US 9,849,163 B2

(12) United States Patent
Chaddock et al.

(10) Patent No.: US 9,849,163 B2
(45) Date of Patent: *Dec. 26, 2017

(54) MODIFIED NON-CYTOTOXIC PROTEASES

(75) Inventors: John Andrew Chaddock, Abingdon (GB); Keith Alan Foster, Abingdon (GB)

(73) Assignee: Ipsen Bioinnovation Limited, Abingdon, Oxfordshire (GB)

(*) Notice: Subject to any disclaimer, the term of this patent is extended or adjusted under 35 U.S.C. 154(b) by 28 days.

This patent is subject to a terminal disclaimer.

(21) Appl. No.: 13/202,696

(22) PCT Filed: Dec. 16, 2009

(86) PCT No.: PCT/GB2009/002892
§ 371 (c)(1),
(2), (4) Date: Nov. 7, 2011

(87) PCT Pub. No.: WO2010/094905
PCT Pub. Date: Aug. 26, 2010

(65) Prior Publication Data
US 2012/0128649 A1    May 24, 2012

(30) Foreign Application Priority Data

Feb. 23, 2009 (GB) .................................. 0903006.5

(51) Int. Cl.
| A61K 38/48 | (2006.01) |
| C12N 9/50 | (2006.01) |
| C12N 9/52 | (2006.01) |
| A61K 38/00 | (2006.01) |

(52) U.S. Cl.
CPC .......... *A61K 38/4893* (2013.01); *C12N 9/50* (2013.01); *C12N 9/52* (2013.01); *C12Y 304/24069* (2013.01); *A61K 38/00* (2013.01); *C07K 2319/06* (2013.01); *C07K 2319/33* (2013.01); *C07K 2319/50* (2013.01)

(58) Field of Classification Search
None
See application file for complete search history.

(56) References Cited

U.S. PATENT DOCUMENTS

| 2007/0184048 A1* | 8/2007 | Foster et al. ............... 424/133.1 |
| 2008/0038274 A1 | 2/2008 | Foster et al. |
| 2009/0023901 A1 | 1/2009 | Steward et al. |

FOREIGN PATENT DOCUMENTS

| JP | 2005-506036 A | 3/2005 | |
| JP | 2008-508364 A | 3/2008 | |
| JP | 2008/511338 A | 4/2008 | |
| JP | 2008-521428 A | 6/2008 | |
| WO | 0114570 A1 | 3/2001 | |
| WO | 0244199 A2 | 6/2002 | |
| WO | WO0244199 * | 6/2002 | ............. C07K 14/33 |
| WO | 2006/026780 A | 3/2006 | |
| WO | 2006/060044 A | 6/2006 | |
| WO | 2006059113 A2 | 6/2006 | |
| WO | 2009150470 A2 | 12/2009 | |

OTHER PUBLICATIONS

Chaddock et al, Protein Expr Purif. Jul. 2002;25(2):219-28. Expression and purification of catalytically active, non-toxic endopeptidase derivatives of Clostridium botulinum toxin type A.*
Wishart et al, A single mutation converts a novel phosphotyrosine binding domain into a dual-specificity phosphatase. J Biol Chem. Nov. 10, 1995;270(45):26782-26785.*
Whisstock et al, Prediction of protein function from protein sequence and structure. Q Rev Biophys. Aug. 2003;36(3):307-40. Review.*
Turton et al, Trends Biochem Sci. Nov. 2002;27(11):552-8. Botulinum and tetanus neurotoxins: structure, function and therapeutic utility.*
A_Geneseq_201215 databse AYI0996 (SEQ ID No. 13) from PCT/GB2009/002892 Chaddock et al, 2010. Alignment with SEQ ID No. 13 herein.*
Li et al, Spectroscopic Analysis of pH-Induced Changes in the Molecular Features of Type A Botulinum Neurotoxin Light Chain. Biochemistry 2000, 39, 6466-6474.*
Lacy and Stevens, 1999, Sequence homology and structural analysis of the clostridial neurotoxins. J. Mol. Biol., 291, 1091-1104.*
United Kingdom Search Report dated Jun. 11, 2009.
International Search Report dated Feb. 7, 2010.
J. A. Chaddock, et al. "Clostridial Neurotoxins: structure-function led design of new therapeutics" CMLS Cellular and Molecular Life Sciences, Birkhauser-Verlag, BA Lnkd. vol. 63, No. 5, Mar. 1, 2006, pp. 540-551.
K. A. Foster, et al. "Re-engineering the target specificity of Clostridial Neurotoxins—a route to novel therapeutics" Neurotoxicity Research, Harwood Academic Publishers, Lausanne, Ch., vol. 9, No. 2-3, Apr. 1, 2006, pp. 101-107.

* cited by examiner

Primary Examiner — Sheridan Swope
(74) Attorney, Agent, or Firm — Hunton & Williams LLP

(57) ABSTRACT

The present invention relates to a modified polypeptide comprising a non-cytotoxic protease, a translocation domain, a destructive protease cleavage site and a Targeting Moiety that binds to a Binding Site on a nerve cell, wherein after cleavage of the destructive cleavage site the polypeptide has reduced potency. The destructive cleavage site is recognized and cleaved by a protease present at or in an off-site target cell, and, in one embodiment, the polypeptide is a modified clostridial neurotoxin. The present invention also relates to the use of said polypeptides for treating a range of conditions, and to nucleic acids encoding said polypeptides.

5 Claims, 21 Drawing Sheets

Figure 1:
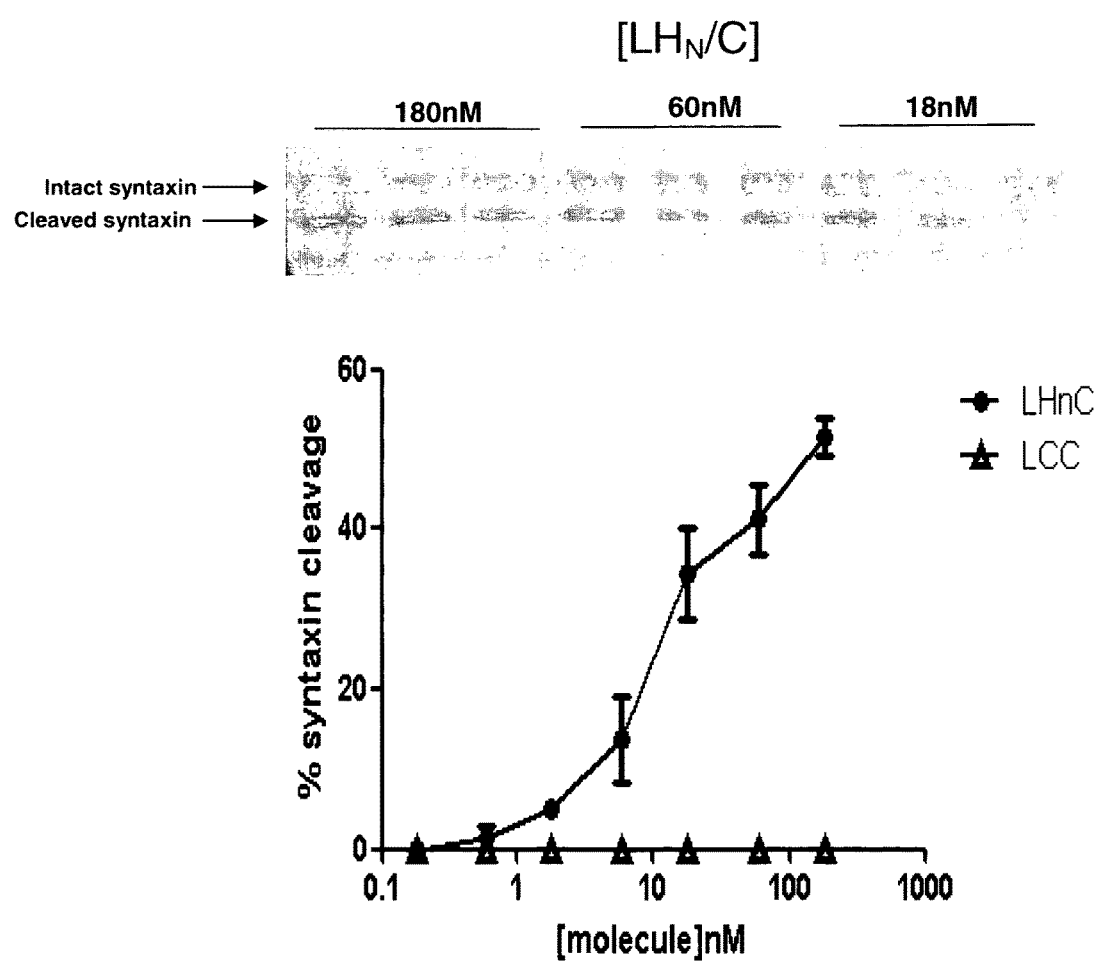

```
LHA : EDTSGKFSVDKLFDKLYKMLTEIYTEDNFVKFFKVLNRKTYLNFDKAVFKIN-IVFKVNYTIYDGFNLRNTNLAANFNGQNTEINMAMFTKLKNFYCGLFEFYKLLCVDGII-- : 435
LHB : EDSEGKYSIDVYSSFDKLYKSLNFGFTETNLAENIKTKASYFSDSLPPVKIKNLLQMEIYTIEEGFMISDKDMEKEIRGQNKAINKQAYEEIS-KEHLAVYKIQMCVDEKK-- : 442
LHC : VESSGEVTVNRNKPVELYNEJTQIPTEENYAKITNVQMRKIYLSNVTPTVTAN-ILDDNVYDIQNGFNIPKSNLRVLFMGQNLSRMPALRKVNP--EMNLYLFTKFCVDAID- : 442
LHD : KDNTGNFVVNIDKFMSLYSDLINVMSEVVYSSQYMVKNRTMHYFSRHYLPVFAM-ILDDMIVTLRDGFNLFMKGFNIENSGQNIERNPALQKLSS--ESVVDLFTKVCVDKSEE : 443
LHE : KDASSGIYSVNFNKFRDIFKKLYS-FTEFDLRKTFQVKCRQTVIGGYKY-FKLSNLLNDSIYNISEGYNIK---NL KYNFRGQNAMLNFPIITPIT-GRGLVKKIIRFCVD-- : 414
LHF : QPSNGNYTVDNISKFNATYKKLFS-FTECDLAQKFQVKRSNYLFHFKP-FRLLDLLDDNIYSISEGFNIG---SLRVNRNGQNIMLNSRIVGPIF--QMGLVERFVGLCVD-- : 423
LHG : EDPNGKYSYNHDKPFDKLYKALMFGFTIKTKYSFYELPFIKTEKLLKLNTEFNQMEKFMIASKMLNTEFNGQEKAVNKEAYEEIS-LEHLVIYRIAMCKF-V-- : 439
       2D3IGN5361624KFIKG5KKLNS6531ETI6AKKS36KMRRK3Y6S21KPP6446N16611M6Y3I2EG5M6314K1646E5NGQN6E6NF2

Fig. 2 (continued)

MODIFIED NON-CYTOTOXIC PROTEASES

The present invention relates to non-cytotoxic proteases having improved efficacy, and to the construction thereof.

Non-cytotoxic proteases are a well-recognised group of proteases, which act on target cells by incapacitating cellular function. Importantly, non-cytotoxic proteases do not kill the target cells upon which they act. Some of the best known examples of non-cytotoxic proteases include clostridial neurotoxins (e.g. botulinum neurotoxin; also known as BOTOX™) and IgA proteases.

Non-cytotoxic proteases act by proteolytically-cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle formation, and thus to secretion of molecules via vesicle transport from a cell. Accordingly, once delivered to a desired target cell, the non-cytotoxic protease is capable of inhibiting cellular secretion from the target cell.

Non-cytotoxic proteases may be employed in their native or substantially native forms (i.e. as holotoxins, such as BOTOX™), in which case targeting of the proteases to specific cell-types is reliant on (i) localised administration of the protease and/or (ii) the inherent binding ability of the native protease. Alternatively, non-cytotoxic proteases may be employed in a re-targeted form in which the native protease is modified to include an exogenous ligand known as a Targeting Moiety (TM). The TM is selected to provide binding specificity for a desired target cell, and, as part of the re-targeting process, the native binding portion of the non-cytotoxic protease may be removed. Re-targeting technology is described, for example, in: EP-B-0689459; EP-B-0939818; U.S. Pat. No. 6,461,617; U.S. Pat. No. 7,192,596; EP-B-0826051; U.S. Pat. No. 5,989,545; U.S. Pat. No. 6,395,513; U.S. Pat. No. 6,962,703; EP-B-0996468; U.S. Pat. No. 7,052,702; EP-B-1107794; and U.S. Pat. No. 6,632,440; all of which are herein incorporated by reference thereto.

In view of the ubiquitous nature of SNARE proteins, non-cytotoxic proteases have been successfully employed in a wide range of therapies.

By way of example, we refer to William J. Lipham, Cosmetic and Clinical Applications of Botulinum Toxin (Slack, Inc., 2004), which describes the use of clostridial toxins, such as botulinum neurotoxins (BoNTs), BoNT/A, BoNT/B, BoNT/C1, BoNT/D, BoNT/E, BoNT/F and BoNT/G, and tetanus neurotoxin (TeNT), to inhibit neuronal transmission in a wide variety of therapeutic and cosmetic applications—as an example, BOTOX™ is currently approved as a therapeutic for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder. In addition, clostridial toxin therapies are described for treating neuromuscular disorders (see U.S. Pat. No. 6,872,397; for treating uterine disorders (see US2004/0175399); for treating ulcers and gastroesophageal reflux disease (see US2004/0086531); for treating dystonia (see U.S. Pat. No. 6,319,505); for treating eye disorders (see US2004/0234532); for treating blepharospasm (see US2004/0151740); for treating strabismus (see US2004/0126396); for treating pain (see U.S. Pat. No. 6,869,610, U.S. Pat. No. 6,641,820, U.S. Pat. No. 6,464,986, U.S. Pat. No. 6,113,915); for treating fibromyalgia (see U.S. Pat. No. 6,623,742, US2004/0062776); for treating lower back pain (see US2004/0037852); for treating muscle injuries (see U.S. Pat. No. 6,423,319); for treating sinus headache (see U.S. Pat. No. 6,838,434); for treating tension headache (see U.S. Pat. No. 6,776,992); for treating headache (see U.S. Pat. No. 6,458,365); for reduction of migraine headache pain (see U.S. Pat. No. 5,714,469); for treating cardiovascular diseases (see U.S. Pat. No. 6,767,544); for treating neurological disorders such as Parkinson's disease (see U.S. Pat. No. 6,620,415, U.S. Pat. No. 6,306,403); for treating neuropsychiatric disorders (see US2004/0180061, US2003/0211121); for treating endocrine disorders (see U.S. Pat. No. 6,827,931); for treating thyroid disorders (see U.S. Pat. No. 6,740,321); for treating a cholinergic influenced sweat Gland (see U.S. Pat. No. 6,683,049); for treating diabetes (see U.S. Pat. No. 6,337,075, U.S. Pat. No. 6,416,765); for treating a pancreatic disorder (see U.S. Pat. No. 6,261,572, U.S. Pat. No. 6,143,306); for treating cancers such as bone tumors (see U.S. Pat. No. 6,565,870, U.S. Pat. No. 6,368,605, U.S. Pat. No. 6,139,845, US2005/0031648); for treating optic disorders (see U.S. Pat. No. 6,358,926, U.S. Pat. No. 6,265,379); for treating autonomic disorders such as gastrointestinal muscle disorders and other smooth muscle dysfunction (see U.S. Pat. No. 5,437,291); for treatment of skin lesions associated with cutaneous cell-proliferative disorders (see U.S. Pat. No. 5,670,484); for management of neurogenic inflammatory disorders (see U.S. Pat. No. 6,063,768); for reducing hair loss and stimulating hair growth (see U.S. Pat. No. 6,299,893); for treating downturned mouth (see U.S. Pat. No. 6,358,917); for reducing appetite (see US2004/40253274); for dental therapies and procedures (see US2004/0115139); for treating neuromuscular disorders and conditions (see US2002/0010138); for treating various disorders and conditions and associated pain (see US2004/0013692) for treating pain (see WO96/33274); for treating conditions resulting from mucus hypersecretion such: as asthma and COPD (see WO00/10598); for treating non-neuronal conditions such as inflammation, endocrine conditions, exocrine conditions, immunological conditions, cardiovascular conditions, bone conditions (see WO01/21213). All of the above publications are herein incorporated by reference thereto.

The use of non-cytotoxic proteases such as clostridial neurotoxins (e.g. BoNTs and TeNT) in therapeutic and cosmetic treatments of humans and other mammals is anticipated to expand to an ever-widening range of diseases and ailments that can benefit from the properties of these toxins.

Administration of a non-cytotoxic protease (including native clostridial neurotoxin clinical products) can be challenging because of a need for larger doses required to achieve a beneficial effect. Larger doses can increase the likelihood that the protease may move, for example, through the interstitial fluids and the circulatory systems (such as the cardiovascular system and the lymphatic system) of the body, resulting in undesirable dispersal of the protease to areas not targeted for treatment. Said dispersal can lead to undesirable side effects, such as inhibition of cellular secretion in cells not targeted for treatment (e.g. inhibition of neurotransmitter release in neurons not targeted for treatment, or paralysis of a muscle not targeted for treatment). By way of specific example, a patient administered a therapeutically effective amount of a BoNT into the neck muscles for torticollis may develop dysphagia because of dispersal of the protease into the oropharynx. Similarly, a patient administered a non-cytotoxic protease to treat a neuromuscular disorder may suffer from undesirable muscle tissue inactivation due to dispersal of the protease into the muscle.

In common with any other drug substances, a therapeutic dosing range exists which identifies the lower and upper limits of safe, effective therapy. Often, the upper limit is determined by the increasing significance of off-target effects that lead to undesirable (e.g. potentially harmful) side-effects of drug treatment. In the case of non-cytotoxic proteases (notably BoNT), this could lead to the paralysis of cellular secretion in off-target cells, which, in turn, could be fatal.

The growing clinical, therapeutic and cosmetic use of non-cytotoxic proteases in therapies requiring larger doses places an ever-increasing requirement on the part of the pharmaceutical industry to develop means for minimising off-target effects, whilst maintaining the potency of the protease, such that the therapeutic dose range can be increased and the patients thus provided with increased doses which will, in turn, lead to increased efficacy of treatment.

There is therefore a need in the art for new therapies and/or new therapeutics capable of specifically addressing undesirable, off-site targeting effects. This need is addressed by the present invention, which solves one or more of the above-mentioned problems.

In WO02/044199, Lin, Wei-Jen, et al., seek to solve this problem by provision of clostridial neurotoxins modified to contain a blood protease cleavage site (ie. a site cleavable by a protease present in blood) in the binding domain of the neurotoxin, such that contact with a blood protease selectively inactivates the neurotoxin. Said binding domain (also referred to as the $H_C$ domain) is illustrated in FIG. 1B of Lin, Wei-Jen, et al. as the region starting at amino acid residue 873. The above-mentioned solution provided by Lin, et al., however, has a number of problems, and does not adequately solve the problem of off-site targeting effects. In this regard, the present inventors have identified that clostridial neurotoxins in which the binding ($H_C$) domain has been removed (or otherwise inactivated) are still toxic and can still effect inhibition at their target neurons—this is confirmed by FIG. 1 (see Example 39) of the present application, which illustrates SNARE protein cleavage by a clostridial neurotoxin molecule (LHN) lacking the binding ($H_C$). A further deficiency associated with WO02/044199 (Lin, Wei-Jen, et al.) is that the described technology is limited to clostridial neurotoxin molecules possessing a $H_C$ binding domain (ie. clostridial holotoxin molecules). As already discussed, however, non-cytotoxic proteases may be employed in a re-targeted form in which the native protease is modified to include an exogenous ligand known as a Targeting Moiety (TM), which provides binding specificity for a desired target cell. Thus, in the context of re-targeted non-cytotoxic proteases, the disclosure of Lin, et al. fails to address the problem of off-site targeting effects.

The present invention addresses the deficiencies of Lin, et al. and provides non-cytotoxic proteases that reduce or prevent unwanted side-effects associated with dispersal into non-targeted areas. These and related advantages are useful for various clinical, therapeutic and cosmetic applications, such as the treatment of neuromuscular disorders, neuropathic disorders, eye disorders, pain, muscle injuries, headache, cardiovascular diseases, neuropsychiatric disorders, endocrine disorders, exocrine disorders, mucus secretion-related disorders such as asthma and COPD, cancers, optic disorders and hyperkinetic facial lines, as well as, other disorders where non-cytotoxic protease administration to a mammal can produce a beneficial effect (e.g. all of the therapies described on pages 2-3 of this specification).

In more detail, a first aspect of the present invention provides a polypeptide, comprising:
  a. a non-cytotoxic protease that is capable of cleaving a SNARE protein;
  b. a translocation domain that is capable of translocating the non-cytotoxic protease from within an endosome of a mammalian cell, across the endosomal membrane thereof and into the cytosol of the mammalian cell;
  c. a first destructive cleavage site that is cleavable by a second protease and not by the non-cytotoxic protease, and wherein after cleavage thereof by the second protease the polypeptide has reduced potency measurable by a reduced ability to cleave said SNARE protein and/or a reduced ability to translocate said non-cytotoxic protease across an endosomal membrane;
  d. a Targeting Moiety (TM) that binds to a Binding Site present on a mammalian neuronal cell, which Binding Site is capable of undergoing endocytosis to be incorporated into an endosome within the mammalian neuronal cell; and
  e. with the proviso that said first destructive cleavage site is not located within said (TM).

Thus, the present invention provides a polypeptide that can be controllably inactivated and/or destroyed at an off-site location.

In one embodiment, the destructive cleavage site is recognised and cleaved by a second protease (i.e. a destructive protease) selected from a circulating protease (e.g. an extracellular protease, such as a serum protease or a protease of the blood clotting cascade), a tissue-associated protease (e.g. a matrix metalloprotease (MMP), such as a MMP of muscle), and an intracellular protease (preferably a protease that is absent from the target cell)).

Thus, in use, should a polypeptide of the present invention become dispersed away from its intended target cell and/or be taken up by a non-target cell, the polypeptide will become inactivated by cleavage of the destructive cleavage site (by the second protease).

In one embodiment, the destructive cleavage site is recognised and cleaved by a second protease that is present within an off-site cell-type. In this embodiment, the off-site cell and the target cell are preferably different cell types. Alternatively (or in addition), the destructive cleavage site is recognised and cleaved by a second protease that is present at an off-site location (e.g. distal to the target cell). Accordingly, when destructive cleavage occurs extracellularly, the target cell and the off-site cell may be either the same or different cell-types. In this regard, the target cell and the off-site cell may each possess a receptor to which the same polypeptide of the invention binds).

By way of example, when treating neuromuscular disorders, a polypeptide of the present invention is targeted to the desired target cell (e.g. to a motor neuron), and includes a destructive protease cleavage site that is cleaved by a second protease present within and/or in close proximity to muscle tissue. Accordingly, the polypeptide demonstrates minimal adverse effects on muscle tissue, and can be used at greater doses than currently tolerable by a patient, thereby leading to enhanced clinical efficacy.

The destructive cleavage site of the present invention provides for inactivation/destruction of the polypeptide when the polypeptide is in or at an off-site location. In this regard, cleavage at the destructive cleavage site minimises the potency of the polypeptide by reducing the inherent ability of the polypeptide (when compared with an identical polypeptide lacking the same destructive cleavage site, or possessing the same destructive site but in an uncleaved form) to translocate the non-cytotoxic component (across the endosomal membrane of a mammalian cell in the direction of the cytosol), and/or to effect SNARE protein cleavage.

In one embodiment, the polypeptide of the invention may include a second (or subsequent) inactivation/destruction site. Said (or subsequent) second site may be located anywhere within the polypeptide (including within the TM component). Said second (or subsequent) site may be cleaved by the same or by a different protease. Said second (or subsequent) site may have a different amino acid recognition sequence that the first inactivation/destruction site, and may be cleaved by the same or by a different protease.

The above-mentioned reduced SNARE cleavage and/or reduced translocation capacity can be readily measured by direct comparison of a polypeptide of the invention with an identical polypeptide (though lacking the same destructive cleavage site, or possessing the same destructive site but in an uncleaved form). In more detail, the polypeptide of the invention and the corresponding uncleaved counterpart may be assayed in parallel in any one of a variety of conventional whole cell or cell free assays. By way of example, reference is made to Examples 1-4. During said assays, the polypeptide of the invention becomes inactivated (via cleavage at the destructive cleavage site), whereas the counterpart polypeptide substantially retains full potency. Thus, in the context of the present invention, when cleaved at the destructive cleavage site, a polypeptide of the invention possesses less than 50% or less than 25%, less than 10% or less than 5%, less than 1% or less than 0.5%, less than 0.1% or less than 0.01%, or less than 0.001% or less than 0.0001% of the SNARE protein cleavage ability and/or reduced translocation ability when compared with the uncleaved counterpart polypeptide.

In the context of whole cell assays, reduced SNARE cleavage and/or reduced translocation ability may be determined by measuring relative SNARE protein cleavage in a mammalian cell. This is reflective of the overall ability of the polypeptide to translocate into and subsequently cleave a SNARE protein within the cytosol of a mammalian cell. There are a variety of ways for measuring SNARE protein cleavage such as, for example, SDS-PAGE and Western Blotting followed by densitometer analysis of the cleaved products.

In the context of cell-free assays, potency can be measured in terms of relative SNARE protein cleavage, or in terms of relative translocation function (e.g. release of $K^+$ or NAD from liposomes, or membrane conductance measurements).

Preferred off-site targets (and thus preferred mammalian cells for the above assays) include: epithelial cells, especially lung epithelial cells; neuronal cells that are not motor neuron cells; and muscle cells.

Referring to Example 39, a modified clostridial neurotoxin ($LH_N$/C) was provided. This neurotoxin mimics the modified neurotoxin of Lin, et al. (ie. as discussed in the background part of this specification) as it lacks a functional $H_C$ binding domain. Said modified neurotoxin was incubated in the presence of a mammalian cell (e.g. an embryonic spinal cord neuron (eSCN)) to assess it's ability to demonstrate residual clostridial neurotoxin activity in the form of SNARE protein cleavage. In parallel, a control neurotoxin consisting solely of the endopeptidase domain of botulinum neurotoxin type C (LC/C) was incubated in the same manner—the control neurotoxin therefore lacked a function $H_N$ translocation domain. Each of the two polypeptides was then assessed for cleavage of a SNARE protein in the test cell. Surprisingly, the $LH_N$/C modified clostridial neurotoxin demonstrated SNARE cleavage (see FIG. 1), and thus confirmed that inactivation of the $H_C$ binding domain of botulinum neurotoxin is not adequate to reduce off-site activity. In contrast, the control neurotoxin (lacking a functional translocation component) demonstrated a lack of SNARE cleavage.

As mentioned above, the polypeptide of the present invention may include one or more (e.g. two, three, four, five or more) destructive protease cleavage sites.

Where more than one destructive cleavage site is included, each cleavage site may be the same or different. In this regard, use of more than one destructive cleavage sites provides improved off-site inactivation. Similarly, use of two or more different destructive cleavage sites provides additional design flexibility. For example, when minimising off-site target effects in muscle tissue, the polypeptide of the present invention may include two different destructive sites, which are recognised and cleaved by two different muscle tissues associated proteases.

The first destructive cleavage site(s) may be engineered into the non-cytotoxic protease component or the translocation component. The second (or subsequent) site(s) may be engineered anywhere into the polypeptide. In this regard, the destructive cleavage site(s) are chosen to ensure minimal adverse effect on the potency of the polypeptide (for example by having minimal effect on the translocation domain, and/or on the non-cytotoxic protease domain) whilst ensuring that the polypeptide is labile away from its target site/target cell.

Preferred destructive cleavage sites (plus the corresponding second proteases) are listed in the Table immediately below. The listed cleavage sites are purely illustrative and are not intended to be limiting to the present invention.

| Second protease | Destructive cleavage site recognition sequence | Tolerated recognition sequence variance P4-P3-P2-P1-▼-P1'-P2'-P3' | | | | | | |
|---|---|---|---|---|---|---|---|---|
| | | P4 | P3 | P2 | P1 | P1' | P2' | P3' |
| Thrombin | LVPR▼GS (SEQ ID NO: 40) | A, F, G, I, L, T, V or M | A, F, G, I, L, T, V, W or A | P | R | Not D or E | Not D or E | — |
| Thrombin | GR▼G | | | | G | R | G | |
| Factor Xa | IEGR▼(SEQ ID NO: 41) | A, F, G, I, L, T, V or M | D or E | G | R | — | — | — |
| ADAM17 | PLAQA▼VRSSS (SEQ ID NO: 42) | | | | | | | |

-continued

| Second protease | Destructive cleavage site recognition sequence | Tolerated recognition sequence variance P4-P3-P2-P1-▼-P1'-P2'-P3' | | | | | | |
|---|---|---|---|---|---|---|---|---|
| | | P4 | P3 | P2 | P1 | P1' | P2' | P3' |
| Human airway trypsin-like protease (HAT) | SKGR▼SLIGRV (SEQ ID NO: 43) | | | | | | | |
| ACE (peptidyl-dipeptidase A) | | — | — | — | — | Not P | Not D or E | N/A |
| Elastase (leukocyte) | MEA▼VTY (SEQ ID NO: 44) | M, R | E | A, H | V, T | V, T, H | Y | — |
| Furin | RXR/KR▼ (SEQ ID NO: 100) | R | X | R or K | R | | | |
| Granzyme | IEPD▼ (SEQ ID NO: 45 | I | E | P | D | — | — | — |
| Caspase 1 | | F, W, Y, L | — | H, A, T | D | Not P, E. D. Q. K or R | — | — |
| Caspase 2 | DVAD▼ (SEQ ID NO: 46) | D | V | A | D | Not P, E. D. Q. K or R | — | — |
| Caspase 3 | DMQD▼ (SEQ ID NO: 47) | D | M | Q | D | Not P, E. D. Q. K or R | — | — |
| Caspase 4 | LEVD▼ (SEQ ID NO: 48) | L | E | V | D | Not P, E. D. Q. K or R | — | — |
| Caspase 5 | | L or W | E | H | D | — | — | — |
| Caspase 6 | | V | E | H or I | D | Not P, E. D. Q. K or R | — | — |
| Caspase 7 | DEVD▼ (SEQ ID NO: 49) | D | E | V | D | Not P, E. D. Q. K or R | — | — |
| Caspase 8 | | I or L | E | T | D | Not P, E. D. Q. K or R | — | — |
| Caspase 9 | LEHD▼ (SEQ ID NO: 50) | L | E | H | D | — | — | — |
| Caspase 10 | IEHD▼ (SEQ ID NO: 51) | I | E | H | D | — | — | — |

The present invention may employ destructive cleavage sites that are cleavable by a mammalian blood protease, such as Thrombin, Coagulation Factor VIIa, Coagulation Factor IXa, Coagulation Factor Xa, Coagulation Factor XIa, Coagulation Factor XIIa, Kallikrein, Protein C, and MBP-associated serine protease.

Lin, et al. describe the use of thrombin or Factor Xa cleavage sites to inactivate the $H_C$ binding domain of a clostridial holotoxin. As discussed above, however, $H_C$ inactivation is inadequate to achieve desirable off-site inactivation, Moreover, due to the pausity of cleavage sites disclosed, the method described by Lin, et al. has limited utility, for example in off-site environments where thrombin and Factor Xa are absent (or only present at low concentrations).

Matrix metalloproteases (MMPs) are a preferred group of destructive proteases in the context of the present invention. Within this group, ADAM17 (EC 3.4.24.86), also known as TACE, is preferred and cleaves a variety of membrane-anchored, cell-surface proteins to "shed" the extracellular domains. Additional, preferred MMPs include adamalysins, serralysins, and astacins.

In one embodiment of the present invention, said destructive cleavage site(s) comprises a recognition sequence having at least 3 or 4, preferably 5 or 6, more preferably 6 or 7, and particularly preferably at least 8 contiguous amino acid residues. In this regard, the longer (in terms of contiguous amino acid residues) the recognition sequence, the less likely non-specific cleavage of the destructive site will occur via an unintended second protease.

The polypeptide of the present invention optionally includes a Targeting Moiety (TM) that binds to a Binding Site on a neuronal (eg. nerve) cell, thereby providing selectivity of the polypeptide to this species of target cell over other cells. In one embodiment, the neuronal cell is a cell of the neuromuscular junction or presynaptic cholinergic peripheral nerve terminal.

The first (and subsequent) destructive cleavage site(s) of the present invention is preferably introduced into the protease component and/or into the translocation component. Of these two components, the protease component is preferred. Accordingly, the polypeptide may be rapidly inactivated by direct destruction of the non-cytotoxic protease and/or translocation components. These insertion positions are preferable over a TM insertion position because, even in the case of total TM inactivation, it has been shown that the resulting polypeptide may not demonstrate adequately reduced potency on off-site cells [Chaddock, J A., et al. Protein Expression Purification 2002, 25, 219-228 and Sutton, J M, et al. Protein Expression & Purification 2005, 40(1), 31-41].

Thus, the polypeptide of the present invention does not comprise a destructive cleavage site(s) solely within the Targeting Moiety component of the polypeptide. Without wishing to be bound by any theory, it is believed that use of a destruction site within the TM component alone does not address non-specific uptake by off-site target cells. Example 39 (see also FIG. 1) demonstrates that a fragment of botulinum neurotoxin type C lacking the binding domain $H_C$ is still able to enter eSCN and cleave its substrate SNARE protein (syntaxin). A further possibility is that cleavage within the TM component might lead to a TM having increased binding affinity for off-site cells, for example, via exposure of a higher affinity binding region within the TM. In summary, the use of a destructive cleavage site(s) within the TM component alone is considered unsatisfactory. First, off-site targeting is not adequately addressed, and, secondly, once delivered to an off-site cell, the polypeptides are still capable of (wild-type/natural) translocation activity and/or SNARE protein cleavage activity.

It is preferred that the TM has no destructive cleavage site. In this regard, it has been shown that the TM component may be particularly susceptible to adverse conformational changes (upon insertion of a destructive cleavage site), which adversely affect desired binding of the polypeptide. This has been shown to be a particular problem when the TM is the native targeting moiety of a clostridial neurotoxin (i.e. $H_C$).

Suitable TMs for use in the polypeptides of the present invention include cytokines, growth factors, neuropeptides, lectins, protein binding scaffolds, and antibodies—this term includes monoclonal antibodies, and antibody fragments such as Fab, F(ab)'$_2$, Fv, ScFv, etc.

The TM is a ligand (preferably a peptide) that binds to a neuronal cell, preferably to a neuronal cell of the neuromuscular junction. In this regard, in one embodiment the TM comprises the binding domain ($H_{CC}$, or $H_C$) of a clostridial neurotoxin (e.g. BoNT, TeNT, or from other *Clostridium* spp.), or a fragment thereof that possesses native neurotoxin binding ability. The clostridial $H_C$ domain has evolved to bind in a highly effective manner to receptors present on neuronal cells. In accordance with this latter embodiment, the present invention provides use and corresponding methods for modifying BOTOX™ to improve its clinical utility. By way of example, suitable TM clostridial $H_{CC}$ reference sequences include:

Botulinum type A neurotoxin—amino acid residues (Y1111-L1296)
Botulinum type B neurotoxin—amino acid residues (Y1098-E1291)
Botulinum type C neurotoxin—amino acid residues (Y1112-E1291)
Botulinum type D neurotoxin—amino acid residues (Y1099-E1276)
Botulinum type E neurotoxin—amino acid residues (Y1086-K1252)
Botulinum type F neurotoxin—amino acid residues (Y1106-E1274)
Botulinum type G neurotoxin—amino acid residues (Y1106-E1297)
Tetanus neurotoxin—amino acid residues (Y1128-D1315).

The above-identified reference sequences should be considered a guide as slight variations may occur according to sub-serotypes.

Similarly, by way of example, suitable TM clostridial $H_C$ domains of reference sequences include: BoNT/A-N872-L1296; BoNT/B-E859-E1291; BoNT/C1-N867-E1291; BoNT/D-S863-E1276; BoNT/E-R846-K1252; BoNT/F-K865-E1274; BoNT/G-N864-E1297; and TeNT-1880-D1315.

In another embodiment, the TM is selected to provide desirable binding to the neuromuscular junction. Suitable TMs are listed in WO 2006/099590, which is herein incorporated by reference thereto, and include: glucagon like hormone, a neurohormone, a neuroregulatory cytokine, a neurotrophin, a growth factor, an axon guidance signaling molecule, a sugar binding protein, a ligand that selectively binds a neurexin, a ligand for neurexin-2α, a ligand for neurexin-2β, a ligand for neurexin-3α, a ligand for neurexin-3β, a WNT, Ng-CAM(LI), NCAM, N-cadherin, a PACAP peptide such as a VIP peptide, Agrin-MUSK, a basement membrane polypeptide, and a variant of any of the foregoing polypeptides, a neuroregulatory cytokine such as ciliary neurotrophic factor (CNTF), glycophorin-A (GPA), leukemia inhibitory factor (LIF), an interleukin (IL), onostatin M, cardiotrophin-1 (CT-1), cardiotrophin-like cytokine (CLC), a neuroleukin, VEGF, an insulin-like growth factors (IGF), an epidermal growth factor (EGF), and a variant of any of the foregoing neuroregulatory cytokines. These and other TMs are selected for use in the present invention because they mimic the binding ability of clostridial neurotoxins.

As mentioned above, the destructive cleavage site(s) are introduced with minimum adverse effect on the biological properties of the polypeptide (notably, endopeptidase activity, and/or membrane translocation activity). In this regard, it is preferred that any potential decrease in potency of the polypeptide (compared with the same polypeptide lacking said destructive cleavage site(s)) is less than 25%, preferably less than 15%, more preferably less than 5% of the original unmodified protein. Potency here may be measured by a comparative assay such as illustrated in Examples 1-4.

When selecting destructive cleavage site(s) in the context of the present invention, it is preferred that the destructive cleavage site(s) are not substrates for any proteases that may be separately used for post-translational modification of the polypeptide of the present invention as part of its manufacturing process. In this regard, the non-cytotoxic proteases of the present invention typically employ a protease activation event (via a separate 'activation' protease cleavage site, which is structurally distinct from the destructive cleavage site of the present invention). The purpose of the activation cleavage site is to cleave a peptide bond between the non-cytotoxic protease and translocation or TM components of the polypeptide of the present invention, thereby providing an 'activated' di-chain polypeptide wherein said two components are linked together via a di-sulfide bond.

In natural clostridial holotoxin, the di-chain loop protease cleavage site occurs at K448-A449 for BoNT/A, at K441-A442 for BoNT/B, at K449-T450 for BoNT/C1, at R445-D446 for BoNT/D, at R422-K423 for BoNT/E, at K439-A440 for BoNT/F, at K446-S447 for BoNT/G, and at A457-S458 for TeNT. Thus, to help ensure that the destructive cleavage site of the polypeptides of the present invention does not adversely affect the 'activation' cleavage site and subsequent di-sulfide bond formation, the former is preferably introduced into polypeptide of the present invention at a position of at least 20, at least 30, at least 40, at least 50, and more preferably at least 60, at least 70, at least 80 (contiguous) amino acid residues away from the 'activation' cleavage site. In this regard, the activation site of a polypeptide of the invention may be readily aligned (via simple, primary sequence alignment) with the activation site positions (listed above) for clostridial holotoxin.

The destructive cleavage site(s) are preferably exogenous (i.e. engineered/artificial) with regard to the native components of the polypeptide. In other words, said cleavages sites are preferably not inherent to the corresponding native components of the polypeptide. By way of example, a protease or translocation component based on BoNT/A L-chain or H-chain (respectively) may be engineered according to the present invention to include a cleavage site(s). Said cleavage site(S) would not, however, be present in the corresponding BoNT native L-chain or H-chain.

In a preferred embodiment of the present invention, the destructive cleavage site(s) and the 'activation' cleavage site are not cleaved by the same protease. In one embodiment, the two cleavage sites differ from one another in that at least one, more preferably at least two, particularly preferably at least three, and most preferably at least four of the tolerated amino acids within the respective recognition sequences is/are different.

By way of example, in the case of a polypeptide chimaera containing a Factor Xa 'activation' site between clostridial L-chain and $H_N$ components, it is preferred to employ a destructive cleavage site(s) that is a site other than a Factor Xa site, which may be inserted elsewhere in the L-chain and/or $H_N$ component(s). In this scenario, the polypeptide may be modified to accommodate an alternative 'activation' site between the L-chain and $H_N$ components (for example, an enterokinase cleavage site), in which case a separate Factor Xa cleavage site(s) may be incorporated elsewhere into the polypeptide as the destructive cleavage site. Alternatively, the existing Factor Xa 'activation' site between the L-chain and $H_N$ components may be retained, and an alternative cleavage site such as a thrombin cleavage site incorporated as the destructive cleavage site(s).

When identifying suitable sites within the primary sequence of any of the components of the present invention for inclusion of cleavage site(s), it is preferable to select a primary sequence that closely matches with the proposed cleavage site(s) that are to be inserted. By doing so, minimal structural changes are introduced' into the polypeptide. By way of example, cleavage sites typically comprise at least 3 contiguous amino acid residues. Thus, in a preferred embodiment, a cleavage site is selected that already possesses (in the correct position(s)) at least one, preferably at least two of the amino acid residues that are required in order to introduce the new cleavage site. By way of example, when the Caspase 3 cleavage site (DMQD SEQ ID 47) is to be introduced, a preferred insertion position may be identified that already includes a primary sequence selected from, for example, Dxxx (SEQ ID 101), xMxx (SEQ ID 102), xxQx (SEQ ID 103), xxxD (SEQ ID 104), DMxx (SEQ ID 105), DxQx (SEQ ID 106), DxxD (SEQ ID 107), xMQx (SEQ ID 108), xMxD (SEQ ID 109), xxQD (SEQ ID 110), DMQx (SEQ ID 111), xMQD (SEQ ID 112), DxQD (SEQ ID 113), and DMxD (SEQ ID 114).

By analysis of the tertiary structure of clostridial neurotoxin, the present inventors have identified a range of suitable exposed regions (in particular exposed loop regions) for insertion of the destructive site sequence(s). This analysis has been based principally on Chaddock & Marks (2006) in Cell & Molecular Life Sciences, 63, 540-551; and with additional reference to Lacy and Stevens, 1999, J. Mol Biol., 291, 1091-1104; and the following Table.

| BoNT Sero-type | PDB ID | PDB Description |
|---|---|---|
| A | 1E1H | Crystal structure of recombinant botulinum neurotoxin type A light chain, self-inhibiting Zn endopeptidase |
| A | 1XTF | Neurotoxin BoNT/A E224Q Y366F mutant |
| A | 1XTG | Crystal structure of neurotoxin BONT/A complexed with synaptosomal-associated protein 25 |
| A | 3BTA | Crystal structure of botulinum neurotoxin serotype A |
| B | 1EPW | Crystal Structure of *Clostridium* neurotoxin type B |
| B | 1F31 | Crystal structure of *Clostridium botulinum* neurotoxin B complexed with a trisaccharide |
| B | 1F82 | Botulinum neurotoxin type B catalytic domain |
| B | 1F83 | Botulinum neurotoxin type B catalytic domain with synaptobrevin-II bound |
| B | 1G9A | Crystal structure of *Clostridium botulinum* B complexed with an inhibitor (Experiment 3) |
| B | 1G9B | Crystal structure of *Clostridium botulinum* neurotoxin B complexed with an inhibitor (Experiment 1) |
| B | 1G9C | Crystal structure of *Clostridium botulinum* neurotoxin B complexed with an inhibitor (Experiment 4) |
| B | 1G9D | Crystal structure of *Clostridium botulinum* neurotoxin B complexed with an inhibitor (Experiment 2) |
| B | 1I1E | Crystal structure of *Clostridium botulinum* neurotoxin B complexed with doxorubicin |
| B | 1S0B | Crystal structure of botulinum neurotoxin type B at pH 4.0 |
| B | 1S0C | Crystal structure of botulinum neurotoxin type B at pH 5.0 |
| B | 1S0D | Crystal structure of botulinum neurotoxin type B at pH 5.5 |
| B | 1S0E | Crystal structure of botulinum neurotoxin type B at pH 6.0 |
| B | 1S0F | Crystal structure of botulinum neurotoxin type B at pH 7.0 |
| B | 1S0G | Crystal structure of botulinum neurotoxin type B apo form |
| B | 1Z0H | N-terminal helix reorients in recombinant C-fragment of *Clostridium botulinum* type B |
| B | 2ETF | Crystal structure of full length botulinum neurotoxin (type B) light chain |
| D | 2FPQ | Crystal structure of botulinum neurotoxin type D light chain |
| E | 1T3A | Crystal structure of *Clostridium botulinum* neurotoxin type E catalytic domain |
| E | 1T3C | *Clostridium botulinum* type E catalytic domain E212Q mutant |
| E | 1ZKW | Crystal structure of Arg347Ala mutant of botulinum neurotoxin E catalytic domain |
| E | 1ZKX | Crystal structure of Glu158Ala/Thr159Ala/Asn160Ala- a triple mutant of *Clostridium botulinum* neurotoxin E catalytic domain |
| E | 1ZL5 | Crystal structure of Glu335Gln mutant of *Clostridium botulinum* neurotoxin E catalytic domain |
| E | 1ZL6 | Crystal structure of Tyr350Ala mutant of *Clostridium botulinum* neurotoxin E catalytic domain |
| E | 1ZN3 | Crystal structure of Glu335Ala mutant of *Clostridium botulinum* neurotoxin type E |
| F | 2A8A | Crystal structure of *Clostridium botulinum* neurotoxin serotype F light chain |
| F | 2A97 | Crystal structure of catalytic domain of *Clostridium botulinum* neurotoxin serotype F |
| G | 1ZB7 | Crystal Structure of botulinum neurotoxin type G light chain |

The above PDB identification refers to the 4 character code used by the Research Collaboratory for Structural Bioinformatics (RCSB) Protein Data Bank to identify a specific entry in the structural database.

Additional techniques employed include use of peptide/antibody mapping information, for example, antibody mapping of sites on the surface of HC/A (Dolimbek, B Z, 2007, Mol Immunol., 44(5):1029-41), HN/A (Atassi M Z, 2004, Protein J. 23(1):39-52), HC/A (Oshima M., 1998, Immunol Lett., 60(1):7-12; Bavari, S 1998, Vaccine, 16(19):1850-6), HC/E (Kubota T, 1997, Appl Environ Microbiol. 63(4): 1214-8)—a list of epitopes within the BoNT serotypes is publicly available and maintained by Pathema; and use of structural prediction software to predict the solvent accessibility of a specific peptide region—examples of publically available software include:

Swiss Model;
ESyPred3D;
and Geno3D.

In one embodiment of the present invention, the destructive cleavage site(s) are introduced at one or more of the following position(s), which are based (for convenience purposes) on the primary amino acid sequence of BoNT/A. Whilst the insertion positions are identified by reference to BoNT/A, the primary amino acid sequences of corresponding protease domains and/or translocation domains for BoNT/B-G etc may be readily aligned with said BoNT/A positions—by way of example, we refer to the serotype alignment illustrated in FIG. 2.

For the protease component, one or more of the following positions is preferred: 27-31, 56-63, 73-75, 78-81, 99-105, 120-124, 137-144, 161-165, 169-173, 187-194, 202-214, 237-241, 243-250, 300-304, 323-335, 375-382, 391-400, and 413-423. The above numbering preferably starts from the N-terminus of the protease component of the present invention. Of these positions, the 99-105 and/or 202-214 are most preferred. In this regard, referring to FIG. 2, positions 99-105 correspond to the sequence "YSTDLGR" (SEQ ID 52) for serotype A, which equates to the region "KSKPLGE" (SEQ ID 53) for serotype B, "NSREIGE" (SEQ ID 54) for serotype C$_1$, "NERDIGK" (SEQ ID 55) for serotype D, "NNNLSGG" (SEQ ID 56) for serotype E, "NSNPAGQ" (SEQ ID 57) for serotype F, and "NSKPSGQ" (SEQ ID 58) for serotype G. Similarly, referring to FIG. 2, positions 202-214 correspond to the sequence "VDTNPLLGAGKFA" (SEQ ID 59) for serotype A, which equates to the region "NKGASIFNRRGYF" (SEQ ID 60) for serotype B, "DVGEGRFSKSEFC" (SEQ ID 61) for serotype C$_1$, "NQSSAVLGKSIFC" (SEQ ID 62) for serotype D, "DNC----MN--EFI" (SEQ ID 115) for serotype E, "DN-----TD--LFI" (SEQ ID 116) for serotype F, and "ENKDTSIFSRRAYF" (SEQ ID 63) for serotype G. and "P" (202) using the numbering at the top of FIG. 2 as and "P", respectively.

In a preferred embodiment, the destructive cleavage site(s) are located at a position greater than 8 amino acid residues, preferably greater than 10 amino acid residues, more preferably greater than 25 amino acid residues, particularly preferably greater than 50 amino acid residues from the N-terminus of the protease component. Similarly, in a preferred embodiment, the destructive cleavage site(s) are located at a position greater than 20 amino acid residues, preferably greater than 30 amino acid residues, more preferably greater than 40 amino acid residues, particularly preferably greater than 50 amino acid residues from the C-terminus of the protease component.

For the translocation component, one or more of the following positions is preferred: 474-479, 483-495, 507-543, 557-567, 576-580, 618-631, 643-650, 669-677, 751-767, 823-834, 845-859. The above numbering preferably acknowledges a starting position of 449 for the N-terminus of the translocation domain component of the present invention, and a starting position of 871 for the C-terminus of the H$_N$ component. Of these positions, the 557-567 and/or 751-767 are most preferred. In this regard, referring to FIG. 2, positions 557-567 correspond to the sequence "QEFEHGKSRIA" (SEQ ID 64) for serotype A, which equates to the region "QTFPLDIRDIS" (SEQ ID 65) for serotype B, "QKLSDNVEDFT" (SEQ ID 66) for serotype C$_1$, "QKLSNNVENIT" (SEQ ID 67) for serotype D, "QKVPEGENNVN" (SEQ ID 68) for serotype E, "QKAPEGESAIS" (SEQ ID 69) for serotype F, and "QTFPSNIENLQ" (SEQ ID 70) for serotype G. Similarly, referring to FIG. 2, positions 751-767 correspond to the sequence "YNQY-TEEEKNNINNID" (SEQ ID 71) for serotype A, which equates to the region "YNIYSEKEKSNIN--IDFN" (SEQ ID 72) for serotype B, "YKKYSGSDKENIKS--QVE" (SEQ ID 73) for serotype C$_1$, "YKKYSGSDKENIKS--QVE" (SEQ ID 73) for serotype D, "YNSYTLEEKNELTNKYDIK" (SEQ ID 74) for serotype E, "YNNYTLDEKNRLRAEYNIY" (SEQ ID 75) for serotype F, and "YNRYSEEDKMNIN--IDFN" (SEQ ID 76) for serotype G.

In a preferred embodiment, the destructive cleavage site(s) are located at a position greater than 10 amino acid residues, preferably greater than 25 amino acid residues, more preferably greater than 40 amino acid residues, particularly preferably greater than 50 amino acid residues from the N-terminus of the translocation component. Similarly, in a preferred embodiment, the destructive cleavage site(s) are located at a position greater than 10 amino acid residues, preferably greater than 25 amino acid residues, more preferably greater than 40 amino acid residues, particularly preferably greater than 50 amino acid residues from the C-terminus of the translocation component.

According to a second aspect of the present invention, there is provided use of a non-cytotoxic polypeptide for treating a range of diverse medical conditions and diseases. Said conditions and diseases have established therapies (see the background part of the present specification) based on very closely related (though unmodified as per the present invention) non-cytotoxic polypeptides. Accordingly, the present invention provides improvements to said therapies by use of a modified non-cytotoxic polypeptide that has a destructive cleavage site and thus reduced off-site effects.

In particular, the present invention provides use and corresponding methods for the treatment of strabismus, blepharospasm, squint, spasmodic and oromandibular dystonia, torticollis, and other beauty therapy (cosmetic) applications benefiting from cell/muscle incapacitation (via SNARE down-regulation or inactivation).

Additional, related therapies are provided for treating a neuromuscular disorder or condition of ocular motility, e.g. concomitant and vertical strabismus, lateral rectus palsy, nystagmus, dysthyroid myopathy, etc.; dystonia, e.g. focal dystonias such as spasmodic torticollis, writer's cramp, blepharospasm, oromandibular dystonia and the symptoms thereof, e.g. bruxism, Wilson's disease, tardive dystonia, laryngeal dystonia etc.; other dystonias, e.g. tremor, tics, segmental myoclonus; spasms, such as spasticity due to chronic multiple sclerosis, spasticity resulting in abnormal bladder control, e.g. in patients with spinal cord injury, animus, back spasm, charley horse etc.; tension headaches; levator pelvic syndrome; spina bifida, tardive dyskinesia; Parkinson's and limb (focal) dystonia and stuttering, etc.

In use, a polypeptide of the invention binds to a surface structure (the Binding Site), which is present on and preferably characteristic of a target cell. Following binding, the polypeptide (at least the protease component thereof) becomes endocytosed into a vesicle, and the translocation component then directs transport of the protease component across the endosomal membrane and into the cytosol of the target cell. Once inside the target cell, the non-cytotoxic protease inhibits the cellular exocytic fusion process, and thereby inhibits release/secretion from the target cell.

The biologically active component of the polypeptides of the present invention is a non-cytotoxic protease. Non-cytotoxic proteases are a discrete class of molecules that do not kill cells; instead, they act by inhibiting cellular processes other than protein synthesis. Non-cytotoxic proteases are produced as part of a larger toxin molecule by a variety of plants, and by a variety of microorganisms such as *Clostridium* sp. and *Neisseria* sp.

Clostridial neurotoxins represent a major group of non-cytotoxic toxin molecules, and comprise two polypeptide chains joined together by a disulphide bond. The two chains are termed the heavy chain (H-chain), which has a molecular mass of approximately 100 kDa, and the light chain (L-chain), which has a molecular mass of approximately 50 kDa. It is the L-chain, which possesses a protease function and exhibits a high substrate specificity for vesicle and/or plasma membrane associated (SNARE) proteins involved in the exocytic process (eg. synaptobrevin, syntaxin or SNAP-25). These substrates are important components of the neurosecretory machinery.

*Neisseria* sp., most importantly from the species *N. gonorrhoeae*, produce functionally similar non-cytotoxic toxin molecules. An example of such a non-cytotoxic protease is IgA protease (see WO99/58571).

The choice of TM determines the specificity of the polypeptide. By way of example, the same (or similar) receptor may be present on several different cells such that one TM will bind to different cell types. In this scenario, it might be desirable only to target a single cell type. Thus, by employing a second protease ('destruction') cleavage site in a polypeptide of the present invention which is cleaved by a protease specific to one or more of the undesired cells (and/or to their environment), it is possible to minimise off-target side effects in the undesired cells.

In another embodiment, polypeptides of the present invention may comprise two or more different TMs capable of binding to different target cell types. Alternatively (or in addition), combinations of polypeptides may be employed having different TMs so as to provide a coordinated targeting of different target cell types.

Polypeptide Preparation

The polypeptides of the present invention comprise 4 principal components: a TM; a non-cytotoxic protease; a translocation domain; and a destructive protease cleavage site. Said polypeptides embrace non-cytotoxic holotoxins such as clostridial neurotoxins, and, when an exogenous TM is present, re-targeted chimaeras (often referred to as re-targeted proteases). Preparation of these molecules is conventional—by way of exemplification, we refer to: WO94/21300; WO96/33273; WO98/07864; WO00/10598; WO01/21213; WO06/059093; WO00/62814; WO00/04926; WO93/15766; WO00/61192; and WO99/58571. All of these publications are herein incorporated by reference thereto.

In more detail, the TM component of the present invention may be fused to either the protease component or the translocation component of the present invention. Said fusion is preferably by way of a covalent bond, for example either a direct covalent bond or via a spacer/linker molecule. The protease component and the translocation component are preferably linked together via a covalent bond, for example either a direct covalent bond or via a spacer/linker molecule. Suitable spacer/linked molecules are well known in the art, and typically comprise an amino acid-based sequence of between 5 and 40, preferably between 10 and 30 amino acid residues in length.

In use, the polypeptides have a di-chain conformation, wherein the protease component and the translocation component are linked together, preferably via a disulphide bond.

The polypeptides of the present invention may be prepared by conventional chemical conjugation techniques, which are well known to a skilled person. By way of example, reference is made to Hermanson, G. T. (1996), Bioconjugate techniques, Academic Press, and to Wong, S. S. (1991), Chemistry of protein conjugation and cross-linking, CRC Press.

Alternatively, the polypeptides may be prepared by recombinant preparation of a single polypeptide fusion protein (see, for example, WO98/07864). This technique is based on the in vivo bacterial mechanism by which native clostridial neurotoxin (ie. holotoxin) is prepared, and results in a fusion protein having the following 'simplified' structural arrangement:

NH$_2$-[protease component]-[translocation component]-[TM]-COOH

According to WO98/07864, the TM is placed towards the C-terminal end of the fusion protein. The fusion protein is then 'activated' by treatment with a protease, which cleaves at a site between the protease component and the translocation component. A di-chain protein is thus produced, comprising the protease component as a single polypeptide chain covalently attached (via a disulphide bridge) to another single polypeptide chain containing the translocation component plus TM.

The WO98/07864 system is particularly suited to the preparation of fusion proteins having a TM that requires a C-terminal domain that is 'free' for interaction with a Binding Site on a target cell.

For fusion proteins having a TM that requires an N-terminal domain that is 'free' for interaction with a Binding Site on a target cell, a modified system may be employed as described in WO06/059113.

In the modified system, the TM component of the fusion protein is located towards the middle of the linear fusion protein sequence, between the protease cleavage site and the translocation component. This ensures that the TM is attached to the translocation domain (ie. as occurs with native clostridial holotoxin), though in this case the two components are reversed in order vis-à-vis native holotoxin. Subsequent cleavage at the protease cleavage site exposes the N-terminal portion of the TM, and provides the di-chain polypeptide fusion protein.

The above-mentioned protease cleavage sequence(s) may be introduced (and/or any inherent cleavage sequence removed) at the DNA level by conventional means, such as by site-directed mutagenesis. Screening to confirm the presence of cleavage sequences may be performed manually or with the assistance of computer software (e.g. the MapDraw program by DNASTAR, Inc.). Whilst any protease cleavage site may be employed (ie. clostridial, or non-clostridial), the following are preferred (either as the 'destructive' cleavage site, or as the 'activation' cleavage site):

```
Enterokinase              (DDDDK↓)   (SEQ ID 77)

Factor Xa                 (IEGR↓  (SEQ ID 41)/
                          IDGR↓)  (SEQ ID 78)

TEV(Tobacco Etch virus)   (ENLYFQ↓G) (SEQ ID 79)

Thrombin                  (LVPR↓GS)  (SEQ ID 40)

PreScission               (LEVLFQ↓GP) (SEQ ID 80).
```

Also embraced by the term protease cleavage site is an intein, which is a self-cleaving sequence. The self-splicing reaction is controllable, for example by varying the concentration of reducing agent present.

In a preferred embodiment, the fusion protein of the present invention may comprise one or more N-terminal and/or C-terminal located purification tags.

Whilst any purification tag may be employed, the following are preferred:

His-tag (e.g. 6×histidine), preferably as a C-terminal and/or N-terminal tag

MBP-tag (maltose binding protein), preferably as an N-terminal tag

GST-tag (glutathione-S-transferase), preferably as an N-terminal tag

His-MBP-tag, preferably as an N-terminal tag

GST-MBP-tag, preferably as an N-terminal tag

Thioredoxin-tag, preferably as an N-terminal tag

CBD-tag (Chitin Binding Domain), preferably as an N-terminal tag.

One or more peptide spacer/linker molecules may be included in the fusion protein. For example, a peptide spacer may be employed between a purification tag and the rest of the fusion protein molecule.

Thus, a third aspect of the present invention provides a nucleic acid (e.g. DNA) sequence encoding a polypeptide as described above.

Said nucleic acid may be included in the form of a vector, such as a plasmid, which may optionally include one or more of an origin of replication, a nucleic acid integration site, a promoter, a terminator, and a ribosome binding site.

The present invention also includes a method for expressing the above-described nucleic acid sequence (i.e. the third aspect of the present invention) in a host cell, in particular in E. coli or via a baculovirus expression system.

The present invention also includes a method for activating a polypeptide of the present invention, said method comprising contacting the polypeptide with a protease that cleaves the polypeptide at a recognition site (cleavage site) located between the non-cytotoxic protease component and the translocation component, thereby converting the polypeptide into a di-chain polypeptide wherein the non-cytotoxic protease and translocation components are joined together by a disulphide bond. In a preferred embodiment, the recognition site is not native to a naturally-occurring clostridial neurotoxin and/or to a naturally-occurring IgA protease.

Polypeptide Delivery

In use, the present invention employs a pharmaceutical composition, comprising a polypeptide, together with at least one component selected from a pharmaceutically acceptable carrier, excipient, adjuvant, propellant and/or salt.

The polypeptides of the present invention may be formulated for oral, parenteral, continuous infusion, inhalation or topical application. Compositions suitable for injection may be in the form of solutions, suspensions or emulsions, or dry powders which are dissolved or suspended in a suitable vehicle prior to use.

In the case of a polypeptide that is to be delivered locally, the polypeptide may be formulated as a cream (eg. for topical application), or for sub-dermal injection.

Local delivery means may include an aerosol, or other spray (eg. a nebuliser). In this regard, an aerosol formulation of a polypeptide enables delivery to the lungs and/or other nasal and/or bronchial or airway passages.

Polypeptides of the invention may be administered to a patient by intrathecal or epidural injection in the spinal column at the level of the spinal segment involved in the innervation of an affected organ.

A preferred route of administration is via laproscopic and/or localised, particularly intramuscular, injection.

In the case of formulations for injection, it is optional to include a pharmaceutically active substance to assist retention at or reduce removal of the polypeptide from the site of administration. One example of such a pharmaceutically active substance is a vasoconstrictor such as adrenaline. Such a formulation confers the advantage of increasing the residence time of polypeptide following administration and thus increasing and/or enhancing its effect.

The dosage ranges for administration of the polypeptides of the present invention are those to produce the desired therapeutic effect. It will be appreciated that the dosage range required depends on the precise nature of the polypeptide or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages (per kg weight of patient) are in the range 0.0001-1 ng/kg, preferably 0.0001-0.5 ng/kg, more preferably 0.002-0.5 ng/kg, and particularly preferably 0.004-0.5 ng/kg. The unit dosage can vary from less that 1 picogram to 30 ng, but typically will be in the region of 0.01 to 1 ng per dose, which may be administered daily or preferably less frequently, such as weekly or six monthly.

A particularly preferred dosing regimen is based on 0.25 ng of polypeptide as the 1× dose. In this regard, preferred dosages are in the range 1×-100× (i.e. 0.25-25 ng).

Fluid dosage forms are typically prepared utilising the polypeptide and a pyrogen-free sterile vehicle. The polypeptide, depending on the vehicle and concentration used, can be either dissolved or suspended in the vehicle. In preparing solutions the polypeptide can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition/s to facilitate uniform distribution of the components.

Administration in accordance with the present invention may take advantage of a variety of delivery technologies including microparticle encapsulation, viral delivery systems or high-pressure aerosol impingement.

Definitions Section

Targeting Moiety (TM) means any chemical structure that functionally interacts with a Binding Site to cause a physical association between the polypeptide of the invention and the surface of a target cell. The term TM embraces any molecule (ie. a naturally occurring molecule, or a chemically/physically modified variant thereof) that is capable of binding to a Binding Site on the target cell, which Binding Site is capable of internalisation (eg. endosome formation)—also referred to as receptor-mediated endocytosis. The TM may possess an endosomal membrane translocation function, in which case separate TM and Translocation Domain components need not be present in an agent of the present invention. Throughout the preceding description, specific TMs have been described. Reference to said TMs is merely exemplary, and the present invention embraces all variants and derivatives thereof, which retain the basic binding (i.e. targeting) ability of the exemplified TMs.

As mentioned previously, preferred TMs include antibodies (eg. antibody fragments) and binding scaffolds; especially commercially available antibodies/fragments and scaffolds designed for the purpose of binding (eg. specifically) to nerve cells.

Protein scaffolds represent a new generation of universal binding frameworks to complement the expanding repertoire of therapeutic monoclonal antibodies and derivatives such as scFvs, Fab molecules, dAbs (single-domain antibodies), diabodies and minibodies, each of which may be employed as a TM of the present invention. Scaffold systems create or modify known protein recognition domains either through creation of novel scaffolds or modification of known protein binding domains. Such scaffolds include but are not limited to:

(i) protein A based scaffolds—affibodies (Nord, K. et al 1997 "Binding proteins selected from combinatorial libraries of an alpha-helical bacterial receptor domain". Nat Biotechnol 15, 772-777);

(ii) lipocalin based scaffolds—anticalins (Skerra 2008 "Alternative binding proteins: anticalins—harnessing the structural plasticity of the lipocalin ligand pocket to engineer novel binding activities". FEBS J. 275:2677-83);

(iii) fibronectin based scaffolds—adnectin (Dineen et al 2008 "The Adnectin CT-322 is a novel VEGF receptor 2 inhibitor that decreases tumor burden in an orthotopic mouse model of pancreatic cancer". BMC Cancer 8:352);

(iv) avimers (Silverman et al 2005 "Multivalent avimer proteins evolved by exon shuffling of a family of human receptor domains". Nat Biotechnol 23:1556-61);

(v) ankyrin based scaffolds—darpins (Zahnd et al 2006 "Selection and characterization of Her2 binding-designed ankyrin repeat proteins". J Biol Chem. 281:35167-75); and (vi) centyrin scaffolds—based on a protein fold that has significant structural homology to Ig domains with loops that are analogous to CDRs. Ig domains are a common module in human proteins and have been widely applied as alternative scaffold proteins. Each of the above 'scaffold' publications is hereby incorporated (in its entirety) by reference thereto.

Binding scaffolds can be used to target particular cell types via interaction with specific cell surface proteins, receptors or other cell surface epitopes such as sugar groups. Such modified scaffolds can be engineered onto recombinant non-cytotoxic protease based polypeptides of the present invention to target specific nerve cell types of interest.

The TM of the present invention binds (preferably specifically binds) to the target cell in question. The term "specifically binds" preferably means that a given TM binds to the target cell with a binding affinity (Ka) of $10^8$ $M^{-1}$ or greater, preferably $10^7$ $M^{-1}$ or greater, more preferably $10^8$ $M^{-1}$ or greater, and most preferably, $10^9$ $M^{-1}$ or greater.

Reference to TM in the present specification embraces fragments and variants thereof, which retain the ability to bind to the target cell in question. By way of example, a variant may have at least 80%, preferably at least 90%, more preferably at least 95%, and most preferably at least 97 or at least 99% amino acid sequence homology with the reference TM. Thus, a variant may include one or more analogues of an amino acid (e.g. an unnatural amino acid), or a substituted linkage. Also, by way of example, the term fragment, when used in relation to a TM, means a peptide having at least ten, preferably at least twenty, more preferably at least thirty, and most preferably at least forty amino acid residues of the reference TM. The term fragment also relates to the above-mentioned variants. Thus, by way of example, a fragment of the present invention may comprise a peptide sequence having at least 10, 20, 30 or 40 amino acids, wherein the peptide sequence has at least 80% sequence homology over a corresponding peptide sequence (of contiguous) amino acids of the reference peptide.

By way of example, ErbB peptide TMs (eg. EGF) may be modified to generate mutein ErbB ligands with improved properties such as increased stability. By way of example, ErbB TM muteins include ErbB peptides having amino acid modifications such as a valine residue at position 46 or 47 (EGFVal46 or 47), which confers stability to cellular proteases. ErbB TMs may also have amino acids deleted or additional amino acids inserted. This includes but is not limited to EGF having a deletion of the two C-terminal amino acids and a neutral amino acid substitution at position 51 (particularly EGF51Gln51; see US20020098178A1), and EGF with amino acids deleted (e.g. rEGF2-48; rEGF3-48 and rEGF4-48). Fragments of ErbB TMs may include fragments of TGFα which contain predicted β-turn regions (e.g. a peptide of the sequence Ac-C-H-S-G-Y-V-G-A-R-C-O-OMe) (SEQ ID 81), fragments of EGF such as [Ala20]EGF (14-31), and the peptide YHWYGYTPQNVI (SEQ ID 82) or GE11. All of the above patent specifications are incorporated herein by reference thereto.

It is routine to confirm that a TM binds to the selected target cell. For example, a simple radioactive displacement experiment may be employed in which tissue or cells representative of the target cell are exposed to labelled (eg. tritiated) TM in the presence of an excess of unlabelled TM. In such an experiment, the relative proportions of non-specific and specific binding may be assessed, thereby allowing confirmation that the TM binds to the target cell. Optionally, the assay may include one or more binding antagonists, and the assay may further comprise observing a loss of TM binding. Examples of this type of experiment can be found in Hulme, E. C. (1990), Receptor-binding studies, a brief outline, pp. 303-311, In Receptor biochemistry, A Practical Approach, Ed. E. C. Hulme, Oxford University Press.

In the context of the present invention, reference to a peptide TM embraces peptide analogues thereof, so long as the analogue binds to the same receptor as the corresponding 'reference' TM. Said analogues may include synthetic residues such as:

β-Nal=β-naphthylalanine

β-Pal=β-pyridylalanine hArg(Bu)=N-guanidino-(butyl)-homoarginine hArg(Et)$_2$=N, N'-guanidino-(dimethyl)-homoarginine hArg($CH_2CF_3$)$_2$=N, N'-guanidino-bis-(2,2,2,-trifluoroethyl)-homoarginine hArg($CH_3$, hexyl)=N, N'-guanidino-(methyl, hexyl)-homoarginine Lys(Me)=N$^e$-methyllysine
Lys(iPr)=N$^e$-isopropyllysine
AmPhe=aminomethylphenylalanine
AChxAla=aminocyclohexylalanine
Abu=α-aminobutyric acid
Tpo=4-thiaproline
MeLeu=N-methylleucine
Orn=ornithine
Nle—norleucine
Nva=norvaline
Trp(Br)=5-bromo-tryptophan
Trp(F)=5-fluoro-tryptophan
Trp(N0$_2$)=5-nitro-tryptophan
Gaba=γ-aminobutyric acid
Bmp=J-mercaptopropionyl
Ac=acetyl
Pen—pencillamine The polypeptides of the present invention may lack a functional H$_C$ (or H$_{CC}$) domain of a clostridial neurotoxin, in which case a non-clostridial TM is typically present to bind the polypeptide to a Binding Site on the nerve cell. The H$_C$ peptide of a native clostridial neurotoxin comprises approximately 400-440 amino acid residues, and consists of two functionally distinct domains of approximately 25 kDa each, namely the N-terminal region (commonly referred to as the H$_{CN}$ peptide or domain) and the C-terminal region (commonly referred to as the H$_{CC}$ peptide or domain). It has been well documented that the C-terminal region (H$_{CC}$), which constitutes the C-terminal 160-200 amino acid residues, is responsible for binding of a clostridial neurotoxin to its natural cell receptors, namely to nerve terminals at the neuromuscular junction—this fact is also confirmed by the above publications. Thus, reference throughout this specification to a clostridial heavy-chain lacking a functional heavy chain H$_C$ peptide (or domain) means that the clostridial heavy-chain simply lacks a functional H$_{CC}$ peptide. In other words, the H$_{CC}$ peptide region is either partially or wholly deleted, or otherwise modified (e.g. through conventional chemical or proteolytic treatment) to inactivate its native binding ability for nerve cells.

Alternatively, a polypeptide of the present invention may contain a functional H$_C$ (or H$_{CC}$) domain of a clostridial neurotoxin as a TM. A variety of clostridial neurotoxin Hcc or Hc regions comprising a binding domain can be useful in aspects of the present invention with the proviso that these active fragments provide the binding activity and binding specificity of the natural neurotoxin. The H$_C$ regions from the heavy chains of clostridial toxins are approximately 400-440 amino acids in length and comprise a binding domain. Research has shown that the entire length of a H$_C$ region from a clostridial toxin heavy chain is not necessary for the binding activity of the binding domain. Thus, aspects of this embodiment can include clostridial toxin H$_C$ regions comprising a binding domain having a length of, for example, at least 350 amino acids, at least 375 amino acids, at least 400 amino acids and at least 425 amino acids. Other aspects of this embodiment can include clostridial toxin H$_C$ regions comprising a binding domain having a length of, for example, at most 350 amino acids, at most 375 amino acids, at most 400 amino acids and at most 425 amino acids.

The protease of the present invention embraces all non-cytotoxic proteases that are capable of cleaving one or more proteins of the exocytic fusion apparatus in eukaryotic cells.

The protease of the present invention is preferably a bacterial protease (or fragment thereof). More preferably the bacterial protease is selected from the genera *Clostridium* or *Neisseria/Streptococcus* (e.g. a clostridial L-chain, or a neisserial IgA protease preferably from *N. gonorrhoeae* or *S. pneumoniae*).

The present invention also embraces variant non-cytotoxic proteases (ie. variants of naturally-occurring protease molecules), so long as the variant proteases still demonstrate the requisite protease activity. By way of example, a variant may have at least 70%, preferably at least 80%, more preferably at least 90%, and most preferably at least 95 or at least 98% amino acid sequence homology with a reference protease sequence. Thus, the term variant includes non-cytotoxic proteases having enhanced (or decreased) endopeptidase activity—particular mention here is made to the increased K$_{cat}$/K$_m$ of BoNT/A mutants Q161A, E54A, and K165L see Ahmed, S. A. (2008) Protein J. DOI 10.1007/s10930-007-9118-8, which is incorporated by reference thereto. The term fragment, when used in relation to a protease, typically means a peptide having at least 150, preferably at least 200, more preferably at least 250, and most preferably at least 300 amino acid residues of the reference protease. As with the TM 'fragment' component (discussed above), protease 'fragments' of the present invention embrace fragments of variant proteases based on a reference sequence.

The protease of the present invention preferably demonstrates a serine or metalloprotease activity (e.g. endopeptidase activity). The protease is preferably specific for a SNARE protein (e.g. SNAP-25, synaptobrevin/VAMP, or syntaxin).

Particular mention is made to the protease domains of neurotoxins, for example the protease domains of bacterial neurotoxins. Thus, the present invention embraces the use of neurotoxin domains, which occur in nature, as well as recombinantly prepared versions of said naturally-occurring neurotoxins.

Exemplary neurotoxins are produced by clostridia, and the term clostridial neurotoxin embraces neurotoxins produced by *C. tetani* (TeNT), and by *C. botulinum* (BoNT) serotypes A-G, as well as the closely related BoNT-like neurotoxins produced by *C. baratii* and *C. butyricum*. The above-mentioned abbreviations are used throughout the present specification. For example, the nomenclature BoNT/A denotes the source of neurotoxin as BoNT (serotype A). Corresponding nomenclature applies to other BoNT serotypes.

BoNTs are the most potent toxins known, with median lethal dose (LD50) values for mice ranging from 0.5 to 5 ng/kg depending on the serotype. BoNTs are adsorbed in the gastrointestinal tract, and, after entering the general circulation, bind to the presynaptic membrane of cholinergic nerve terminals and prevent the release of their neurotransmitter acetylcholine. BoNT/B, BoNT/D, BoNT/F and BoNT/G cleave synaptobrevin/vesicle-associated membrane protein (VAMP); BoNT/C, BoNT/A and BoNT/E cleave the synaptosomal-associated protein of 25 kDa (SNAP-25); and BoNT/C cleaves syntaxin.

BoNTs share a common structure, being di-chain proteins of ~150 kDa, consisting of a heavy chain (H-chain) of ~100 kDa covalently joined by a single disulphide bond to a light chain (L-chain) of ~50 kDa. The H-chain consists of two domains, each of ~50 kDa. The C-terminal domain (H$_C$) is required for the high-affinity neuronal binding, whereas the N-terminal domain (H$_N$) is proposed to be involved in membrane translocation. The L-chain is a zinc-dependent metalloprotease responsible for the cleavage of the substrate SNARE protein.

The term L-chain fragment means a component of the L-chain of a neurotoxin, which fragment demonstrates a metalloprotease activity and is capable of proteolytically cleaving a vesicle and/or plasma membrane associated protein, involved in cellular exocytosis.

Examples of suitable protease (reference) sequences include:
Botulinum type A neurotoxin—amino acid residues (1-448)
Botulinum type B neurotoxin—amino acid residues (1-440)
Botulinum type C neurotoxin—amino acid residues (1-441)
Botulinum type D neurotoxin—amino acid residues (1-445)
Botulinum type E neurotoxin—amino acid residues (1-422)
Botulinum type F neurotoxin—amino acid residues (1-439)
Botulinum type G neurotoxin—amino acid residues (1-441)
Tetanus neurotoxin—amino acid residues (1-457)
IgA protease—amino acid residues (1-959)*

* Pohlner, J. et al. (1987). Nature 325, pp. 458-462, which is hereby incorporated by reference thereto.

The above-identified reference sequence should be considered a guide as slight variations may occur according to sub-serotypes. By way of example, US 2007/0166332 (hereby incorporated by reference thereto) cites slightly different clostridial sequences:
Botulinum type A neurotoxin—amino acid residues (M1-K448)
Botulinum type B neurotoxin—amino acid residues (M1-K441)
Botulinum type C neurotoxin—amino acid residues (M1-K449)
Botulinum type D neurotoxin—amino acid residues (M1-R445)
Botulinum type E neurotoxin—amino acid residues (M1-R422)
Botulinum type F neurotoxin—amino acid residues (M1-K439)
Botulinum type G neurotoxin—amino acid residues (M1-K446)
Tetanus neurotoxin—amino acid residues (M1-A457)

A variety of clostridial toxin fragments comprising the light chain can be useful in aspects of the present invention with the proviso that these light chain fragments can specifically target the core components of the neurotransmitter release apparatus and thus participate in executing the overall cellular mechanism whereby a clostridial toxin proteolytically cleaves a substrate. The light chains of clostridial toxins are approximately 420-460 amino acids in length and comprise an enzymatic domain. Research has shown that the entire length of a clostridial toxin light chain is not necessary for the enzymatic activity of the enzymatic domain. As a non-limiting example, the first eight amino acids of the BoNT/A light chain are not required for enzymatic activity. As another non-limiting example, the first eight amino acids of the TeNT light chain are not required for enzymatic activity. Likewise, the carboxyl-terminus of the light chain is not necessary for activity. As a non-limiting example, the last 32 amino acids of the BoNT/A light chain (residues 417-448) are not required for enzymatic activity. As another non-limiting example, the last 31 amino acids of the TeNT light chain (residues 427-457) are not required for enzymatic activity. Thus, aspects of this embodiment can include clostridial toxin light chains comprising an enzymatic domain having a length of, for example, at least 350 amino acids, at least 375 amino acids, at least 400 amino acids, at least 425 amino acids and at least 450 amino acids. Other aspects of this embodiment can include clostridial toxin light chains comprising an enzymatic domain having a length of, for example, at most 350 amino acids, at most 375 amino acids, at most 400 amino acids, at most 425 amino acids and at most 450 amino acids.

The polypeptides of the present invention, especially the protease component thereof, may be PEGylated—this may help to increase stability, for example duration of action of the protease component. PEGylation is particularly preferred when the protease comprises a BoNT/A, B or $C_1$ protease. PEGylation preferably includes the addition of PEG to the N-terminus of the protease component. By way of example, the N-terminus of a protease may be extended with one or more amino acid (e.g. cysteine) residues, which may be the same or different. One or more of said amino acid residues may have its own PEG molecule attached (e.g. covalently attached) thereto. An example of this technology is described in WO2007/104567, which is incorporated in its entirety by reference thereto.

A Translocation Domain is a molecule that enables translocation of a protease into a target cell such that a functional expression of protease activity occurs within the cytosol of the target cell. Whether any molecule (e.g. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of $K^+$ and/or labelled NAD, which may be readily monitored [see Shone C. (1987) Eur. J. Biochem; vol. 167(1): pp. 175-180].

A further example is provided by Blaustein R. (1987), which describes a simple in vitro assay employing planar phospholipid bilayer membranes. The membranes are challenged with a test molecule and the requisite translocation function is confirmed by an increase in conductance across said membranes [see Blaustein (1987) FEBS Letts; vol. 226, no. 1: pp. 115-120].

Additional methodology to enable assessment of membrane fusion and thus identification of Translocation Domains suitable for use in the present invention are provided by Methods in Enzymology Vol 220 and 221, Membrane Fusion Techniques, Parts A and B, Academic Press 1993.

The present invention also embraces variant translocation domains, so long as the variant domains still demonstrate the requisite translocation activity. By way of example, a variant may have at least 70%, preferably at least 80%, more preferably at least 90%, and most preferably at least 95% or at least 98% amino acid sequence homology with a reference translocation domain. The term fragment, when used in relation to a translocation domain, means a peptide having at least 20, preferably at least 40, more preferably at least 80, and most preferably at least 100 amino acid residues of the reference translocation domain. In the case of a clostridial translocation domain, the fragment preferably has at least 100, preferably at least 150, more preferably at least 200, and most preferably at least 250 amino acid residues of the reference translocation domain (eg. $H_N$ domain). As with the TM 'fragment' component (discussed above), translocation 'fragments' of the present invention embrace fragments of variant translocation domains based on the reference sequences.

The Translocation Domain is preferably capable of formation of ion-permeable pores in lipid membranes under conditions of low pH. Preferably it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, such as the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. The H-chain lacks the natural binding function of the $H_C$ component of the H-chain. In this regard, the $H_C$ function may be removed by deletion of the $H_C$ amino acid sequence (either at the DNA synthesis level, or at the post-synthesis level by nuclease or protease treatment). Alternatively, the $H_C$ function may be inactivated by chemical or biological treatment. Thus, the H-chain is incapable of binding to the Binding Site on a target cell to which native clostridial neurotoxin (i.e. holotoxin) binds.

Examples of suitable (reference) Translocation Domains include:
  Botulinum type A neurotoxin—amino acid residues (449-871)
  Botulinum type B neurotoxin—amino acid residues (441-858)
  Botulinum type C neurotoxin—amino acid residues (442-866)
  Botulinum type D neurotoxin—amino acid residues (446-862)
  Botulinum type E neurotoxin—amino acid residues (423-845)
  Botulinum type F neurotoxin—amino acid residues (440-864)
  Botulinum type G neurotoxin—amino acid residues (442-863)
  Tetanus neurotoxin—amino acid residues (458-879)

The above-identified reference sequence should be considered a guide as slight variations may occur according to sub-serotypes. By way of example, US 2007/0166332 (hereby incorporated by reference thereto) cites slightly different clostridial sequences:
  Botulinum type A neurotoxin—amino acid residues (A449-K871)
  Botulinum type B neurotoxin—amino acid residues (A442-S858)
  Botulinum type C neurotoxin—amino acid residues (T450-N866)
  Botulinum type D neurotoxin—amino acid residues (D446-N862)
  Botulinum type E neurotoxin—amino acid residues (K423-K845)
  Botulinum type F neurotoxin—amino acid residues (A440-K864)
  Botulinum type G neurotoxin—amino acid residues (S447-S863)
  Tetanus neurotoxin—amino acid residues (S458-V879)

In the context of the present invention, a variety of Clostridial toxin $H_N$ regions comprising a translocation domain can be useful in aspects of the present invention with the proviso that these active fragments can facilitate the release of a non-cytotoxic protease (e.g. a clostridial L-chain) from intracellular vesicles into the cytoplasm of the target cell and thus participate in executing the overall cellular mechanism whereby a clostridial toxin proteolytically cleaves a substrate. The $H_N$ regions from the heavy chains of Clostridial toxins are approximately 410-430 amino acids in length and comprise a translocation domain. Research has shown that the entire length of a $H_N$ region from a Clostridial toxin heavy chain is not necessary for the translocating activity of the translocation domain. Thus, aspects of this embodiment can include clostridial toxin $H_N$ regions comprising a translocation domain having a length of, for example, at least 350 amino acids, at least 375 amino acids, at least 400 amino acids and at least 425 amino acids. Other aspects of this embodiment can include clostridial toxin $H_N$ regions comprising translocation domain having a length of, for example, at most 350 amino acids, at most 375 amino acids, at most 400 amino acids and at most 425 amino acids.

For further details on the genetic basis of toxin production in *Clostridium botulinum* and *C. tetani*, we refer to Henderson et al (1997) in *The Clostridia: Molecular Biology and Pathogenesis*, Academic press.

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin. Examples of non-clostridial (reference) Translocation Domain origins include, but not be restricted to, the translocation domain of diphtheria toxin [O=Keefe et al., Proc. Natl. Acad. Sci. USA (1992) 89, 6202-6206; Silverman et al., J. Biol. Chem. (1993) 269, 22524-22532; and London, E. (1992) *Biochem. Biophys. Acta.*, 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) PNAS, 89, pp. 7934-7938], and amphiphilic peptides [Murata et al (1992) *Biochem.*, 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral (reference) Translocation Domains suitable for use in the present invention include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded Aspike proteins have particular application in the context of the present invention, for example, the E1 protein of SFV and the G protein of the G protein of VSV.

Use of the (reference) Translocation Domains listed in Table (below) includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

| Translocation Domain source | Amino acid residues | References |
|---|---|---|
| Diphtheria toxin | 194-380 | Silverman et al., 1994, J. Biol. Chem. 269, 22524-22532 London E., 1992, Biochem. Biophys. Acta., 1113, 25-51 |
| Domain II of pseudomonas exotoxin | 405-613 | Prior et al., 1992, Biochemistry 31, 3555-3559 Kihara & Pastan, 1994, Bioconj Chem. 5, 532-538 |
| Influenza virus haemagglutinin | GLFGAIAGFIENGWE GMIDGWYG, and Variants thereof | Plank et al., 1994, J. Biol. Chem. 269, 12918-12924 Wagner et al., 1992, PNAS, 89, 7934-7938 Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

The polypeptides of the present invention may further comprise a translocation facilitating domain. Said domain facilitates delivery of the non-cytotoxic protease into the cytosol of the target cell and are described, for example, in WO 08/008803 and WO 08/008805, each of which is herein incorporated by reference thereto.

By way of example, suitable translocation facilitating domains include an enveloped virus fusogenic peptide domain, for example, suitable fusogenic peptide domains include influenzavirus fusogenic peptide domain (eg. influenza A virus fusogenic peptide domain of 23 amino acids), alphavirus fusogenic peptide domain (eg. Semliki Forest virus fusogenic peptide domain of 26 amino acids), vesiculovirus fusogenic peptide domain (eg. vesicular stomatitis virus fusogenic peptide domain of 21 amino acids), respirovirus fusogenic peptide domain (eg. Sendai virus fusogenic peptide domain of 25 amino acids), morbiliivirus fusogenic peptide domain (eg. Canine distemper virus fusogenic peptide domain of 25 amino acids), avulavirus fusogenic peptide domain (eg. Newcastle disease virus fusogenic peptide domain of 25 amino acids), henipavirus fusogenic peptide domain (eg. Hendra virus fusogenic peptide domain of 25 amino acids), metapneumovirus fusogenic peptide domain (eg. Human metapneumovirus fusogenic peptide domain of 25 amino acids) or spumavirus fusogenic peptide domain such as simian foamy virus fusogenic peptide domain; or fragments or variants thereof.

By way of further example, a translocation facilitating domain may comprise a Clostridial toxin $H_{CN}$ domain or a fragment or variant thereof. In more detail, a Clostridial toxin $H_{CN}$ translocation facilitating domain may have a length of at least 200 amino acids, at least 225 amino acids, at least 250 amino acids, at least 275 amino acids. In this regard, a Clostridial toxin $H_{CN}$ translocation facilitating domain preferably has a length of at most 200 amino acids, at most 225 amino acids, at most 250 amino acids, or at most 275 amino acids. Specific (reference) examples include:

Botulinum type A neurotoxin—amino acid residues (872-1110)
Botulinum type B neurotoxin—amino acid residues (859-1097)
Botulinum type C neurotoxin—amino acid residues (867-1111)
Botulinum type D neurotoxin—amino acid residues (863-1098)
Botulinum type E neurotoxin—amino acid residues (846-1085)
Botulinum type F neurotoxin—amino acid residues (865-1105)
Botulinum type G neurotoxin—amino acid residues (864-1105)
Tetanus neurotoxin—amino acid residues (880-1127)

The above sequence positions may vary a little according to serotype/sub-type, and further examples of suitable (reference) Clostridial toxin $H_{CN}$ domains include:

Botulinum type A neurotoxin—amino acid residues (874-1110)
Botulinum type B neurotoxin—amino acid residues (861-1097)
Botulinum type C neurotoxin—amino acid residues (869-1111)
Botulinum type D neurotoxin—amino acid residues (865-1098)
Botulinum type E neurotoxin—amino acid residues (848-1085)
Botulinum type F neurotoxin—amino acid residues (867-1105)
Botulinum type G neurotoxin—amino acid residues (866-1105)
Tetanus neurotoxin—amino acid residues (882-1127)

Any of the above-described facilitating domains may be combined with any of the previously described translocation domain peptides that are suitable for use in the present invention. Thus, by way of example, a non-clostridial facilitating domain may be combined with non-clostridial translocation domain peptide or with clostridial translocation domain peptide. Alternatively, a Clostridial toxin $H_{CN}$ translocation facilitating domain may be combined with a non-clostridial translocation domain peptide. Alternatively, a Clostridial toxin $H_{CN}$ facilitating domain may be combined or with a clostridial translocation domain peptide, examples of which include:

Botulinum type A neurotoxin—amino acid residues (449-1110)
Botulinum type B neurotoxin—amino acid residues (442-1097)
Botulinum type C neurotoxin—amino acid residues (450-1111)

Botulinum type D neurotoxin—amino acid residues (446-1098)

Botulinum type E neurotoxin—amino acid residues (423-1085)

Botulinum type F neurotoxin—amino acid residues (440-1105)

Botulinum type G neurotoxin—amino acid residues (447-1105)

Tetanus neurotoxin—amino acid residues (458-1127)

Sequence Homology:

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics: 1428-1435 (2004).

Thus, percent sequence identity is determined by conventional methods. See, for example, Altschul et al., *Bull. Math. Bio.* 48: 603-16, 1986 and Henikoff and Henikoff, *Proc. Natl. Acad. Sci. USA* 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment Scores for Determining Sequence Identity

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{Total number of identical matches}}{\left[\begin{array}{c}\text{length of the longer sequence plus the number of}\\ \text{gaps introduced into the longer sequence in order}\\ \text{to align the two sequences}\end{array}\right]} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions
Basic: arginine
  lysine
  histidine
Acidic: glutamic acid
  aspartic acid
Polar: glutamine
  asparagine
Hydrophobic: leucine
  isoleucine
  valine
Aromatic: phenylalanine
  tryptophan
  tyrosine
Small: glycine
  alanine
  serine
  threonine
  methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for clostridial polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* oocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., *Biochem.* 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, *Science* 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-12, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (*Proc. Natl. Acad. Sci. USA* 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., DNA 7:127, 1988).

Multiple amino acid substitutions can be made and tested using known methods of mutagenesis and screening, such as those disclosed by Reidhaar-Olson and Sauer (*Science* 241: 53-7, 1988) or Bowie and Sauer (*Proc. Natl. Acad. Sci. USA* 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

There now follows a brief description of the Figures, which illustrate aspects and/or embodiments of the present invention.

Cultured rat embryonic spinal cord neurons were treated with varying concentrations of $LH_N/C$ and LC/C (which cleaves the SNARE protein syntaxin) for 24 hours before lysis in a detergent buffer. A Western blot was then performed using an anti-syntaxin antibody which recognises full-length and cleaved forms of the protein. Percent cleavage was calculated by comparative quantification of the two species. The results are shown in FIG. 1 which shows % syntaxin cleavage as a function of concentration of LC/C and $LH_N$.

FIG. 1 illustrates the surprising neurotoxin activity retained by a modified clostridial neurotoxin ($LH_N$). Said modified neurotoxin lacks a functional $H_C$ binding domain and is therefore equivalent to the modified clostridial neurotoxins described by LIN, et al. (WO02/044199). In contrast, no neurotoxin activity was detected for a modified clostridial neurotoxin (LC/C), which lacks a function $H_N$ translocation domain.

FIG. 2—illustrates a simply amino acid sequence homology alignment for the various BoNT serotypes. From this alignment, amino acid residues or regions from one serotype (eg. from serotype A) may be compared with corresponding residues/regions across the serotypes by way of simple vertical alignment.

Figure 3:
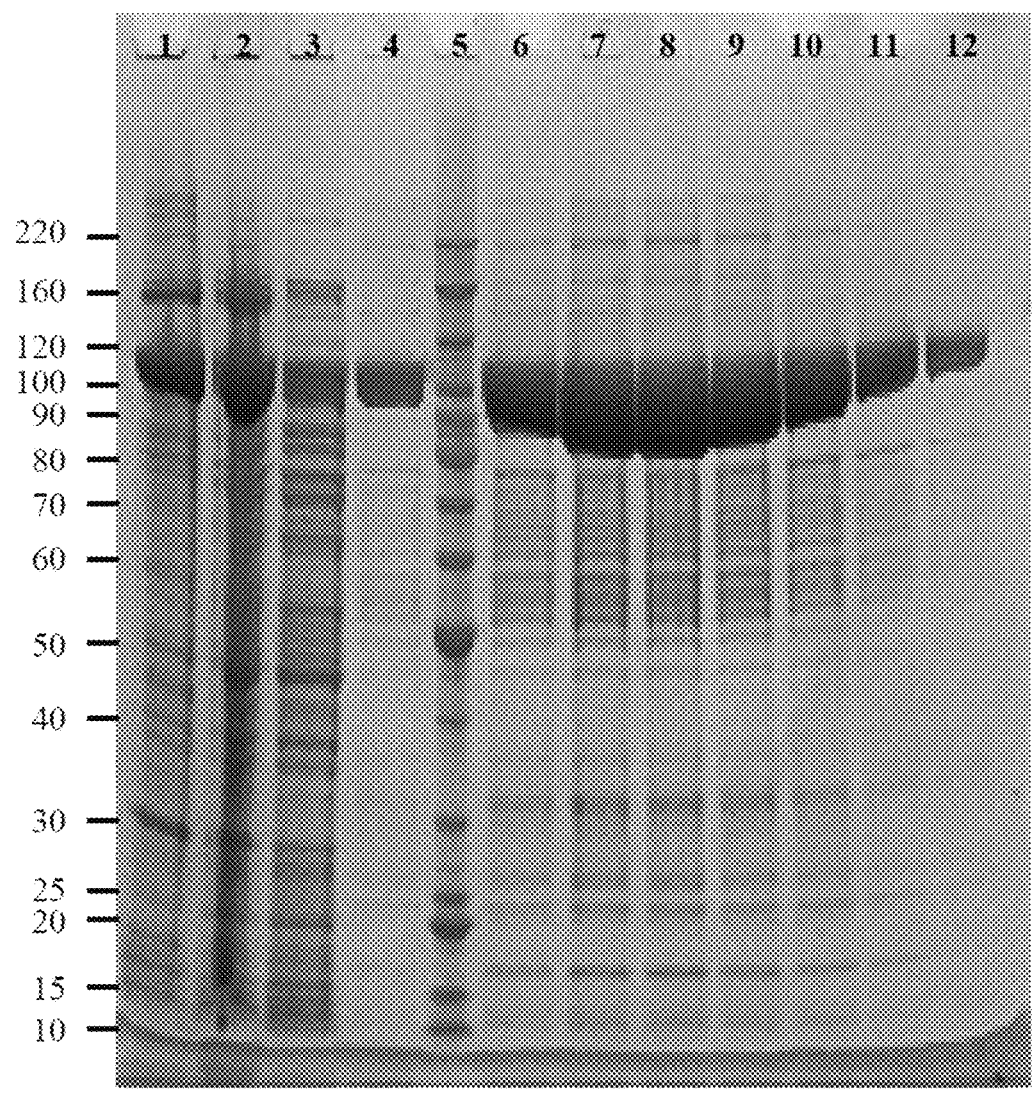

FIG. 3—SDS-PAGE analysis of the purification of a L(#FXa)HC-EGF chimaeric protein. Lane 1 illustrates the clarified cell lysate; Lane 2 illustrates the column flow through; Lane 3 illustrates the fraction eluted following washing the column; Lanes 4, 6-12 are fractions eluted on addition of 250 mM imidazole. Lane 5 is molecular mass markers (Benchmark)

Figure 4:
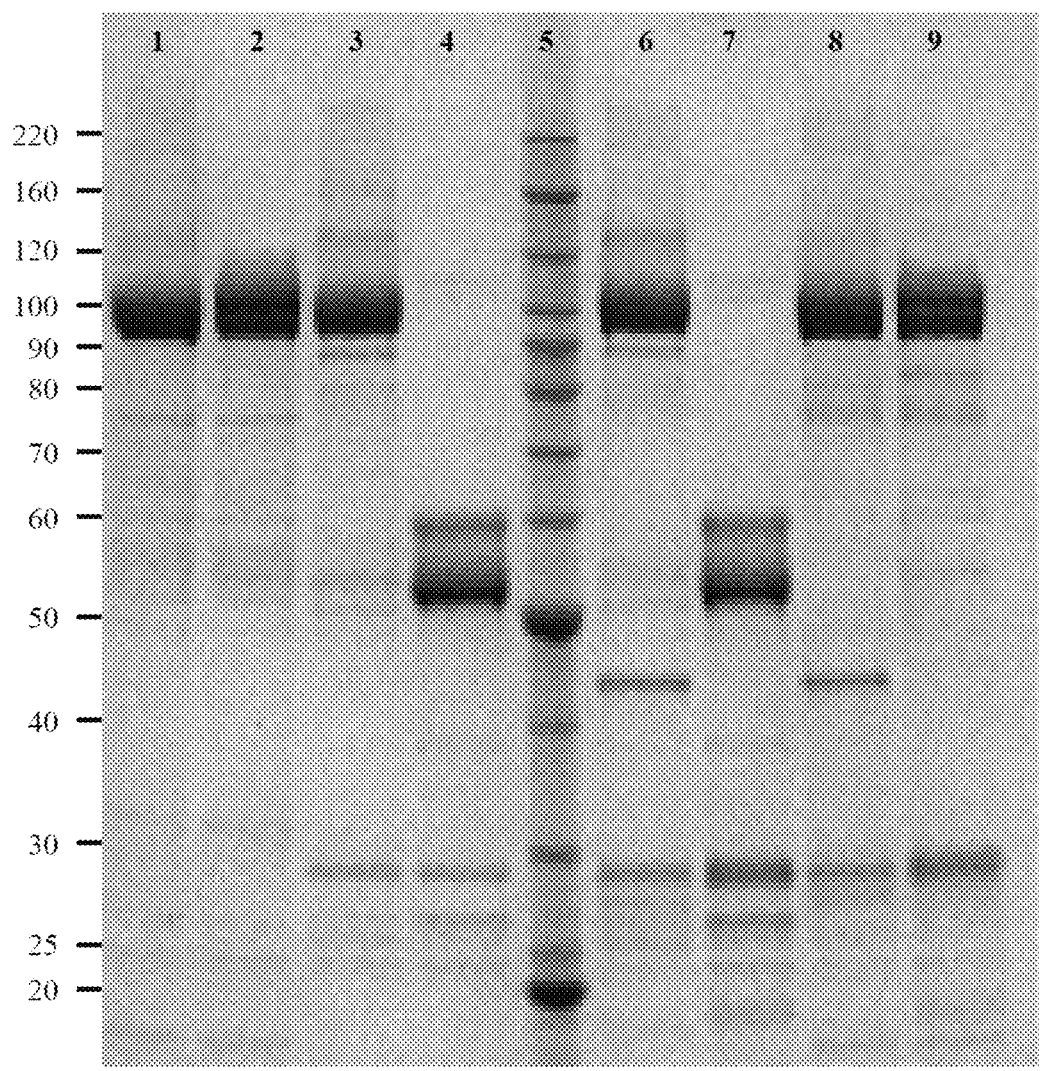

FIG. 4—SDS-PAGE analysis of the proteolysis of a L(#FXa)HC-EGF chimaeric protein by FXa. Lanes 1 & 2 illustrate the purified protein prior to enterokinase activation at the LC-$H_N$ junction, in the absence and presence of DTT respectively; Lanes 3&4 illustrate the protein post enterokinase activation at the LC-$H_N$ junction, in the absence and presence of DTT respectively; Lane 5 is molecular mass markers (benchmark); Lanes 6 & 7 illustrate the enterokinase activated protein treated with Factor Xa, in the absence and presence of DTT respectively; Lanes 8 & 9 illustrate the result of FXa treatment of the protein that has not been activated with enterokinase, in the absence and presence of DTT respectively. Fragmentation of the protein following treatment with Factor Xa is clearly seen in Lanes 6 and 8.

Figure 5:
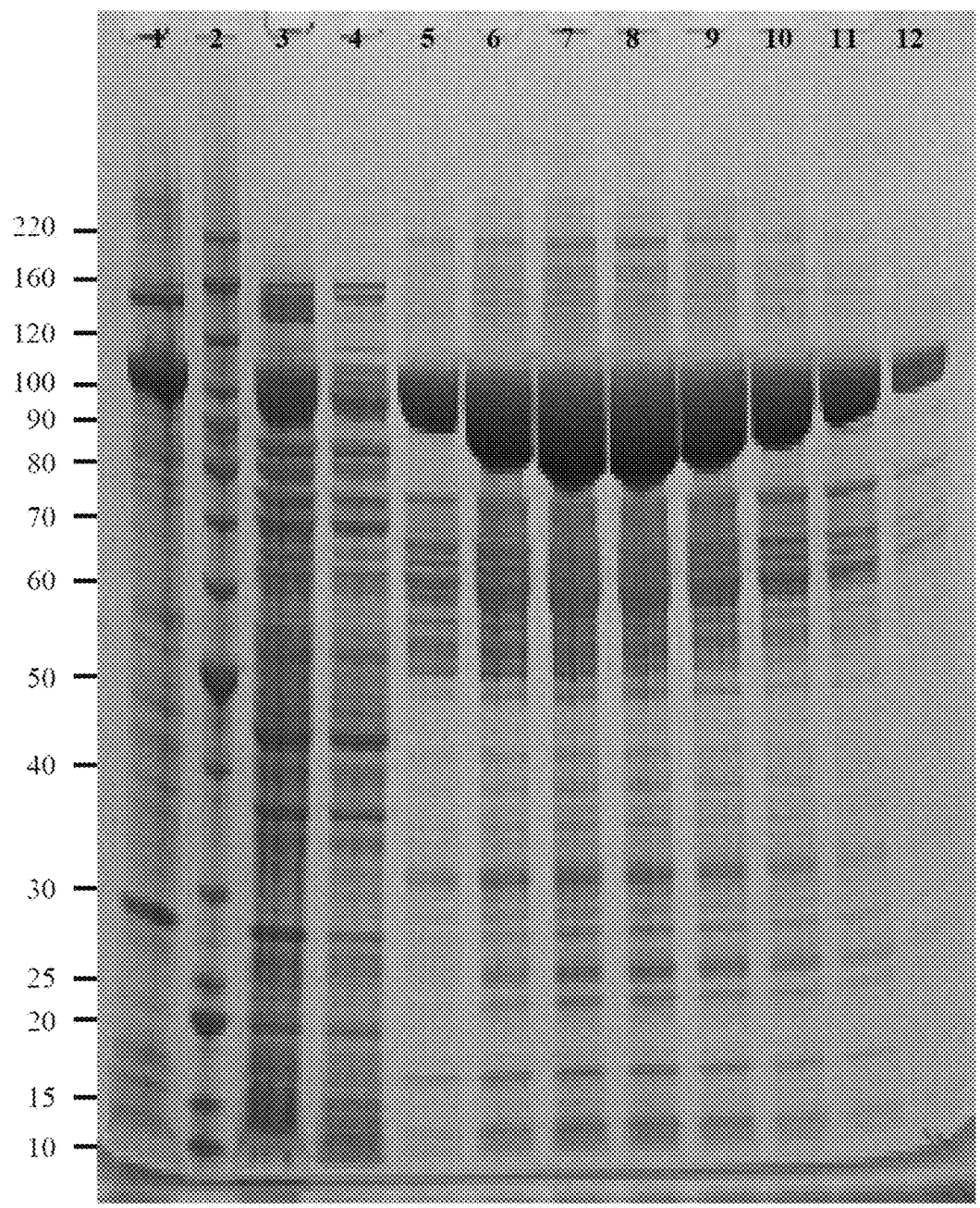

FIG. 5—SDS-PAGE analysis of the purification of a LH(#FXa)C-EGF chimaeric protein (as prepared in Example 20). Lane 1 illustrates the clarified cell lysate; Lane 2 is molecular mass markers (Benchmark); Lane 3 illustrates the column flow through; Lane 4 illustrates the fraction eluted following washing the column; Lanes 5-12 are fractions eluted on addition of 250 mM imidazole.

Figure 6:
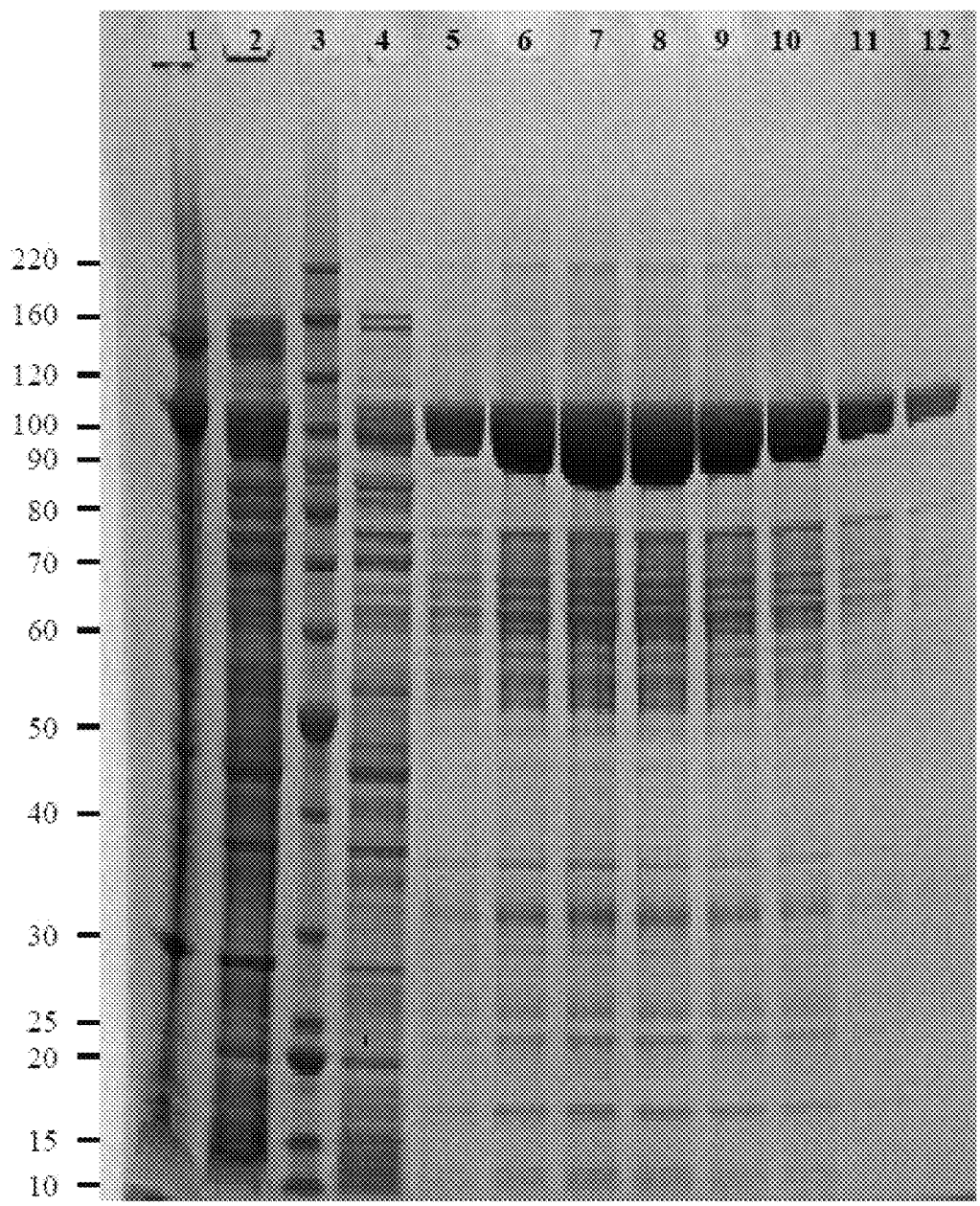

FIG. 6—SDS-PAGE analysis of the purification of a LH(#FXa)C-EGF chimaeric protein (as prepared in Example 21). Lane 1 illustrates the clarified cell lysate; Lane 2 illustrates the column flow through; Lane 3 is molecular mass markers (Benchmark); Lane 4 illustrates the fraction eluted following washing the column; Lanes 5-12 are fractions eluted on addition of 250 mM imidazole.

Figure 7:
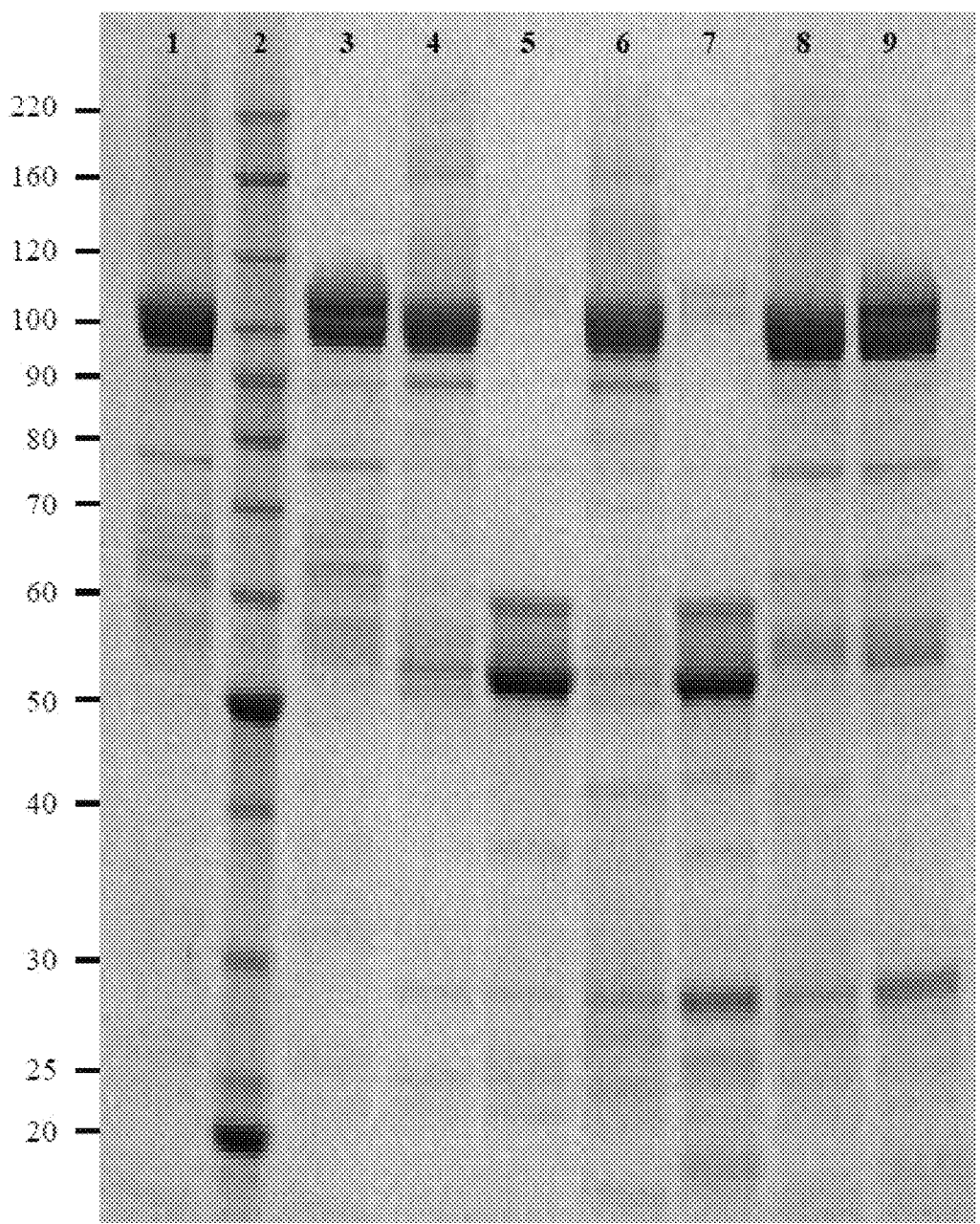

FIG. 7—SDS-PAGE analysis of the proteolysis of a LH(#FXa)C-EGF chimaeric protein (as prepared in Example 20) by FXa. Lanes 1 & 3 illustrate the purified protein prior to enterokinase activation at the LC-$H_N$ junction, in the absence and presence of DTT respectively; Lanes 4 & 5 illustrate the protein post enterokinase activation at the LC-$H_N$ junction, in the absence and presence of DTT respectively; Lanes 6 & 7 illustrate the enterokinase activated protein treated with Factor Xa, in the absence and presence of DTT respectively; Lanes 8 & 9 illustrate the result of FXa treatment of the protein that has not been activated with enterokinase, in the absence and presence of DTT respectively. Fragmentation of the protein following treatment with Factor Xa is clearly seen in Lanes 7 and 9. Lane 2 is molecular mass markers (Benchmark).

Figure 8:
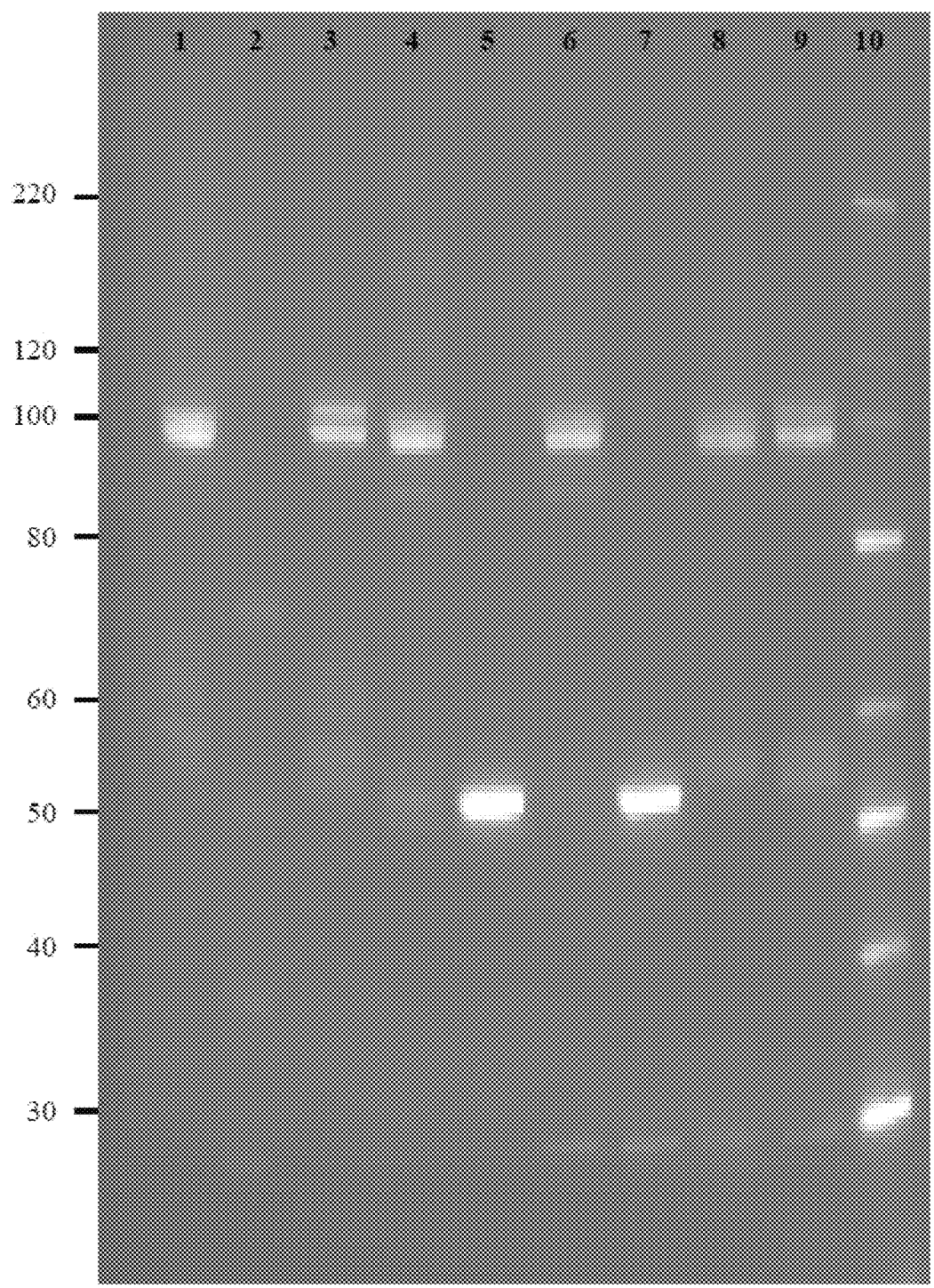

FIG. 8—Western blot analysis of the proteolysis of a LH(#FXa)C-EGF chimaeric protein (as prepared in Example 20) by FXa. Lanes 1 & 3 illustrate the purified protein prior to enterokinase activation at the LC-$H_N$ junction, in the absence and presence of DTT respectively; Lanes 4 & 5 illustrate the protein post enterokinase activation at the LC-$H_N$ junction, in the absence and presence of DTT respectively; Lanes 6 & 7 illustrate the enterokinase activated protein treated with Factor Xa, in the absence and presence of DTT respectively; Lanes 8 & 9 illustrate the result of FXa treatment of the protein that has not been activated with enterokinase, in the absence and presence of DTT respectively. Fragmentation of the protein following treatment with Factor Xa is clearly seen in Lanes 6, 7, 8 & 9 by the visualisation of a Histidine immunoreactive band at the anticipated size. Lane 2 is molecular mass markers suitable for detection by staining (Benchmark). Lane 10 is molecular mass markers suitable for Western blot visualisation (Magic Markers).

Figure 9:
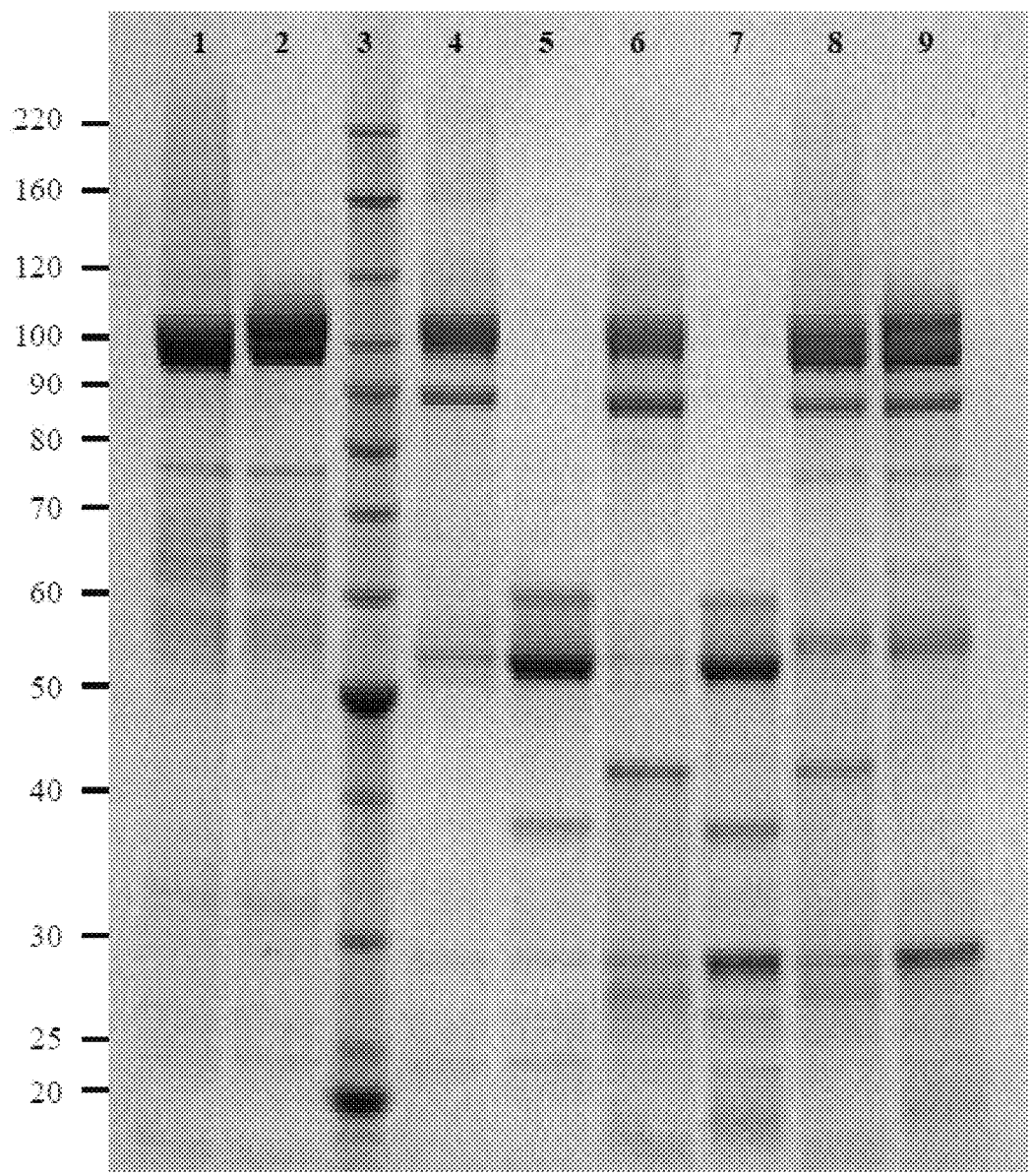

FIG. 9—SDS-PAGE analysis of the proteolysis of a LH(#FXa)C-EGF chimaeric protein (as prepared in Example 21) by FXa. Lanes 1 & 2 illustrate the purified protein prior to enterokinase activation at the LC-$H_N$ junction, in the absence and presence of DTT respectively; Lanes 4 & 5 illustrate the protein post enterokinase activation at the LC-$H_N$ junction, in the absence and presence of DTT respectively; Lanes 6 & 7 illustrate the enterokinase activated protein treated with Factor Xa, in the absence and presence of DTT respectively; Lanes 8 & 9 illustrate the result of FXa treatment of the protein that has not been activated with enterokinase, in the absence and presence of DTT respectively. Fragmentation of the protein following treatment with Factor Xa is clearly seen in Lanes 7 and 9. Lane 3 is molecular mass markers (Benchmark).

Figure 10:
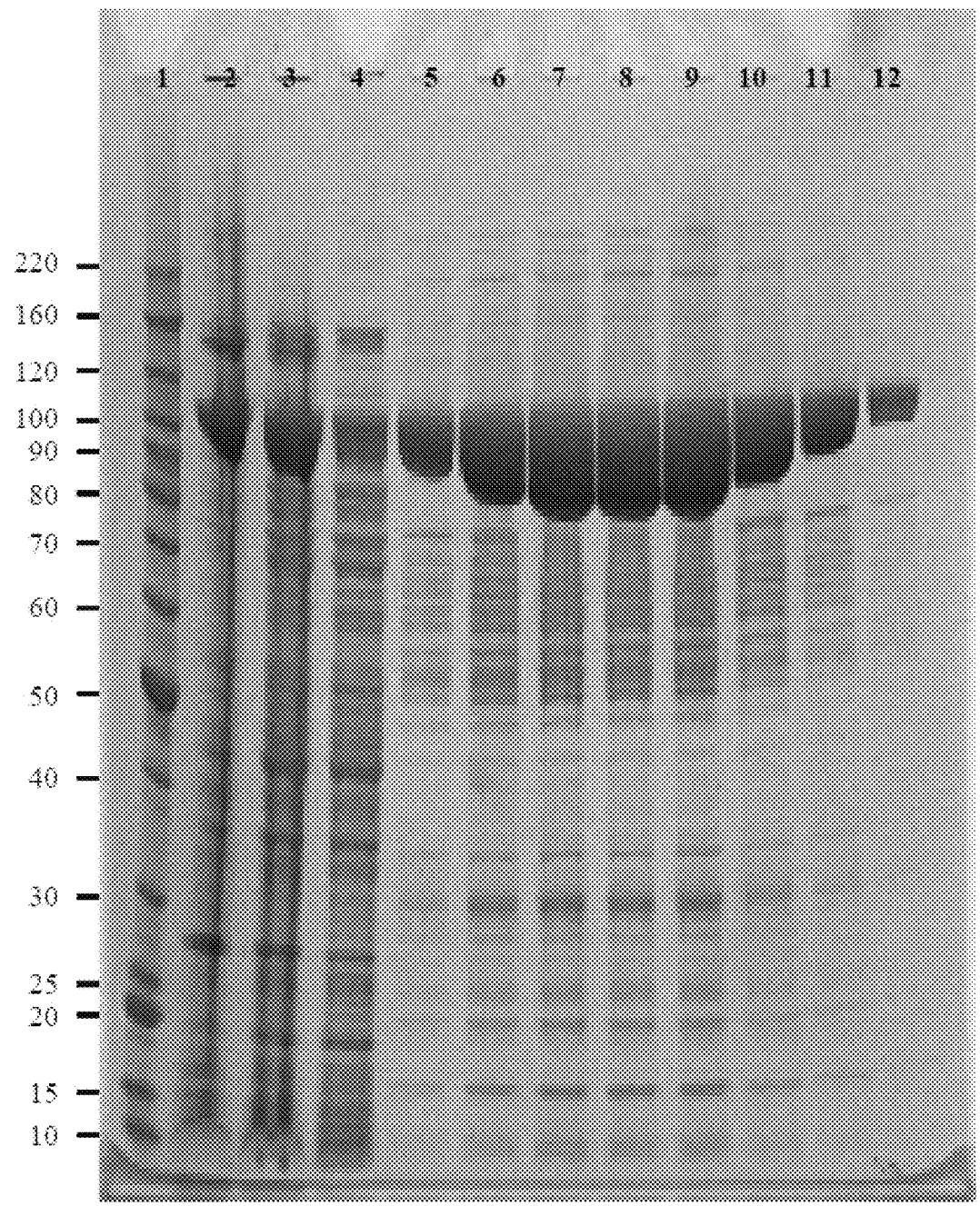

FIG. 10—SDS-PAGE analysis of the purification of a L(#Thr)HC-EGF chimaeric protein (as prepared in Example 19). Lane 1 is molecular mass markers (Benchmark); Lane 2 illustrates the clarified cell lysate; Lane 3 illustrates the column flow through; Lane 4 illustrates the fraction eluted following washing the column; Lanes 5-12 are fractions eluted on addition of 250 mM imidazole.

Figure 11:
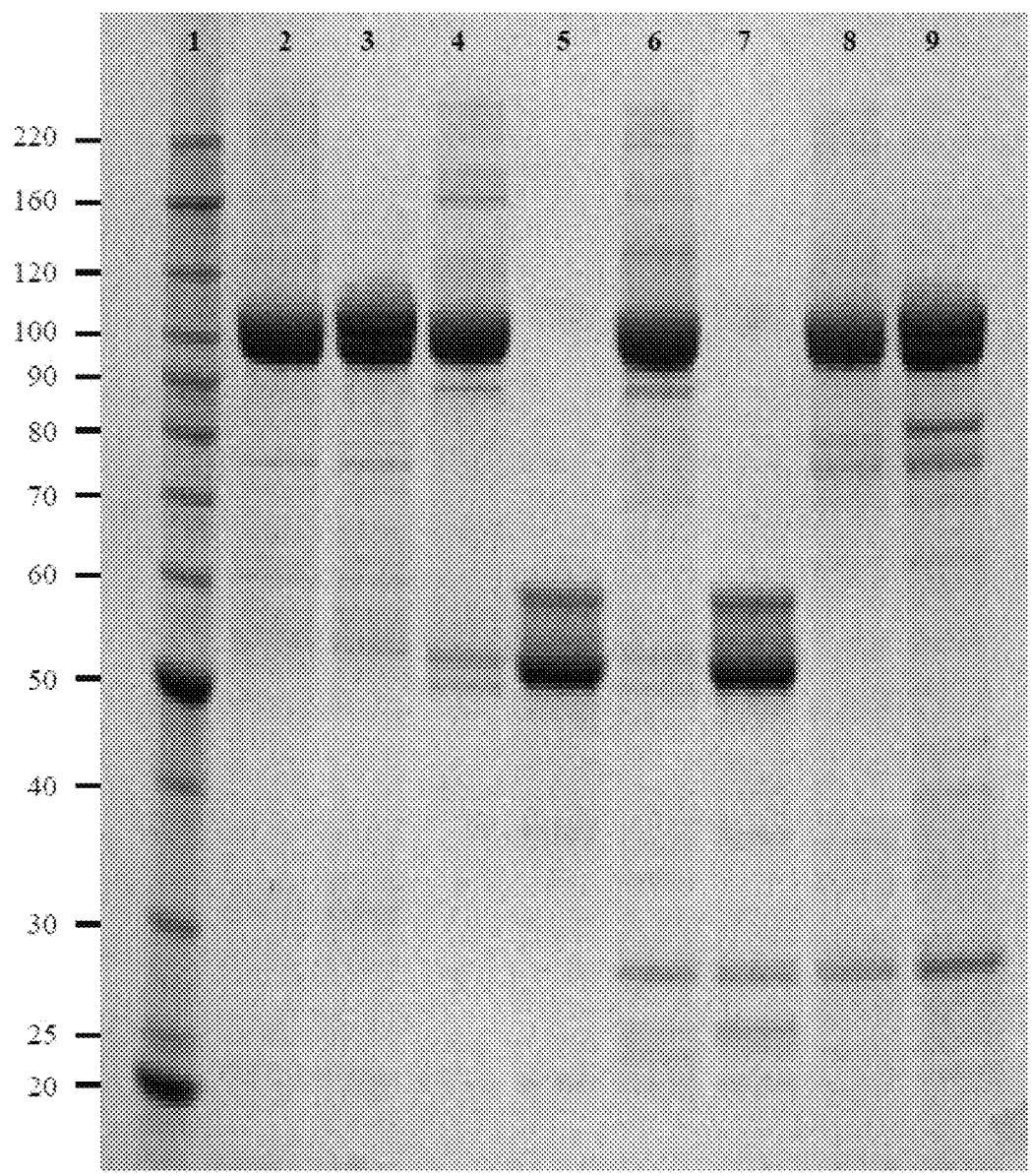

FIG. 11—SDS-PAGE analysis of the proteolysis of a L(#Thr)HC-EGF chimaeric protein (as prepared in Example 19) by Thrombin. Lane 1 is molecular mass markers (Benchmark). Lanes 2 & 3 illustrate the purified protein prior to enterokinase activation at the LC-$H_N$ junction, in the absence and presence of DTT respectively; Lanes 4 & 5 illustrate the protein post enterokinase activation at the LC-$H_N$ junction, in the absence and presence of DTT respectively; Lanes 6 & 7 illustrate the enterokinase activated protein treated with Factor Xa, in the absence and presence of DTT respectively; Lanes 8 & 9 illustrate the result of FXa treatment of the protein that has not been activated with enterokinase, in the absence and presence of DTT respectively. Fragmentation of the protein following treatment with Thrombin is clearly seen in Lanes 6, 7, 8 and 9.

Figure 12:
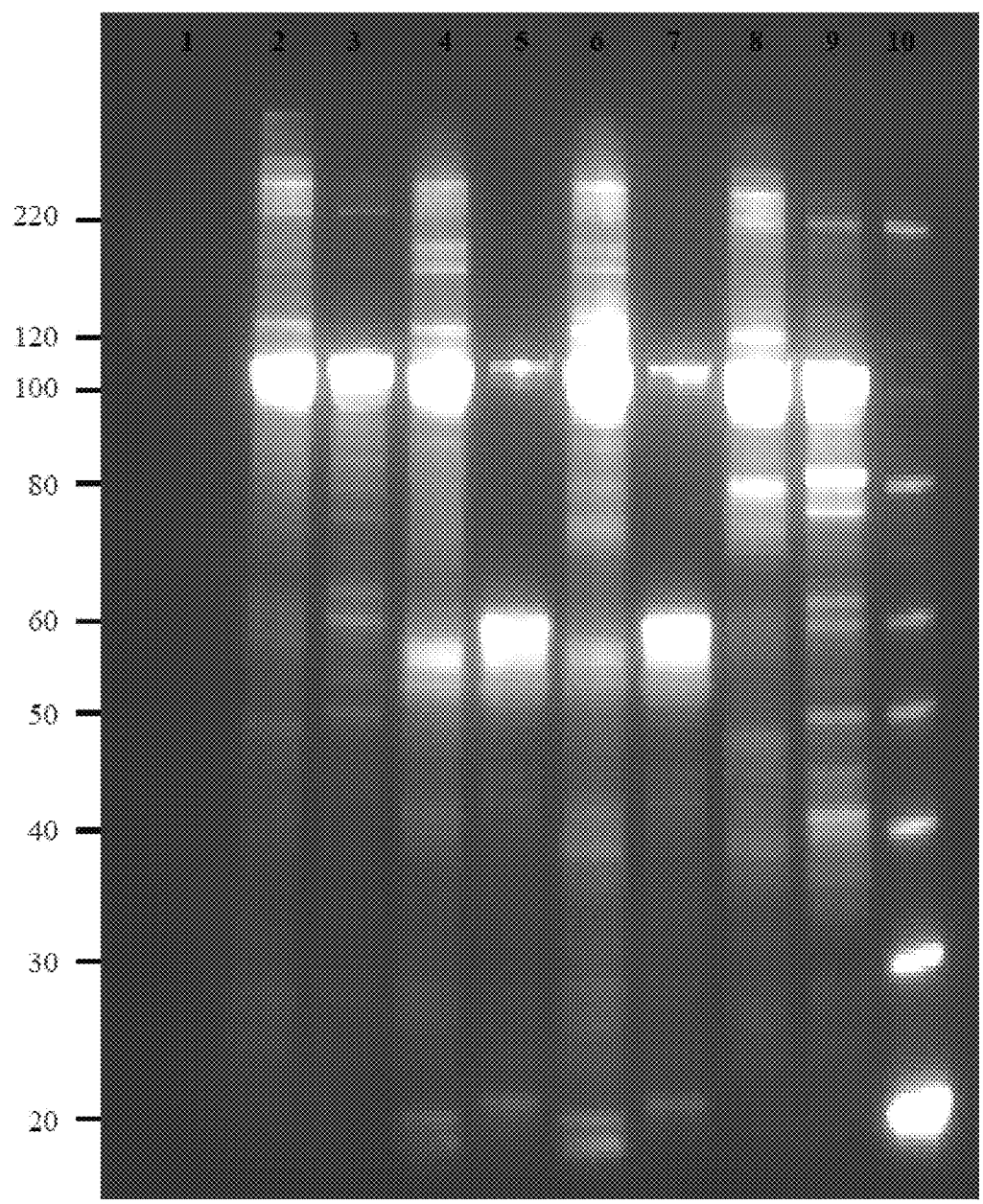

FIG. 12—Western blot analysis of the proteolysis of a L(#Thr)HC-EGF chimaeric protein (as prepared in Example 19) by Thrombin. Lane 1 is molecular mass markers (Benchmark), which are poorly visible by Western blotting. Lanes 2 & 3 illustrate the purified protein prior to enterokinase activation at the LC-$H_N$ junction, in the absence and presence of DTT respectively; Lanes 4 & 5 illustrate the protein post enterokinase activation at the LC-$H_N$ junction, in the absence and presence of DTT respectively; Lanes 6 & 7 illustrate the enterokinase activated protein treated with Factor Xa, in the absence and presence of DTT respectively; Lanes 8 & 9 illustrate the result of FXa treatment of the protein that has not been activated with enterokinase, in the absence and presence of DTT respectively. Fragmentation of the protein following treatment with Thrombin to release an ~85 kDa fragment that retains the EGF domain but lacks ~20 Kda of the N-terminus of the LC is clearly seen in Lanes 8 and 9.

Figure 13:
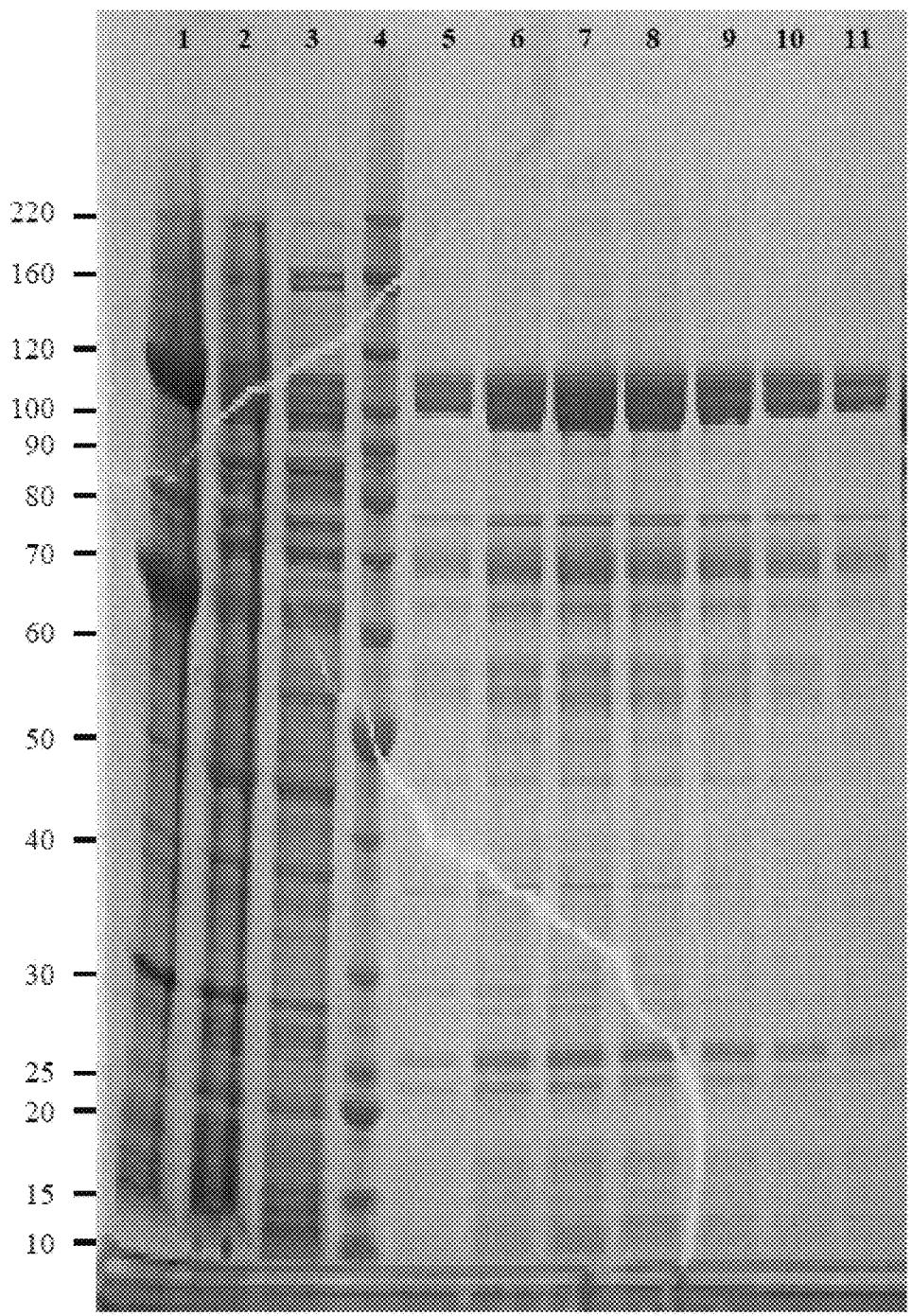

FIG. 13—SDS-PAGE analysis of the purification of a L(#Thr)HA-EGF chimaeric protein (as prepared in Example 24). Lane 1 illustrates the clarified cell lysate; Lane 2 illustrates the column flow through; Lane 3 illustrates the fraction eluted following washing the column; Lane 4 is molecular mass markers (Benchmark); Lanes 5-11 are fractions eluted on addition of 250 mM imidazole FIG. 14—SDS-PAGE analysis of the proteolysis of a L(#Thr)HA-EGF chimaeric protein (as prepared in Example 24) by Thrombin. Lane 4 is molecular mass markers (Benchmark). Lanes 1 & 2 illustrate the purified protein prior to enterokinase activation at the LC-$H_N$ junction, in the absence and presence of DTT respectively; Lanes 3 & 5 illustrate the protein post enterokinase activation at the LC-$H_N$ junction, in the absence and presence of DTT respectively; Lanes 6 & 7 illustrate the enterokinase activated protein treated with Thrombin in the absence and presence of DTT respectively; Lanes 8 & 9 illustrate the result of Thrombin treatment of the protein that has not been activated with enterokinase, in the absence and presence of DTT respectively. Fragmentation of the protein following treatment with Thrombin is clearly seen in Lanes 6, 7, 8 and 9

Figure 15:
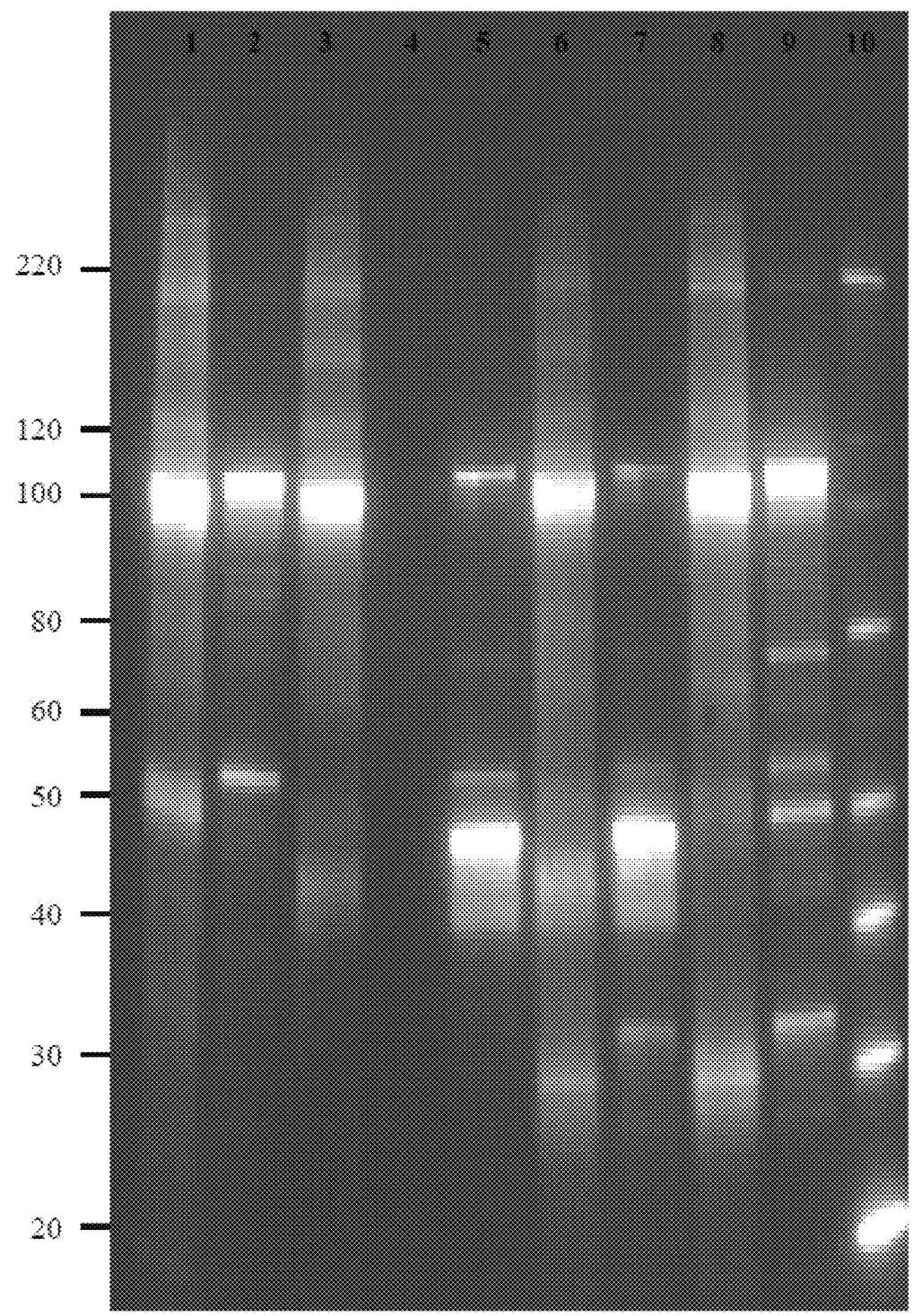

FIG. 15—Western blot analysis of the proteolysis of a L(#Thr)HA-EGF chimaeric protein (as prepared in Example 24) by Thrombin. Lane 4 is molecular mass markers (Benchmark). Lanes 1 & 2 illustrate the purified protein prior to enterokinase activation at the LC-$H_N$ junction, in the absence and presence of DTT respectively; Lanes 3 & 5 illustrate the protein post enterokinase activation at the LC-$H_N$ junction, in the absence and presence of DTT respectively; Lanes 6 & 7 illustrate the enterokinase activated protein treated with Thrombin in the absence and presence of DTT respectively; Lanes 8 & 9 illustrate the result of Thrombin treatment of the protein that has not been activated with enterokinase, in the absence and presence of DTT respectively. Fragmentation of the protein following treatment with Thrombin is clearly seen in Lanes 7 and 9.

Figure 16:
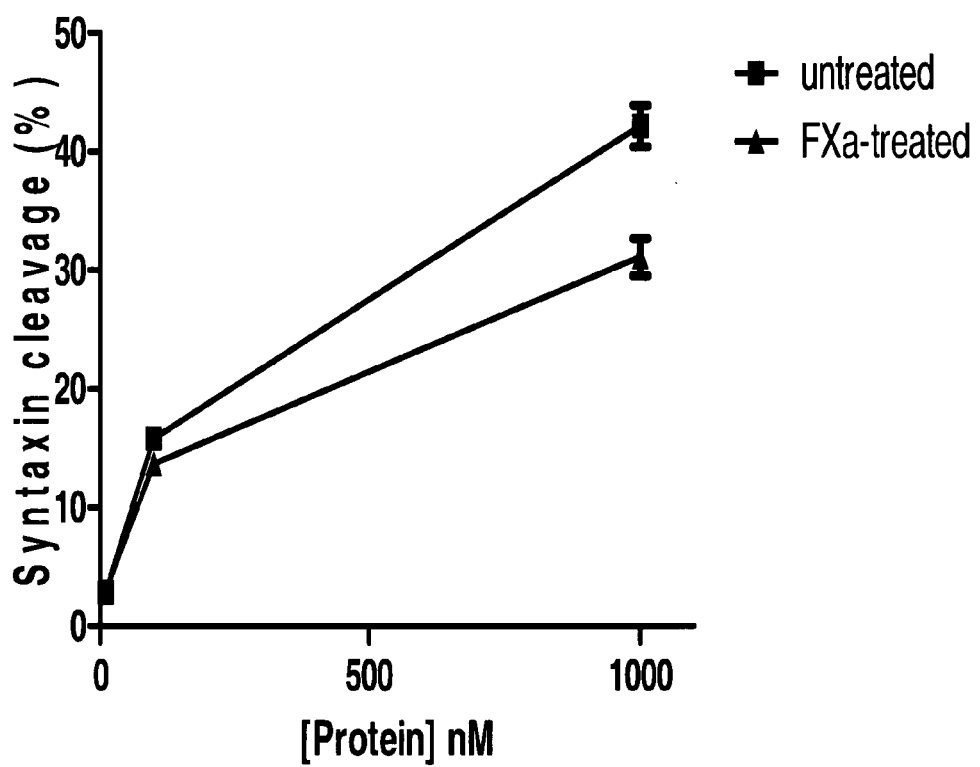

FIG. 16—illustrates the result obtained following exposure of SCN with FXa-treated L(FXa)HC-EGF compared to untreated L(FXa)HC-EGF. The protein that had been treated with Factor Xa is clearly less effective at cleaving Syntaxin than the protein that was not treated with FXa. The invention has therefore enabled a reduction in the efficacy of the modified protein.

Figure 17:
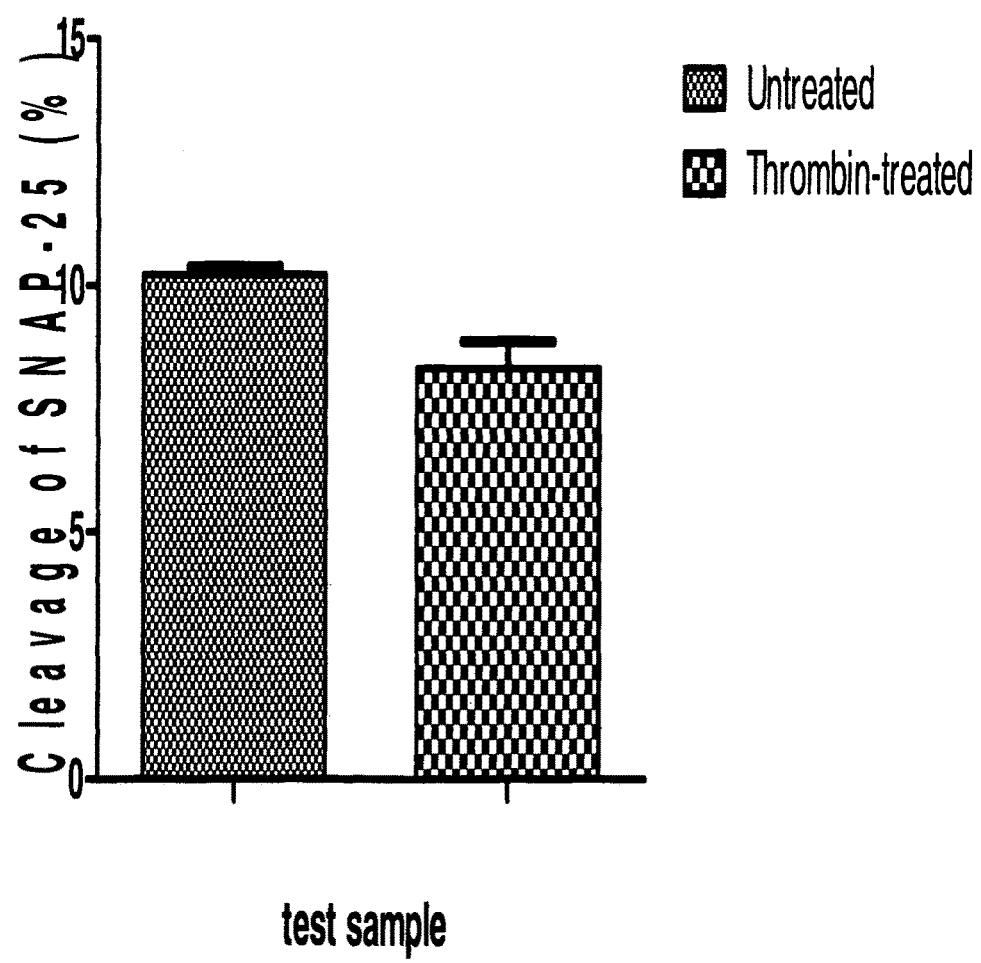

FIG. 17—illustrates the result obtained following exposure of SCN with 10 nM Thrombin-treated L(Thr)HA-EGF compared to 10 nM untreated L(Thr)HA-EGF. The protein that had been treated with thrombin is clearly less effective at cleaving SNAP-25 than the protein that was not treated with thrombin. The invention has therefore enabled a reduction in the efficacy of the modified protein.

There now follows description of specific embodiments of the invention, illustrated by the Examples.

Example 1—Assessment of polypeptides of the invention when exposed to a mammalian cell (muscle).

Example 2—Assessment of polypeptides of the invention when exposed to a mammalian cell having first exposed the polypeptide to circulatory proteases.

Example 3—Assessment of the catalytic activity of polypeptides of the invention.

Example 4—Assessment of the translocation ability of polypeptides of the invention.

Example 5—Creation of an LHC-EGF chimaeric protein that incorporates a Factor Xa recognition site into the LC.

Example 6—Purification of an LHC-EGF chimaeric protein that incorporates a Factor Xa recognition site into the LC.

Example 7—Demonstration of enhanced protease sensitivity in an LHC-EGF chimaeric protein that incorporates a Factor Xa recognition site into the LC.

Example 8—Creation of an LHC-EGF chimaeric protein that incorporates a Thrombin recognition site into the LC.

Example 9—Creation of an LHA-EGF chimaeric protein that incorporates a Thrombin recognition site into the LC, wherein LHA is the $LH_N$ fragment of BoNT/A.

Example 10—Creation of an LHC-EGF chimaeric protein that incorporates a furin recognition site into the LC.

Example 11—Creation of an LHA-EGF chimaeric protein that incorporates a Factor Xa recognition site into the $H_N$ domain.

Example 12—Creation of a LHA-EGF chimaeric protein that incorporates an ADAM17 recognition site into the LC domain.

Example 13—Creation of a recombinant BoNT/A protein that incorporates an ADAM17 recognition site into the LC Example 14—Creation of a recombinant BoNT/A protein that incorporates a furin recognition site into the $H_N$.

Example 15—Treatment of a patient suffering from dystonia (Spasmodic Torticollis).

Example 16—Treatment of a patient suffering from blepharospasm.

Example 17—Creation of a LHC-EGF chimaeric protein that incorporates a Factor Xa recognition site into the LC at position 210

Example 18—Creation of a LHC-EGF chimaeric protein that incorporates a Thrombin recognition site into the LC at position 195

Example 19—Creation of a LHC-EGF chimaeric protein that incorporates a Thrombin recognition site into the LC at position 210

Example 20—Creation of a LHC-EGF chimaeric protein that incorporates a Factor Xa recognition site into the $H_N$ domain at position 742 of the $H_N$ Example 21—Creation of a LHC-EGF chimaeric protein that incorporates a Factor Xa recognition site into the $H_N$ domain at position 750 of the $H_N$ Example 22—Creation of a LHC-EGF chimaeric protein that incorporates a Thrombin recognition site into the $H_N$ domain at position 750 of the $H_N$ Example 23—Creation of a LHD-VIPr chimaeric protein that incorporates a Factor Xa recognition site into the $H_N$ domain at position 798 of the $H_N$ Example 24—Creation of an LHA-EGF chimaeric protein that incorporates a Thrombin recognition site into the LC domain Example 25—Demonstration of specific cleavage of a purified LHC-EGF chimaeric protein that is engineered to incorporate a Factor Xa recognition site into the LC.

Example 26—Demonstration of specific cleavage of a purified LHC-EGF chimaeric protein that is engineered to incorporate a Factor Xa recognition site into the $H_N$.

Example 27—Demonstration of specific cleavage of a purified LHC-EGF chimaeric protein that is engineered to incorporate a Thrombin recognition site into the LC Example 28—Demonstration of specific cleavage of a purified LHA-EGF chimaeric protein that is engineered to incorporate a Thrombin recognition site into the LC Example 29—Demonstration of reduced in vitro cellular activity of a protein engineered to incorporate a Factor Xa protease cleavage site into the LC domain of L(FXa)HC-EGF Example 30—Demonstration of reduced in vitro cellular activity of a protein engineered to incorporate a Thrombin protease cleavage site into the LC domain of L(Thr)HA-EGF Example 31—Creation of a recombinant BoNT/A protein that incorporates a Thrombin recognition site into the LC Example 32—Creation of a recombinant BoNT/A protein that incorporates a Factor Xa recognition site into the LC.

Example 33—Creation of a recombinant BoNT/A protein that incorporates a Factor Xa recognition site into the $H_N$ Example 34—Creation of a recombinant BoNT/E protein that incorporates a Thrombin recognition site into the LC Example 35—Creation of a recombinant BoNT/E protein that incorporates a Factor Xa recognition site into the $H_N$.

Example 36—Creation of an LHE-VIPr chimaeric protein that incorporates a Thrombin recognition site into the LC.

Example 37—Creation of an LHE-VIPr chimaeric protein that incorporates a Factor Xa recognition site into the $H_N$.

Example 38—Creation of an LHE-VIPr chimaeric protein that incorporates a Factor Xa recognition site into the LC.

Example 39—Cleavage of SNARE protein by a modified clostridial neurotoxin ($LH_N$) having the properties described by LIN, et al. (WO02/044199)

Summary of SEQ ID NOs
SEQ ID 1 DNA sequence of LHC-EGF
SEQ ID 2 Protein sequence of LHC-EGF
SEQ ID 3 DNA sequence of L(#FXa)HC-EGF
SEQ ID 4 Protein sequence of L(#FXa)HC-EGF
SEQ ID 5 DNA sequence of L(#Thr)HC-EGF
SEQ ID 6 Protein sequence of L(#Thr)HC-EGF
SEQ ID 7 DNA sequence of LHA-EGF
SEQ ID 8 Protein sequence of LHA-EGF
SEQ ID 9 DNA sequence of L(#Thr)HA-EGF
SEQ ID 10 Protein sequence of L(#Thr)HA-EGF
SEQ ID 11 Protein sequence of L(#furin)HC-EGF
SEQ ID 12 DNA sequence of LH(#FXa)A-EGF
SEQ ID 13 Protein sequence of LH(#FXa)A-EGF
SEQ ID 14 DNA sequence of L(#ADAM17)HA-EGF
SEQ ID 15 Protein sequence of L(#ADAM17)HA-EGF
SEQ ID 16 DNA sequence of LHA-$H_C$/A
SEQ ID 17 Protein sequence of LHA-$H_C$/A
SEQ ID 18 DNA sequence of L(#ADAM17)HA-$H_C$/A
SEQ ID 19 Protein sequence of L(#ADAM17)HA-$H_C$/A
SEQ ID 20 DNA sequence of L(#furin)HA-$H_C$/A
SEQ ID 21 Protein sequence of L(#furin)HA-$H_C$/A
SEQ ID 22 DNA sequence of L(#FXa)HC-EGF (SXN1975)
SEQ ID 23 Protein sequence of L(#FXa)HC-EGF (SXN1975)
SEQ ID 24 Protein sequence of L(#Thr)HC-EGF (SXN1931)
SEQ ID 25 Protein sequence of L(#Thr)HC-EGF (SXN1932)
SEQ ID 26 Protein sequence of LH(#FXa)C-EGF (SXN1937)
SEQ ID 27 Protein sequence of LH(#FXa)C-EGF (SXN1938)
SEQ ID 28 Protein sequence of LH(#Thr)C-EGF (SXN1939)
SEQ ID 29 Protein sequence of LH(#FXa)D-VIPr (SXN1930)
SEQ ID 30 Protein sequence of L(#Thr)HA-EGF (SXN1974)
SEQ ID 31 Protein sequence of L(#Thr)HA-EGF (SXN1974)
SEQ ID 32 Protein sequence of L(#Thr)HA-$H_C$/A
SEQ ID 33 Protein sequence of L(#FXa)HA-$H_C$/A
SEQ ID 34 Protein sequence of LH(FXa)A-$H_C$/A
SEQ ID 35 Protein sequence of L(#Thr)HE-$H_C$/E
SEQ ID 36 Protein sequence of LH(#FXa)E-$H_C$/E
SEQ ID 37 Protein sequence of L(#Thr)HE-VIPr
SEQ ID 38 Protein sequence of LH(#FXa)E-VIPr
SEQ ID 39 Protein sequence of L(#FXa)HE-VIPr (mutation at K228D)

EXAMPLES

Example 1—Assessment of Polypeptides of the Invention when Exposed to a Mammalian Muscle Cell A purified protein created according to Example 13 is incubated in the presence of a mammalian muscle cell (coronary smooth muscle primary culture or HSkMC (150-05f) cell (available from ECACC)). In parallel, a second polypeptide (identical to the first polypeptide other than for the fact that it lacks the same destructive cleavage site) is incubated under identical conditions in the presence of the same test cell-type.

Each of the two polypeptides is then assessed for cleavage by ADAM17 (inherent to the coronary smooth muscle primary culture/HSkMC cell) by SDS-PAGE and subsequent Western blot analysis. In this regard, a greater observed cleavage for the first polypeptide versus that observed for the second polypeptide confirms controllable inactivation of the present invention.

Example 2—Assessment of Polypeptides of the Invention when Exposed to a Mammalian Cell Having First Exposed the Polypeptide to a Circulatory Protease A first polypeptide (SEQ ID 4); prepared according to Example 5 of the present invention) is taken and incubated in the presence of a target cell having first exposed the polypeptide to circulatory proteases (for example, Factor Xa, Thrombin) in vitro. In parallel, a second polypeptide (SEQ ID2; identical to the first polypeptide other than for the fact that it lacks the protease cleavage site) is incubated in the same manner as for the first polypeptide.

Each of the two polypeptides is then assessed for cleavage of syntaxin in an embryonic spinal cord neuron (eSCN). In this regard, a lesser observed cleavage for the first polypeptide versus that observed for the second polypeptide confirms controllable inactivation of the present invention.

Example 3—Assessment of the Catalytic Activity of Polypeptides of the Invention

A first polypeptide (SEQ ID 10; prepared according to Example 9 of the present invention) is incubated in vitro in the presence of a protease (thrombin) that cleaves the polypeptide at a destructive cleavage site introduced into the protease domain of the polypeptide. In parallel, a second polypeptide (SEQ ID 8: identical to the first polypeptide other than for the fact that it lacks the protease cleavage site) is incubated in an identical manner in the presence of the same protease.

Each of the two polypeptides is then challenged in an in vitro cell-free system (as described by Hallis et al 1996, J. Clin. Microbiol. 34 1934-1938) containing immobilised SNAP-25, and cleavage of SNAP-25 protein is measured by using specific antisera raised to the cleavage product. In this regard, a lesser observed SNARE protein cleavage for the first polypeptide versus that observed for the second polypeptide confirms controllable inactivation of the present invention.

Example 4—Assessment of the Translocation Ability of Polypeptides of the Invention A first polypeptide (according to the present invention) is incubated in the presence of a protease that cleaves the polypeptide at a destructive cleavage site introduced into the translocation (e.g. $H_N$) domain. In parallel, a second polypeptide (identical to the first polypeptide other than for the fact that it lacks the protease cleavage site) is incubated in an identical manner in the presence of the same protease.

Each of the two polypeptides is then challenged in an in vitro system containing a lipid bilayer membrane, and transport across the membrane is measured. For example, Shone C. (1987) describes an in vitro assay employing liposomes, which are challenged with a test molecule. Presence of the requisite translocation function is confirmed by release from the liposomes of K+ and/or labelled NAD, which may be readily monitored [see Shone C. (1987) Eur. J. Biochem; vol. 167(1): pp. 175-180]. A further example is provided by Blaustein R. (1987), which describes a simple in vitro assay employing planar phospholipid bilayer membranes. The membranes are challenged with a test molecule and the requisite translocation function is confirmed by an increase in conductance across said membranes [see Blaustein (1987) FEBS Letts; vol. 226, no. 1: pp. 115-120].

This method is applied to study the protease inactivation of the $H_N$ domain of serotype D BoNT. The protein of Example 23 is expressed and purified and is exposed to Factor Xa to result in cleavage of the protein within the $H_N$ domain. The cleaved protein is assessed in the in vitro system described above and compared to the protein that has not been treated with Factor Xa. The experiment determines that the transport across the membrane for the Factor Xa-treated polypeptide is significantly less than that of the untreated polypeptide.

Example 5—Creation of an LHC-EGF Chimaeric Protein that Incorporates a Factor Xa Recognition Site into the LC The primary sequence of a chimaeric protein constructed by a genetic fusion of the $LH_N$ fragment of BoNT/C and the human epidermal growth factor sequence (SEQ ID 2) is reviewed for the presence of amino acid strings that bear resemblance to the prototypical recognition site for Factor Xa (IEGR) (SEQ ID 41). Simple text character analysis of the primary sequence identified the sequence 210GEGR213 (SEQ ID 97) within the LC domain. The location of the peptide in the tertiary structure of the LC/C is predicted from examination of the location of the homologous peptide sequence in the LC/A using the X-ray crystal structure of BoNT/A (pdb: 3BTA) as the guide. Freely available software (such as FirstGlance in Jmol) are used to identify that the LC/A equivalent peptide sequence is located on the surface of the LC. The location is therefore a good region for accessibility by proteases.

Site directed mutagenesis of the SEQ ID 1 (encoding SEQ ID 2) using a primer designed to switch the codon for G210 (GGC) to one that encodes Ile (ATC) was achieved utilising standard molecular tools for performing mutagenesis (for example, the Stratagene Quickchange mutagenesis methodology). E. coli codon usage was assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA was incorporated into a standard cloning vector, for example pCR4, prior to transformation into E. coli host. The integrity of the ORF DNA was checked by sequencing. The final ORF incorporating the Factor Xa site is illustrated as SEQ ID 3 and the amino acid sequence of the expression product is illustrated in SEQ ID 4.

Example 6—Purification of an LHC-EGF Chimaeric Protein that Incorporates a Factor Xa Recognition Site into the LC The ORF created in Example 17 was cloned into an E. coli expression vector (a pET (Novagen) vector that has been modified to ensure mobilisation deficiency) and transformed into an E. coli host strain, most commonly BL21. The vector was modified to include expression of a Histidine tag at the N-terminus of the LHC-EGF ORF.

Expression of the LHC-EGF fusion protein is achieved using the following protocol. Inoculate 100 ml of modified TB containing 0.2% glucose and 100 µg/ml ampicillin in a 250 ml flask with a single colony from the LHC-EGF expression strain. Grow the culture at 37° C., 225 rpm for 16 hours. Inoculate 1 L of modified TB containing 0.2% glucose and 100 µg/ml ampicillin in a 2 L flask with 10 ml of overnight culture. Grow cultures at 37° C. until an approximate OD600 nm of 0.5 is reached at which point reduce the temperature to 16° C. After 1 hour induce the cultures with 1 mM IPTG and grow at 16° C. for a further 16 hours.

Purification of the LHC-EGF fusion is achieved by affinity chromatography. In detail, a falcon tube containing 25 ml 50 mM HEPES pH 7.2 200 mM NaCl and approximately 10 g of E. coli BL21 cell paste is defrosted. Sonicate the cell paste on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M NiSO4 charged Chelating column (20-30 ml column is sufficient) equilibrated with 50 mM HEPES pH 7.2 200 mM NaCl. Using a step gradient of 10 and 40 mM imidazole, wash away the non-specific bound protein and elute the fusion protein with 100 mM imidazole. Dialyse the eluted fusion protein against 5 L of 50 mM HEPES pH 7.2 200 mM NaCl at 4° C. overnight and measure the OD of the dialysed fusion protein. Add 6.4 ng enterokinase/mg fusion protein and incubate at 25° C. static overnight. Load onto a 0.1 M NiSO4 charged Chelating column (20-30 ml column is sufficient) equilibrated with 50 mM HEPES pH 7.2 200 mM NaCl. Wash column to baseline with 50 mM HEPES pH 7.2 200 mM NaCl. Using a step gradient of 10 and 40 mM imidazole, wash away the non-specific bound protein and elute the fusion protein with 100 mM imidazole. Dialyse the eluted fusion protein against 5 L of 50 mM HEPES pH 7.2 200 mM NaCl at 4° C. overnight and concentrate the fusion to about 2 mg/ml, aliquot sample and freeze at −20° C. Test purified protein using OD, BCA and purity analysis.

Example 7—Demonstration of Enhanced Protease Sensitivity in an LHC-EGF Chimaeric Protein that Incorporates a Factor Xa Recognition Site into the LC The purified chimaeric protein of Example 6 is assessed for its stability in the presence of protease using the methodology outlines in Example 2 and 3. In summary, the LHC-EGF chimaeric protein is exposed to a range of concentrations of Factor Xa protease (obtained, for example, from New England Biolabs #P8010L) in vitro over a period of 1-120 minutes. The proteolysis is terminated by addition of a specific inhibitor of Factor Xa (for example Dansyl-glu-gly-arg-chloromethyl ketone (CALBIOCHEM, #251700)). A control protein chimaera of LHC-EGF that does not include the additional Factor Xa site is used to compare the effect of the protease on LC activity (using Example 3), and functionality of the chimaera when exposed to a target cell (using Example 2 and measuring syntaxin cleavage in an embryonic spinal cord neuron (eSCN)).

Example 8—Creation of an LHC-EGF Chimaeric Protein that Incorporates a Thrombin Recognition Site into the LC The primary sequence of a chimaeric protein constructed by a genetic fusion of the $LH_N$ fragment of BoNT/C and the human epidermal growth factor sequence (SEQ ID 2) is reviewed for the presence of amino acid strings that bear resemblance to the prototypical recognition site for Thrombin (LVPRGS) (SEQ ID 40). Simple text character analysis of the primary sequence identified the sequence 194ISPRFM199 (SEQ ID 84) within the LC domain. The location of the peptide in the tertiary structure of the LC/C is predicted from examination of the location of the homologous peptide sequence in the LC/A using the X-ray crystal structure of BoNT/A (pdb: 3BTA) as the guide. Freely available software (such as FirstGlance in Jmol) are used to identify that the LC/A equivalent peptide sequence is located near the surface of the LC. The location is therefore a good region for accessibility by proteases.

Site directed mutagenesis of the SEQ ID 1 (encoding SEQ ID 2) using a primer designed to switch the codons for $S_{195}$ to Val (TCT to GTT) and $M_{195}$ to Ser (ATG to TCC) changes the region $_{194}$ISPRFM$_{199}$ (SEQ ID 84) to IVPRFS (SEQ ID 85) to make it a substrate for Thrombin cleavage. Mutagenesis was achieved utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The final ORF incorporating the Thrombin site is illustrated as SEQ ID 5 and the amino acid sequence of the expression product is illustrated in SEQ ID 6.

Example 9—Creation of an LHA-EGF Chimaeric Protein that Incorporates a Thrombin Recognition Site into the LC The primary sequence of a chimaeric protein constructed by a genetic fusion of the $LH_N$ fragment of BoNT/A and the EGF sequence (SEQ ID 8) is reviewed for the presence of amino acid strings that bear resemblance to the prototypical recognition site for Thrombin (GRG). Simple text character analysis of the primary sequence identified the sequence 103GRM105 within the LC domain. The location of the peptide in the tertiary structure of the LC/A is predicted from the X-ray crystal structure of BoNT/A (pdb: 3BTA) as the guide. Freely available software (such as FirstGlance in Jmol) are used to identify that the LC/A peptide sequence is located on the surface. The location is therefore a good region for accessibility by proteases.

Site directed mutagenesis of the SEQ ID 7 (encoding the ORF of SEQ ID 8) using a primer designed to switch the codon for Met105 (ATG) to one that encodes Gly (GGT) was achieved utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The final ORF incorporating the Thrombin site is illustrated as SEQ ID 9 and the amino acid sequence of the expression product is illustrated in SEQ ID 10.

Example 10—Creation of an LHC-EGF Chimaeric Protein that Incorporates a Furin Recognition Site into the LC The primary sequence of a chimaeric protein constructed by a genetic fusion of the $LH_N$ fragment of BoNT/C and the human epidermal growth factor sequence (SEQ ID 2) is reviewed for the presence of amino acid strings that bear resemblance to the prototypical recognition site for furin (RXR▼K/R) (SEQ ID 100). Simple text character analysis of the primary sequence identified the sequence 210GEGR213 (SEQ ID 97) within the LC domain. The location of the peptide in the tertiary structure of the LC/C is predicted from examination of the location of the homologous peptide sequence in the LC/A using the X-ray crystal structure of BoNT/A (pdb: 3BTA) as the guide. Freely available software (such as FirstGlance in Jmol) are used to identify that the LC/A equivalent peptide sequence is located on the surface of the LC. The location is therefore a good region for accessibility by proteases.

Site directed mutagenesis of the SEQ ID 1 (encoding SEQ ID 2) using a primer designed to switch the peptide region from GEGR (SEQ ID 97) to RSRR (SEQ ID 87) was achieved utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The amino acid sequence of the expression product is illustrated in SEQ ID 11.

Example 11—Creation of an LHA-EGF Chimaeric Protein that Incorporates a Factor Xa Recognition Site into the $H_N$ Domain The primary sequence of a chimaeric protein constructed by a genetic fusion of the $LH_N$ fragment of BoNT/A and the human epidermal growth factor sequence (SEQ ID 8) is reviewed for the presence of amino acid strings that bear resemblance to the prototypical recognition site for Factor Xa (IEGR) (SEQ ID 41). Simple text character analysis of the primary sequence identified the sequence 562GKSR565 (SEQ ID 99) within the FIN domain. The location of the peptide in the tertiary structure of the HN/A is predicted from the X-ray crystal structure of BoNT/A (pdb: 3BTA) as the guide. Freely available software (such as FirstGlance in Jmol) are used to identify that the HN peptide sequence is located on the surface. The location is therefore a good region for accessibility by proteases.

Site directed mutagenesis of the SEQ ID 7 (encoding SEQ ID 8) using a primer designed to switch the peptide region from GKSR (SEQ ID 99) to IEGR (SEQ ID 41) was achieved utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into E. coli host. The integrity of the ORF DNA is checked by sequencing. The final ORF incorporating the Factor Xa site is illustrated as SEQ ID 12 and the amino acid sequence of the expression product is illustrated in SEQ ID 13.

Example 12—Creation of a LHA-EGF Chimaeric Protein that Incorporates an ADAM17 Recognition Site into the LC Domain The primary sequence of a chimaeric protein constructed by a genetic fusion of the $LH_N$ fragment of BoNT/A and the human epidermal growth factor sequence (SEQ ID 8) is reviewed for the presence of amino acid strings that bear resemblance to the prototypical recognition site for ADAM17 (PLAQAVRSSS) (SEQ ID 42). Simple text character analysis of the primary sequence identifies a region of the structure (206PLLGAGKFAT215 (SEQ ID 86) within the LC domain) that is amenable to protein engineering. The location of the peptide in the tertiary structure of the LC is predicted from the X-ray crystal structure of BoNT/A (pdb: 3BTA) as the guide. Freely available software (such as FirstGlance in Jmol) are used to identify that the LC peptide sequence is located on the surface. The location is therefore good for accessibility by proteases.

Site directed mutagenesis of the SEQ ID 7 (which encodes SEQ ID 8) was achieved utilising standard molecular tools for performing mutagenesis (for example, the Stratagene Quickchange mutagenesis methodology). The mutagenesis of the LC was performed to modify the coding region from $_{206}$PLLGAGKFAT$_{215}$ (SEQ ID 86) to PLAQAVRSSS (SEQ ID 42).

E. coli codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into E. coli host. The integrity of the ORF DNA is checked by sequencing. The final ORF incorporating the additional ADAM17 sites is illustrated as SEQ ID 14 and the amino acid sequence of the expression product is illustrated in SEQ ID 15.

Example 13—Creation of a Recombinant BoNT/A Protein that Incorporates an ADAM17 Recognition Site into the LC Domain The primary sequence of a recombinant endopeptidase active BoNT/A containing an engineered activation protease site specific for enterokinase (SEQ ID 17) is reviewed for the presence of amino acid strings that bear resemblance to the prototypical recognition site for ADAM17 (PLAQAVRSSS) (SEQ ID 42). Simple text character analysis of the primary sequence identifies a region of the BoNT structure (206PLLGAGKFAT215 (SEQ ID 86) within the LC domain) that is amenable to protein engineering. The location of the peptide in the tertiary structure of the LC is predicted from the X-ray crystal structure of BoNT/A (pdb: 3BTA) as the guide. Freely available software (such as FirstGlance in Jmol) are used to identify that the LC peptide sequence is located on the surface. The location is therefore good for accessibility by proteases.

Site directed mutagenesis of the SEQ ID 16 (which encodes SEQ ID 17) was achieved utilising standard molecular tools for performing mutagenesis (for example, the Stratagene Quickchange mutagenesis methodology). The mutagenesis of the LC was performed to modify the coding region from $_{206}$PLLGAGKFAT$_{215}$ (SEQ ID 86) to PLAQAVRSSS (SEQ ID 42).

E. coli codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into E. coli host. The integrity of the ORF DNA is checked by sequencing. The final ORF incorporating the additional ADAM17 sites is illustrated as SEQ ID 18 and the amino acid sequence of the expression product is illustrated in SEQ ID 19.

Example 14—Creation of a Recombinant BoNT/A Protein that Incorporates a Furin Recognition Site into the $H_N$ The primary sequence of a recombinant endopeptidase active BoNT/A containing an engineered activation protease site specific for enterokinase (SEQ ID 17) is reviewed for the presence of amino acid strings that bear resemblance to the prototypical recognition site for furin (RXR▼K/R) (SEQ ID 100). Simple text character analysis of the primary sequence identified the sequence 563KSR565 within the $H_N$ domain that is amenable to protein engineering. The location of the peptide in the tertiary structure of the $H_N$ domain is predicted from the X-ray crystal structure of BoNT/A (pdb: 3BTA) as the guide. Freely available software (such as FirstGlance in Jmol) are used to identify that the HN peptide sequence is located on the surface. The location is therefore good for accessibility by proteases.

Site directed mutagenesis of the SEQ ID 16 (which encodes SEQ ID 17) using a primer designed to switch the codon for $K_{563}$ (AAA) to Arg (CGT) and to insert an Arg (CGC) after the existing $R_{565}$ changes the sequence $_{563}$KSR$_{565}$ to RSRR (SEQ ID 87) which is a substrate for cleavage by furin. Mutagenesis was achieved utilising standard molecular tools for performing mutagenesis (for example, the Stratagene Quickchange mutagenesis methodology).

E. coli codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into E. coli host. The integrity of the ORF DNA is checked by sequencing. The final ORF incorporating the additional ADAM17 sites is illustrated as SEQ ID 20 and the amino acid sequence of the expression product is illustrated in SEQ ID 21.

Example 15—Treatment of a Patient Suffering from Dystonia (Spasmodic Torticollis)

A male, suffering from spasmodic torticollis, as manifested by spasmodic or tonic contractions of the neck musculature, producing stereotyped abnormal deviations of the head, the chin being rotated to one side, and the shoulder being elevated toward the side at which the head is rotated, had previously been treated with a therapeutically effective amount of BoNT/A into the neck muscles for torticollis, but developed dysphagia because of dispersal of the protease into the oropharynx. The patient is subsequently treated by injection with up to about 300 units, or more, of polypeptide of the present invention (eg. a botulinum toxin type A neurotoxin modified to include a Factor Xa protease sensitive site), in the dystonic neck muscles. After 3-7 days the symptoms are substantially alleviated and the patient is able to hold his head and shoulder in a normal position for at least 3 months. Following the treatment with the modified neurotoxin the patient does not experience any dysphagia. By utilising the modified botulinum toxin type A, the physician is able to inject more product into the area requiring therapy without fear of an increase in side effects. Enhanced dose leads to enhanced duration of action and therefore improved therapy.

Example 16—Treatment of a Patient Suffering from Blepharospasm

A 58 year old female with blepharospasm is treated by injecting between about 1 to about 5 units of a polypeptide of the present invention (eg. a botulinum toxin type A neurotoxin modified to include a ADAM17 protease sensitive site, as described in Example 13) into the lateral pre-tarsal orbicularis oculi muscle of the upper lid and the lateral pre-tarsal orbicularis oculi of the lower lid, the amount injected varying based upon both the size of the muscle to be injected and the extent of muscle paralysis desired. Alleviation of the blepharospasm occurs in about 1 to about 7 days. By utilising the modified botulinum toxin type A, the physician is able to inject more product into the area requiring therapy without fear of an increase in side effects. Enhanced dose leads to enhanced duration of action and therefore improved therapy.

Example 17—Creation of a LHC-EGF Chimaeric Protein that Incorporates a Factor Xa Recognition Site into the LC at Position 210 [SXN101975]

The primary sequence of a chimaeric protein constructed by a genetic fusion of the $LH_N$ fragment of BoNT/C and the human epidermal growth factor sequence (SEQ ID 2) is reviewed for the presence of amino acid strings that bear resemblance to the prototypical recognition site for Factor Xa (IEGR) (SEQ ID 41). A site for insertion of a Factor Xa site is identified in the primary sequence $_{210}$GEGR (SEQ ID 97) within the LC domain. The location of the peptide in the tertiary structure of the LC/C is predicted from examination of the location of the homologous peptide sequence in the LC/A using the X-ray crystal structure of BoNT/A (pdb: 3BTA) as the guide. Freely available software (such as FirstGlance in Jmol) are used to identify that the LC/A equivalent peptide sequence is located near the surface of the LC. The location is therefore a good region for accessibility by proteases.

Site directed mutagenesis of the SEQ ID 1 (encoding SEQ ID 2) was achieved using a primer designed to switch the codons for $_{210}$G to I to make it a substrate for Factor Xa cleavage. Mutagenesis was achieved utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The final ORF incorporating the Factor Xa site is illustrated as SEQ ID 22 and the amino acid sequence of the expression product is illustrated in SEQ ID 23.

Example 18—Creation of a LHC-EGF Chimaeric Protein that Incorporates a Thrombin Recognition Site into the LC at Position 195 [SXN101931]

The primary sequence of a chimaeric protein constructed by a genetic fusion of the $LH_N$ fragment of BoNT/C and the human epidermal growth factor sequence (SEQ ID 2) is reviewed for the presence of amino acid strings that bear resemblance to the prototypical recognition site for Thrombin. A site for insertion of a Thrombin site is identified in the primary sequence $_{194}$ISPRFM$_{199}$ (SEQ ID 84) within the LC domain. The location of the peptide in the tertiary structure of the LC/C is predicted from examination of the location of the homologous peptide sequence in the LC/A using the X-ray crystal structure of BoNT/A (pdb: 3BTA) as the guide. Freely available software (such as FirstGlance in Jmol) are used to identify that the LC/A equivalent peptide sequence is located near the surface of the LC. The location is therefore a good region for accessibility by proteases.

Site directed mutagenesis of the SEQ ID 1 (encoding SEQ ID 2) using a primer designed to switch the codons for $S_{195}$ to Val (TCT to GTT) and $M_{195}$ to Ser (ATG to TCC) changes the region $_{194}$ISPRFM$_{199}$ (SEQ ID 84) to IVPRFS (SEQ ID 85) to make it a substrate for Thrombin cleavage. Mutagenesis was achieved utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The final ORF incorporating the Thrombin site is used to encode the amino acid sequence of the expression product is illustrated in SEQ ID 24.

Example 19—Creation of a LHC-EGF Chimaeric Protein that Incorporates a Thrombin Recognition Site into the LC at Position 210 [SXN101932]

The primary sequence of a chimaeric protein constructed by a genetic fusion of the $LH_N$ fragment of BoNT/C and the human epidermal growth factor sequence (SEQ ID 2) is reviewed for the presence of amino acid strings that bear resemblance to the prototypical recognition site for Thrombin. A site for insertion of a Thrombin site is identified in the primary sequence $_{210}$GEGRFS (SEQ ID 88) within the LC domain. The location of the peptide in the tertiary structure of the LC/C is predicted from examination of the location of the homologous peptide sequence in the LC/A using the X-ray crystal structure of BoNT/A (pdb: 3BTA) as the guide. Freely available software (such as FirstGlance in Jmol) are used to identify that the LC/A equivalent peptide sequence is located near the surface of the LC. The location is therefore a good region for accessibility by proteases.

Site directed mutagenesis of the SEQ ID 1 (encoding SEQ ID 2) using a primer designed to switch the codons $_{211}$EGR to TPR to create a sequence GTPRFS (SEQ ID 89) which is a substrate for Thrombin cleavage. Mutagenesis was achieved utilising standard molecular tools for performing mutagenesis (for example, the Stratagene Quickchange mutagenesis methodology). E. coli codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into E. coli host. The integrity of the ORF DNA is checked by sequencing. The final ORF incorporating the Thrombin site is used to encode the amino acid sequence of the expression product is illustrated in SEQ ID 25.

Example 20—Creation of a LHC-EGF Chimaeric Protein that Incorporates a Factor Xa Recognition Site into the $H_N$ Domain at Position 742 of the $H_N$ [SXN101937]

The primary sequence of a chimaeric protein constructed by a genetic fusion of the $LH_N$ fragment of BoNT/C and the human epidermal growth factor sequence (SEQ ID 2) is reviewed and a site for insertion of a Factor Xa site is identified in the primary sequence $_{742}$IDLE$_{755}$ (SEQ ID 98) within the $H_N$ domain. The location of the peptide in the tertiary structure of the $H_N$/C is predicted from examination of the location of the homologous peptide sequence in the $H_N$/A using the X-ray crystal structure of BoNT/A (pdb: 3BTA) as the guide. Freely available software (such as FirstGlance in Jmol) are used to identify that the $H_N$/A equivalent peptide sequence is located near the surface of the $H_N$. The location is therefore a good region for accessibility by proteases.

Site directed mutagenesis of the SEQ ID 1 (encoding SEQ ID 2) using a primer designed to switch the codons for $_{742}$LE to GR to make it a substrate for Factor Xa cleavage. Mutagenesis was achieved utilising standard molecular tools for performing mutagenesis (for example, the Stratagene Quickchange mutagenesis methodology). E. coli codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into E. coli host. The integrity of the ORF DNA is checked by sequencing. The final ORF incorporating the Thrombin site is used to encode the amino acid sequence of the expression product is illustrated in SEQ ID 26.

Example 21—Creation of a LHC-EGF Chimaeric Protein that Incorporates a Factor Xa Recognition Site into the $H_N$ Domain at Position 750 of the $H_N$ [SXN101938]

The primary sequence of a chimaeric protein constructed by a genetic fusion of the $LH_N$ fragment of BoNT/C and the human epidermal growth factor sequence (SEQ ID 2) is reviewed and a site for insertion of a Factor Xa site is identified in the primary sequence $_{750}$SGSD$_{753}$ (SEQ ID 90) within the $H_N$ domain. The location of the peptide in the tertiary structure of the $H_N$/C is predicted from examination of the location of the homologous peptide sequence in the $H_N$/A using the X-ray crystal structure of BoNT/A (pdb: 3BTA) as the guide. Freely available software (such as FirstGlance in Jmol) are used to identify that the $H_N$/A equivalent peptide sequence is located near the surface of the $H_N$. The location is therefore a good region for accessibility by proteases.

Site directed mutagenesis of the SEQ ID 1 (encoding SEQ ID 2) using a primer designed to switch the codons for $_{750}$SGSD (SEQ ID 90) to IDGR (SEQ ID 78) make it a substrate for Factor Xa cleavage. Mutagenesis was achieved utilising standard molecular tools for performing mutagenesis (for example, the Stratagene Quickchange mutagenesis methodology). E. coli codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into E. coli host. The integrity of the ORF DNA is checked by sequencing. The final ORF incorporating the Factor Xa site is used to encode the amino acid sequence of the expression product is illustrated in SEQ ID 27.

Example 22—Creation of a LHC-EGF Chimaeric Protein that Incorporates a Thrombin Recognition Site into the $H_N$ Domain at Position 750 of the $H_N$ [SXN101939]

The primary sequence of a chimaeric protein constructed by a genetic fusion of the $LH_N$ fragment of BoNT/C and the human epidermal growth factor sequence (SEQ ID 2) is reviewed and a site for insertion of a Thrombin site is identified in the primary sequence $_{750}$SGSD$_{753}$ (SEQ ID 90) within the $H_N$ domain. The location of the peptide in the tertiary structure of the $H_N$/C is predicted from examination of the location of the homologous peptide sequence in the $H_N$/A using the X-ray crystal structure of BoNT/A (pdb: 3BTA) as the guide. Freely available software (such as FirstGlance in Jmol) are used to identify that the $H_N$/A equivalent peptide sequence is located near the surface of the $H_N$. The location is therefore a good region for accessibility by proteases.

Site directed mutagenesis of the SEQ ID 1 (encoding SEQ ID 2) using a primer designed to switch the codons for SGSD (SEQ ID 90) to GVPR (SEQ ID 91) to make it a substrate for Thrombin cleavage. Mutagenesis was achieved utilising standard molecular tools for performing mutagenesis (for example, the Stratagene Quickchange mutagenesis methodology). E. coli codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The final ORF incorporating the Thrombin site is used to encode the amino acid sequence of the expression product is illustrated in SEQ ID 28.

Example 23—Creation of a LHD-VIPr Chimaeric Protein that Incorporates a Factor Xa Recognition Site into the $H_N$ Domain at Position 798 of the $H_N$ [SXN101930]

The primary sequence of a chimaeric protein constructed by a genetic fusion of the $LH_N$ fragment of BoNT/D and an analogue of the human vasoactive intestinal peptide (VIPr) is reviewed and a site for insertion of a Factor Xa site is identified in the primary sequence $_{798}$SGSD (SEQ ID 90) within the $H_N$ domain. The location of the peptide in the tertiary structure of the $H_N$/D is predicted from examination of the location of the homologous peptide sequence in the $H_N$/A using the X-ray crystal structure of BoNT/A (pdb: 3BTA) as the guide. Freely available software (such as FirstGlance in Jmol) are used to identify that the $H_N$/A equivalent peptide sequence is located near the surface of the $H_N$. The location is therefore a good region for accessibility by proteases.

Site directed mutagenesis of the gene using a primer designed to switch the codons for $_{798}$SGSD (SEQ ID 90) to IDGR (SEQ ID 78) to make it a substrate for Factor Xa cleavage is performed. Mutagenesis was achieved utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The final ORF incorporating the Factor Xa site is used to encode the amino acid sequence of the expression product is illustrated in SEQ ID 29.

Example 24—Creation of an LHA-EGF Chimaeric Protein that Incorporates a Thrombin Recognition Site into the LC Domain [SXN1974]

The primary sequence of a chimaeric protein constructed by a genetic fusion of the $LH_N$ fragment of BoNT/A and the human epidermal growth factor sequence (SEQ ID 8) is reviewed for the presence of amino acid strings that bear resemblance to the prototypical recognition site for Thrombin (GRG). Simple text character analysis of the primary sequence identified the sequence $_{103}$GRM$_{105}$ within the LC domain. The location of the peptide in the tertiary structure of the LC is predicted from the X-ray crystal structure of BoNT/A (pdb: 3BTA) as the guide. Freely available software (such as FirstGlance in Jmol) are used to identify that the LC peptide sequence is located on the surface. The location is therefore a good region for accessibility by proteases.

Site directed mutagenesis of the SEQ ID 7 (encoding SEQ ID 8) using a primer designed to switch the peptide region from GRM to GRG was achieved utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The final ORF incorporating the Thrombin site is used to encode the amino acid sequence of the expression product is illustrated in SEQ ID 31.

Example 25—Demonstration of Specific Cleavage of a Purified LHC-EGF Chimaeric Protein that is Engineered to Incorporate a Factor Xa Recognition Site into the LC [SXN1975]

A novel molecule incorporating a Factor Xa recognition site into the LC of LHC-EGF is constructed according to Example 17. Using methodology similar to that described in Example 6, the protein of Example 17 is expressed and purified. The methodology was adapted for use on an AKTA Xpress purification system. Essentially, the clarified *E. coli* lysates were applied to a 5 ml HisTrap FF Crude column on the Xpress system. The program was set to wash the columns with 10 column volumes of binding buffer (50 mM Tris pH8.0, 200 mM NaCl) and 10 col. vols. of 40 mM imidazole in binding buffer (collected together with the flow through). Elution was with 5 col. vols. of 250 mM imidazole in binding buffer. The protein was collected in a loop and held until system was ready to desalt (in 50 mM Tris pH8.0, 150 mM NaCl). The desalted protein was collected in a 2 ml 96 well plate. FIG. 3 illustrates purification of LHC-EGF from *E. coli*.

Using methodology described in Example 7, the protein is treated with Factor Xa protease and samples analysed by SDS-PAGE. FIG. 4 illustrates the cleavage of the protein in the presence of Factor Xa. Cleavage products are observed in the non-reduced and reduced samples. The estimated mass of the cleavage products is in agreement with the anticipated cleavage point of the engineered protein

Example 26—Demonstration of Specific Cleavage of a Purified LHC-EGF Chimaeric Protein that is Engineered to Incorporate a Factor Xa Recognition Site into the $H_N$ [SXN1937 & SXN1938]

A novel molecule incorporating a Factor Xa recognition site into the $H_N$ of LHC-EGF is constructed according to Example 20, and a second novel jmolecule incorporating a Factor Xa recognition site into a different location within the $H_N$ of LHC-EGF is constructed according to Example 21. Using methodology similar to that described in Example 24, the proteins of Example 20 and 21 are expressed and purified. FIG. 5 illustrates purification of LHC-EGF from Example 20 from *E. coli*, and FIG. 6 illustrates purification of LHC-EGF from Example 21 from *E. coli*.

Using methodology described in Example 7, the protein of Example 20 is treated with Factor Xa protease and samples analysed by SDS-PAGE. FIG. 7 illustrates cleavage of the protein in the presence of Factor Xa, as assessed by staining of SDS-PAGE gels. FIG. 8 illustrates the profile of the samples when assessed by Western blotting using anti-His tag antibodies to probe for the presence of the His tag. The estimated mass of the cleavage products is in agreement with the anticipated cleavage point of the engineered protein.

Using methodology described in Example 7, the protein of Example 21 is treated with Factor Xa protease and samples analysed by SDS-PAGE. FIG. 9 illustrates the cleavage of the protein in the presence of Factor Xa. The estimated mass of the cleavage products is in agreement with the anticipated cleavage point of the engineered protein.

Example 27—Demonstration of Specific Cleavage of a Purified LHC-EGF Chimaeric Protein that is Engineered to Incorporate a Thrombin Recognition Site into the LC [SXN1932]

A novel molecule incorporating a Thrombin recognition site into the LC of LHC-EGF is constructed according to Example 19. Using methodology similar to that described in Example 25, the protein of Example 19 is expressed and purified. FIG. 10 illustrates purification of LHC-EGF from E. coli.

Using methodology described in Example 7, the protein is treated with Thrombin protease and samples analysed by SDS-PAGE. FIG. 11 illustrates the cleavage of the protein in the presence of Thrombin, as assessed by SDS-PAGE. FIG. 12 illustrates the cleavage of the protein in the presence of Thrombin, as assessed by Western blotting using anti-EGF antibodies. The estimated mass of the cleavage products is in agreement with the anticipated cleavage point of the engineered protein Example 28—Demonstration of Specific Cleavage of a Purified LHA-EGF Chimaeric Protein that is Engineered to Incorporate a Thrombin Recognition Site into the LC [SXN1974]

A novel molecule incorporating a Factor Xa recognition site into the LC of LHA-EGF is constructed according to Example 24. Using methodology similar to that described in Example 25, the protein of Example 24 is expressed and purified. FIG. 13 illustrates purification of LHA-EGF from E. coli.

Figure 14:
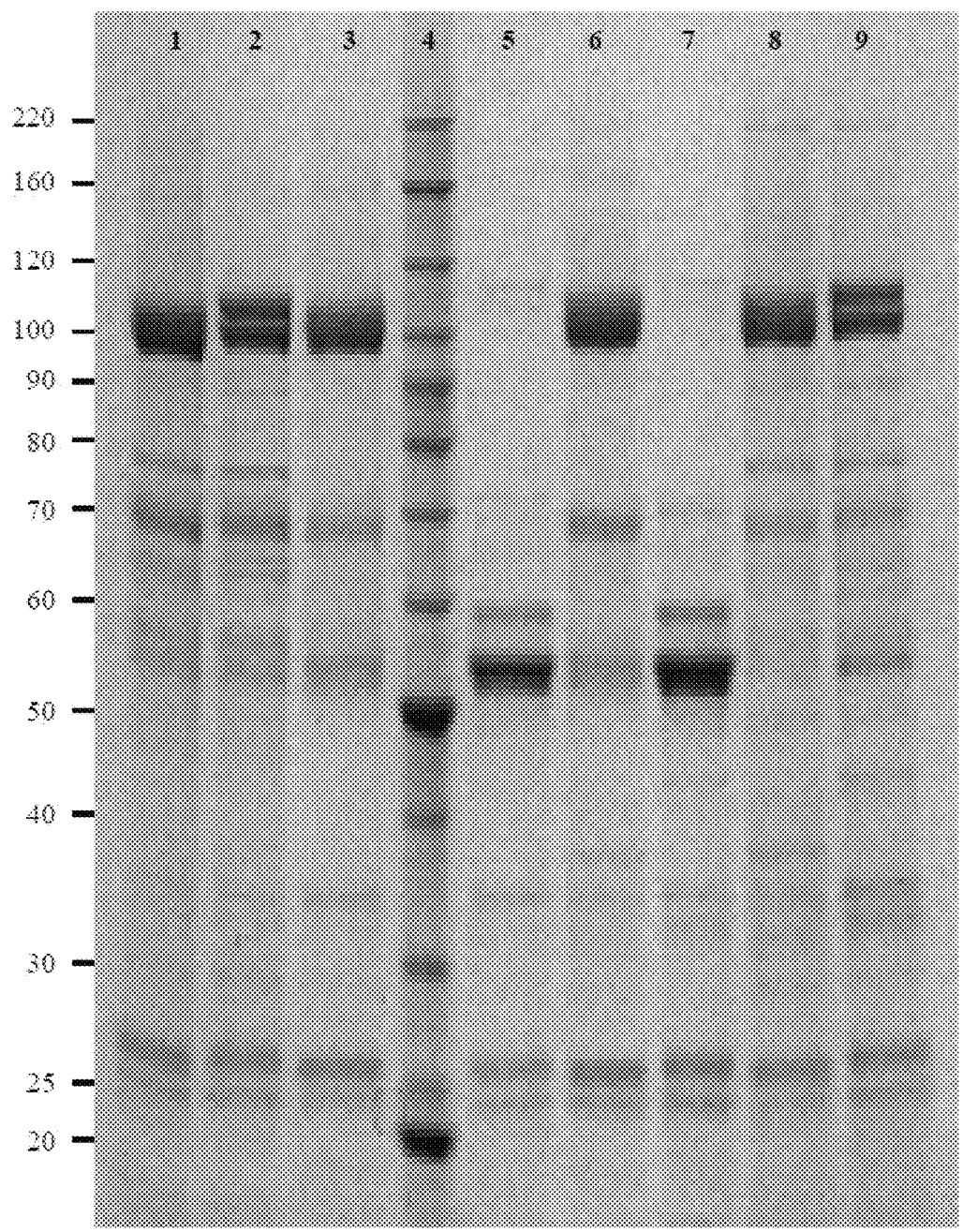

Using methodology described in Example 7, the protein is treated with Thrombin protease and samples analysed by SDS-PAGE. FIG. 14 illustrates the cleavage of the protein in the presence of Thrombin. FIG. 15 illustrates the Western blot profile of the same PAGE, using anti-EGF as primary antibody. The estimated mass of the cleavage products is in agreement with the anticipated cleavage point of the engineered protein Example 29—Demonstration of Reduced In Vitro Cellular Activity of a Protein Engineered to Incorporate a FXa Protease Cleavage Site into the LC Domain of LHC-EGF [SXN1975]

The protein product of Example 25 is expressed and purified. The purified protein is exposed to FXa protease for prior to assessment in an in vitro spinal cord neuron (SCN) assay. The preparation of SCN is a well established technique and is described in the literature [B. R. Ransom, E. Neale, M. Henkart, P. N. Bullock, P. G. Nelson, Mouse spinal cord in cell culture. I. Morphology and intrinsic neuronal electrophysiologic properties, J. Neurophysiol. 40 (1977) 1132-1150; S. C. Fitzgerald, A Dissection and Tissue Culture Manual of the Nervous System, Alan R. Liss Inc, New York, 1989]. Test protein is prepared at a variety of concentrations by dilution into culture media. SCNs are exposed to the test proteins for 24 hr prior to removal of media and preparation of the cellular material for analysis by SDS-PAGE and Western blotting. Following separation of cellular proteins on Novex 4-20% Tris-glycine polyacrylamide gels, the proteins are transferred to nitrocellulose and subsequently probed for the presence of the appropriate SNARE protein using antibodies obtained from commercial sources. In this case, the antibodies were specific for the SNARE syntaxin.

Referring to FIG. 16, the protein that has been treated with Factor Xa is clearly less effective at cleaving Syntaxin than the protein that was not treated with FXa. The invention has therefore enabled a reduction in the efficacy of the modified protein.

Example 30—Demonstration of Reduced In Vitro Cellular Activity of a Protein Engineered to Incorporate a Thrombin Protease Cleavage Site into the LC Domain of LHA-EGF [SXN1974]

The protein product of Example 24 is expressed and purified. The purified protein is exposed to Thrombin protease for prior to assessment in an in vitro spinal cord neuron (SCN) assay. The preparation of SCN is a well established technique and is described in the literature [B. R. Ransom, E. Neale, M. Henkart, P. N. Bullock, P. G. Nelson, Mouse spinal cord in cell culture. I. Morphology and intrinsic neuronal electrophysiologic properties, J. Neurophysiol. 40 (1977) 1132-1150; S. C. Fitzgerald, A Dissection and Tissue Culture Manual of the Nervous System, Alan R. Liss Inc, New York, 1989]. Test protein is prepared at a variety of concentrations by dilution into culture media. SCNs are exposed to the test proteins for 24 hr prior to removal of media and preparation of the cellular material for analysis by SDS-PAGE and Western blotting. Following separation of cellular proteins on Novex 4-20% Tris-glycine polyacrylamide gels, the proteins are transferred to nitrocellulose and subsequently probed for the presence of the appropriate SNARE protein using antibodies obtained from commercial sources. In this case, the antibodies were specific for the SNARE SNAP-25. FIG. 17 demonstrates SNAP-25-cleavage by thrombin-treated L(Thr)HA-EGF compared to untreated L(Thr)HA-EGF.

Example 31—Creation of a Recombinant BoNT/a Protein that Incorporates a Thrombin Recognition Site into the LC The primary sequence of a recombinant endopeptidase active BoNT/A containing an engineered activation protease site specific for enterokinase (SEQ ID 17) is reviewed for the presence of amino acid strings that bear resemblance to the prototypical recognition site for thrombin (GRG). Simple text character analysis of the primary sequence identified the sequence $_{103}GRM_{105}$ within the LC domain that is amenable to protein engineering. The location of the peptide in the tertiary structure of the $H_N$ domain is predicted from the X-ray crystal structure of BoNT/A (pdb: 3BTA) as the guide. Freely available software (such as FirstGlance in Jmol) are used to identify that the $H_N$ peptide sequence is located on the surface. The location is therefore good for accessibility by proteases.

Site directed mutagenesis of the SEQ ID 16 (which encodes SEQ ID 17) using a primer designed to switch the codons for $M_{105}$ to G changes the sequence $_{103}GRM_{105}$ to GRG which is a substrate for cleavage by thrombin. Mutagenesis was achieved utilising standard molecular tools for performing mutagenesis (for example, the Stratagene Quickchange mutagenesis methodology).

E. coli codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into E. coli host. The integrity of the ORF DNA is checked by sequencing. The final amino acid sequence of the expression product is illustrated in SEQ ID 32.

Example 32—Creation of a Recombinant BoNT/a Protein that Incorporates a Factor Xa Recognition Site into the LC The primary sequence of a recombinant endopeptidase active BoNT/A containing an engineered activation protease site specific for enterokinase (SEQ ID 17) is reviewed for the presence of amino acid strings that bear resemblance to the prototypical recognition site for Factor Xa (IEGR) (SEQ ID 41). Simple text character analysis of the primary sequence identified the sequence IDSL (SEQ ID 92) within the LC domain that is amenable to protein engineering. The location of the peptide in the tertiary structure of the LC domain is predicted from the X-ray crystal structure of BoNT/A (pdb: 3BTA) as the guide. Freely available software (such as FirstGlance in Jmol) are used to identify that the LC peptide sequence is located on the surface. The location is therefore good for accessibility by proteases.

Site directed mutagenesis of the SEQ ID 16 (which encodes SEQ ID 17) using a primer designed to switch the codons for $_{276}SL$ to GR changes the sequence IDSL (SEQ ID 92) to IDGR (SEQ ID 78) which is a substrate for cleavage by Factor Xa. Mutagenesis was achieved utilising standard molecular tools for performing mutagenesis (for example, the Stratagene Quickchange mutagenesis methodology).

E. coli codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into E. coli host. The integrity of the ORF DNA is checked by sequencing. The final amino acid sequence of the expression product is illustrated in SEQ ID 33.

Example 33—Creation of a Recombinant BoNT/a Protein that Incorporates a Factor Xa Recognition Site into the $H_N$ The primary sequence of a recombinant endopeptidase active BoNT/A containing an engineered activation protease site specific for enterokinase (SEQ ID 17) is reviewed for the presence of amino acid strings that bear resemblance to the prototypical recognition site for Factor Xa (IEGR) (SEQ ID 41). Simple text character analysis of the primary sequence identified the sequence $_{562}GKSR_{565}$ within the $H_N$ domain that is amenable to protein engineering. The location of the peptide in the tertiary structure of the $H_N$ domain is predicted from the X-ray crystal structure of BoNT/A (pdb: 3BTA) as the guide. Freely available software (such as FirstGlance in Jmol) are used to identify that the LC peptide sequence is located on the surface. The location is therefore good for accessibility by proteases.

Site directed mutagenesis of the SEQ. ID 16 (which encodes SEQ ID 17) using a primer designed to switch the peptide region from GKSR (SEQ ID 99) to IEGR (SEQ ID 41) which is a substrate for cleavage by Factor Xa. Mutagenesis was achieved utilising standard molecular tools for performing mutagenesis (for example, the Stratagene Quickchange mutagenesis methodology).

E. coli codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into E. coli host. The integrity of the ORF DNA is checked by sequencing. The final amino acid sequence of the expression product is illustrated in SEQ ID 34.

Example 34—Creation of a Recombinant BoNT/E Protein that Incorporates a Thrombin Recognition Site into the LC The primary sequence of a recombinant endopeptidase active BoNT/E [nucleotide accession AM695755; Uniprot number A8Y867] is reviewed for the presence of amino acid strings that bear resemblance to the prototypical recognition site for Thrombin (LVPRGS) (SEQ ID 40). Simple text character analysis of the primary sequence identified the sequence $_{186}FSPEYS_{191}$ (SEQ ID 93) within the LC domain that is amenable to protein engineering. The location of the peptide in the tertiary structure of the $H_N$ domain is predicted from the X-ray crystal structure of BoNT/A (pdb: 3BTA) as the guide. Freely available software (such as FirstGlance in Jmol) are used to identify that the LC peptide sequence is located on the surface. The location is therefore good for accessibility by proteases.

Site directed mutagenesis is achieved using a primer designed to switch the peptide region from FSPEYS (SEQ ID 93) to IVPRFS (SEQ ID 85) which is a substrate for cleavage by Thrombin. Mutagenesis was achieved utilising standard molecular tools for performing mutagenesis (for example, the Stratagene Quickchange mutagenesis methodology).

E. coli codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into E. coli host. The integrity of the ORF DNA is checked by sequencing. The final amino acid sequence of the expression product is illustrated in SEQ ID 35.

Example 35—Creation of a Recombinant BoNT/E Protein that Incorporates a Factor Xa Recognition Site into the $H_N$ The primary sequence of BoNT/E [nucleotide accession AM695755; Uniprot number A8Y867] is reviewed for a potential insertion site for a Factor Xa recognition peptide (IEGR) (SEQ ID 41). Comparison of the primary sequence of BoNT/E with that of BoNT/A and the corresponding location of the peptide in the tertiary structure of the $H_N$ domain predicted from the X-ray crystal structure of BoNT/A (pdb: 3BTA), concludes that the region $_{727}$TLEE (SEQ ID 94) is suitable for protein engineering to IEGR (SEQ ID 41).

Site directed mutagenesis is achieved using a primer designed to switch the peptide region from TLEE (SEQ ID 94) to IEGR (SEQ ID 41) which is a substrate for cleavage by Factor Xa. Mutagenesis was achieved utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The final amino acid sequence of the expression product is illustrated in SEQ ID 36.

Example 36—Creation of an LHE-VIPr Chimaeric Protein that Incorporates a Thrombin Recognition Site into the LC The primary sequence of a chimaeric protein constructed by a genetic fusion of the $LH_N$ fragment of BoNT/E and an analogue of the human vasoactive intestinal peptide (VIPr) sequence is reviewed for the presence of amino acid strings that bear resemblance to the prototypical recognition site for Thrombin (GRG). Simple text character analysis of the primary sequence identified the sequence $_{103}$GGI$_{105}$ within the LC domain of the chimaera. The location of the peptide in the tertiary structure of the LC/E is predicted from the X-ray crystal structure of LC/E (pdb: 1T3A) as the guide. Freely available software (such as Jmol are used to identify that the LC peptide sequence is located on the surface. The location is therefore a good region for accessibility by proteases.

Site directed mutagenesis is achieved using a primer designed to switch the peptide region from GGI to GRG utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The final ORF incorporating the Thrombin site is used to encode the amino acid sequence of the expression product is illustrated in SEQ ID 37.

Example 37—Creation of an LHE-VIPr Chimaeric Protein that Incorporates a Factor Xa Recognition Site into the $H_N$ The primary sequence of a chimaeric protein constructed by a genetic fusion of the $LH_N$ fragment of BoNT/E and an analogue of vasoactive intestinal peptide (VIPr) sequence is reviewed for the presence of amino acid strings that bear resemblance to the prototypical recognition site for Factor Xa (IEGR) (SEQ ID 41).

Simple text character analysis of the primary sequence identified the sequence $_{585}$GENN (SEQ ID 95) within the $H_N$ domain. The location of the peptide in the tertiary structure of the $H_N$/E is predicted from the X-ray crystal structure of BoNT/A (pdb: 3BTA) as the guide. Freely available software (such as FirstGlance in Jmol) are used to identify that the LC peptide sequence is located on the surface. The location is therefore a good region for accessibility by proteases.

Site directed mutagenesis is achieved using a primer designed to switch the peptide region from GENN (SEQ ID 95) to IEGR (SEQ ID 41) utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example GenBank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The final ORF incorporating the Factor Xa site is used to encode the amino acid sequence of the expression product is illustrated in SEQ ID 38.

Example 38—Creation of an LHE-VIPr Chimaeric Protein that Incorporates a Factor Xa Recognition Site into the LC The primary sequence of a chimaeric protein constructed by a genetic fusion of the $LH_N$ fragment of BoNT/E (incorporating a mutated substrate recognition domain (K228D) and an analogues of the human vasoactive intestinal peptide (VIPr) is reviewed for the presence of amino acid strings that are exposed on the surface of the protein and can be engineered to resemble the prototypical recognition site for Factor Xa (IEGR) (SEQ ID 41).

Analysis of the primary sequence identified the sequence $_{268}$VAQY (SEQ ID 96) within the LC domain. The location of the peptide in the tertiary structure of the LC/E is predicted from the X-ray crystal structure of BoNT/E (pdb: 1T3A) as the guide. Freely available software (such as Jmol) are used to identify that the LC peptide sequence is located on the surface. The location is therefore a good region for accessibility by proteases.

Site directed mutagenesis is achieved using a primer designed to switch the peptide region from VAQY (SEQ ID 96) to IEGR (SEQ ID 41) utilising standard molecular tools for performing mutagenesis (for example, the Stratagene Quickchange mutagenesis methodology). *E. coli* codon usage is assessed by reference to software programs such as Graphical Codon Usage Analyser (Geneart), and the % GC content and codon usage ratio assessed by reference to published codon usage tables (for example Gen Bank Release 143, Sep. 13, 2004) to ensure that the mutagenesis does not result in poor codon utilisation. The mutagenised DNA is incorporated into a standard cloning vector, for example pCR4, prior to transformation into *E. coli* host. The integrity of the ORF DNA is checked by sequencing. The

Example 39—Cleavage of SNARE Protein by a Modified Clostridial Neurotoxin (LH$_N$) Having the Properties Described by LIN, et al. (WO02/044199)

Embryonic spinal cord neurons were prepared by dissection from E15 Sprague Dawley rats and dissociated before plating onto Matrigel-coated 96 well plates at 125,000 cells per well in medium (MEM buffered with sodium bicarbonate, 5% inactivated horse serum, 0.6% D-glucose, 2% N1 medium supplement, 40 ng/ml corticosterone, 20 ng/ml tri-iodothryronine).

After three weeks the cells were incubated with fresh medium containing either recombinant light chain of serotype C (LC/C) or a modified clostridial neurotoxin consisting of the translocation and light chains of serotype C (LHn/C) at half log concentrations between 180 nM and 0.18 nM) for 24 hrs at 37° C. in a humidified, 5% $CO_2$ atmosphere.

Cells were lysed with SDS PAGE loading buffer containing DTT. Proteins were separated by SDS PAGE (12% Tris-Bis), transferred to nitrocellulose membrane and syntaxin detected using rabbit anti-syntaxin 2 antibody (Synaptic Systems, cat#110022). Bound antibody was detected with anti-rabbit IgG-peroxidase conjugate, followed by Westdura for fluorescent signal. Images were scanned and quantitated using Syngene software (GeneTools). The FIG. 1 shows cleaved syntaxin as a percentage of total syntaxin, and confirms a neurotoxin activity for the modified clostridial neurotoxin lacking a functional $H_C$ binding domain (LHn/C), but no detectable neurotoxin activity for the modified clostridial neurotoxin lacking a functional $H_N$ translocation domain (LC/C).

SEQUENCE LISTING

SEQ ID NO: 1

```
ATGATTTCCGAATTTGGCTCGGAGTTCATGCCAATTACGATTAACAATTTTAACTATAGTGATCCGGTGG
ATAATAAAACATTTTATACCTGGATACCCACTTGAATACTCTTGCCAATGAGCCTGAAAAAGCCTTTCG
CATAACGGGTAACATTTGGGTCATTCCGGACCGTTTTAGCCGGAACTCTAACCCTAATCTGAATAAACCT
CCGCGTGTCACGTCTCCGAAAAGTGGGTATTACGATCCAAATTATCTGAGTACCGATTCAGACAAGGATA
CGTTTCTGAAAGAAATCATAAAACTTTTCAAAAGAATCAACTCCCGTGAAATCGGTGAAGAGCTGATCTA
CCGTCTGTCGACGGACATTCCTTTTCCGGGAAACAATAACACTCCCATTAATACCTTCGACTTTGATGTC
GATTTCAACTCAGTCGATGTGAAAACCCGCCAGGGTAATAACTGGGTTAAAACTGGATCCATTAACCCGT
CCGTTATTATCACAGGTCCTCGTGAAAATATTATAGATCCTGAGACCTCCACGTTCAAGCTGACGAATAA
CACTTTTGCGGCACAGGAAGGGTTTGGTGCCCTTTCAATTATCTCTATCTCTCCGCGCTTCATGTTAACG
TATTCTAACGCAACCAACGATGTTGGCGAGGGCCGCTTCAGCAAAAGTGAATTCTGTATGGATCCCATTC
TGATCTTGATGCATGAGCTTAACCACGCTATGCATAATCTTTATGGTATTGCAATCCCAAACGATCAGAC
GATCTCCAGCGTTACATCTAACATATTCTACAGCCAATATAATGTGAAGCTCGAATATGCAGAGATTTAC
GCCTTCGGTGGGCCGACCATTGACCTCATTCCAAAGTCTGCCCGTAAGTACTTTGAGGAAAAAGCGTTGG
ATTACTATCGTAGCATCGCGAAACGCCTGAATTCAATTACAACTGCAAACCCATCTAGCTTCAACAAATA
CATCGGAGAATATAAACAAAAGCTGATACGCAAATATCGCTTTGTGGTCGAATCGTCCGGGGAAGTGACA
GTTAATCGAAATAAATTTGTTGAACTCTATAATGAATTAACGCAGATCTTCACAGAATTTAATTATGCTA
AAATCTATAATGTACAGAACCGGAAAATTTATCTCAGTAATGTATACACACCGGTGACTGCTAACATTCT
GGACGATAACGTCTACGATATTCAAAATGGCTTTAATATCCCGAAGAGCAACTTGAATGTCCTCTTCATG
GGGCAGAACTTGTCACGTAACCCAGCGCTGCGAAAAGTTAACCCAGAAAATATGTTGTACCTCTTTACAA
AATTCTGTGTAGACGCCGACGATGACGATAAACTGTACAACAAAACCCTGCAATGCCGTGAACTTCTGGT
TAAGAACACCGACCTGCCGTTCATTGGGGACATCAGTGATGTCAAAACGGATATTTTTCTTCGGAAGGAT
ATTAATGAGGAAACCGAAGTGATACCTGACAATGTGTCGGTAGATCAGGTAATCCTGAGTAAGAACACCA
GCGAGCATGGGCAGCTGGATCTGTTGTATCCGAGCATTGACAGCGAGTCGGAAATACTGCCCGGCGAAAA
TCAAGTTTTTTATGACAATCGGACCCAGAATGTTGATTATCTGAATAGTTACTATTACTTGGAGAGCCAA
AAATTATCAGATAATGTGGAAGACTTTACCTTTACCCGGTCTATCGAAGAGGCGCTGGATAACAGCGCGA
AAGTTTACACTTATTTTCCCACGCTCGCAAACAAAGTTAATGCTGGCGTACAGGGTGGATTATTTCTTAT
GTGGGCGAATGATGTGGTAGAGGACTTTACAACCAACATCCTGCGCAAAGACACTTTAGACAAAATTTCT
GACGTCTCGGCCATTATCCCGTATATAGGTCCGGCCTTAAACATAAGCAATTCGGTTCGCCGTGGCAACT
```

```
TCACAGAAGCCTTCGCTGTGACTGGTGTGACCATTCTGTTGGAAGCATTTCCTGAGTTTACGATCCCGGC

TCTGGGCGCATTTGTAATTTACTCTAAAGTTCAGGAACGAAATGAAATTATAAAAACTATCGATAATTGC

CTGGAACAGCGTATCAAGAGATGGAAGGATTCCTATGAGTGGATGATGGGGACCTGGCTGTCAAGAATTA

TCACACAGTTTAATAACATATCCTATCAAATGTATGATAGCTTAAACTATCAAGCAGGAGCGATAAAGGC

GAAAATTGACCTGGAATACAAGAAATATTCTGGTTCGGATAAAGAGAATATTAAAGTCAGGTGGAAAAT

CTGAAAAATAGTTTAGATGTCAAAATTTCTGAGGCGATGAATAACATTAACAAATTCATCCGCGAGTGCA

GTGTAACTTATTTGTTTAAGAATATGTTACCCAAAGTTATCGACGAACTGAATGAATTTGATCGTAATAC

CAAAGCCAAATTGATCAACCTCATCGACTCTCATAACATCATTCTGGTGGGAGAAGTCGACAAACTGAAA

GCTAAGGTGAATAACAGCTTCCAGAATACAATTCCGTTTAATATTTTCTCATACACCAATAACTCGCTGC

TTAAAGATATTATCAACGAATATTTTAATCTGGAGGGTGGCGGTGGCAGTGGCGGTGGCGGATCCGGCGG

TGGCGGTAGCGCACTGGATAATTCAGATTCCGAATGTCCACTGTCACACGATGGTTATTGTCTTCATGAT

GGCGTGTGCATGTATATAGAAGCGTTAGATAAATACGCTTGCAACTGCGTGGTTGGCTATATCGGCGAAC

GTTGTCAGTATCGTGATTTAAAGTGGTGGGAATTACGCTAATGA
```

SEQ ID NO: 2
```
ISEFGSEFMPITINNFNYSDPVDNKNILYLDTHLNTLANEPEKAFRITGNIWVIPDRFSRNSNPNLNKPP

RVTSPKSGYYDPNYLSTDSDKDTFLKEIIKLFKRINSREIGEELIYRLSTDIPFPGNNNTPINTFDFDVD

ENSVDVKTRQGNNWVKTGSINPSVIITGPRENIIDPETSTFKLTNNTFAAQEGFGALSIISISPRFMLTY

SNATNDVGEGRFSKSEFCMDPILILMHELNHAMHNLYGIAIPNDQTISSVTSNIFYSQYNVKLEYAEIYA

FGGPTIDLIPKSARKYFEEKALDYYRSIAKRLNSITTANPSSFNKYIGEYKQKLIRKYRFVVESSGEVTV

NRNKFVELYNELTQIFTEFNYAKIYNVQNRKIYLSNVYTPVTANILDDNVYDIQNGFNIPKSNLNVLFMG

QNLSRNPALRKVNPENMLYLFTKFCVDADDDDKLYNKTLQCRELLVKNTDLPFIGDISDVKTDIFLRKDI

NEETEVIPDNVSVDQVILSKNTSEHGQLDLLYPSIDSESEILPGENQVFYDNRTQNVDYLNSYYYLESQK

LSDNVEDFTFTRSIEEALDNSAKVYTYFPTLANKVNAGVQGGLFLMWANDVVEDFTTNILRKDTLDKISD

VSAIIPYIGPALNISNSVRRGNFTEAFAVTGVTILLEAFPEFTIPALGAFVIYSKVQERNEIIKTIDNCL

EQRIKRWKDSYEWMMGTWLSRIITQFNNISYQMYDSLNYQAGAIKAKIDLEYKKYSGSDKENIKSQVENL

KNSLDVKISEAMNNINKFIRECSVTYLFKNMLPKVIDELNEFDRNTKAKLINLIDSHNIILVGEVDKLKA

KVNNSFQNTIPFNIFSYTNNSLLKDIINEYFNLEGGGGSGGGGSGGGGSALDNSDSECPLSHDGYCLHDG

VCMYIEALDKYACNCVVGYIGERCQYRDLKWWELR
```

SEQ ID NO: 3
```
ATGATTTCCGAATTTGGCTCGGAGTTCATGCCAATTACGATTAACAATTTTAACTATAGTGATCCGGTGG

ATAATAAAAACATTTTATACCTGGATACCCACTTGAATACTCTTGCCAATGAGCCTGAAAAAGCCTTTCG

CATAACGGGTAACATTTGGGTCATTCCGGACCGTTTTAGCCGGAACTCTAACCCTAATCTGAATAAACCT

CCGCGTGTCACGTCTCCGAAAAGTGGGTATTACGATCCAAATTATCTGAGTACCGATTCAGACAAGGATA

CGTTTCTGAAAGAAATCATAAAACTTTTCAAAAGAATCAACTCCCGTGAAATCGGTGAAGAGCTGATCTA

CCGTCTGTCGACGGACATTCCTTTTCCGGGAAACAATAACACTCCCATTAATACCTTCGACTTTGATGTC

GATTTCAACTCAGTCGATGTGAAAACCCGCCAGGGTAATAACTGGGTTAAAACTGGATCCATTAACCCGT

CCGTTATTATCACAGGTCCTCGTGAAAATATTATAGATCCTGAGACCTCCACGTTCAAGCTGACGAATAA

CACTTTTGCGGCACAGGAAGGGTTTGGTGCCCTTTCAATTATCTCTATCTCTCCGCGCTTCATGTTAACG

TATTCTAACGCAACCAACGATGTTATCGAGGGCCGCTTCAGCAAAAGTGAATTCTGTATGGATCCCATTC

TGATCTTGATGCATGAGCTTAACCACGCTATGCATAATCTTTATGGTATTGCAATCCCAAACGATCAGAC
```

```
GATCTCCAGCGTTACATCTAACATATTCTACAGCCAATATAATGTGAAGCTCGAATATGCAGAGATTTAC

GCCTTCGGTGGGCCGACCATTGACCTCATTCCAAAGTCTGCCCGTAAGTACTTTGAGGAAAAAGCGTTGG

ATTACTATCGTAGCATCGCGAAACGCCTGAATTCAATTACAACTGCAAACCCATCTAGCTTCAACAAATA

CATCGGAGAATATAAACAAAAGCTGATACGCAAATATCGCTTTGTGGTCGAATCGTCCGGGGAAGTGACA

GTTAATCGAAATAAATTTGTTGAACTCTATAATGAATTAACGCAGATCTTCACAGAATTTAATTATGCTA

AAATCTATAATGTACAGAACCGGAAAATTTATCTCAGTAATGTATACACACCGGTGACTGCTAACATTCT

GGACGATAACGTCTACGATATTCAAAATGGCTTTAATATCCCGAAGAGCAACTTGAATGTCCTCTTCATG

GGGCAGAACTTGTCACGTAACCCAGCGCTGCGAAAAGTTAACCCAGAAAATATGTTGTACCTCTTTACAA

AATTCTGTGTAGACGCCGACGATGACGATAAACTGTACAACAAAACCCTGCAATGCCGTGAACTTCTGGT

TAAGAACACCGACCTGCCGTTCATTGGGGACATCAGTGATGTCAAAACGGATATTTTTCTTCGGAAGGAT

ATTAATGAGGAAACCGAAGTGATACCTGACAATGTGTCGGTAGATCAGGTAATCCTGAGTAAGAACACCA

GCGAGCATGGGCAGCTGGATCTGTTGTATCCGAGCATTGACAGCGAGTCGGAAATACTGCCCGGCGAAAA

TCAAGTTTTTTATGACAATCGGACCCAGAATGTTGATTATCTGAATAGTTACTATTACTTGGAGAGCCAA

AAATTATCAGATAATGTGGAAGACTTTACCTTTACCCGGTCTATCGAAGAGGCGCTGGATAACAGCGCGA

AAGTTTACACTTATTTTCCCACGCTCGCAAACAAAGTTAATGCTGGCGTACAGGGTGGATTATTTCTTAT

GTGGGCGAATGATGTGGTAGAGGACTTTACAACCAACATCCTGCGCAAAGACACTTTAGACAAAATTTCT

GACGTCTCGGCCATTATCCCGTATATAGGTCCGGCCTTAAACATAAGCAATTCGGTTCGCCGTGGCAACT

TCACAGAAGCCTTCGCTGTGACTGGTGTGACCATTCTGTTGGAAGCATTTCCTGAGTTTACGATCCCGGC

TCTGGGCGCATTTGTAATTTACTCTAAAGTTCAGGAACGAAATGAATTATAAAAACTATCGATAATTGC

CTGGAACAGCGTATCAAGAGATGGAAGGATTCCTATGAGTGGATGATGGGGACCTGGCTGTCAAGAATTA

TCACACAGTTTAATAACATATCCTATCAAATGTATGATAGCTTAAACTATCAAGCAGGAGCGATAAAGGC

GAAAATTGACCTGGAATACAAGAAATATTCTGGTTCGGATAAAGAGAATATTAAAGTCAGGTGGAAAAT

CTGAAAAATAGTTTAGATGTCAAAATTTCTGAGGCGATGAATAACATTAACAAATTCATCCGCGAGTGCA

GTGTAACTTATTTGTTTAAGAATATGTTACCCAAAGTTATCGACGAACTGAATGAATTTGATCGTAATAC

CAAAGCCAAATTGATCAACCTCATCGACTCTCATAACATCATTCGGTGGGAGAAGTCGACAAACTGAAA

GCTAAGGTGAATAACAGCTTCCAGAATACAATTCCGTTTAATATTTTCTCATACACCAATAACTCGCTGC

TTAAAGATATTATCAACGAATATTTTAATCTGGAGGGTGGCGGTGGCAGTGGCGGTGGCGGATCCGGCGG

TGGCGGTAGCGCACTGGATAATTCAGATTCCGAATGTCCACTGTCACACGATGGTTATTGTCTTCATGAT

GGCGTGTGCATGTATATAGAAGCGTTAGATAAATACGCTTGCAACTGCGTGGTTGGCTATATCGGCGAAC

GTTGTCAGTATCGTGATTTAAAGTGGTGGGAATTACGCTAATGA
```

SEQ ID NO: 4

```
MISEFGSEFMPITINNFNYSDPVDNKNILYLDTHLNTLANEPEKAFRITGNIWVIPDRFSRNSNPNLNKP

PRVTSPKSGYYDPNYLSTDSDKDTFLKEIIKLFKRINSREIGEELIYRLSTDIPFPGNNNTPINTFDFDV

DFNSVDVKTRQGNNWVKTGSINPSVIITGPRENIIDPETSTFKLTNNTFAAQEGFGALSIISISPRFMLT

YSNATNDVIEGRFSKSEFCMDPILILMHELNHAMHNLYGIAIPNDQTISSVTSNIFYSQYNVKLEYAEIY

AFGGPTIDLIPKSARKYFEEKALDYYRSIAKRLNSITTANPSSFNKYIGEYKQKLIRKYRFVVESSGEVT

VNRNKFVELYNELTQIFTEFNYAKIYNVQNRKIYLSNVYTPVTANILDDNVYDIQNGFNIPKSNLNVLFM

GQNLSRNPALRKVNPENMLYLFTKFCVDADDDDKLYNKTLQCRELLVKNTDLPFIGDISDVKTDIFLRKD

INEETEVIPDNVSVDQVILSKNTSEHGQLDLLYPSIDSESEILPGENQVFYDNRTQNVDYLNSYYYLESQ

KLSDNVEDFTFTRSIEEALDNSAKVYTYFPTLANKVNAGVQGGLFLMWANDVVEDFTTNILRKDTLDKIS
```

DVSAIIPYIGPALNISNSVRRGNFTEAFAVTGVTILLEAFPEFTIPALGAFVIYSKVQERNEIIKTIDNC
LEQRIKRWKDSYEWMMGTWLSRIITQFNNISYQMYDSLNYQAGAIKAKIDLEYKKYSGSDKENIKSQVEN
LKNSLDVKISEAMNNINKFIRECSVTYLFKNMLPKVIDELNEFDRNTKAKLINLIDSHNIILVGEVDKLK
AKVNNSFQNTIPFNIFSYTNNSLLKDIINEYFNLEGGGGSGGGGSGGGGSALDNSDSECPLSHDGYCLHD
GVCMYIEALDKYACNCVVGYIGERCQYRDLKWWELR

SEQ ID NO: 5

ATGATTTCCGAATTTGGCTCGGAGTTCATGCCAATTACGATTAACAATTTTAACTATAGTGATCCGGTGG
ATAATAAAAACATTTTATACCTGGATACCCACTTGAATACTCTTGCCAATGAGCCTGAAAAAGCCTTTCG
CATAACGGGTAACATTTGGGTCATTCCGGACCGTTTTAGCCGGAACTCTAACCCTAATCTGAATAAACCT
CCGCGTGTCACGTCTCCGAAAAGTGGGTATTACGATCCAAATTATCTGAGTACCGATTCAGACAAGGATA
CGTTTCTGAAAGAAATCATAAAACTTTTCAAAAGAATCAACTCCCGTGAAATCGGTGAAGAGCTGATCTA
CCGTCTGTCGACGGACATTCCTTTTCCGGGAAACAATAACACTCCCATTAATACCTTCGACTTTGATGTC
GATTTCAACTCAGTCGATGTGAAAACCCGCCAGGGTAATAACTGGGTTAAAACTGGATCCATTAACCCGT
CCGTTATTATCACAGGTCCTCGTGAAAATATTATAGATCCTGAGACCTCCACGTTCAAGCTGACGAATAA
CACTTTTGCGGCACAGGAAGGGTTTGGTGCCCTTTCAATTATCTCTATCGTTCCGCGCTTCTCCTTAACG
TATTCTAACGCAACCAACGATGTTGGCGAGGGCCGCTTCAGCAAAAGTGAATTCTGTATGGATCCCATTC
TGATCTTGATGCATGAGCTTAACCACGCTATGCATAATCTTTATGGTATTGCAATCCCAAACGATCAGAC
GATCTCCAGCGTTACATCTAACATATTCTACAGCCAATATAATGTGAAGCTCGAATATGCAGAGATTTAC
GCCTTCGGTGGGCCGACCATTGACCTCATTCCAAAGTCTGCCCGTAAGTACTTTGAGGAAAAAGCGTTGG
ATTACTATCGTAGCATCGCGAAACGCCTGAATTCAATTACAACTGCAAACCCATCTAGCTTCAACAAATA
CATCGGAGAATATAAACAAAAGCTGATACGCAAATATCGCTTTGTGGTCGAATCGTCCGGGGAAGTGACA
GTTAATCGAAATAAATTTGTTGAACTCTATAATGAATTAACGCAGATCTTCACAGAATTTAATTATGCTA
AAATCTATAATGTACAGAACCGGAAAATTTATCTCAGTAATGTATACACACCGGTGACTGCTAACATTCT
GGACGATAACGTCTACGATATTCAAAATGGCTTTAATATCCCGAAGAGCAACTTGAATGTCCTCTTCATG
GGGCAGAACTTGTCACGTAACCCAGCGCTGCGAAAAGTTAACCCAGAAAATATGTTGTACCTCTTTACAA
AATTCTGTGTAGACGCCGACGATGACGATAAACTGTACAACAAAACCCTGCAATGCCGTGAACTTCTGGT
TAAGAACACCGACCTGCCGTTCATTGGGGACATCAGTGATGTCAAAACGGATATTTTTCTTCGGAAGGAT
ATTAATGAGGAAACCGAAGTGATACCTGACAATGTGTCGGTAGATCAGGTAATCCTGAGTAAGAACACCA
GCGAGCATGGGCAGCTGGATCTGTTGTATCCGAGCATTGACAGCGAGTCGGAAATACTGCCCGGCGAAAA
TCAAGTTTTTTATGACAATCGGACCCAGAATGTTGATTATCTGAATAGTTACTATTACTTGGAGAGCCAA
AAATTATCAGATAATGTGGAAGACTTTACCTTTACCCGGTCTATCGAAGAGGCGCTGGATAACAGCGCGA
AAGTTTACACTTATTTTCCCACGCTCGCAAACAAAGTTAATGCTGGCGTACAGGGTGGATTATTCTTAT
GTGGGCGAATGATGTGGTAGAGGACTTTACAACCAACATCCTGCGCAAAGACACTTTAGACAAAATTTCT
GACGTCTCGGCCATTATCCCGTATATAGGTCCGGCCTTAAACATAAGCAATTCGGTTCGCCGTGGCAACT
TCACAGAAGCCTTCGCTGTGACTGGTGTGACCATTCTGTTGGAAGCATTTCCTGAGTTTACGATCCCGGC
TCTGGGCGCATTTGTAATTTACTCTAAAGTTCAGGAACGAAATGAATTATAAAAACTATCGATAATTGC
CTGGAACAGCGTATCAAGAGATGGAAGGATTCCTATGAGTGGATGATGGGGACCTGGCTGTCAAGAATTA
TCACACAGTTTAATAACATATCCTATCAAATGTATGATAGCTTAAACTATCAAGCAGGAGCGATAAAGGC
GAAAATTGACCTGGAATACAAGAAATATTCTGGTTCGGATAAAGAGAATATTAAAAGTCAGGTGGAAAAT
CTGAAAAATAGTTTAGATGTCAAAATTTCTGAGGCGATGAATAACATTAACAAATTCATCCGCGAGTGCA

```
GTGTAACTTATTTGTTTAAGAATATGTTACCCAAAGTTATCGACGAACTGAATGAATTTGATCGTAATAC

CAAAGCCAAATTGATCAACCTCATCGACTCTCATAACATCATTCTGGTGGGAGAAGTCGACAAACTGAAA

GCTAAGGTGAATAACAGCTTCCAGAATACAATTCCGTTTAATATTTTCTCATACACCAATAACTCGCTGC

TTAAAGATATTATCAACGAATATTTTAATCTGGAGGGTGGCGGTGGCAGTGGCGGTGGCGGATCCGGCGG

TGGCGGTAGCGCACTGGATAATTCAGATTCCGAATGTCCACTGTCACACGATGGTTATTGTCTTCATGAT

GGCGTGTGCATGTATATAGAAGCGTTAGATAAATACGCTTGCAACTGCGTGGTTGGCTATATCGGCGAAC

GTTGTCAGTATCGTGATTTAAAGTGGTGGGAATTACGCTAATGA
```

SEQ ID NO: 6

```
MISEFGSEFMPITINNFNYSDPVDNKNILYLDTHLNTLANEPEKAFRITGNIWVIPDRFSRNSNPNLNKP

PRVTSPKSGYYDPNYLSTDSDKDTFLKEIIKLFKRINSREIGEELIYRLSTDIPFPGNNNTPINTFDFDV

DFNSVDVKTRQGNNWVKTGSINPSVIITGPRENIIDPETSTFKLTNNTFAAQEGFGALSIISIVPRFSLT

YSNATNDVGEGRFSKSEFCMDPILILMHELNHAMHNLYGIAIPNDQTISSVTSNIFYSQYNVKLEYAEIY

AFGGPTIDLIPKSARKYFEEKALDYYRSIAKRLNSITTANPSSFNKYIGEYKQKLIRKYRFVVESSGEVT

VNRNKFVELYNELTQIFTEFNYAKIYNVQNRKIYLSNVYTPVTANILDDNVYDIQNGFNIPKSNLNVLFM

GQNLSRNPALRKVNPENMLYLFTKFCVDADDDDKLYNKTLQCRELLVKNTDLPFIGDISDVKTDIFLRKD

INEETEVIPDNVSVDQVILSKNTSEHGQLDLLYPSIDSESEILPGENQVFYDNRTQNVDYLNSYYYLESQ

KLSDNVEDFTFTRSIEEALDNSAKVYTYFPTLANKVNAGVQGGLFLMWANDVVEDFTTNILRKDTLDKIS

DVSAIIPYIGPALNISNSVRRGNFTEAFAVTGVTILLEAFPEFTIPALGAFVIYSKVQERNEIIKTIDNC

LEQRIKRWKDSYEWMMGTWLSRIITQFNNISYQMYDSLNYQAGAIKAKIDLEYKKYSGSDKENIKSQVEN

LKNSLDVKISEAMNNINKFIRECSVTYLFKNMLPKVIDELNEFDRNTKAKLINLIDSHNIILVGEVDKLK

AKVNNSFQNTIPFNIFSYTNNSLLKDIINEYFNLEGGGGSGGGGSGGGGSALDNSDSECPLSHDGYCLHD

GVCMYIEALDKYACNCVVGYIGERCQYRDLKWWELR
```

SEQ ID NO: 7

```
atgggatccatggagttcgttaacaaacagttcaactataaagacccagttaacggtgttgacattgctt acatcaaaatcccgaacgctggccagatgcagccggtaaaggcattcaaaatccacaacaaatctgggt tatcccggaacgtgatacctttactaacccggaagaaggtgacctgaacccgccaccggaagcgaaacag gtgccggtatcttactatgactccacctacctgtctaccgataacgaaaaggacaactacctgaaaggtg ttactaaactgttcgagcgtatttactccaccgacctgggccgtatgctgctgactagcatcgttcgcgg tatcccgttctggggcggttctaccatcgataccgaactgaaagtaatcgacactaactgcatcaacgtt attcagccggacggttcctatcgttccgaagaactgaacctggtgatcatcggcccgtctgctgatatca tccagttcgagtgtaagagctttggtcacgaagttctgaacctcacccgtaacggctacggttccactca gtacatccgtttctctccggacttcaccttcggttttgaagaatccctggaagtagacacgaacccactg ctgggcgctggtaaattcgcaactgatcctgcggttaccctggctcacgaactgattcatgcaggccacc gcctgtacggtatcgccatcaatccgaaccgtgtcttcaaagttaacaccaacgcgtattacgagatgtc cggtctggaagttagcttcgaagaactgcgtacttttggcggtcacgacgctaaattcatcgactctctg caagaaaacgagttccgtctgtactactataacaagttcaaagatatcgcatccaccctgaacaaagcga aatccatcgtgggtaccactgcttctctccagtacatgaagaacgttttttaaagaaaaatacctgctcag cgaagacacctccggcaaattctctgtagacaagttgaaattcgataaactttacaaaatgctgactgaa atttacaccgaagacaacttcgttaagttcttttaaagttctgaaccgcaaaacctatctgaacttcgaca aggcagtattcaaaatcaacatcgtgccgaaagttaactacactatctacgatggtttcaacctgcgtaa caccaacctggctgctaattttaacggccagaacacggaaatcaacaacatgaacttcacaaaactgaaa
```

-continued

```
aacttcactggtctgttcgagttttacaagctgctgtgcGTCGACGGCATCATTACCTCCAAAACTAAAT
CTGACGATGACGATAAAAACAAAGCGCTGAACCTGCAGtgtatcaaggttaacaactgggatttattctt
cagcccgagtgaagacaacttcaccaacgacctgaacaaaggtgaagaaatcacctcagatactaacatc
gaagcagccgaagaaaacatctcgctggacctgatccagcagtactacctgacctttaatttcgacaacg
agccggaaaacatttctatcgaaaacctgagctctgatatcatcggccagctggaactgatgccgaacat
cgaacgtttcccaaacggtaaaaagtacgagctggacaaatataccatgttccactacctgcgcgcgcag
gaatttgaacacggcaaatcccgtatcgcactgactaactccgttaacgaagctctgctcaacccgtccc
gtgtatacaccttcttctctagcgactacgtgaaaaaggtcaacaaagcgactgaagctgcaatgttctt
gggttgggttgaacagcttgtttatgattttaccgacgagacgtccgaagtatctactaccgacaaaatt
gcggatatcactatcatcatcccgtacatcggtccggctctgaacattggcaacatgctgtacaaagacg
acttcgttggcgcactgatcttctccggtgcggtgatcctgctggagttcatcccggaaatcgccatccc
ggtactgggcacctttgctctggtttcttacattgcaaacaaggttctgactgtacaaaccatcgacaac
gcgctgagcaaacgtaacgaaaaatgggatgaagtttacaaatatatcgtgaccaactggctggctaagg
ttaatactcagatcgacctcatccgcaaaaaaatgaaagaagcactggaaaaccaggcggaagctaccaa
ggcaatcattaactaccagtacaaccagtacaccgaggaagaaaaaaacaacatcaacttcaacatcgac
gatctgtcctctaaactgaacgaatccatcaacaaagctatgatcaacatcaacaagttcctgaaccagt
gctctgtaagctatctgatgaactccatgatcccgtacggtgttaaacgtctggaggacttcgatgcgtc
tctgaaagacgccctgctgaaatacatttacgacaaccgtggcactctgatcggtcaggttgatcgtctg
aaggacaaagtgaacaatacc ttatcgaccgacatccc ttttcagctcagtaaatatgtcgataaccaac
gccttttgtccactctagaaggtggcggtgggtccggtggcggtggctcaggcggggcggtagcgcact
agacaactctgactctgaatgcccgctgtctcacgacggttactgcctgcacgacggtgtttgcatgtac
atcgaagctctggacaaatacgcttgcaactgcgttgttggttacatcggtgaacgttgccagtaccgtg
acctgaaatggtgggaactgcgtgcgctagaagcaCACCATCATCACcaccatcaccatcaccattaatg
a
```

MGSMEFVNKQFNYKDPVNGVDIAYIKIPNAGQMQPVKAFKIHNKIWVIPERDTFTNPEEGDLNPPPEAKQ
VPVSYYDSTYLSTDNEKDNYLKGVTKLFERIYSTDLGRMLLTSIVRGIPFWGGSTIDTELKVIDTNCINV
IQPDGSYRSEELNLVIIGPSADIIQFECKSFGHEVLNLTRNGYGSTQYIRFSPDFTFGFEESLEVDTNPL
LGAGKFATDPAVTLAHELIHAGHRLYGIAINPNRVFKVNTNAYYEMSGLEVSFEELRTFGGHDAKFIDSL
QENEFRLYYYNKFKDIASTLNKAKSIVGTTASLQYMKNVFKEKYLLSEDTSGKFSVDKLKFDKLYKMLTE
IYTEDNFVKFFKVLNRKTYLNFDKAVFKINIVPKVNYTIYDGFNLRNTNLAANFNGQNTEINNMNFTKLK
NFTGLFEFYKLLCVDGIITSKTKSDDDDKNKALNLQCIKVNNWDLFFSPSEDNFTNDLNKGEEITSDTNI
EAAEENISLDLIQQYYLTFNFDNEPENISIENLSSDIIGQLELMPNIERFPNGKKYELDKYTMFHYLRAQ
EFEHGKSRIALTNSVNEALLNPSRVYTFFSSDYVKKVNKATEAAMFLGWVEQLVYDFTDETSEVSTTDKI
ADITIIIPYIGPALNIGNMLYKDDFVGALIFSGAVILLEFIPEIAIPVLGTFALVSYIANKVLTVQTIDN
ALSKRNEKWDEVYKYIVTNWLAKVNTQIDLIRKKMKEALENQAEATKAIINYQYNQYTEEEKNNINFNID
DLSSKLNESINKAMININKFLNQCSVSYLMNSMIPYGVKRLEDFDASLKDALLKYIYDNRGTLIGQVDRL
KDKVNNTLSTDIPFQLSKYVDNQRLLSTLEGGGGSGGGGSGGGGSALDNSDECPLSHDGYCLHDGVCMY
IEALDKYACNCVVGYIGERCQYRDLKWWELRALEAHHHHHHHHHH

SEQ ID NO: 8

SEQ ID NO: 9 atgggatccatggagttcgttaacaaacagttcaactataaagacccagttaacggtgttgacattgctt acatcaaaatcccgaacgctggccagatgcagccggtaaaggcattcaaaatccacaacaaaatctgggt tatcccggaacgtgatacctttactaacccggaagaaggtgacctgaacccgccaccggaagcgaaacag gtgccggtatcttactatgactccacctacctgtctaccgataacgaaaaggacaactacctgaaaggtg ttactaaactgttcgagcgtatttactccaccgacctgggccgtggtctgctgactagcatcgttcgcgg tatcccgttctggggcggttctaccatcgataccgaactgaaagtaatcgacactaactgcatcaacgtt attcagccggacggttcctatcgttccgaagaactgaacctggtgatcatcggcccgtctgctgatatca tccagttcgagtgtaagagctttggtcacgaagttctgaacctcacccgtaacggctacggttccactca gtacatccgtttctctccggacttcaccttcggttttgaagaatccctggaagtagacacgaacccactg ctgggcgctggtaaattcgcaactgatcctgcggttaccctggctcacgaactgattcatgcaggccacc gcctgtacggtatcgccatcaatccgaaccgtgtcttcaaagttaacaccaacgcgtattacgagatgtc cggtctggaagttagcttcgaagaactgcgtacttttggcggtcacgacgctaaattcatcgactctctg caagaaaacgagttccgtctgtactactataacaagttcaaagatatcgcatccaccctgaacaaagcga aatccatcgtgggtaccactgcttctctccagtacatgaagaacgttttttaaagaaaaatacctgctcag cgaagacacctccggcaaattctctgtagacaagttgaaattcgataaactttacaaaatgctgactgaa atttacaccgaagacaacttcgttaagttcttttaaagttctgaaccgcaaaacctatctgaacttcgaca aggcagtattcaaaatcaacatcgtgccgaaagttaactacactatctacgatggtttcaacctgcgtaa caccaacctggctgctaatttttaacggccagaacacggaaatcaacaacatgaacttcacaaaactgaaa aacttcactggtctgttcgagttttacaagctgctgtgcGTCGACGGCATCATTACCTCCAAAACTAAAT CTGACGATGACGATAAAAACAAAGCGCTGAACCTGCAGtgtatcaaggttaacaactgggatttattctt cagcccgagtgaagacaacttcaccaacgacctgaacaaaggtgaagaaatcacctcagatactaacatc gaagcagccgaagaaaacatctcgctggacctgatccagcagtactacctgacctttaatttcgacaacg agccggaaaacatttctatcgaaaacctgagctctgatatcatcggccagctggaactgatgccgaacat cgaacgtttcccaaacggtaaaaagtacgagctggacaaatataccatgttccactacctgcgcgcgcag gaatttgaacacggcaaatcccgtatcgcactgactaactccgttaacgaagctctgctcaacccgtccc gtgtatacaccttcttctctagcgactacgtgaaaaaggtcaacaaagcgactgaagctgcaatgttctt gggttgggttgaacagcttgtttatgattttaccgacgagacgtccgaagtatctactaccgacaaaatt gcggatatcactatcatcatcccgtacatcggtccggctctgaacattggcaacatgctgtacaaagacg acttcgttggcgcactgatcttctccggtgcggtgatcctgctggagttcatcccggaaatcgccatccc ggtactgggcacctttgctctggttttcttacattgcaaacaaggttctgactgtacaaaccatcgacaac gcgctgagcaaacgtaacgaaaaatgggatgaagtttacaaatatatcgtgaccaactggctggctaagg ttaatactcagatcgacctcatccgcaaaaaaatgaaagaagcactggaaaaccaggcggaagctaccaa ggcaatcattaactaccagtacaaccagtacaccgaggaagaaaaaaacaacatcaacttcaacatcgac gatctgtcctctaaactgaacgaatccatcaacaaagctatgatcaacatcaacaagttcctgaaccagt gctctgtaagctatctgatgaactccatgatcccgtacggtgttaaacgtctggaggacttcgatgcgtc tctgaaagacgccctgctgaaatacatttacgacaaccgtggcactctgatcggtcaggttgatcgtctg aaggacaaagtgaacaataccttatcgaccgacatcccttttcagctcagtaaatatgtcgataaccaac gccttttgtccactctagaaggtggcggtgggtccggtggcggtggctcaggcggggcggtagcgcact agacaactctgactctgaatgcccgctgtctcacgacggttactgcctgcacgacggtgtttgcatgtac atcgaagctctggacaaatacgcttgcaactgcgttgttggttacatcggtgaacgttgccagtaccgtg acctgaaatggtgggaactgcgtgcgctagaagcaCACCATCATCACcaccatcaccatcaccattaatg a

SEQ ID NO: 10

MGSMEFVNKQFNYKDPVNGVDIAYIKIPNAGQMQPVKAFKIHNKIWVIPERDTFTNPEEGDLNPPPEAKQ

VPVSYYDSTYLSIDNEKDNYLKGVTKLFERIYSTDLGRGLLTSIVRGIPFWGGSTIDTELKVIDTNCINV

IQPDGSYRSEELNLVIIGPSADIIQFECKSFGHEVLNLTRNGYGSTQYIRFSPDFTFGFEESLEVDTNPL

LGAGKFATDPAVTLAHELIHAGHRLYGIAINPNRVFKVNTNAYYEMSGLEVSFEELRIFGGHDAKFIDSL

QENEFRLYYYNKFKDIASTLNKAKSIVGTTASLQYMKNVFKEKYLLSEDTSGKFSVDKLKFDKLYKMLTE

IYTEDNFVKFFKVLNRKTYLNFDKAVFKINIVPKVNYTIYDGFNLRNTNLAANFNGQNTEINNMNFTKLK

NFTGLFEFYKLLCVDGIITSKTKSDDDDKNKALNLQCIKVNNWDLFFSPSEDNFTNDLNKGEEITSDTNI

EAAEENISLDLIQQYYLTFNFDNEPENISIENLSSDIIGQLELMPNIERFPNGKKYELDKYTMFHYLRAQ

EFEHGKSRIALTNSVNEALLNPSRVYTFFSSDYVKKVNKATEAAMFLGWVEQLVYDFTDETSEVSTTDKI

ADITIIIPYIGPALNIGNMLYKDDFVGALIFSGAVILLEFIPEIAIPVLGTFALVSYIANKVLIVQTIDN

ALSKRNEKWDEVYKYIVTNWLAKVNTQIDLIRKKMKEALENQAEATKAIINYQYNQYTEEEKNNINFNID

DLSSKLNESINKAMININKFLNQCSVSYLMNSMIPYGVKRLEDFDASLKDALLKYIYDNRGTLIGQVDRL

KDKVNNTLSTDIPFQLSKYVDNQRLLSTLEGGGGSGGGGSGGGGSALDNSDSECPLSHDGYCLHDGVCMY

IEALDKYACNCVVGYIGERCQYRDLKWWELRALEAHHHHHHHHH

SEQ ID 11

ISEFGSEFMPITINNFNYSDPVDNKNILYLDTHLNTLANEPEKAFRITGNIWVIPDRFSRNSNPNLNKPP

RVISPKSGYYDPNYLSTDSDKDIFLKEIIKLFKRINSREIGEELIYRLSTDIPFPGNNNTPINTFDFDVD

FNSVDVKTRQGNNWVKIGSINPSVIITGPRENIIDPETSTFKLTNNTFAAQEGFGALSIISISPRFMLTY

SNAINDVRSRRFSKSEFCMDPILILMHELNHAMHNLYGIAIPNDQTISSVTSNIFYSQYNVKLEYAEIYA

FGGPTIDLIPKSARKYFEEKALDYYRSIAKRLNSITTANPSSFNKYIGEYKQKLIRKYRFVVESSGEVTV

NRNKFVELYNELTQIFTEFNYAKIYNVQNRKIYLSNVYTPVTANILDDNVYDIQNGFNIPKSNLNVLFMG

QNLSRNPALRKVNPENMLYLFTKFCVDADDDDKLYNKTLQCRELLVKNTDLPFIGDISDVKIDIFLRKDI

NEETEVIPDNVSVDQVILSKNTSEHGQLDLLYPSIDSESEILPGENQVFYDNRTQNVDYLNSYYYLESQK

LSDNVEDFTFTRSIEEALDNSAKVYTYFPTLANKVNAGVQGGLFLMWANDVVEDFTTNILRKDILDKISD

VSAIIPYIGPALNISNSVRRGNFTEAFAVTGVTILLEAFPEFTIPALGAFVIYSKVQERNEIIKTIDNCL

EQRIKRWKDSYEWMMGTWLSRIITQFNNISYQMYDSLNYQAGAIKAKIDLEYKKYSGSDKENIKSQVENL

KNSLDVKISEAMNNINKFIRECSVTYLFKNMLPKVIDELNEFDRNTKAKLINLIDSHNIILVGEVDKLKA

KVNNSFQNTIPFNIFSYTNNSLLKDIINEYFNLEGGGGSGGGGSGGGGSALDNSDSECPLSHDGYCLHDG

VCMYIEALDKYACNCVVGYIGERCQYRDLKWWELR

SEQ ID 12 atgggatccatggagttcgttaacaaacagttcaactataaagacccagttaacggtgttgacattgctt acatcaaaatcccgaacgctggccagatgcagccggtaaaggcattcaaaatccacaacaaaatctgggt tatcccggaacgtgatacctttactaacccggaagaaggtgacctgaacccgccaccggaagcgaaacag gtgccggtatcttactatgactccacctacctgtctaccgataacgaaaaggacaactacctgaaaggtg ttactaaactgttcgagcgtatttactccaccgacctgggccgtatgctgctgactagcatcgttcgcgg tatcccgttctggggcggttctaccatcgataccgaactgaaagtaatcgacactaactgcatcaacgtt attcagccggacggttcctatcgttccgaagaactgaacctggtgatcatcggcccgtctgctgatatca -continued

```
tccagttcgagtgtaagagctttggtcacgaagttctgaacctcacccgtaacggctacggttccactca
gtacatccgtttctctccggacttcaccttcggttttgaagaatccctggaagtagacacgaacccactg
ctgggcgctggtaaattcgcaactgatcctgcggttaccctggctcacgaactgattcatgcaggccacc
gcctgtacggtatcgccatcaatccgaaccgtgtcttcaaagttaacaccaacgcgtattacgagatgtc
c'ggtctggaagttagcttcgaagaactgcgtacttttggcggtcacgacgctaaattcatcgactctctg
caagaaaacgagttccgtctgtactactataacaagttcaaagatatcgcatccaccctgaacaaagcga
atccatcgtgggtaccactgcttctctccagtacatgaagaacgtttttaaagaaaaatacctgctcag
cgaagacacctccggcaaattctctgtagacaagttgaaattcgataaactttacaaaatgctgactgaa
atttacaccgaagacaacttcgttaagttcttttaaagttctgaaccgcaaaacctatctgaacttcgaca
aggcagtattcaaaatcaacatcgtgccgaaagttaactacactatctacgatggtttcaacctgcgtaa
caccaacctggctgctaattttaacggccagaacacggaaatcaacaacatgaacttcacaaaactgaaa
aacttcactggtctgttcgagttttacaagctgctgtgcGTCGACGGCATCATTACCTCCAAAACTAAAT
CTGACGATGACGATAAAAACAAAGCGCTGAACCTGCAGtgtatcaaggttaacaactgggatttattctt
cagcccgagtgaagacaacttcaccaacgacctgaacaaaggtgaagaaatcacctcagatactaacatc
gaagcagccgaagaaaacatctcgctggacctgatccagcagtactacctgacctttaatttcgacaacg
agccggaaaacatttctatcgaaaacctgagctctgatatcatcggccagctggaactgatgccgaacat
cgaacgtttcccaaacggtaaaaagtacgagctggacaaatataccatgttccactacctgcgcgcgcag
gaatttgaacacATcGaaGGccgtatcgcactgactaactccgttaacgaagctctgctcaacccgtccc
gtgtatacaccttcttctctagcgactacgtgaaaaaggtcaacaaagcgactgaagctgcaatgttctt
gggttggttgaacagcttgtttatgattttaccgacgagacgtccgaagtatctactaccgacaaaatt
gcggatatcactatcatcatcccgtacatcggtccggctctgaacattggcaacatgctgtacaaagacg
acttcgttggcgcactgatcttctccggtgcggtgatcctgctggagttcatcccggaaatcgccatccc
ggtactgggcacctttgctctggtttcttacattgcaaacaaggttctgactgtacaaaccatcgacaac
gcgctgagcaaacgtaacgaaaaatgggatgaagtttacaaatatcgtgaccaactggctggctaagg
ttaatactcagatcgacctcatccgcaaaaaaatgaaagaagcactggaaaaccaggcggaagctaccaa
ggcaatcattaactaccagtacaaccagtacaccgaggaagaaaaaaacaacatcaacttcaacatcgac
gatctgtcctctaaactgaacgaatccatcaacaaagctatgatcaacatcaacaagttcctgaaccagt
gctctgtaagctatctgatgaactccatgatcccgtacggtgttaaacgtctggaggacttcgatgcgtc
tctgaaagacgccctgctgaaatacatttacgacaacgtggcactctgatcggtcaggttgatcgtctg
aaggacaaagtgaacaatacccttatcgaccgacatccctttttcagctcagtaaatatgtcgataaccaac
gccttttgtccactctagaaggtggcggtgggtccggtggcggtggctcaggcggggcggtagcgcact
agacaactctgactctgaatgcccgctgtctcacgacggttactgcctgcacgacggtgtttgcatgtac
atcgaagctctggacaaatacgcttgcaactgcgttgttggttacatcggtgaacgttgccagtaccgtg
acctgaaatggtgggaactgcgtgcgctagaagcaCACCATCATCACcaccatcaCcatcaccattaatg
a
```

SEQ ID 13

GSMEFVNKQFNYKDPVNGVDIAYIKIPNAGQMQPVKAFKIHNKIWVIPERDTFTNPEEGDLNPPPEAKQV

PVSYYDSTYLSTDNEKDNYLKGVTKLFERIYSTDLGRMLLTSIVRGIPFWGGSTIDTELKVIDTNCINVI

QPDGSYRSEELNLVIIGPSADITQFECKSFGHEVLNLTRNGYGSTQYIRFSPDFTFGFEESLEVDTNPLL

GAGKFATDPAVTLAHELIHAGHRLYGIAINPNRVFKVNTNAYYEMSGLEVSFEELRTFGGHDAKFIDSLQ

ENEFRLYYYNKFKDIASTLNKAKSIVGTTASLQYMKNVFKEKYLLSEDTSGKFSVDKLKFDKLYKMLTEI
YTEDNFVKFFKVLNRKTYLNFDKAVFKINIVPKVNYTIYDGFNLRNTNLAANFNGQNTEINNMNFTKLKN
FTGLFEFYKLLCVDGIITSKTKSDDDDKNKALNLQCIKVNNWDLFFSPSEDNFTNDLNKGEEITSDTNIE
AAEENISLDLIQQYYLTFNFDNEPENISIENLSSDITGQLELMPNIERFPNGKKYELDKYTMFHYLRAQE
FEHIEGRIALTNSVNEALLNPSRVYTFFSSDYVKKVNKATEAAMFLGWVEQLVYDFTDETSEVSTTDKIA
DITIIPYIGPALNIGNMLYKDDFVGALIFSGAVILLEFIPETAIPVLGTFALVSYIANKVLTVQTIDNA
LSKRNEKWDEVYKYIVTNWLAKVNTQIDLIRKKMKEALENQAEATKAIINYQYNQYTEEEKNNINFNIDD
LSSKLNESINKAMININKFLNQCSVSYLMNSMIPYGVKRLEDFDASLKDALLKYIYDNRGTLIGQVDRLK
DKVNNTLSTDIPFQLSKYVDNQRLLSTLEGGGGSGGGGSGGGGSALDNSDSECPLSHDGYCLHDGVCMYI
EALDKYACNCVVGYIGERCQYRDLKWWELRALEAHHHHHHHHH

SEQ ID 14 atgggatccatggagttcgttaacaaacagttcaactataaagacccagttaacggtgttgacattgctt
acatcaaaatcccgaacgctggccagatgcagccggtaaaggcattcaaaatccacaacaaaatctgggt
tatcccggaacgtgatacctttactaaccggaagaaggtgacctgaacccgccaccggaagcgaaacag
gtgccggtatcttactatgactccacctacctgtctaccgataacgaaaaggacaactacctgaaaggtg
ttactaaactgttcgagcgtatttactccaccgacctgggccgtatgctgctgactagcatcgttcgcgg
tatcccgttctggggcggttctaccatcgataccgaactgaaagtaatcgacactaactgcatcaacgtt
attcagccggacggttcctatcgttccgaagaactgaacctggtgatcatcggcccgtctgctgatatca
tccagttcgagtgtaagagctttggtcacgaagttctgaacctcacccgtaacggctacggttccactca
gtacatccgtttctctccggacttcaccttcggttttgaagaatccctggaagtagacacgaacccactg
GCGCAGgctgTTCGTTCCTCTTCTgatcctgcggttaccctggctcacgaactgattcatgcaggccacc
gcctgtacggtatcgccatcaatccgaacgtgtcttcaaagttaacaccaacgcgtattacgagatgtc
cggtctggaagttagcttcgaagaactgcgtacttttggcggtcacgacgctaaattcatcgactctctg
caagaaaacgagttccgtctgtactactataacaagttcaaagatatcgcatccaccctgaacaaagcga
atccatcgtgggtaccactgcttctctccagtacatgaagaacgttttttaaagaaaaatacctgctcag
cgaagacacctccggcaaattctctgtagacaagttgaaattcgataaactttacaaaatgctgactgaa
atttacaccgaagacaacttcgttaagttctttaaagttctgaaccgcaaaacctatctgaacttcgaca
aggcagtattcaaaatcaacatcgtgccgaaagttaactacactatctacgatggtttcaacctgcgtaa
caccaacctggctgctaattttaacggccagaacacggaaatcaacaacatgaacttcacaaaactgaaa
aacttcactggtctgttcgagttttacaagctgctgtgcGTCGACGGCATCATTACCTCCAAAACTAAAT
CTGACGATGACGATAAAAACAAAGCGCTGAACCTGCAGtgtatcaaggttaacaactgggatttattctt
cagcccgagtgaagacaacttcaccaacgacctgaacaaaggtgaagaaatcacctcagatactaacatc
gaagcagccgaagaaaacatctcgctggacctgatccagcagtactacctgaccttaatttcgacaacg
agccggaaaacatttctatcgaaaacctgagctctgatatcatcggccagctggaactgatgccgaacat
cgaacgtttcccaaacggtaaaaagtacgagctggacaaatataccatgttccactacctgcgcgcgcag
gaatttgaacacggcaaatcccgtatcgcactgactaactccgttaacgaagctctgctcaacccgtccc
gtgtatacaccttcttctctagcgactacgtgaaaaaggtcaacaaagcgactgaagctgcaatgttctt
gggttgggttgaacagcttgtttatgattttaccgacgagacgtccgaagtatctactaccgacaaaatt
gcggatatcactatcatcatcccgtacatcggtccggctctgaacattggcaacatgctgtacaaagacg
acttcgttggcgcactgatcttctccggtgcggtgatcctgctggagttcatcccggaaatcgccatccc -continued

```
ggtactgggcacctttgctctggtttcttacattgcaaacaaggttctgactgtacaaccatcgacaac gcgctgagcaaacgtaacgaaaaatgggatgaagtttacaaatatatcgtgaccaactggctggctaagg ttaatactcagatcgacctcatccgcaaaaaatgaaagaagcactggaaaaccaggcggaagctaccaa ggcaatcattaactaccagtacaaccagtacaccgaggaagaaaaaaacaacatcaacttcaacatcgac gatctgtcctctaaactgaacgaatccatcaacaaagctatgatcaacatcaacaagttcctgaaccagt gctctgtaagctatctgatgaactccatgatcccgtacggtgttaaacgtctggaggaCttcgatgcgtc tctgaaagacgccctgctgaaatacatttacgacaaccgtggcactctgatcggtcaggttgatcgtctg aaggacaaagtgaacaatacctatcgaccgacatccctttttcagctcagtaaatatgtcgataaccaac gccttttgtccactctagaaggtggcggtgggtccggtggcggtggctcaggcggggcggtagcgcact agacaactctgactctgaatgcccgctgtctcacgacggttactgcctgcacgacggtgtttgcatgtac atcgaagctctggacaaatacgcttgcaactgcgttgttggttacatcggtgaacgttgccagtaccgtg acctgaaatggtgggaactgcgtgcgctagaagcaCACCATCATCACcaccatcaccatcaccattaatg
a
```

SEQ ID 15

```
GSMEFVNKQFNYKDPVNGVDIAYIKIPNAGQMQPVKAFKIHNKIWVIPERDTFTNPEEGDLNPPPEAKQV

PVSYYDSTYLSTDNEKDNYLKGVTKLFERIYSTDLGRMLLTSIVRGIPFWGGSTIDTELKVIDTNCINVI

QPDGSYRSEELNLVIIGPSADIIQFECKSFGHEVLNLTRNGYGSTQYIRFSPDFTFGFEESLEVDTNPLA

QAVRSSSDPAVTLAHELIHAGHRLYGIAINPNRVFKVNTNAYYEMSGLEVSFEELRTFGGHDAKFIDSLQ

ENEFRLYYYNKFKDIASTLNKAKSIVGTTASLQYMKNVFKEKYLLSEDTSGKFSVDKLKFDKLYKMLTEI

YTEDNFVKFFKVLNRKTYLNFDKAVFKINIVPKVNYTIYDGFNLRNTNLAANFNGQNTEINNMNFTKLKN

FTGLFEFYKLLCVDGIITSKTKSDDDDKNKALNLQCIKVNNWDLFFSPSEDNFTNDLNKGEEITSDTNIE

AAEENISLDLIQQYYLTFNFDNEPENISIENLSSDIIGQLELMPNIERFPNGKKYELDKYTMFHYLRAQE

FEHGKSRIALTNSVNEALLNPSRVYTFFSSDYVKKVNKATEAAMFLGWVEQLVYDFTDETSEVSTTDKIA

DITIIIPYIGPALNIGNMLYKDDFVGALIFSGAVILLEFIPEIAIPVLGTFALVSYIANKVLTVQTIDNA

LSKRNEKWDEVYKYIVINWLAKVNTQIDLIRKKMKEALENQAEATKAIINYQYNQYTEEEKNNINFNIDD

LSSKLNESINKAMININKFLNQCSVSYLMNSMIPYGVKRLEDFDASLKDALLKYIYDNRGTLIGQVDRLK

DKVNNTLSTDIPFQLSKYVDNQRLLSTLEGGGGSGGGGSGGGGSALDNSDSECPLSHDGYCLHDGVCMYI

EALDKYACNCVVGYIGERCQYRDLKWWELRALEAHHHHHHHHHH
```

SEQ ID 16

```
atgggatccatggagttcgttaacaaacagttcaactataaagacccagttaacggtgttgacattgcttacatcaaaatccccgaacgc tggccagatgcagccggtaaaggcattcaaaatccacaacaaatctgggttatcccggaacgtgatacctttactaacccggaag aaggtgacctgaacccgccaccggaagcgaaacaggtgccggtatcttactatgactccacctacctgtctaccgataacgaaaag gacaactacctgaaaggtgttactaaactgttcgagcgtatttactccaccgacctgggccgtatgctgctgactagcatcgttcgcggt atcccgttctggggcggttctaccatcgataccgaactgaaagtaatcgacactaactgcatcaacgttattcagccggacggttcctat cgttccgaagaactgaacctggtgatcatcggcccgtctgctgatatcatccagttcgagtgtaagagctttggtcacgaagttctgaac ctcacccgtaacggctacggttccactcagtacatccgtttctctccggacttcacct-
tcggttttgaagaatccctggaagtagacacga acccactgctgggcgctggtaaaattcgcaactgatcctgcggttaccctggctcacgaactgattcatgcaggccaccgcctgtacggt atcgccatcaatccgaaccgtgtcttcaaagttaacaccaacgcgtattacgagatgtccggtctggaagttagcttcgaagaactgcg tactttttggcggtcacgacgctaaattcatcgactctctgcaagaaaacgagttccgtctgtactactataacaagttcaaagatatcgc atccaccctgaacaaagcgaaatccatcgtgggtaccactgcttctctccagtacatgaagaacgttttttaaagaaaaatacctgctca
``` gcgaagacacctccggcaaattctctgtagacaagttgaaattcgataaactttacaaaatgctgactgaaatttacaccgaagacaa cttcgttaagttctttaaagttctgaaccgcaaaacctatctgaacttcgacaaggcagtattcaaaatcaacatcgtgccgaaagttaa ctacactatctacgatggtttcaacctgcgtaacaccaacctggctgctaattttaacggccagaacacggaaatcaacaacatgaac ttcacaaaactgaaaaacttcactggtctgttcgagttttacaagctgctgtgcGTCGACGGCATCATTACCTCCAAAA CTAAATCTGACGATGACGATAAAAACAAAGCGCTGAACCTGCAGtgtatcaaggttaacaactgggattt attcttcagcccgagtgaagacaacttcaccaacgacctgaacaaaggtgaagaaatcacctcagatactaacatcgaagcagcc gaagaaaacatctcgctggacctgatccagcagtactacctgacctttaatttcgacaacgagccggaaaacatttctatcgaaacc tgagctctgatatcatcggccagctggaactgatgccgaacatcgaacgtttcccaaacggtaaaaagtacgagctggacaaatata ccatgttccactacctgcgcgcgcaggaatttgaacacggcaaatcccgtatcgcactgactaactccgttaacgaagctctgctcaa cccgtcccgtgtatacaccttcttctctagcgactacgtgaaaaaggtcaacaaagcgactgaagctgcaatgttcttgggttgggttga acagcttgtttatgattttaccgacgagacgtccgaagtatctactaccgacaaaatt-
gcggatatcactatcatcatcccgtacatcggt ccggctctgaacattggcaacatgctgtacaaagacgacttcgttggcgcactgatcttctccggtgcggtgatcctgctggagttcatc ccggaaatcgccatcccggtactgggcacctttgctctggtttcttacattgcaaacaaggttctgactgtacaaaccatcgacaacgc gctgagcaaacgtaacgaaaaatgggatgaagtttacaaatatatcgtgaccaactggctggctaaggttaatactcagatcgacctc atccgcaaaaaaatgaaagaagcactggaaaaccaggcggaagctaccaaggcaatcattaactaccagtacaaccagtacac cgaggaagaaaaaaacaacatcaacttcaacatcgacgatctgtcctctaaactgaacgaatccatcaacaaagctatgatcaac atcaacaagttcctgaaccagtgctctgtaagctatctgatgaactccatgatcccgtacggtgttaaacgtctggaggacttcgatgcg tctctgaaagacgccctgctgaaatacatttacgacaaccgtggcactctgatcggtcaggttgatcgtctgaaggacaaagtgaaca ataccttatcgaccgacatccctttcagctcagtaaatatgtcgataaccaacgc-
ctttgtccactttcaccgaatacatcaaaaacat catcaacaccagtctagaaATCCTGAACCTGCGTTACGAATCTAACCACCTGATCGACCTGTCTCG

TTACGCTTCTAAAATCAACATCGGTTCTAAAGTTAACTTCGACCCGATCGACAAAAACCAG

ATCCAGCTGTTCAACCTGGAATCTTCTAAAATCGAAGTTATCCTGAAAAACGCTATCGTTTA

CAACTCTATGTACGAAAACTTCTCTACCTCTTTCTGGATTCGTATCCCGAAATACTTTAACT

CTATCTCTCTGAACAACGAATACACCATCATCAACTGCATGGAAAACAACTCTGGTTGGAA

AGTTTCTCTGAACTACGGTGAAATCATCTGGACCCTGCAAGACACCCAGGAAATCAAACAG

CGTGTTGTTTTCAAATACTCTCAGATGATCAACATCTCTGACTACATCAACCGTTGGATCTT

CGTTACCATCACCAACAACCGTCTGAACAACTCTAAAATCTACATCAACGGTCGTCTGATC

GACCAGAAACCGATCTCTAACCTGGGTAACATCCACGCTTCTAACAACATCATGTTCAAAC

TGGACGGTTGCCGTGACACCCACCGTTACATCTGGATCAAATACTTCAACCTGTTCGACAA

AGAACTGAACGAAAAGAAATCAAAGACCTGTACGACAACCAGTCTAACTCTGGTgcactagtg

ATTTTGAAGGACTTTTGGGGCGACTATCTCCAGTACGACAAACCTTACTATATGCTGAATT

TGTATGATCCCAACAAATATGTGGATGTGAATAACGTTGGTATTAGGGGTTACATGTATTT

GAAGGGTCCAAGGGGGTCAGTCATGACAACCAATATCTACTTAAATTCCTCTCTTTACCGA

GGGACAAAATTCATTATCAAAAAGTATGCTAGTGGAAATAAAGATAATATAGTCAGAAACAA

TGATCGCGTTTACATTAACGTGGTAGTCAAAAATAAGGAGTATAGACTAGCTACGAATGCA

TCGCAGGCGGGAGTGGAGAAGATACTGAGCGCACTAGAAATACCTGACGTAGGAAACTTA

AGCCAGGTTGTCGTTATGAAATCAAAGAACGATCAAGGAATTACTAATAAGTGTAAGATGA

ACTTACAAGATAACAATGGCAATGATATAGGCTTCATCGGGTTTCATCAATTTAACAACATA

GCGAAACTCGTAGCCTCTAACTGGTACAACCGTCAAATCGAACGAAGTTCCCGTACTCTA

```
GGTTGCTCGTGGGAGTTCATCCCAGTAGACGACGGGTGGGGCGAACGGCCGCTTgcgctag caCACCATCATCACcaccatcaccatcaccattaatga
```

SEQ ID 17

HMGSMEFVNKQFNYKDPVNGVDIAYIKIPNAGQMQPVKAFKIHNKIVVVIPERDTFTNPEEGDLN

PPPEAKQVPVSYYDSTYLSTDNEKDNYLKGVTKLFERIYSTDLGRMLLTSIVRGIPFWGGSTIDT

ELKVIDTNCINVIQPDGSYRSEELNLVIIGPSADIIQFECKSFGHEVLNLTRNGYGSTQYIRFSPDF

TFGFEESLEVDTNPLLGAGKFATDPAVTLAHELIHAGHRLYGIAINPNRVFKVNTNAYYEMSGLE

VSFEELRTFGGHDAKFIDSLQENEFRLYYYNKFKDIASTLNKAKSIVGTTASLQYMKNVFKEKYL

LSEDTSGKFSVDKLKFDKLYKMLTEIYTEDNFVKFFKVLNRKTYLNFDKAVFKINIVPKVNYTIYD

GFNLRNTNLAANFNGQNTEINNMNFTKLKNFTGLFEFYKLLCVDGIITSKTKSDDDDKNKALNL

QCIKVNNWDLFFSPSEDNFTNDLNKGEEITSDTNIEAAEENISLDLIQQYYLTFNFDNEPENISIE

NLSSDIIGQLELMPNIERFPNGKKYELDKYTMFHYLRAQEFEHGKSRIALTNSVNEALLNPSRVY

TFFSSDYVKKVNKATEAAMFLGVVVEQLVYDFTDETSEVSTTDKIADITIIPYIGPALNIGNMLYK

DDFVGALIFSGAVILLEFIPEIAIPVLGTFALVSYIANKVLTVQTIDNALSKRNEKWDEVYKYIVTN

WLAKVNTQIDLIRKKMKEALENQAEATKAIINYQYNQYTEEEKNNINFNIDDLSSKLNESINKAMI

NINKFLNQCSVSYLMNSMIPYGVKRLEDFDASLKDALLKYIYDNRGTLIGQVDRLKDKVNNTLST

DIPFQLSKYVDNQRLLSTFTEYIKNIINTSLEILNLRYESNHLIDLSRYASKINIGSKVNFDPIDKNQI

QLFNLESSKIEVILKNAIVYNSMYENFSTSFWIRIPKYFNSISLNNEYTIINCMENNSGWKVSLNY

GEIIVVTLQDTQEIKQRVVFKYSQMINISDYINRWIFVTITNNRLNNSKIYINGRLIDQKPISNLGNIH

ASNNIMFKLDGCRDTHRYIWIKYFNLFDKELNEKEIKDLYDNQSNSGALVILKDFWGDYLQYDK

PYYMLNLYDPNKYVDVNNVGIRGYMYLKGPRGSVMTTNIYLNSSLYRGTKFIIKKYASGNKDNIV

RNNDRVYINVVVKNKEYRLATNASQAGVEKILSALEIPDVGNLSQVVVMKSKNDQGITNKCKMN

LQDNNGNDIGFIGFHQFNNIAKLVASNVVYNRQIERSSRTLGCSWEFIPVDDGWGERPLALAHH

HHHHHHHH

SEQ ID 18 atgggatccatggagttcgttaacaaacagttcaactataaagacccagttaacggtgttgacattgctt acatcaaaatcccgaacgctggccagatgcagccggtaaaggcattcaaaatccacaacaaatctgggt tatcccggaacgtgatacctttactaacccggaagaaggtgacctgaacccgccaccggaagcgaaacag gtgccggtatcttactatgactccacctacctgtctaccgataacgaaaaggacaactacctgaaaggtg ttactaaactgttcgagcgtatttactccaccgacctgggccgtatgctgctgactagcatcgttcgcgg tatcccgttctggggcggttctaccatcgataccgaactgaaagtaatcgacactaactgcatcaacgtt attcagccggacggttcctatcgttccgaagaactgaacctggtgatcatcggcccgtctgctgatatca tccagttcgagtgtaagagctttggtcacgaagttctgaacctcacccgtaacggctacggttccactca gtacatccgtttctctccggacttcaccttcggttttgaagaatccctggaagtagacacgaacccactg GCGCAGgctGTTCGTTCCTCTTCTgatcctgcggttaccctggctcacgaactgattcatgcaggccacc gcctgtacggtatcgccatcaatccgaaccgtgtcttcaaagttaacaccaacgcgtattacgagatgtc cggtctggaagttagcttcgaagaactgcgtacttttggcggtcacgacgctaaattcatcgactctctg caagaaaacgagttccgtctgtactactataacaagttcaaagatatcgcatccaccctgaacaaagcga aatccatcgtgggtaccactgcttctctccagtacatgaagaacgtttttaaagaaaaatacctgctcag cgaagacacctccggcaaattctctgtagacaagttgaaattcgataaactttacaaaatgctgactgaa atttacaccgaagacaacttcgttaagttctttaaagttctgaaccgcaaaacctatctgaacttcgaca aggcagtattcaaaatcaacatcgtgccgaaagttaactacactatctacgatggtttcaacctgcgtaa caccaacctggctgctaattttaacggccagaacacggaaatcaacaacatgaacttcacaaaactgaaa aacttcactggtctgttcgagttttacaagctgctgtgcGTCGACGGCATCATTACCTCCAAAACTAAAT CTGACGATGACGATAAAAACAAAGCGCTGAACCTGCAGtgtatcaaggttaacaactgggatttattctt cagcccgagtgaagacaacttcaccaacgacctgaacaaaggtgaagaaatccctcagatactaacatc gaagcagccgaagaaaacatctcgctggacctgatccagcagtactacctgacctttaatttcgacaacg agccggaaaacatttctatcgaaaacctgagctctgatatcatcggccagctggaactgatgccgaacat cgaacgtttcccaaacggtaaaaagtacgagctggacaaatataccatgttccactacctgcgcgcgcag gaatttgaacacggcaaatcccgtatcgcactgactaactccgttaacgaagctctgctcaacccgtccc gtgtatacaccttcttctctagcgactacgtgaaaaaggtcaacaaagcgactgaagctgcaatgttctt gggttgggttgaacagcttgtttatgattttaccgacgagacgtccgaagtatctactaccgacaaaatt goggatatcactatcatcatcccgtacatcggtccggctctgaacattggcaacatgctgtacaaagacg acttcgttggcgcactgatcttctccggtgcggtgatcctgctggagttcatcccggaaatcgccatccc ggtactgggcacctttgctctggtttcttacattgcaaacaaggttctgactgtacaaaccatcgacaac gcgctgagcaaacgtaacgaaaaatgggatgaagtttacaaatatatcgtgaccaactggctggctaagg ttaatactcagatcgacctcatccgcaaaaaaatgaaagaagcactggaaaaccaggcggaagctaccaa ggcaatcattaactaccagtacaaccagtacaccgaggaagaaaaaaacaacatcaacttcaacatcgac gatctgtoctctaaactgaacgaatccatcaacaaagctatgatcaacatcaacaagttcctgaaccagt gctctgtaagctatctgatgaactccatgatcccgtacggtgttaaacgtctggaggacttcgatgcgtc tctgaaagacgccctgctgaaatacatttacgacaaccgtggcactctgatcggtcaggttgatcgtctg aaggacaaagtgaacaataccttatcgaccgacatccctttcagctcagtaaatatgtcgataaccaac gccttttgtccactttcaccgaatacatcaaaaacatcatcaacaccagtctagaaATCCTGAACCTGCG

TTACGAATCTAACCACCTGATCGACCTGTCTCGTTACGCTTCTAAAATCAACATCGGTTCTAAAGTTAAC

TTCGACCCGATCGACAAAAACCAGATCCAGCTGTTCAACCTGGAATCTTCTAAAATCGAAGTTATCCTGA

AAAACGCTATCGTTTACAACTCTATGTACGAAAACTTCTCTACCTCTTTCTGGATTCGTATCCCGAAATA

CTTTAACTCTATCTCTCTGAACAACGAATACACCATCATCAACTGCATGGAAAACAACTCTGGTTGGAAA

GTTTCTCTGAACTACGGTGAAATCATCTGGACCCTGCAAGACACCCAGGAAATCAAACAGCGTGTTGTTT

TCAAATACTCTCAGATGATCAACATCTCTGACTACATCAACCGTTGGATCTTCGTTACCATCACCAACAA

CCGTCTGAACAACTCTAAAATCTACATCAACGGTCGTCTGATCGACCAGAAACCGATCTCTAACCTGGGT

AACATCCACGCTTCTAACAACATCATGTTCAAACTGGACGGTTGCCGTGACACCCACCGTTACATCTGGA

TCAAATACTTCAACCTGTTCGACAAAGAACTGAACGAAAAAGAAATCAAAGACCTGTACGACAACCAGTC

TAACTCTGGTgcactagtgATTTTGAAGGACTTTTGGGGCGACTATCTCCAGTACGACAAACCTTACTAT

ATGCTGAATTTGTATGATCCCAACAAATATGTGGATGTGAATAACGTTGGTATTAGGGGTTACATGTATT

TGAAGGGTCCAAGGGGGTCAGTCATGACAACCAATATCTACTTAAATTCCTCTCTTTACCGAGGGACAAA

ATTCATTATCAAAAAGTATGCTAGTGGAAATAAAGATAATATAGTCAGAAACAATGATCGCGTTTACATT

AACGTGGTAGTCAAAAATAAGGAGTATAGACTAGCTACGAATGCATCGCAGGCGGGAGTGGAGAAGATAC

TGAGCGCACTAGAAATACCTGACGTAGGAAACTTAAGCCAGGTTGTCGTTATGAAATCAAAGAACGATCA

AGGAATTACTAATAAGTGTAAGATGAACTTACAAGATAACAATGGCAATGATATAGGCTTCATCGGGTTT

CATCAATTTAACAACATAGCGAAACTCGTAGCCTCTAACTGGTACAACCGTCAAATCGAACGAAGTTCCC

```
GTACTCTAGGTTGCTCGTGGGAGTTCATCCCAGTAGACGACGGGTGGGGCGAACGGCCGCTTgcgctagc aCACCATCATCACcaccatcaccatcaccattaatga
```

SEQ ID 19

```
GSMEFVNKQENYKDPVNGVDIAYIKIPNAGQMQPVKAFKIHNKIWVIPERDTFTNPEEGDLNPPPEAKQV

PVSYYDSTYLSTDNEKDNYLKGVTKLFERTYSTDLGRMLLTSIVRGIPFWGGSTIDTELKVIDTNCINVI

QPDGSYRSEELNLVIIGPSADIIQFECKSFGHEVLNLTRNGYGSTQYIRFSPDFTFGFEESLEVDTNPLA

QAVRSSSDPAVTLAHELIHAGHRLYGIAINPNRVEKVNTNAYYEMSGLEVSFEELRTFGGHDAKFIDSLQ

ENEFRLYYYNKFKDIASTLNKAKSIVGTTASLQYMKNVFKEKYLLSEDTSGKFSVDKLKFDKLYKMLTEI

YTEDNEVKFFKVLNRKTYLNEDKAVFKINIVPKVNYTIYDGFNLRNTNLAANFNGQNTEINNMNFTKLKN

FTGLFEFYKLLCVDGIITSKTKSDDDDKNKALNLQCIKVNNWDLFFSPSEDNFTNDLNKGEEITSDTNIE

AAEENISLDLIQQYYLTFNEDNEPENISIENLSSDITGQLELMPNIERFPNGKKYELDKYTMFHYLRAQE

FEHGKSRIALTNSVNEALLNPSRVYTFFSSDYVKKVNKATEAAMFLGWVEQLVYDFTDETSEVSTTDKIA

DITIIIPYIGPALNIGNMLYKDDEVGALIFSGAVILLEFIPETAIPVLGTFALVSYIANKVLTVQTIDNA

LSKRNEKWDEVYKYIVTNWLAKVNTQIDLIRKKMKEALENQAEATKAIINYQYNQYTEEEKNNINFNIDD

LSSKLNESINKAMININKFLNQCSVSYLMNSMIPYGVKRLEDFDASLKDALLKYIYDNRGTLIGQVDRLK

DKVNNTLSTDIPFQLSKYVDNQRLLSTFTEYIKNIINTSLEILNLRYESNHLIDLSRYASKINIGSKVNF

DPIDKNQIQLFNLESSKIEVILKNAIVYNSMYENFSTSFWIRIPKYFNSISLNNEYTIINCMENNSGWKV

SLNYGETIWTLQDTQEIKQRVVEKYSQMINISDYINRWIFVTITNNRLNNSKIYINGRLIDQKPISNLGN

IHASNNIMFKLDGCRDTHRYIWIKYFNLEDKELNEKEIKDLYDNQSNSGALVILKDFWGDYLQYDKPYYM

LNLYDPNKYVDVNNVGIRGYMYLKGPRGSVMTTNIYLNSSLYRGTKFIIKKYASGNKDNIVRNNDRVYIN

VVVKNKEYRLATNASQAGVEKILSALEIPDVGNLSQVVVMKSKNDQGITNKCKMNLQDNNGNDIGFIGFH

QFNNIAKLVASNWYNRQIERSSRTLGCSWEFIPVDDGWGERPLALAHHHHHHHHH
```

SEQ ID 20

```
atgggatccatggagttcgttaacaaacagttcaactataaagacccagttaacggtgttgacattgctt acatcaaaatcccgaacgctggccagatgcagccggtaaaggcattcaaaatccacaacaaatctgggt tatcccggaacgtgatacctttactaacccggaagaaggtgacctgaacccgccaccggaagcgaaacag gtgccggtatcttactatgactccacctacctgtctaccgataacgaaaaggacaactacctgaaaggtg ttactaaactgttcgagcgtatttactccaccgacctgggccgtatgctgctgactagcatcgttcgcgg tatcccgttctggggcggttctaccatcgataccgaactgaaagtaatcgacactaactgcatcaacgtt attcagccggacggttcctatcgttccgaagaactgaacctggtgatcatcggcccgtctgctgatatca tccagttcgagtgtaagagctttggtcacgaagttctgaacctcacccgtaacggctacggttccactca gtacatccgtttctctccggacttcaccttcggttttgaagaatccctggaagtagacacgaacccactg ctgggcgctggtaaattcgcaactgatcctgcggttaccctggctcacgaactgattcatgcaggccacc gcctgtacggtatcgccatcaatccgaaccgtgtcttcaaagttaacaccaacgcgtattacgagatgtc cggtctggaagttagcttcgaagaactgcgtacttttggcggtcacgacgctaaattcatcgactctctg caagaaaacgagttccgtctgtactactataacaagttcaaagatatcgcatccaccctgaacaaagcga aatccatcgtgggtaccactgcttctctccagtacatgaagaacgttttttaaagaaaaatacctgctcag cgaagacacctccggcaaattctctgtagacaagttgaaattcgataaactttacaaaatgctgactgaa atttacaccgaagacaacttcgttaagttctttaaagttctgaaccgcaaaacctatctgaacttcgaca aggcagtattcaaaatcaacatcgtgccgaaagttaactacactatctacgatggtttcaacctgcgtaa caccaacctggctgctaattttaacggccagaacacggaaatcaacaacatgaacttcacaaaactgaaa
```

-continued

```
aacttcactggtctgttcgagttttacaagctgctgtgcGTCGACGGCATCATTACCTCCAAAACTAAAT
CTGACGATGACGATAAAAACAAAGCGCTGAACCTGCAGtgtatcaaggttaacaactgggatttattctt
cagcccgagtgaagacaacttcaccaacgacctgaacaaaggtgaagaaatcacctcagatactaacatc
gaagcagccgaagaaaacatctcgctggacctgatccagcagtactacctgacctttaatttcgacaacg
agccggaaaacatttctatcgaaaacctgagctctgatatcatcggccagctggaactgatgccgaacat
cgaacgtttcccaaacggtaaaaagtacgagctggacaaatataccatgttccactacctgcgcgcgcag
gaatttgaacacggcCGTtcccgtCGCatcgcactgactaactccgttaacgaagctctgctcaacccgt
cccgtgtatacaccttcttctctagcgactacgtgaaaaaggtcaacaaagcgactgaagctgcaatgtt
cttgggttgggttgaacagcttgtttatgattttaccgacgagacgtccgaagtatctactaccgacaaa
attgcggatatcactatcatcatcccgtacatcggtccggctctgaacattggcaacatgctgtacaaag
acgacttcgttggcgcactgatcttctccggtgcggtgatcctgctggagttcatcccggaaatcgccat
cccggtactgggcacctttgctctggtttcttacattgcaaacaaggttctgactgtacaaaccatcgac
aacgcgctgagcaaacgtaacgaaaaatgggatgaagtttacaaatatatcgtgaccaactggctggcta
aggttaatactcagatcgacctcatccgcaaaaaaatgaaagaagcactggaaaaccaggcggaagctac
caaggcaatcattaactaccagtacaaccagtacaccgaggaagaaaaaaacaacatcaacttcaacatc
gacgatctgtcctctaaactgaacgaatccatcaacaaagctatgatcaacatcaacaagttcctgaacc
agtgctctgtaagctatctgatgaactccatgatcccgtacggtgttaaacgtctggaggacttcgatgc
gtctctgaaagacgccctgctgaaatacatttacgacaaccgtggcactctgatcggtcaggttgatcgt
ctgaaggacaaagtgaacaatacettatcgaccgacatccettttcagctcagtaaatatgtcgataacc
aacgcettttgtccactttcaccgaatacatcaaaaacatcatcaacaccagtctagaaATCCTGAACCT
GCGTTACGAATCTAACCACCTGATCGACCTGTCTCGTTACGCTTCTAAAATCAACATCGGTTCTAAAGTT
AACTTCGACCCGATCGACAAAAACCAGATCCAGCTGTTCAACCTGGAATCTTCTAAAATCGAAGTTATCC
TGAAAAACGCTATCGTTTACAACTCTATGTACGAAAACTTCTCTACCTCTTTCTGGATTCGTATCCCGAA
ATACTTTAACTCTATCTCTCTGAACAACGAATACACCATCATCAACTGCATGGAAAACAACTCTGGTTGG
AAAGTTTCTCTGAACTACGGTGAAATCATCTGGACCCTGCAAGACACCCAGGAAATCAAACAGCGTGTTG
TTTTCAAATACTCTCAGATGATCAACATCTCTGACTACATCAACCGTTGGATCTTCGTTACCATCACCAA
CAACCGTCTGAACAACTCTAAAATCTACATCAACGGTCGTCTGATCGACCAGAAACCGATCTCTAACCTG
GGTAACATCCACGCTTCTAACAACATCATGTTCAAACTGGACGGTTGCCGTGACACCCACCGTTACATCT
GGATCAAATACTTCAACCTGTTCGACAAAGAACTGAACGAAAAAGAAATCAAAGACCTGTACGACAACCA
GTCTAACTCTGGTgcactagtgATTTTGAAGGACTTTTGGGGCGACTATCTCCAGTACGACAAACCTTAC
TATATGCTGAATTTGTATGATCCCAACAAATATGTGGATGTGAATAACGTTGGTATTAGGGGTTACATGT
ATTTGAAGGGTCCAAGGGGGTCAGTCATGACAACCAATATCTACTTAAATTCCTCTCTTTACCGAGGGAC
AAAATTCATTATCAAAAAGTATGCTAGTGGAAATAAAGATAATATAGTCAGAAACAATGATCGCGTTTAC
ATTAACGTGGTAGTCAAAAATAAGGAGTATAGACTAGCTACGAATGCATCGCAGGCGGGAGTGGAGAAGA
TACTGAGCGCACTAGAAATACCTGACGTAGGAAACTTAAGCCAGGTTGTCGTTATGAAATCAAAGAACGA
TCAAGGAATTACTAATAAGTGTAAGATGAACTTACAAGATAACAATGGCAATGATATAGGCTTCATCGGG
TTTCATCAATTTAACAACATAGCGAAACTCGTAGCCTCTAACTGGTACAACCGTCAAATCGAACGAAGTT
CCCGTACTCTAGGTTGCTCGTGGGAGTTCATCCCAGTAGACGACGGGTGGGGCGAACGGCCGCTTgcgct
agcaCACCATCATCACcaccatcaccatcaccattaatga
```

-continued

SEQ ID 21

GSMEFVNKQFNYKDPVNGVDIAYIKIPNAGQMQPVKAFKIHNKIWVIPERDTFTNPEEGDLNPPPEAKQV

PVSYYDSTYLSTDNEKDNYLKGVTKLFERTYSTDLGRMLLTSIVRGIPFWGGSTIDTELKVIDTNCINVI

QPDGSYRSEELNLVIIGPSADIIQFECKSFGHEVLNLTRNGYGSTQYIRFSPDFTFGFEESLEVDTNPLL

GAGKFATDPAVTLAHELIHAGHRLYGIAINPNRVFKVNTNAYYEMSGLEVSFEELRTFGGHDAKFIDSLQ

ENEFRLYYYNKFKDIASTLNKAKSIVGTTASLQYMKNVFKEKYLLSEDTSGKFSVDKLKEDKLYKMLTEI

YTEDNFVKFEKVLNRKTYLNEDKAVFKINIVPKVNYTIYDGFNLRNTNLAANENGQNTEINNMNFTKLKN

FTGLFEFYKLLCVDGIITSKTKSDDDDKNKALNLQCIKVNNWDLFFSPSEDNFTNDLNKGEEITSDTNIE

AAEENISLDLIQQYYLTFNEDNEPENISIENLSSDIIGQLELMPNIERFPNGKKYELDKYTMFHYLRAQE

FEHGRSRRIALTNSVNEALLNPSRVYTFFSSDYVKKVNKATEAAMFLGWVEQLVYDFTDETSEVSTTDKI

ADITIIIPYIGPALNIGNMLYKDDFVGALIFSGAVILLEFIPEIAIPVLGTFALVSYIANKVLTVQTIDN

ALSKRNEKWDEVYKYIVTNWLAKVNTQIDLIRKKMKEALENQAEATKAIINYQYNQYTEEEKNNINFNID

DLSSKLNESINKAMININKFLNQCSVSYLMNSMIPYGVKRLEDFDASLKDALLKYIYDNRGTLIGQVDRL

KDKVNNTLSTDIPFQLSKYVDNQRLLSTFTEYIKNIINTSLEILNLRYESNHLIDLSRYASKINIGSKVN

FDPIDKNQIQLFNLESSKIEVILKNAIVYNSMYENFSTSFWIRIPKYFNSISLNNEYTIINCMENNSGWK

VSLNYGEIIWTLQDTQEIKQRVVFKYSQMINISDYINRWIFVTITNNRLNNSKIYINGRLIDQKPISNLG

NIHASNNIMFKLDGCRDTHRYIWIKYFNLEDKELNEKEIKDLYDNQSNSGALVILKDFWGDYLQYDKPYY

MLNLYDPNKYVDVNNVGIRGYMYLKGPRGSVMTTNIYLNSSLYRGTKFIIKKYASGNKDNIVRNNDRVYI

NVVVKNKEYRLATNASQAGVEKILSALEIPDVGNLSQVVVMKSKNDQGITNKCKMNLQDNNGNDIGFIGF

HQFNNIAKLVASNWYNRQIERSSRTLGCSWEFIPVDDGWGERPLALAHHHHHHHHH

SEQ ID 22 atgccgatcaccatcaacaacttcaactacagcgatccggtggataacaaaaacatcctgtacctggata cccatctgaataccctggcgaacgaaccggaaaaagcgtttcgtatcaccggcaacatttgggttattcc ggatcgttttagccgtaacagcaacccgaatctgaataaaccgccgcgtgttaccagcccgaaaagcggt tattacgatccgaactatctgagcaccgatagcgataaagataccttcctgaaagaaatcatcaaactgt tcaaacgcatcaacagccgtgaaattggcgaagaactgatctatcgcctgagcaccgatattccgtttcc gggcaacaacaacaccccgatcaacacctttgatttcgatgtggatttcaacagcgttgatgttaaaacc cgccagggtaacaattgggtgaaaaccggcagcattaacccgagcgtgattattaccggtccgcgcgaaa acattattgatccggaaaccagcacctttaaactgaccaacaacaccttttgcggcgcaggaaggttttgg cgcgctgagcattattagcattagcccgcgctttatgctgacctatagcaacgcgaccaacgatgttatt gaaggccgtttcagcaaaagcgaattttgcatggacccgatcctgatcctgatgcatgaactgaaccatg cgatgcataacctgtatggcatcgcgattccgaacgatcagaccattagcagcgtgaccagcaacatctt ttacagccagtacaacgtgaaactggaatatgcggaaatctatgcgtttggcggtccgaccattgatctg attccgaaaagcgcgcgcaaatacttcgaagaaaaagcgctggattactatcgcagcattgcgaaacgtc tgaacagcattaccaccgcgaatccgagcagcttcaacaaatatatcggcgaatataaacagaaactgat ccgcaaatatcgctttgtggtggaaagcagcggcgaagttaccgttaaccgcaataaattcgtggaactg tacaacgaactgacccagatcttcaccgaatttaactatgcgaaaatctataacgtgcagaaccgtaaaa tctacctgagcaacgtgtataccccggtgaccgcgaatattctggatgataacgtgtacgatatccagaa cggctttaacatcccgaaaagcaacctgaacgttctgtttatgggccagaacctgagccgtaatccggcg ctgcgtaaagtgaacccggaaaacatgctgtacctgttcaccaaattttgcGTCGAcGCGGACGATGACG ATAAACTGTACAACAAACCCTGCAGtgtcgtgaactgctggtgaaaaacaccgatctgccgtttattgg cgatatcagcgatgtgaaaaccgatatcttcctgcgcaaagatatcaacgaagaaaccgaagtgatcccg gataacgtgagcgttgatcaggtgatcctgagcaaaaacaccagcgaacatggtcagctggatctgctgt atccgagcattgatagcgaaagcgaaattctgccgggcgaaaaccaggtgttttacgataaccgtaccca gaacgtggattacctgaacagctattactacctggaaagccagaaactgagcgataacgtggaagatttt acctttacccgcagcattgaagaagcgctggataacagcgcgaaagtttacacctattttccgaccctgg cgaacaaagttaatgcgggtgttcagggcggtctgtttctgatgtgggcgaacgatgtggtggaagattt caccaccaacatcctgcgtaaagataccctggataaaatcagcgatgttagcgcgattattccgtatatt ggtccggcgctgaacattagcaatagcgtgcgtcgtggcaattttaccgaagcgtttgcggttaccggtg tgaccattctgctggaagcgtttccggaatttaccattccggcgctgggtgcgtttgtgatctatagcaa agtgcaggaacgcaacgaaatcatcaaaaccatcgataactgcctggaacagcgtattaaacgctggaaa gatagctatgaatggatgatgggcacctggctgagccgtattatcacccagttcaacaacatcagctacc agatgtacgatagcctgaactatcaggcgggtgcgattaaagcgaaaatcgatctggaatacaaaaaata cagcggcagcgataagaaaacatcaaaagccaggttgaaaacctgaaaaacagcctggatgtgaaaatt agcgaagcgatgaataacatcaacaaattcatccgcgaatgcagcgtgaccTacctgttcaaaaacatgc tgccgaaagtgatcgatgaactgaacgaatttgatcgcaacaccaaagcgaaactgatcaacctgatcga tagccacaacattattctggtgggcgaagtggataaactgaaagcgaaagttaacaacagcttccagaac accatcccgtttaacatcttcagctataccaacaacagcctgctgaaagatatcatcaacgaatacttca atctagaaggtggcggtgggtccggtggcggtggctcaggcggggcggtagcgcactagacaactctga ctctgaatgcccgctgtctcacgacggttactgcctgcacgacggtgtttgcatgtacatcgaagctctg gacaaatacgcttgcaactgcgttgttggttacatcggtgaacgttgccagtaccgtgacctgaaatggt gggaactgcgt

SEQ ID 23

MPITINNFNYSDPVDNKNILYLDTHLNTLANEPEKAFRITGNIWVIPDRFSRNSNPNLNKPPRVTSPKSG

YYDPNYLSTDSDKDTFLKEIIKLFKRINSREIGEELIYRLSTDIPFPGNNNTPINTFDFDVDFNSVDVKT

RQGNNWVKTGSINPSVIITGPRENIIDPETSTFKLTNNTFAAQEGFGALSIISISPRFMLTYSNATNDVI

EGRFSKSEFCMDPILILMHELNHAMHNLYGIAIPNDQTISSVTSNIFYSQYNVKLEYAEIYAFGGPTIDL

IPKSARKYFEEKALDYYRSIAKRLNSITTANPSSFNKYIGEYKQKLIRKYRFVVESSGEVTVNRNKFVEL

YNELTQIFTEFNYAKIYNVQNRKIYLSNVYTPVTANILDDNVYDIQNGFNIPKSNLNVLFMGQNLSRNPA

LRKVNPENMLYLFTKFCVDADDDDKLYNKTLQCRELLVKNTDLPFIGDISDVKTDIFLRKDINEETEVIP

DNVSVDQVILSKNTSEHGQLDLLYPSIDSESEILPGENQVFYDNRTQNVDYLNSYYYLESQKLSDNVEDF

TFTRSIEEALDNSAKVYTYFPTLANKVNAGVQGGLFLMWANDVVEDFTTNILRKDTLDKISDVSAIIPYI

GPALNISNSVRRGNFTEAFAVTGVTILLEAFPEFTIPALGAFVIYSKVQERNEIIKTIDNCLEQRIKRWK

DSYEWMMGTWLSRIITQFNNISYQMYDSLNYQAGAIKAKIDLEYKKYSGSDKENIKSQVENLKNSLDVKI

SEAMNNINKFIRECSVTYLFKNMLPKVIDELNEFDRNTKAKLINLIDSHNIILVGEVDKLKAKVNNSFQN

TIPFNIFSYTNNSLLKDIINEYFNLEGGGGSGGGGSGGGGSALDNSDSECPLSHDGYCLHDGVCMYIEAL

DKYACNCVVGYIGERCQYRDLKWWELR

SEQ ID 24

MPITINNFNYSDPVDNKNILYLDTHLNTLANEPEKAFRITGNIWVIPDRFSRNSNPNLNKPPRVTSPKSG

YYDPNYLSTDSDKDTFLKEIIKLFKRINSREIGEELIYRLSTDIPFPGNNNTPINTFDFDVDFNSVDVKT

RQGNNWVKTGSINPSVIITGPRENIIDPETSTFKLTNNTFAAQEGFGALSIISIVPRFSLTYSNATNDVG

-continued

EGRFSKSEFCMDPILILMHELNHAMHNLYGIAIPNDQTISSVTSNIFYSQYNVKLEYAEIYAFGGPTIDL
IPKSARKYFEEKALDYYRSIAKRLNSITTANPSSFNKYIGEYKQKLIRKYRFVVESSGEVTVNRNKFVEL
YNELTQIFTEFNYAKIYNVQNRKIYLSNVYTPVTANILDDNVYDIQNGFNIPKSNLNVLFMGQNLSRNPA
LRKVNPENMLYLFTKFCVDADDDDKLYNKTLQCRELLVKNTDLPFIGDISDVKTDIFLRKDINEETEVIY
YPDNVSVDQVILSKNTSEHGQLDLLYPSIDSESEILPGENQVFYDNRTQNVDYLNSYYYLESQKLSDNVE
DFTFTRSIEEALDNSAKVYTYFPTLANKVNAGVQGGLFLMWANDVVEDFTTNILRKDTLDKISDVSAIIP
YIGPALNISNSVRRGNFTEAFAVTGVTILLEAFPEFTIPALGAFVIYSKVQERNEIIKTIDNCLEQRIKR
WKDSYEWMMGTWLSRIITQFNNISYQMYDSLNYQAGAIKAKIDLEYKKYSGSDKENIKSQVENLKNSLDV
KISEAMNNINKFIRECSVTYLFKNMLPKVIDELNEFDRNTKAKLINLIDSHNIILVGEVDKLKAKVNNSF
QNTIPFNIFSYTNNSLLKDIINEYFNLEGGGGSGGGGSGGGGSALDNSDSECPLSHDGYCLHDGVCMYIE
ALDKYACNCVVGYIGERCQYRDLKWWELR

SEQ ID 25

MPITINNFNYSDPVDNKNILYLDTHLNTLANEPEKAFRITGNIWVIPDRFSRNSNPNLNKPPRVISPKSG
YYDPNYLSTDSDKDTFLKEIIKLFKRINSREIGEELIYRLSTDIPFPGNNNTPINTFDFDVDENSVDVKT
RQGNNWVKTGSINPSVIITGPRENIIDPETSTFKLTNNTFAAQEGFGALSIISISPRFMLTYSNATNDVG
TPRFSKSEFCMDPILILMHELNHAMHNLYGIAIPNDQTISSVTSNIFYSQYNVKLEYAEIYAFGGPTIDL
IPKSARKYFEEKALDYYRSIAKRLNSITTANPSSFNKYIGEYKQKLIRKYRFVVESSGEVTVNRNKFVEL
YNELTQIFTEFNYAKIYNVQNRKIYLSNVYTPVTANILDDNVYDIQNGFNIPKSNLNVLFMGQNLSRNPA
LRKVNPENMLYLFTKFCVDADDDDKLYNKTLQCRELLVKNIDLPFIGDISDVKTDIFLRKDINEETEVIY
YPDNVSVDQVILSKNTSEHGQLDLLYPSIDSESEILPGENQVFYDNRTQNVDYLNSYYYLESQKLSDNVE
DFTFIRSIEEALDNSAKVYTYFPTLANKVNAGVQGGLFLMWANDVVEDFTTNILRKDTLDKISDVSAIIP
YIGPALNISNSVRRGNFTEAFAVTGVTILLEAFPEFTIPALGAFVIYSKVQERNEIIKTIDNCLEQRIKR
WKDSYEWMMGTWLSRIITQFNNISYQMYDSLNYQAGAIKAKIDLEYKKYSGSDKENIKSQVENLKNSLDV
KISEAMNNINKFIRECSVTYLFKNMLPKVIDELNEFDRNTKAKLINLIDSHNIILVGEVDKLKAKVNNSF
QNTIPFNIFSYTNNSLLKDIINEYENLEGGGGSGGGGSGGGGSALDNSDSECPLSHDGYCLHDGVCMYIE
ALDKYACNCVVGYIGERCQYRDLKWWELR

SEQ ID 26

MPITINNFNYSDPVDNKNILYLDTHLNTLANEPEKAFRITGNIWVIPDRFSRNSNPNLNKPPRVTSPKSG
YYDPNYLSTDSDKDTFLKEIIKLFKRINSREIGEELIYRLSTDIPFPGNNNTPINTFDEDVDENSVDVKT
RQGNNWVKTGSINPSVIITGPRENIIDPETSTFKLTNNTFAAQEGFGALSIISISPRFMLTYSNATNDVG
EGRFSKSEFCMDPILILMHELNHAMHNLYGIAIPNDQTISSVTSNIFYSQYNVKLEYAEIYAFGGPTIDL
IPKSARKYFEEKALDYYRSIAKRLNSITTANPSSFNKYIGEYKQKLIRKYRFVVESSGEVTVNRNKFVEL
YNELTQIFTEENYAKIYNVQNRKIYLSNVYTPVTANILDDNVYDIQNGENIPKSNLNVLFMGQNLSRNPA
LRKVNPENMLYLFTKFCVDADDDDKLYNKTLQCRELLVKNTDLPFIGDISDVKTDIFLRKDINEETEVIY
YPDNVSVDQVILSKNTSEHGQLDLLYPSIDSESEILPGENQVFYDNRTQNVDYLNSYYYLESQKLSDNVE
DFTFIRSIEEALDNSAKVYTYFPTLANKVNAGVQGGLFLMWANDVVEDFTTNILRKDTLDKISDVSAIIP
YIGPALNISNSVRRGNFTEAFAVTGVTILLEAFPEFTIPALGAFVIYSKVQERNEIIKTIDNCLEQRIKR
WKDSYEWMMGTWLSRIITQFNNISYQMYDSLNYQAGAIKAKIDGRYKKYSGSDKENIKSQVENLKNSLDV
KISEAMNNINKFIRECSVTYLEKNMLPKVIDELNEFDRNTKAKLINLIDSHNIILVGEVDKLKAKVNNSF

QNTIPFNIFSYTNNSLLKDIINEYFNLEGGGGSGGGGSGGGGSALDNSDSECPLSHDGYCLHDGVCMYIE

ALDKYACNCVVGYIGERCQYRDLKWWELR

SEQ ID 27

MPITINNFNYSDPVDNKNILYLDTHLNTLANEPEKAFRITGNIWVIPDRFSRNSNPNLNKPPRVTSPKSG

YYDPNYLSTDSDKDTFLKEIIKLFKRINSREIGEELIYRLSTDIPFPGNNNTPINTFDFDVDFNSVDVKT

RQGNNWVKTGSINPSVIITGPRENIIDPETSTFKLTNNTFAAQEGFGALSIISISPRFMLTYSNATNDVG

EGRFSKSEFCMDPILILMHELNHAMHNLYGIAIPNDQTISSVTSNIFYSQYNVKLEYAEIYAFGGPTIDL

IPKSARKYFEEKALDYYRSIAKRLNSITTANPSSFNKYIGEYKQKLIRKYRFVVESSGEVTVNRNKFVEL

YNELTQIFTEFNYAKIYNVQNRKIYLSNVYTPVTANILDDNVYDIQNGFNIPKSNLNVLFMGQNLSRNPA

LRKVNPENMLYLFTKFCVDADDDDKLYNKTLQCRELLVKNTDLPFIGDISDVKTDIFLRKDINEETEVIY

YPDNVSVDQVILSKNTSEHGQLDLLYPSIDSESEILPGENQVFYDNRTQNVDYLNSYYYLESQKLSDNVE

DFTFTRSIEEALDNSAKVYTYFPTLANKVNAGVQGGLFLMWANDVVEDFTTNILRKDTLDKISDVSAIIP

YIGPALNISNSVRRGNFTEAFAVTGVTILLEAFPEFTIPALGAFVIYSKVQERNEIIKTIDNCLEQRIKR

WKDSYEWMMGTWLSRIITQFNNISYQMYDSLNYQAGAIKAKIDLEYKKYIDGRKENIKSQVENLKNSLDV

KISEAMNNINKFIRECSVTYLFKNMLPKVIDELNEFDRNTKAKLINLIDSHNIILVGEVDKLKAKVNNSF

QNTIPFNIFSYTNNSLLKDIINEYFNLEGGGGSGGGGSGGGGSALDNSDSECPLSHDGYCLHDGVCMYIE

ALDKYACNCVVGYIGERCQYRDLKWWELR

SEQ ID 28

MPITINNFNYSDPVDNKNILYLDTHLNTLANEPEKAFRITGNIWVIPDRFSRNSNPNLNKPPRVTSPKSG

YYDPNYLSTDSDKDTFLKEIIKLFKRINSREIGEELIYRLSTDIPFPGNNNTPINTFDFDVDFNSVDVKT

RQGNNWVKTGSINPSVIITGPRENIIDPETSTFKLTNNTFAAQEGFGALSIISISPRFMLTYSNATNDVG

EGRFSKSEFCMDPILILMHELNHAMHNLYGIAIPNDQTISSVTSNIFYSQYNVKLEYAEIYAFGGPTIDL

IPKSARKYFEEKALDYYRSIAKRLNSITTANPSSFNKYIGEYKQKLIRKYRFVVESSGEVTVNRNKFVEL

YNELTQIFTEFNYAKIYNVQNRKIYLSNVYTPVTANILDDNVYDIQNGFNIPKSNLNVLFMGQNLSRNPA

LRKVNPENMLYLFTKFCVDADDDDKLYNKTLQCRELLVKNTDLPFIGDISDVKTDIFLRKDINEETEVIY

YPDNVSVDQVILSKNTSEHGQLDLLYPSIDSESEILPGENQVFYDNRTQNVDYLNSYYYLESQKLSDNVE

DFTFTRSIEEALDNSAKVYTYFPTLANKVNAGVQGGLFLMWANDVVEDFTTNILRKDTLDKISDVSAIIP

YIGPALNISNSVRRGNFTEAFAVTGVTILLEAFPEFTIPALGAFVIYSKVQERNEIIKTIDNCLEQRIKR

WKDSYEWMMGTWLSRIITQFNNISYQMYDSLNYQAGAIKAKIDLEYKKYGVPRKENIKSQVENLKNSLDV

KISEAMNNINKFIRECSVTYLFKNMLPKVIDELNEFDRNTKAKLINLIDSHNIILVGEVDKLKAKVNNSF

QNTIPFNIFSYTNNSLLKDIINEYFNLEGGGGSGGGGSGGGGSALDNSDSECPLSHDGYCLHDGVCMYIE

ALDKYACNCVVGYIGERCQYRDLKWWELR

SEQ ID 29

MTWPVKDFNYSDPVNDNDILYLRIPQNKLITTPVKAFMITQNIWVIPERFSSDTNPSLSKPPRPTSKYQS

YYDPSYLSTDEQKDTFLKGIIKLFKRINERDIGKKLINYLVVGSPFMGDSSTPEDTFDFTRHTTNIAVEK

FENGSWKVTNIITPSVLIFGPLPNILDYTASLTLQGGQQSNPSFEGFGTLSILKVAPEFLLTFSDVTSNQS

SAVLGKSIFCMDPVIALMHELTHSLHQLYGINIPSDKRIRPQVSEGFFSQDGPNVQFEELYTFGGLDVEI

IPQIERSQLREKALGHYKDIAKRLNNINKTIPSSWISNIDKYKKIFSEKYNFDKDNTGNFVVNIDKFNSL

YSDLTNVMSEVVYSSQYNVKNRTHYFSRHYLPVFANILDDNIYTIRDGFNLTNKGFNIENSGQNIERNPA

LQKLSSESVVDLFTKVCDGGGSADDDDKHSDAVFTDNYTRLRRQLAVRRYLNSILNALAGGGGSGGGG

SGGGGSALALQCIKVKNNRLPYVADKDSISQEIFENKIITDETNVQNYSDKFSLDESILDGQVPINPEIV

DPLLPNVNMEPLNLPGEEIVFYDDITKYVDYLNSYYYLESQKLSNNVENITLTTSVEEALGYSNKIYTFL

PSLAEKVNKGVQAGLFLNWANEVVEDFTTNIMKKDTLDKISDVSVIIPYIGPALNIGNSALRGNFNQAFA

TAGVAFLLEGFPEFTIPALGVFTFYSSIQEREKIIKTIENCLEQRVKRWKDSYQWMVSNWLSRITTQFNH

INYQMYDSLSYQADAIKAKIDLEYKKYIDGRKENIKSQVENLKNSLDVKISEAMNNINKFIRECSVTYLF

KNMLPKVIDELNKFDLRTKTELINLIDSHNIILVGEVDRLKAKVNESFENTMPFNIFSYTNNSLLKDIIN

EYFNLEA

SEQ ID 30

MEFVNKQFNYKDPVNGVDIAYIKIPNAGQMQPVKAFKIHNKIWVIPERDTFTNPEEGDLNPPPEAKQVPV

SYYDSTYLSTDNEKDNYLKGVTKLFERIYSTDLGRGLLTSIVRGIPFWGGSTIDTELKVIDTNCINVIQP

DGSYRSEELNLVIIGPSADIIQFECKSFGHEVLNLTRNGYGSTQYIRFSPDFTFGFEESLEVDTNPLLGA

GKFATDPAVTLAHELIHAGHRLYGIAINPNRVFKVNTNAYYEMSGLEVSFEELRTFGGHDAKFIDSLQEN

EFRLYYYNKFKDIASTLNKAKSIVGTTASLQYMKNVFKEKYLLSEDTSGKFSVDKLKFDKLYKMLTEIYT

EDNFVKFFKVLNRKTYLNFDKAVFKINIVPKVNYTIYDGFNLRNTNLAANFNGQNTEINNMNFTKLKNFT

GLFEFYKLLCVDGIITSKTKSDDDDKNKALNLQCIKVNNWDLFFSPSEDNFTNDLNKGEEITSDTNIEAA

EENISLDLIQQYYLTFNFDNEPENISIENLSSDIIGQLELMPNIERFPNGKKYELDKYTMFHYLRAQEFE

HGKSRIALTNSVNEALLNPSRVYTFFSSDYVKKVNKATEAAMFLGWVEQLVYDFTDETSEVSTTDKIADI

TIIIPYIGPALNIGNMLYKDDFVGALIFSGAVILLEFIPEIAIPVLGTFALVSYIANKVLTVQTIDNALS

KRNEKWDEVYKYIVTNWLAKVNTQIDLIRKKMKEALENQAEATKAIINYQYNQYTEEEKNNINFNIDDLS

SKLNESINKAMININKFLNQCSVSYLMNSMIPYGVKRLEDFDASLKDALLKYIYDNRGTLIGQVDRLKDK

VNNTLSTDIPFQLSKYVDNQRLLSTLEGGGGSGGGGSGGGGSALDNSDSECPLSHDQYCLHDGVCMYIEA

LDKYACNCVVGYIGERCQYRDLKWWELR

SEQ ID 31

MEFVNKQFNYKDPVNGVDIAYIKIPNAGQMQPVKAFKIHNKIWVIPERDTFTNPEEGDLNPPPEAKQVPV

SYYDSTYLSTDNEKDNYLKGVTKLFERIYSTDLGRGLLTSIVRGIPFWGGSTIDTELKVIDTNCINVIQP

DGSYRSEELNLVIIGPSADIIQFECKSFGHEVLNLTRNGYGSTQYIRFSPDFTFGFEESLEVDTNPLLGA

GKFATDPAVTLAHELIHAGHRLYGIAINPNRVFKVNTNAYYEMSGLEVSFEELRTFGGHDAKFIDSLQEN

EFRLYYYNKFKDIASTLNKAKSIVGTTASLQYMKNVFKEKYLLSEDTSGKFSVDKLKFDKLYKMLTEIYT

EDNFVKFFKVLNRKTYLNFDKAVFKINIVPKVNYTIYDGFNLRNTNLAANFNGQNTEINNMNFTKLKNFT

GLFEFYKLLCVDGIITSKTKSDDDDKNKALNLQCIKVNNWDLFFSPSEDNFTNDLNKGEEITSDTNIEAA

EENISLDLIQQYYLTFNFDNEPENISIENLSSDIIGQLELMPNIERFPNGKKYELDKYTMFHYLRAQEFE

HGKSRIALTNSVNEALLNPSRVYTFFSSDYVKKVNKATEAAMFLGWVEQLVYDFTDETSEVSTTDKIADI

TIIIPYIGPALNIGNMLYKDDFVGALIFSGAVILLEFIPEIAIPVLGTFALVSYIANKVLTVQTIDNALS

KRNEKWDEVYKYIVTNWLAKVNTQIDLIRKKMKEALENQAEATKAIINYQYNQYTEEEKNNINFNIDDLS

SKLNESINKAMININKFLNQCSVSYLMNSMIPYGVKRLEDFDASLKDALLKYIYDNRGTLIGQVDRLKDK

VNNTLSTDIPFQLSKYVDNQRLLSTLEGGGGSGGGGSGGGGSALDNSDSECPLSHDQYCLHDGVCMYIEA

LDKYACNCVVGYIGERCQYRDLKWWELR

SEQ ID 32

HMGSMEFVNKQFNYKDPVNGVDIAYIKIPNAGQMQPVKAFKIHNKIWVIPERDTFTNPEEGDLNPPPEAK

QVPVSYYDSTYLSTDNEKDNYLKGVTKLFERIYSTDLGRGLLTSIVRGIPFWGGSTIDTELKVIDTNCIN

VIQPDGSYRSEELNLVIIGPSADIIQFECKSFGHEVLNLTRNGYGSTQYIRFSPDFTFGFEESLEVDTNP

LLGAGKFATDPAVTLAHELIHAGHRLYGIAINPNRVFKVNTNAYYEMSGLEVSFEELRTFGGHDAKFIDS

```
LQENEFRLYYYNKFKDIASTLNKAKSIVGTTASLQYMKNVFKEKYLLSEDTSGKFSVDKLKFDKLYKMLT

EIYTEDNFVKFFKVLNRKTYLNFDKAVFKINIVPKVNYTIYDGFNLRNTNLAANFNGQNTEINNMNFTKL

KNFTGLFEFYKLLCVDGIITSKTKSDDDDKNKALNLQCIKVNNWDLFFSPSEDNFTNDLNKGEEITSDTN

IEAAEENISLDLIQQYYLTFNFDNEPENISIENLSSDIIGQLELMPNIERFPNGKKYELDKYTMFHYLRA

QEFEHGKSRIALTNSVNEALLNPSRVYTETSSDYVKKVNKATEAAMFLGWVEQLVYDFTDETSEVSTTDK

IADITIIIPYIGPALNIGNMLYKDDFVGALIFSGAVILLEFIPEIAIPVLGTFALVSYIANKVLTVQTID

NALSKRNEKWDEVYKYIVINWLAKVNTQIDLIRKKMKEALENQAEATKAIINYQYNQYTEEEKNNINFNI

DDLSSKLNESINKAMININKFLNQCSVSYLMNSMIPYGVKRLEDFDASLKDALLKYIYDNRGTLIGQVDR

LKDKVNNTLSTDIPFQLSKYVDNQRLLSTFTEYIKNIINTSLEILNLRYESNHLIDLSRYASKINIGSKV

NFDPIDKNQIQLFNLESSKIEVILKNAIVYNSMYENFSTSFWIRIPKYFNSISLNNEYTIINCMENNSGW

KVSLNYGEIIWTLQDTQEIKQRVVFKYSQMINISDYINRWIFVTITNNRLNNSKIYINGRLIDQKPISNL

GNIHASNNIMFKLDGCRDTHRYIWIKYFNLFDKELNEKEIKDLYDNQSNSGALVILKDFWGDYLQYDKPY

YMLNLYDPNKYVDVNNVGIRGYMYLKGPRGSVMTTNIYLNSSLYRGTKFIIKKYASGNKDNIVRNNDRVY

INVVVKNKEYRLATNASQAGVEKILSALEIPDVGNLSQVVVMKSKNDQGITNKCKMNLQDNNGNDIGFIG

FHQFNNIAKLVASNWYNRQIERSSRTLGCSWEFIPVDDGWGERPLALAHHHHHHHHHH

SEQ ID 33
HMGSMEFVNKQFNYKDPVNGVDIAYIKIPNAGQMQPVKAFKIHNKIWVIPERDTFTNPEEGDLNPPPEAK

QVPVSYYDSTYLSTDNEKDNYLKGVTKLFERIYSTDLGRMLLTSIVRGIPFWGGSTIDTELKVIDTNCIN

VIQPDGSYRSEELNLVIIGPSADIIQFECKSFGHEVLNLTRNGYGSTQYIRFSPDFTFGFEESLEVDTNP

LLGAGKFATDPAVTLAHELIHAGHRLYGIAINPNRVFKVNTNAYYEMSGLEVSFEELRTFGGHDAKFIDG

RQENEFRLYYYNKFKDIASTLNKAKSIVGTTASLQYMKNVFKEKYLLSEDTSGKFSVDKLKFDKLYKMLT

EIYTEDNFVKFFKVLNRKTYLNFDKAVFKINIVPKVNYTIYDGFNLRNTNLAANFNGQNTEINNMNFTKL

KNFTGLFEFYKLLCVDGIITSKTKSDDDDKNKALNLQCIKVNNWDLFFSPSEDNFTNDLNKGEEITSDTN

IEAAEENISLDLIQQYYLTFNFDNEPENISIENLSSDIIGQLELMPNIERFPNGKKYELDKYTMFHYLRA

QEFEHGKSRIALTNSVNEALLNPSRVYTFFSSDYVKKVNKATEAAMFLGWVEQLVYDFTDETSEVSTTDK

IADITIIIPYIGPALNIGNMLYKDDFVGALIFSGAVILLEFIPEIAIPVLGTFALVSYIANKVLTVQTID

NALSKRNEKWDEVYKYIVTNWLAKVNTQIDLIRKKMKEALENQAEATKAIINYQYNQYTEEEKNNINFNI

DDLSSKLNESINKAMININKFLNQCSVSYLMNSMIPYGVKRLEDFDASLKDALLKYIYDNRGTLIGQVDR

LKDKVNNTLSTDIPFQLSKYVDNQRLLSTFTEYIKNIINTSLEILNLRYESNHLIDLSRYASKINIGSKV

NFDPIDKNQIQLFNLESSKIEVILKNAIVYNSMYENFSTSFWIRIPKYFNSISLNNEYTIINCMENNSGW

KVSLNYGEIIWTLQDTQEIKQRVVFKYSQMINISDYINRWIFVTITNNRLNNSKIYINGRLIDQKPISNL

GNIHASNNIMFKLDGCRDTHRYIWIKYFNLFDKELNEKEIKDLYDNQSNSGALVILKDFWGDYLQYDKPY

YMLNLYDPNKYVDVNNVGIRGYMYLKGPRGSVMTTNIYLNSSLYRGTKFIIKKYASGNKDNIVRNNDRVY

INVVVKNKEYRLATNASQAGVEKILSALEIPDVGNLSQVVVMKSKNDQGITNKCKMNLQDNNGNDIGFIG

FHQFNNIAKLVASNWYNRQIERSSRTLGCSWEFIPVDDGWGERPLALAHHHHHHHHHH

SEQ ID 34
HMGSMEFVNKQFNYKDPVNGVDIAYIKIPNAGQMQPVKAFKIHNKIWVIPERDTFTNPEEGDLNPPPEAK

QVPVSYYDSTYLSTDNEKDNYLKGVTKLFERIYSTDLGRMLLTSIVRGIPFWGGSTIDTELKVIDTNCIN

VIQPDGSYRSEELNLVIIGPSADIIQFECKSFGHEVLNLTRNGYGSTQYIRFSPDFTFGFEESLEVDTNP

LLGAGKFATDPAVTLAHELIHAGHRLYGIAINPNRVFKVNTNAYYEMSGLEVSFEELRTFGGHDAKFIDS
```

LQENEFRLYYYNKFKDIASTLNKAKSTVGTTASLQYMKNVFKEKYLLSEDTSGKFSVDKLKFDKLYKMLT

EIYTEDNFVKFFKVLNRKTYLNFDKAVFKINIVPKVNYTIYDGFNLRNTNLAANFNGQNTEINNMNFTKL

KNFTGLFEFYKLLCVDGIITSKTKSDDDDKNKALNLQCIKVNNWDLFFSPSEDNFTNDLNKGEEITSDTN

IEAAEENISLDLIQQYYLTFNFDNEPENISIENLSSDIIGQLELMPNIERFPNGKKYELDKYTMFHYLRA

QEFEHIEGRIALTNSVNEALLNPSRVYTFFSSDYVKKVNKATEAAMFLGWVEQLVYDFTDETSEVSTTDK

IADITIIIPYIGPALNIGNMLYKDDFVGALIFSGAVILLEFIPEIAIPVLGTFALVSYIANKVLTVQTID

NALSKRNEKWDEVYKYIVTNWLAKVNTQIDLIRKKMKEALENQAEATKAIINYQYNQYTEEEKNNINFNI

DDLSSKLNESINKAMININKFLNQCSVSYLMNSMIPYGVKRLEDFDASLKDALLKYIYDNRGTLIGQVDR

LKDKVNNTLSTDIPFQLSKYVDNQRLLSTFTEYIKNIINTSLEILNLRYESNHLIDLSRYASKINIGSKV

NFDPIDKNQIQLFNLESSKIEVILKNAIVYNSMYENFSTSFWIRIPKYFNSISLNNEYTIINCMENNSGW

KVSLNYGEIIWTLQDTQEIKQRVVFKYSQMINISDYINRWIFVTITNNRLNNSKIYINGRLIDQKPISNL

GNIHASNNIMFKLDGCRDTHRYIWIKYFNLFDKELNEKEIKDLYDNQSNSGALVILKDFWGDYLQYDKPY

YMLNLYDPNKYVDVNNVGIRGYMYLKGPRGSVMTTNIYLNSSLYRGTKFIIKKYASGNKDNIVRNNDRVY

INVVVKNKEYRLATNASQAGVEKILSALEIPDVGNLSQVVVMKSKNDQGITNKCKMNLQDNNGNDIGFIG

FHQFNNIAKLVASNWYNRQIERSSRTLGCSWEFIPVDDGWGERPLALAHHHHHHHHH

SEQ ID 35

MPKINSFNYNDPVNDRTILYIKPGGCQEFYKSFNIMKNIWIIPERNVIGTTPQDFHPPTSLKNGDSSYYD

PNYLQSDEEKDRFLKIVTKIFNRINNNLSGGILLEELSKANPYLGNDNTPDNQFHIGDASAVEIKFSNGS

QHILLPNVIIMGAEPDLFETNSSNISLRNNYMPSNHGFGSIAIVTIVPRFSFRFNDNSINEFIQDPALTL

MHELIHSLHGLYGAKGITTTCIITQQQNPLITNRKGINIEEFLTFGGNDLNIITVAQYNDIYTNLLNDYR

KIASKLSKVQVSNPQLNPYKDIFQEKYGLDKDASGIYSVNINKFDDILKKLYSFTEFDLATKFQVKCRET

YIGQYKYFKLSNLLNDSIYNISEGYNINNLKVNFRGQNANLNPRIIKPITGRGLVKKIIRFCKNIVSVKG

IRKSICIEINNGELFFVASENSYNDDNINTPKEIDDTVTSNNNYENDLDQVILNFNSESAPGLSDEKLNL

TIQNDAYIPKYDSNGTSDIEQHDVNELNVFFYLDAQKVPEGENNVNLTSSIDTALLEQPKIYTFFSSEFI

NNVNKPVQAALFVSWIQQVLVDFTTEANQKSTVDKIADISIVVPYIGLALNIGNEAQKGNFKDALELLGA

GILLEFEPELLIPTILVFTIKSFLGSSDNKNKVIKAINNALKERDEKWKEVYSFIVSNWMTKINTQFNKR

KEQMYQALQNQVNAIKTIIESKYNSYTLEEKNELTNKYDIKQIENELNQKVSIAMNNIDRFLTESSISYL

MKLINEVKINKLREYDENVKTYLLNYIIQHGSILGESQQELNSMVTDTLNNSIPFKLSSYTDDKILISYF

NKFFKRIKSSSVLNMRYKNDKYVDTSGYDSNININGDVYKYPTNKNQFGIYNDKLSEVNISQNDYIIYDN

KYKNFSISFWVRIPNYDNKIVNVNNEYTIINCMRDNNSGWKVSLNHNEIIWTLQDNAGINQKLAFNYGNA

NGISDYINKWIFVTITNDRLGDSKLYINGNLIDQKSILNLGNIHVSDNILFKIVNCSYTRYIGIRYFNIF

DKELDETEIQTLYSNEPNTNILKDFWGNYLLYDKEYYLLNVLKPNNFIDRRKDSTLSINNIRSTILLANR

LYSGIKVKIQRVNNSSTNDNLVRKNDQVYINFVASKTHLFPLYADTATTNKEKTIKISSSGNRFNQVVVM

NSVGNNCTMNFKNNNGNNIGLLGFKADTVVASTWYYTHMRDHTNSNGCFWNFISEEHGWQEK

SEQ ID 36

MPKINSFNYNDPVNDRTILYIKPGGCQEFYKSFNIMKNIWIIPERNVIGTTPQDFHPPTSLKNGDSSYYD

PNYLQSDEEKDRFLKIVTKIFNRINNNLSGGILLEELSKANPYLGNDNTPDNQFHIGDASAVEIKFSNGS

QHILLPNVIIMGAEPDLFETNSSNISLRNNYMPSNHGFGSIAIVTFSPEYSFRFNDNSINEFIQDPALTL

MHELIHSLHGLYGAKGITTTCIITQQQNPLITNRKGINIEEFLTFGGNDLNIITVAQYNDIYTNLLNDYR

KIASKLSKVQVSNPQLNPYKDIFQEKYGLDKDASGIYSVNINKFDDILKKLYSFTEFDLATKFQVKCRET

YIGQYKYFKLSNLLNDSIYNISEGYNINNLKVNFRGQNANLNPRIIKPITGRGLVKKIIRFCKNIVSVKG

-continued

IRKSICIEINNGELFFVASENSYNDDNINTPKEIDDTVTSNNNYENDLDQVILNFNSESAPGLSDEKLNL
TIQNDAYIPKYDSNGTSDIEQHDVNELNVFFYLDAQKVPEGENNVNLTSSIDTALLEQPKIYTFFSSEFI
NNVNKPVQAALFVSWIQQVLVDFTTEANQKSTVDKIADISIVVPYIGLALNIGNEAQKGNFKDALELLGA
GILLEFEPELLIPTILVFTIKSFLGSSDNKNKVIKAINNALKERDEKWKEVYSFIVSNWMTKINTQFNKR
KEQMYQALQNQVNAIKTIIESKYNSYIEGRKNELTNKYDIKQIENELNQKVSIAMNNIDRFLTESSISYL
MKLINEVKINKLREYDENVKTYLLNYIIQHGSILGESQQELNSMVTDTLNNSIPFKLSSYTDDKILISYF
NKFFKRIKSSSVLNMRYKNDKYVDTSGYDSNININGDVYKYPTNKNQFGIYNDKLSEVNISQNDYIIYDN
KYKNFSISFWVRIPNYDNKIVNVNNEYTIINCMRDNNSGWKVSLNHNEIIWTLQDNAGINQKLAFNYGNA
NGISDYINKWIFVTITNDRLGDSKLYINGNLIDQKSILNLGNIHVSDNILFKIVNCSYTRYIGIRYFNIF
DKELDETEIQTLYSNEPNTNILKDFWGNYLLYDKEYYLLNVLKPNNFIDRRKDSTLSINNIRSTILLANR
LYSGIKVKIQRVNNSSTNDNLVRKNDQVYINFVASKTHLFPLYADTATTNKEKTIKISSSGNRFNQVVVM
NSVGNNCTMNFKNNNGNNIGLLGFKADTVVASTWYYTHMRDHTNSNGCFWNFISEEHGWQEK

SEQ ID 37

MGSMPKINSFNYNDPVNDRTILYIKPGGCQEFYKSFNIMKNIWIIPERNVIGTTPQDFHPPTSLKNGDSS
YYDPNYLQSDEEKDRFLKIVTKIFNRINNNLSGRGLLEELSKANPYLGNDNTPDNQFHIGDASAVEIKFS
NGSQHILLPNVIIMGAEPDLFETNSSNISLRNNYMPSNHGFGSIAIVTFSPEYSFRFNDNSINEFIQDPA
LTLMHELIHSLHGLYGAKGITTTCIITQQQNPLITNRKGINIEEFLTFGGNDLNIITVAQYNDIYTNLLN
DYRKIASKLSKVQVSNPQLNPYKDIFQEKYGLDKDASGIYSVNINKFDDILKKLYSFTEFDLATKFQVKC
RETYIGQYKYFKLSNLLNDSIYNISEGYNINNLKVNFRGQNANLNPRIIKPITGRGLVKKIIRFCVDGGG
GSADDDDKHSDAVFTDNYTRLRRQLAVRRYLNSILNALAGGGGSGGGGSGGGGSALVLQCIEINNGELFF
VASENSYNDDNINTPKEIDDTVTSNNNYENDLDQVILNFNSESAPGLSDEKLNLTIQNDAYIPKYDSNGT
SDIEQHDVNELNVFFYLDAQKVPEGENNVNLTSSIDTALLEQPKIYTFFSSEFINNVNKPVQAALFVSWI
QQVLVDFTTEANQKSTVDKIADISIVVPYIGLALNIGNEAQKGNFKDALELLGAGILLEFEPELLIPTIL
VFTIKSFLGSSDNKNKVIKAINNALKERDEKWKEVYSFIVSNWMTKINTQFNKRKEQMYQALQNQVNAIK
TIIESKYNSYTLEEKNELTNKYDIKQIENELNQKVSIAMNNIDRFLTESSISYLMKIINEVKINKLREYD
ENVKTYLLNYIIQHGSILGESQQELNSMVTDTLNNSIPFKLSSYTDDKILISYFNKFFKG

SEQ ID 38

MGSMPKINSFNYNDPVNDRTILYIKPGGCQEFYKSFNIMKNIWIIPERNVIGTTPQDFHPPTSLKNGDSS
YYDPNYLQSDEEKDRFLKIVTKIFNRINNNLSGGILLEELSKANPYLGNDNTPDNQFHIGDASAVEIKFS
NGSQHILLPNVIIMGAEPDLFETNSSNISLRNNYMPSNHGFGSIAIVTFSPEYSFRFNDNSINEFIQDPA
LTLMHELIHSLHGLYGAKGITTTCIITQQQNPLITNRKGINIEEFLTFGGNDLNIITVAQYNDIYTNLLN
DYRKIASKLSKVQVSNPQLNPYKDIFQEKYGLDKDASGIYSVNINKFDDILKKLYSFTEFDLATKFQVKC
RETYIGQYKYFKLSNLLNDSIYNISEGYNINNLKVNFRGQNANLNPRIIKPITGRGLVKKIIRFCVDGGG
GSADDDDKHSDAVFTDNYTRLRRQLAVRRYLNSILNALAGGGGSGGGGSGGGGSALVLQCIEINNGELFF
VASENSYNDDNINTPKEIDDTVISNNNYENDLDQVILNFNSESAPGLSDEKLNLTIQNDAYIPKYDSNGT
SDIEQHDVNELNVFFYLDAQKVPEIEGRVNLTSSIDTALLEQPKIYTFFSSEFINNVNKPVQAALFVSWI
QQVLVDFTTEANQKSTVDKIADISIVVPYIGLALNIGNEAQKGNFKDALELLGAGILLEFEPELLIPTIL
VFTIKSFLGSSDNKNKVIKAINNALKERDEKWKEVYSFIVSNWMTKINTQFNKRKEQMYQALQNQVNAIK
TIIESKYNSYTLEEKNELTNKYDIKQIENELNQKVSIAMNNIDRFLTESSISYLMKIINEVKINKLREYD
ENVKTYLLNYIIQHGSILGESQQELNSMVTDTLNNSIPFKLSSYTDDKILISYFNKFFKG

SEQ ID 39

```
MGSMPKINSFNYNDPVNDRTILYIKPGGCQEFYKSFNIMKNIWIIPERNVIGTTPQDFHPPTSLKNGDSS
YYDPNYLQSDEEKDRFLKIVTKIFNRINNNLSGGILLEELSKANPYLGNDNTPDNQFHIGDASAVEIKFS
NGSQHILLPNVIIMGAEPDLFETNSSNISLRNNYMPSNHGFGSIAIVTFSPEYSFRFNDNSINEFIQDPA
LTLMHELIHSLHGLYGADGITTTCIITQQQNPLITNRKGINIEEFLTFGGNDLNIITIEGRNDIYTNLLN
DYRKIASKLSKVQVSNPQLNPYKDIFQEKYGLDKDASGIYSVNINKFDDILKKLYSFTEFDLATKFQVKC
RETYIGQYKYFKLSNLLNDSIYNISEGYNINNLKVNFRGQNANLNPRIIKPITGRGLVKKIIRFCVDGGG
GSADDDDKHSDAVFTDNYTRLRRQLAVRRYLNSILNALAGGGGSGGGGSGGGGSALVLQCIEINNGELFF
VASENSYNDDNINTPKEIDDTVTSNNNYENDLDQVILNFNSESAPGLSDEKLNLTIQNDAYIPKYDSNGT
SDIEQHDVNELNVFFYLDAQKVPEGENNVNLTSSIDTALLEQPKIYTFFSSEFINNVNKPVQAALFVSWI
QQVLVDFTTEANQKSTVDKIADISIVVPYIGLALNIGNEAQKGNFKDALELLGAGILLEFEPELLIPTIL
VFTIKSFLGSSDNKNKVIKAINNALKERDEKWKEVYSFIVSNWMTKINTQFNKRKEQMYQALQNQVNAIK
TIIESKYNSYTLEEKNELTNKYDIKQIENELNQKVSIAMNNIDRFLTESSISYLMKIINEVKINKLREYD
ENVKTYLLNYIIQHGSILGESQQELNSMVTDTLNNSIPFKLSSYTDDKILISYFNKFFKG.
```

---

SEQUENCE LISTING

<160> NUMBER OF SEQ ID NOS: 123

<210> SEQ ID NO 1
<211> LENGTH: 2844
<212> TYPE: DNA
<213> ORGANISM: Artificial sequence
<220> FEATURE:
<223> OTHER INFORMATION: DNA sequence of BoNT/C with Human EGF Targeting
      Moiety

<400> SEQUENCE: 1

```
atgatttccg aatttggctc ggagttcatg ccaattacga ttaacaattt taactatagt      60
gatccggtgg ataataaaaa cattttatac ctggataccc acttgaatac tcttgccaat     120
gagcctgaaa agccttttcg cataacgggt aacatttggg tcattccgga ccgttttagc     180
cggaactcta accctaatct gaataaacct ccgcgtgtca cgtctccgaa aagtgggtat     240
tacgatccaa attatctgag taccgattca gacaaggata cgtttctgaa agaaatcata     300
aaacttttca aaagaatcaa ctcccgtgaa atcggtgaag agctgatcta ccgtctgtcg     360
acggacattc cttttccggg aaacaataac actcccatta ataccttcga ctttgatgtc     420
gatttcaact cagtcgatgt gaaaacccgc cagggtaata ctgggttaa actggatcc      480
attaacccgt ccgttattat cacaggtcct cgtgaaaata ttatagatcc tgagacctcc     540
acgttcaagc tgacgaataa cacttttgcg gcacaggaag ggtttggtgc cctttcaatt     600
atctctatct ctccgcgctt catgttaacg tattctaacg caaccaacga tgttggcgag     660
ggccgcttca gcaaaagtga attctgtatg gatcccattc tgatcttgat gcatgagctt     720
aaccacgcta tgcataatct ttatggtatt gcaatcccaa acgatcagac gatctccagc     780
gttacatcta acatattcta cagccaatat aatgtgaagc tcgaatatgc agagatttac     840
gccttcggtg ggccgaccat tgacctcatt ccaaagtctg cccgtaagta ctttgaggaa     900
aaagcgttgg attactatcg tagcatcgcg aaacgcctga attcaattac aactgcaaac     960
ccatctagct tcaacaaata catcggagaa tataaacaaa agctgatacg caaatatcgc    1020
```

```
tttgtggtcg aatcgtccgg ggaagtgaca gttaatcgaa ataaatttgt tgaactctat    1080
aatgaattaa cgcagatctt cacagaattt aattatgcta aaatctataa tgtacagaac    1140
cggaaaattt atctcagtaa tgtatacaca ccggtgactg ctaacattct ggacgataac    1200
gtctacgata ttcaaaatgg ctttaatatc ccgaagagca acttgaatgt cctcttcatg    1260
gggcagaact tgtcacgtaa cccagcgctg cgaaaagtta acccagaaaa tatgttgtac    1320
ctctttacaa aattctgtgt agacgccgac gatgacgata aactgtacaa caaaaccctg    1380
caatgccgtg aacttctggt taagaacacc gacctgccgt tcattgggga catcagtgat    1440
gtcaaaacgg atattttttct tcggaaggat attaatgagg aaaccgaagt gataccctgac  1500
aatgtgtcgg tagatcaggt aatcctgagt aagaacacca gcgagcatgg gcagctggat    1560
ctgttgtatc cgagcattga cagcgagtcg gaaatactgc ccggcgaaaa tcaagttttt    1620
tatgacaatc ggacccagaa tgttgattat ctgaatagtt actattactt ggagagccaa    1680
aaattatcag ataatgtgga agactttacc tttacccggt ctatcgaaga ggcgctggat    1740
aacagcgcga aagtttacac ttatttttccc acgctcgcaa acaaagttaa tgctggcgta    1800
cagggtggat tattcttat gtgggcgaat gatgtggtag aggactttac aaccaacatc    1860
ctgcgcaaag acactttaga caaaatttct gacgtctcgg ccattatccc gtatataggt    1920
ccggccttaa acataagcaa ttcggttcgc cgtggcaact tcacagaagc cttcgctgtg    1980
actggtgtga ccattctgtt ggaagcattt cctgagttta cgatcccggc tctgggcgca    2040
tttgtaattt actctaaagt tcaggaacga aatgaaatta taaaaactat cgataattgc    2100
ctggaacagc gtatcaagag atggaaggat tcctatgagt ggatgatggg gacctggctg    2160
tcaagaatta tcacacagtt taataacata tcctatcaaa tgtatgatag cttaaactat    2220
caagcaggag cgataaaggc gaaaattgac ctggaataca gaaatattc tggttcggat    2280
aaagagaata ttaaaagtca ggtggaaaat ctgaaaaata gtttagatgt caaaatttct    2340
gaggcgatga taacattaa caaattcatc cgcgagtgca gtgtaactta tttgtttaag    2400
aatatgttac ccaaagttat cgacgaactg aatgaatttg atcgtaatac aaagccaaa    2460
ttgatcaacc tcatcgactc tcataacatc attctggtgg agaagtcga caaactgaaa    2520
gctaaggtga ataacagctt ccagaataca attccgttta atatttttctc atacaccaat    2580
aactcgctgc ttaaagatat tatcaacgaa tatttttaatc tggagggtgg cggtggcagt    2640
ggcggtggcg gatccggcgg tggcggtagc gcactggata attcagattc cgaatgtcca    2700
ctgtcacacg atggttattg tcttcatgat ggcgtgtgca tgtatataga agcgttagat    2760
aaatacgctt gcaactgcgt ggttggctat atcggcgaac gttgtcagta tcgtgattta    2820
aagtggtggg aattacgcta atga                                           2844
```

<210> SEQ ID NO 2
<211> LENGTH: 945
<212> TYPE: PRT
<213> ORGANISM: Artificial sequence
<220> FEATURE:
<223> OTHER INFORMATION: Protein sequence of BoNT/C with Human EGF
      Targeting Moiety

<400> SEQUENCE: 2

Ile Ser Glu Phe Gly Ser Glu Phe Met Pro Ile Thr Ile Asn Asn Phe
1               5                   10                  15

Asn Tyr Ser Asp Pro Val Asp Asn Lys Asn Ile Leu Tyr Leu Asp Thr
            20                  25                  30

-continued

```
His Leu Asn Thr Leu Ala Asn Glu Pro Glu Lys Ala Phe Arg Ile Thr
         35                  40                  45
Gly Asn Ile Trp Val Ile Pro Asp Arg Phe Ser Arg Asn Ser Asn Pro
 50                  55                  60
Asn Leu Asn Lys Pro Pro Arg Val Thr Ser Pro Lys Ser Gly Tyr Tyr
 65                  70                  75                  80
Asp Pro Asn Tyr Leu Ser Thr Asp Ser Asp Lys Asp Thr Phe Leu Lys
                 85                  90                  95
Glu Ile Ile Lys Leu Phe Lys Arg Ile Asn Ser Arg Glu Ile Gly Glu
             100                 105                 110
Glu Leu Ile Tyr Arg Leu Ser Thr Asp Ile Pro Phe Pro Gly Asn Asn
             115                 120                 125
Asn Thr Pro Ile Asn Thr Phe Asp Phe Asp Val Asp Phe Asn Ser Val
 130                 135                 140
Asp Val Lys Thr Arg Gln Gly Asn Asn Trp Val Lys Thr Gly Ser Ile
 145                 150                 155                 160
Asn Pro Ser Val Ile Ile Thr Gly Pro Arg Glu Asn Ile Ile Asp Pro
                 165                 170                 175
Glu Thr Ser Thr Phe Lys Leu Thr Asn Asn Thr Phe Ala Ala Gln Glu
             180                 185                 190
Gly Phe Gly Ala Leu Ser Ile Ile Ser Ile Ser Pro Arg Phe Met Leu
             195                 200                 205
Thr Tyr Ser Asn Ala Thr Asn Asp Val Gly Glu Gly Arg Phe Ser Lys
             210                 215                 220
Ser Glu Phe Cys Met Asp Pro Ile Leu Ile Leu Met His Glu Leu Asn
 225                 230                 235                 240
His Ala Met His Asn Leu Tyr Gly Ile Ala Ile Pro Asn Asp Gln Thr
                 245                 250                 255
Ile Ser Ser Val Thr Ser Asn Ile Phe Tyr Ser Gln Tyr Asn Val Lys
             260                 265                 270
Leu Glu Tyr Ala Glu Ile Tyr Ala Phe Gly Gly Pro Thr Ile Asp Leu
             275                 280                 285
Ile Pro Lys Ser Ala Arg Lys Tyr Phe Glu Glu Lys Ala Leu Asp Tyr
             290                 295                 300
Tyr Arg Ser Ile Ala Lys Arg Leu Asn Ser Ile Thr Thr Ala Asn Pro
 305                 310                 315                 320
Ser Ser Phe Asn Lys Tyr Ile Gly Glu Tyr Lys Gln Lys Leu Ile Arg
                 325                 330                 335
Lys Tyr Arg Phe Val Val Glu Ser Ser Gly Glu Val Thr Val Asn Arg
             340                 345                 350
Asn Lys Phe Val Glu Leu Tyr Asn Glu Leu Thr Gln Ile Phe Thr Glu
             355                 360                 365
Phe Asn Tyr Ala Lys Ile Tyr Asn Val Gln Asn Arg Lys Ile Tyr Leu
             370                 375                 380
Ser Asn Val Tyr Thr Pro Val Thr Ala Asn Ile Leu Asp Asp Asn Val
 385                 390                 395                 400
Tyr Asp Ile Gln Asn Gly Phe Asn Ile Pro Lys Ser Asn Leu Asn Val
                 405                 410                 415
Leu Phe Met Gly Gln Asn Leu Ser Arg Asn Pro Ala Leu Arg Lys Val
             420                 425                 430
Asn Pro Glu Asn Met Leu Tyr Leu Phe Thr Lys Phe Cys Val Asp Ala
             435                 440                 445
Asp Asp Asp Asp Lys Leu Tyr Asn Lys Thr Leu Gln Cys Arg Glu Leu
```

-continued

```
            450                 455                 460
Leu Val Lys Asn Thr Asp Leu Pro Phe Ile Gly Asp Ile Ser Asp Val
465                 470                 475                 480

Lys Thr Asp Ile Phe Leu Arg Lys Asp Ile Asn Glu Glu Thr Glu Val
                485                 490                 495

Ile Pro Asp Asn Val Ser Val Asp Gln Val Ile Leu Ser Lys Asn Thr
                500                 505                 510

Ser Glu His Gly Gln Leu Asp Leu Leu Tyr Pro Ser Ile Asp Ser Glu
            515                 520                 525

Ser Glu Ile Leu Pro Gly Glu Asn Gln Val Phe Tyr Asp Asn Arg Thr
            530                 535                 540

Gln Asn Val Asp Tyr Leu Asn Ser Tyr Tyr Leu Glu Ser Gln Lys
545                 550                 555                 560

Leu Ser Asp Asn Val Glu Asp Phe Thr Phe Thr Arg Ser Ile Glu Glu
                565                 570                 575

Ala Leu Asp Asn Ser Ala Lys Val Tyr Thr Tyr Phe Pro Thr Leu Ala
                580                 585                 590

Asn Lys Val Asn Ala Gly Val Gln Gly Gly Leu Phe Leu Met Trp Ala
            595                 600                 605

Asn Asp Val Val Glu Asp Phe Thr Thr Asn Ile Leu Arg Lys Asp Thr
            610                 615                 620

Leu Asp Lys Ile Ser Asp Val Ser Ala Ile Pro Tyr Ile Gly Pro
625                 630                 635                 640

Ala Leu Asn Ile Ser Asn Ser Val Arg Arg Gly Asn Phe Thr Glu Ala
                645                 650                 655

Phe Ala Val Thr Gly Val Thr Ile Leu Leu Glu Ala Phe Pro Glu Phe
                660                 665                 670

Thr Ile Pro Ala Leu Gly Ala Phe Val Ile Tyr Ser Lys Val Gln Glu
            675                 680                 685

Arg Asn Glu Ile Ile Lys Thr Ile Asp Asn Cys Leu Glu Gln Arg Ile
            690                 695                 700

Lys Arg Trp Lys Asp Ser Tyr Glu Trp Met Met Gly Thr Trp Leu Ser
705                 710                 715                 720

Arg Ile Ile Thr Gln Phe Asn Asn Ile Ser Tyr Gln Met Tyr Asp Ser
                725                 730                 735

Leu Asn Tyr Gln Ala Gly Ala Ile Lys Ala Lys Ile Asp Leu Glu Tyr
                740                 745                 750

Lys Lys Tyr Ser Gly Ser Asp Lys Glu Asn Ile Lys Ser Gln Val Glu
            755                 760                 765

Asn Leu Lys Asn Ser Leu Asp Val Lys Ile Ser Glu Ala Met Asn Asn
            770                 775                 780

Ile Asn Lys Phe Ile Arg Glu Cys Ser Val Thr Tyr Leu Phe Lys Asn
785                 790                 795                 800

Met Leu Pro Lys Val Ile Asp Glu Leu Asn Glu Phe Asp Arg Asn Thr
                805                 810                 815

Lys Ala Lys Leu Ile Asn Leu Ile Asp Ser His Asn Ile Ile Leu Val
                820                 825                 830

Gly Glu Val Asp Lys Leu Lys Ala Lys Val Asn Asn Ser Phe Gln Asn
            835                 840                 845

Thr Ile Pro Phe Asn Ile Phe Ser Tyr Thr Asn Asn Ser Leu Leu Lys
            850                 855                 860

Asp Ile Ile Asn Glu Tyr Phe Asn Leu Glu Gly Gly Gly Ser Gly
865                 870                 875                 880
```

Gly Gly Gly Ser Gly Gly Gly Ser Ala Leu Asp Asn Ser Asp Ser
            885                 890                 895

Glu Cys Pro Leu Ser His Asp Gly Tyr Cys Leu His Asp Gly Val Cys
        900                 905                 910

Met Tyr Ile Glu Ala Leu Asp Lys Tyr Ala Cys Asn Cys Val Val Gly
    915                 920                 925

Tyr Ile Gly Glu Arg Cys Gln Tyr Arg Asp Leu Lys Trp Trp Glu Leu
    930                 935                 940

Arg
945

<210> SEQ ID NO 3
<211> LENGTH: 2844
<212> TYPE: DNA
<213> ORGANISM: Artificial sequence
<220> FEATURE:
<223> OTHER INFORMATION: DNA sequence of BoNT/C with Human EGF Targeting
      Moiety and Factor Xa Protease Cleavage Site

<400> SEQUENCE: 3

```
atgatttccg aatttggctc ggagttcatg ccaattacga ttaacaattt taactatagt     60
gatccggtgg ataataaaaa cattttatac ctggataccc acttgaatac tcttgccaat    120
gagcctgaaa aagcctttcg cataacgggt aacatttggg tcattccgga ccgttttagc    180
cggaactcta accctaatct gaataaacct ccgcgtgtca cgtctccgaa aagtgggtat    240
tacgatccaa attatctgag taccgattca gacaaggata cgtttctgaa agaaatcata    300
aaacttttca aaagaatcaa ctcccgtgaa atcggtgaag agctgatcta ccgtctgtcg    360
acggacattc cttttccggg aaacaataac actcccatta ataccttcga ctttgatgtc    420
gatttcaact cagtcgatgt gaaaacccgc cagggtaata actgggttaa aactggatcc    480
attaacccgt ccgttattat cacaggtcct cgtgaaaata ttatagatcc tgagacctcc    540
acgttcaagc tgacgaataa cacttttgcg gcacaggaag ggtttggtgc cctttcaatt    600
atctctatct ctccgcgctt catgttaacg tattctaacg caaccaacga tgttatcgag    660
ggccgcttca gcaaaagtga attctgtatg gatcccattc tgatcttgat gcatgagctt    720
aaccacgcta tgcataatct ttatggtatt gcaatcccaa acgatcagac gatctccagc    780
gttacatcta acatattcta cagccaatat aatgtgaagc tcgaatatgc agagatttac    840
gccttcggtg ggccgaccat tgacctcatt ccaaagtctg cccgtaagta ctttgaggaa    900
aaagcgttgg attactatcg tagcatcgcg aaacgcctga attcaattac aactgcaaac    960
ccatctagct tcaacaaata catcggagaa tataaacaaa agctgatacg caaatatcgc   1020
tttgtggtcg aatcgtccgg ggaagtgaca gttaatcgaa ataaatttgt tgaactctat   1080
aatgaattaa cgcagatctt cacagaattt aattatgcta aaatctataa tgtacagaac   1140
cggaaaattt atctcagtaa tgtatacaca ccggtgactg ctaacattct ggacgataac   1200
gtctacgata ttcaaaatgg ctttaatatc ccgaagagca acttgaatgt cctcttcatg   1260
gggcagaact tgtcacgtaa cccagcgctg cgaaaagtta acccagaaaa tatgttgtac   1320
ctctttacaa aattctgtgt agacgccgac gatgacgata aactgtacaa caaaaccctg   1380
caatgccgtg aacttctggt taagaacacc gacctgccgt tcattgggga catcagtgat   1440
gtcaaaacgg atatttttct tcggaaggat attaatgagg aaaccgaagt gatacctgac   1500
aatgtgtcgg tagatcaggt aatcctgagt aagaacacca gcgagcatgg gcagctggat   1560
```

| ctgttgtatc cgagcattga cagcgagtcg gaaatactgc ccggcgaaaa tcaagttttt | 1620 |
| tatgacaatc ggacccagaa tgttgattat ctgaatagtt actattactt ggagagccaa | 1680 |
| aaattatcag ataatgtgga agactttacc tttacccggt ctatcgaaga ggcgctggat | 1740 |
| aacagcgcga agtttacac ttattttccc acgctcgcaa acaaagttaa tgctggcgta | 1800 |
| cagggtggat tatttcttat gtgggcgaat gatgtggtag aggactttac aaccaacatc | 1860 |
| ctgcgcaaag acactttaga caaaatttct gacgtctcgg ccattatccc gtatataggt | 1920 |
| ccggccttaa acataagcaa ttcggttcgc cgtggcaact tcacagaagc cttcgctgtg | 1980 |
| actggtgtga ccattctgtt ggaagcattt cctgagtta cgatcccggc tctgggcgca | 2040 |
| tttgtaattt actctaaagt tcaggaacga atgaaatta taaaaactat cgataattgc | 2100 |
| ctggaacagc gtatcaagag atggaaggat tcctatgagt ggatgatggg gacctggctg | 2160 |
| tcaagaatta tcacacagtt taataacata tcctatcaaa tgtatgatag cttaaactat | 2220 |
| caagcaggag cgataaaggc gaaaattgac ctggaataca agaaatattc tggttcggat | 2280 |
| aaagagaata ttaaaagtca ggtggaaaat ctgaaaaata gtttagatgt caaaatttct | 2340 |
| gaggcgatga ataacattaa caaattcatc cgcgagtgca gtgtaactta tttgtttaag | 2400 |
| aatatgttac ccaagttat cgacgaactg aatgaatttg atcgtaatac aaagccaaa | 2460 |
| ttgatcaacc tcatcgactc tcataacatc attctggtgg gagaagtcga caactgaaa | 2520 |
| gctaaggtga ataacagctt ccagaataca attccgttta tattttctc atacaccaat | 2580 |
| aactcgctgc ttaaagatat tatcaacgaa tattttaatc tggagggtgg cggtggcagt | 2640 |
| ggcggtggcg gatccggcgg tggcggtagc gcactggata ttcagattc cgaatgtcca | 2700 |
| ctgtcacacg atggttattg tcttcatgat ggcgtgtgca tgtatataga agcgttagat | 2760 |
| aaatacgctt gcaactgcgt ggttggctat atcggcgaac gttgtcagta tcgtgattta | 2820 |
| aagtggtggg aattacgcta atga | 2844 |

<210> SEQ ID NO 4
<211> LENGTH: 946
<212> TYPE: PRT
<213> ORGANISM: Artificial sequence
<220> FEATURE:
<223> OTHER INFORMATION: Protein sequence of BoNT/C with Human EGF
      Targeting Moiety and Factor Xa Protease Cleavage Site

<400> SEQUENCE: 4

```
Met Ile Ser Glu Phe Gly Ser Glu Phe Met Pro Ile Thr Ile Asn Asn
1               5                   10                  15

Phe Asn Tyr Ser Asp Pro Val Asp Lys Asn Ile Leu Tyr Leu Asp
            20                  25                  30

Thr His Leu Asn Thr Leu Ala Asn Glu Pro Glu Lys Ala Phe Arg Ile
        35                  40                  45

Thr Gly Asn Ile Trp Val Ile Pro Asp Arg Phe Ser Arg Asn Ser Asn
    50                  55                  60

Pro Asn Leu Asn Lys Pro Pro Arg Val Thr Ser Pro Lys Ser Gly Tyr
65                  70                  75                  80

Tyr Asp Pro Asn Tyr Leu Ser Thr Asp Ser Asp Lys Asp Thr Phe Leu
                85                  90                  95

Lys Glu Ile Ile Lys Leu Phe Lys Arg Ile Asn Ser Arg Glu Ile Gly
            100                 105                 110

Glu Glu Leu Ile Tyr Arg Leu Ser Thr Asp Ile Pro Phe Pro Gly Asn
        115                 120                 125
```

```
Asn Asn Thr Pro Ile Asn Thr Phe Asp Phe Asp Val Asp Phe Asn Ser
    130                 135                 140

Val Asp Val Lys Thr Arg Gln Gly Asn Asn Trp Val Lys Thr Gly Ser
145                 150                 155                 160

Ile Asn Pro Ser Val Ile Ile Thr Gly Pro Arg Glu Asn Ile Ile Asp
                165                 170                 175

Pro Glu Thr Ser Thr Phe Lys Leu Thr Asn Asn Thr Phe Ala Ala Gln
            180                 185                 190

Glu Gly Phe Gly Ala Leu Ser Ile Ile Ser Ile Ser Pro Arg Phe Met
        195                 200                 205

Leu Thr Tyr Ser Asn Ala Thr Asn Asp Val Ile Glu Gly Arg Phe Ser
    210                 215                 220

Lys Ser Glu Phe Cys Met Asp Pro Ile Leu Ile Leu Met His Glu Leu
225                 230                 235                 240

Asn His Ala Met His Asn Leu Tyr Gly Ile Ala Ile Pro Asn Asp Gln
                245                 250                 255

Thr Ile Ser Ser Val Thr Ser Asn Ile Phe Tyr Ser Gln Tyr Asn Val
            260                 265                 270

Lys Leu Glu Tyr Ala Glu Ile Tyr Ala Phe Gly Gly Pro Thr Ile Asp
        275                 280                 285

Leu Ile Pro Lys Ser Ala Arg Lys Tyr Phe Glu Glu Lys Ala Leu Asp
    290                 295                 300

Tyr Tyr Arg Ser Ile Ala Lys Arg Leu Asn Ser Ile Thr Thr Ala Asn
305                 310                 315                 320

Pro Ser Ser Phe Asn Lys Tyr Ile Gly Glu Tyr Lys Gln Lys Leu Ile
                325                 330                 335

Arg Lys Tyr Arg Phe Val Val Glu Ser Ser Gly Glu Val Thr Val Asn
            340                 345                 350

Arg Asn Lys Phe Val Glu Leu Tyr Asn Glu Leu Thr Gln Ile Phe Thr
        355                 360                 365

Glu Phe Asn Tyr Ala Lys Ile Tyr Asn Val Gln Asn Arg Lys Ile Tyr
    370                 375                 380

Leu Ser Asn Val Tyr Thr Pro Val Thr Ala Asn Ile Leu Asp Asp Asn
385                 390                 395                 400

Val Tyr Asp Ile Gln Asn Gly Phe Asn Ile Pro Lys Ser Asn Leu Asn
                405                 410                 415

Val Leu Phe Met Gly Gln Asn Leu Ser Arg Asn Pro Ala Leu Arg Lys
            420                 425                 430

Val Asn Pro Glu Asn Met Leu Tyr Leu Phe Thr Lys Phe Cys Val Asp
        435                 440                 445

Ala Asp Asp Asp Lys Leu Tyr Asn Lys Thr Leu Gln Cys Arg Glu
    450                 455                 460

Leu Leu Val Lys Asn Thr Asp Leu Pro Phe Ile Gly Asp Ile Ser Asp
465                 470                 475                 480

Val Lys Thr Asp Ile Phe Leu Arg Lys Asp Ile Asn Glu Glu Thr Glu
                485                 490                 495

Val Ile Pro Asp Asn Val Ser Val Asp Gln Val Ile Leu Ser Lys Asn
            500                 505                 510

Thr Ser Glu His Gly Gln Leu Asp Leu Leu Tyr Pro Ser Ile Asp Ser
        515                 520                 525

Glu Ser Glu Ile Leu Pro Gly Glu Asn Gln Val Phe Tyr Asp Asn Arg
    530                 535                 540

Thr Gln Asn Val Asp Tyr Leu Asn Ser Tyr Tyr Tyr Leu Glu Ser Gln
```

```
            545                 550                 555                 560
        Lys Leu Ser Asp Asn Val Glu Asp Phe Thr Phe Thr Arg Ser Ile Glu
                            565                 570                 575
        Glu Ala Leu Asp Asn Ser Ala Lys Val Tyr Thr Tyr Phe Pro Thr Leu
                            580                 585                 590
        Ala Asn Lys Val Asn Ala Gly Val Gln Gly Gly Leu Phe Leu Met Trp
                            595                 600                 605
        Ala Asn Asp Val Val Glu Asp Phe Thr Thr Asn Ile Leu Arg Lys Asp
                            610                 615                 620
        Thr Leu Asp Lys Ile Ser Asp Val Ser Ala Ile Ile Pro Tyr Ile Gly
        625                 630                 635                 640
        Pro Ala Leu Asn Ile Ser Asn Ser Val Arg Arg Gly Asn Phe Thr Glu
                            645                 650                 655
        Ala Phe Ala Val Thr Gly Val Thr Ile Leu Leu Glu Ala Phe Pro Glu
                            660                 665                 670
        Phe Thr Ile Pro Ala Leu Gly Ala Phe Val Ile Tyr Ser Lys Val Gln
                            675                 680                 685
        Glu Arg Asn Glu Ile Ile Lys Thr Ile Asp Asn Cys Leu Glu Gln Arg
                            690                 695                 700
        Ile Lys Arg Trp Lys Asp Ser Tyr Glu Trp Met Met Gly Thr Trp Leu
        705                 710                 715                 720
        Ser Arg Ile Ile Thr Gln Phe Asn Asn Ile Ser Tyr Gln Met Tyr Asp
                            725                 730                 735
        Ser Leu Asn Tyr Gln Ala Gly Ala Ile Lys Ala Lys Ile Asp Leu Glu
                            740                 745                 750
        Tyr Lys Lys Tyr Ser Gly Ser Asp Lys Glu Asn Ile Lys Ser Gln Val
                            755                 760                 765
        Glu Asn Leu Lys Asn Ser Leu Asp Val Lys Ile Ser Glu Ala Met Asn
                            770                 775                 780
        Asn Ile Asn Lys Phe Ile Arg Glu Cys Ser Val Thr Tyr Leu Phe Lys
        785                 790                 795                 800
        Asn Met Leu Pro Lys Val Ile Asp Glu Leu Asn Glu Phe Asp Arg Asn
                            805                 810                 815
        Thr Lys Ala Lys Leu Ile Asn Leu Ile Asp Ser His Asn Ile Ile Leu
                            820                 825                 830
        Val Gly Glu Val Asp Lys Leu Lys Ala Lys Val Asn Asn Ser Phe Gln
                            835                 840                 845
        Asn Thr Ile Pro Phe Asn Ile Phe Ser Tyr Thr Asn Asn Ser Leu Leu
                            850                 855                 860
        Lys Asp Ile Ile Asn Glu Tyr Phe Asn Leu Glu Gly Gly Gly Gly Ser
        865                 870                 875                 880
        Gly Gly Gly Gly Ser Gly Gly Gly Ser Ala Leu Asp Asn Ser Asp
                            885                 890                 895
        Ser Glu Cys Pro Leu Ser His Asp Gly Tyr Cys Leu His Asp Gly Val
                            900                 905                 910
        Cys Met Tyr Ile Glu Ala Leu Asp Lys Tyr Ala Cys Asn Cys Val Val
                            915                 920                 925
        Gly Tyr Ile Gly Glu Arg Cys Gln Tyr Arg Asp Leu Lys Trp Trp Glu
                            930                 935                 940
        Leu Arg
        945

<210> SEQ ID NO 5
```

<211> LENGTH: 2844
<212> TYPE: DNA
<213> ORGANISM: Artificial sequence
<220> FEATURE:
<223> OTHER INFORMATION: DNA sequence of BoNT/C with Human EGF Targeting
Moiety and Thrombin Protease Cleavage Site

<400> SEQUENCE: 5
atgatttccg aatttggctc ggagttcatg ccaattacga ttaacaattt taactatagt 60
gatccggtgg ataataaaaa cattttatac ctggataccc acttgaatac tcttgccaat 120
gagcctgaaa aagcctttcg cataacgggt aacatttggg tcattccgga ccgttttagc 180
cggaactcta accctaatct gaataaacct ccgcgtgtca cgtctccgaa aagtgggtat 240
tacgatccaa attatctgag taccgattca gacaaggata cgtttctgaa agaaatcata 300
aaacttttca aaagaatcaa ctcccgtgaa atcggtgaag agctgatcta ccgtctgtcg 360
acggacattc cttttccggg aaacaataac actcccatta ataccttcga ctttgatgtc 420
gatttcaact cagtcgatgt gaaaacccgc cagggtaata actgggttaa aactggatcc 480
attaacccgt ccgttattat cacaggtcct cgtgaaaata ttatagatcc tgagacctcc 540
acgttcaagc tgacgaataa cacttttgcg gcacaggaag ggtttggtgc cctttcaatt 600
atctctatcg ttccgcgctt ctccttaacg tattctaacg caaccaacga tgttggcgag 660
ggccgcttca gcaaaagtga attctgtatg gatcccattc tgatcttgat gcatgagctt 720
aaccacgcta tgcataatct ttatggtatt gcaatcccaa acgatcagac gatctccagc 780
gttacatcta acatattcta cagccaatat aatgtgaagc tcgaatatgc agagatttac 840
gccttcggtg ggccgaccat tgacctcatt ccaaagtctg cccgtaagta ctttgaggaa 900
aaagcgttgg attactatcg tagcatcgcg aaacgcctga attcaattac aactgcaaac 960
ccatctagct tcaacaaata catcggagaa tataaacaaa agctgatacg caaatatcgc 1020
tttgtggtcg aatcgtccgg ggaagtgaca gttaatcgaa ataaatttgt tgaactctat 1080
aatgaattaa cgcagatctt cacagaattt aattatgcta aaatctataa tgtacagaac 1140
cggaaaattt atctcagtaa tgtatacaca ccggtgactg ctaacattct ggacgataac 1200
gtctacgata ttcaaaatgg ctttaatatc ccgaagagca acttgaatgt cctcttcatg 1260
gggcagaact tgtcacgtaa cccagcgctg cgaaaagtta acccagaaaa tatgttgtac 1320
ctctttacaa aattctgtgt agacgccgac gatgacgata aactgtacaa caaaaccctg 1380
caatgccgtg aacttctggt taagaacacc gacctgccgt tcattgggga catcagtgat 1440
gtcaaaacgg atatttttct tcggaaggat attaatgagg aaaccgaagt gatacctgac 1500
aatgtgtcgg tagatcaggt aatcctgagt aagaacacca gcgagcatgg gcagctggat 1560
ctgttgtatc cgagcattga cagcgagtcg gaaatactgc ccggcgaaaa tcaagttttt 1620
tatgacaatc ggacccagaa tgttgattat ctgaatagtt actattactt ggagagccaa 1680
aaattatcag ataatgtgga agactttacc tttacccggt ctatcgaaga ggcgctggat 1740
aacagcgcga aagtttacac ttattttccc acgctcgcaa acaaagttaa tgctggcgta 1800
cagggtggat tatttcttat gtgggcgaat gatgtggtag aggactttac aaccaacatc 1860
ctgcgcaaag acactttaga caaaatttct gacgtctcgg ccattatccc gtatataggt 1920
ccggccttaa acataagcaa ttcggttcgc cgtggcaact tcacagaagc cttcgctgtg 1980
actggtgtga ccattctgtt ggaagcattt cctgagttta cgatcccggc tctgggcgca 2040
tttgtaattt actctaaagt tcaggaacga aatgaaatta taaaaactat cgataattgc 2100

```
ctggaacagc gtatcaagag atggaaggat ccctatgagt ggatgatggg gacctggctg    2160
tcaagaatta tcacacagtt taataacata tcctatcaaa tgtatgatag cttaaactat    2220
caagcaggag cgataaaggc gaaaattgac ctggaataca agaaatattc tggttcggat    2280
aaagagaata ttaaaagtca ggtggaaaat ctgaaaaata gtttagatgt caaaatttct    2340
gaggcgatga ataacattaa caattcatc cgcgagtgca gtgtaactta tttgtttaag    2400
aatatgttac ccaaagttat cgacgaactg aatgaatttg atcgtaatac caaagccaaa    2460
ttgatcaacc tcatcgactc tcataacatc attctggtgg gagaagtcga caaactgaaa    2520
gctaaggtga ataacagctt ccagaataca attccgttta atattttctc atacaccaat    2580
aactcgctgc ttaaagatat tatcaacgaa tattttaatc tggagggtgg cggtggcagt    2640
ggcggtggcg gatccggcgg tggcggtagc gcactggata attcagattc cgaatgtcca    2700
ctgtcacacg atggttattg tcttcatgat ggcgtgtgca tgtatataga agcgttagat    2760
aaatacgctt gcaactgcgt ggttggctat atcggcgaac gttgtcagta tcgtgattta    2820
aagtggtggg aattacgcta atga                                           2844
```

<210

-continued

```
Lys Ser Glu Phe Cys Met Asp Pro Ile Leu Ile Leu Met His Glu Leu
225                 230                 235                 240

Asn His Ala Met His Asn Leu Tyr Gly Ile Ala Ile Pro Asn Asp Gln
            245                 250                 255

Thr Ile Ser Ser Val Thr Ser Asn Ile Phe Tyr Ser Gln Tyr Asn Val
        260                 265                 270

Lys Leu Glu Tyr Ala Glu Ile Tyr Ala Phe Gly Gly Pro Thr Ile Asp
    275                 280                 285

Leu Ile Pro Lys Ser Ala Arg Lys Tyr Phe Glu Glu Lys Ala Leu Asp
    290                 295                 300

Tyr Tyr Arg Ser Ile Ala Lys Arg Leu Asn Ser Ile Thr Thr Ala Asn
305                 310                 315                 320

Pro Ser Ser Phe Asn Lys Tyr Ile Gly Glu Tyr Lys Gln Lys Leu Ile
            325                 330                 335

Arg Lys Tyr Arg Phe Val Val Glu Ser Ser Gly Glu Val Thr Val Asn
        340                 345                 350

Arg Asn Lys Phe Val Glu Leu Tyr Asn Glu Leu Thr Gln Ile Phe Thr
    355                 360                 365

Glu Phe Asn Tyr Ala Lys Ile Tyr Asn Val Gln Asn Arg Lys Ile Tyr
370                 375                 380

Leu Ser Asn Val Tyr Thr Pro Val Thr Ala Asn Ile Leu Asp Asp Asn
385                 390                 395                 400

Val Tyr Asp Ile Gln Asn Gly Phe Asn Ile Pro Lys Ser Asn Leu Asn
            405                 410                 415

Val Leu Phe Met Gly Gln Asn Leu Ser Arg Asn Pro Ala Leu Arg Lys
        420                 425                 430

Val Asn Pro Glu Asn Met Leu Tyr Leu Phe Thr Lys Phe Cys Val Asp
    435                 440                 445

Ala Asp Asp Asp Lys Leu Tyr Asn Lys Thr Leu Gln Cys Arg Glu
    450                 455                 460

Leu Leu Val Lys Asn Thr Asp Leu Pro Phe Ile Gly Asp Ile Ser Asp
465                 470                 475                 480

Val Lys Thr Asp Ile Phe Leu Arg Lys Asp Ile Asn Glu Glu Thr Glu
            485                 490                 495

Val Ile Pro Asp Asn Val Ser Val Asp Gln Val Ile Leu Ser Lys Asn
        500                 505                 510

Thr Ser Glu His Gly Gln Leu Asp Leu Leu Tyr Pro Ser Ile Asp Ser
    515                 520                 525

Glu Ser Glu Ile Leu Pro Gly Glu Asn Gln Val Phe Tyr Asp Asn Arg
530                 535                 540

Thr Gln Asn Val Asp Tyr Leu Asn Ser Tyr Tyr Tyr Leu Glu Ser Gln
545                 550                 555                 560

Lys Leu Ser Asp Asn Val Glu Asp Phe Thr Phe Thr Arg Ser Ile Glu
            565                 570                 575

Glu Ala Leu Asp Asn Ser Ala Lys Val Tyr Thr Tyr Phe Pro Thr Leu
        580                 585                 590

Ala Asn Lys Val Asn Ala Gly Val Gln Gly Gly Leu Phe Leu Met Trp
    595                 600                 605

Ala Asn Asp Val Val Glu Asp Phe Thr Thr Asn Ile Leu Arg Lys Asp
    610                 615                 620

Thr Leu Asp Lys Ile Ser Asp Val Ser Ala Ile Ile Pro Tyr Ile Gly
625                 630                 635                 640

Pro Ala Leu Asn Ile Ser Asn Ser Val Arg Arg Gly Asn Phe Thr Glu
```

```
                645                 650                 655

Ala Phe Ala Val Thr Gly Val Thr Ile Leu Leu Glu Ala Phe Pro Glu
            660                 665                 670

Phe Thr Ile Pro Ala Leu Gly Ala Phe Val Ile Tyr Ser Lys Val Gln
        675                 680                 685

Glu Arg Asn Glu Ile Ile Lys Thr Ile Asp Asn Cys Leu Glu Gln Arg
    690                 695                 700

Ile Lys Arg Trp Lys Asp Ser Tyr Glu Trp Met Met Gly Thr Trp Leu
705                 710                 715                 720
Ser Arg Ile Ile Thr Gln Phe Asn Asn Ile Ser Tyr Gln Met Tyr Asp
                725                 730                 735

Ser Leu Asn Tyr Gln Ala Gly Ala Ile Lys Ala Lys Ile Asp Leu Glu
            740                 745                 750

Tyr Lys Lys Tyr Ser Gly Ser Asp Lys Glu Asn Ile Lys Ser Gln Val
        755                 760                 765

Glu Asn Leu Lys Asn Ser Leu Asp Val Lys Ile Ser Glu Ala Met Asn
    770                 775                 780

Asn Ile Asn Lys Phe Ile Arg Glu Cys Ser Val Thr Tyr Leu Phe Lys
785                 790                 795                 800
Asn Met Leu Pro Lys Val Ile Asp Glu Leu Asn Glu Phe Asp Arg Asn
                805                 810                 815

Thr Lys Ala Lys Leu Ile Asn Leu Ile Asp Ser His Asn Ile Ile Leu
            820                 825                 830

Val Gly Glu Val Asp Lys Leu Lys Ala Lys Val Asn Asn Ser Phe Gln
        835                 840                 845

Asn Thr Ile Pro Phe Asn Ile Phe Ser Tyr Thr Asn Asn Ser Leu Leu
    850                 855                 860

Lys Asp Ile Ile Asn Glu Tyr Phe Asn Leu Glu Gly Gly Gly Gly Ser
865                 870                 875                 880

Gly Gly Gly Gly Ser Gly Gly Gly Gly Ser Ala Leu Asp Asn Ser Asp
                885                 890                 895

Ser Glu Cys Pro Leu Ser His Asp Gly Tyr Cys Leu His Asp Gly Val
            900                 905                 910

Cys Met Tyr Ile Glu Ala Leu Asp Lys Tyr Ala Cys Asn Cys Val Val
        915                 920                 925

Gly Tyr Ile Gly Glu Arg Cys Gln Tyr Arg Asp Leu Lys Trp Trp Glu
    930                 935                 940

Leu Arg
945
```

<210> SEQ ID NO 7
<211> LENGTH: 2871
<212> TYPE: DNA
<213> ORGANISM: Artificial sequence
<220> FEATURE:
<223> OTHER INFORMATION: DNA sequence of BoNT/A with Human EGF Targeting Moiety

<400> SEQUENCE: 7

```
atgggatcca tggagttcgt taacaaacag ttcaactata aagacccagt taacggtgtt     60
gacattgctt acatcaaaat cccgaacgct ggccagatgc agccggtaaa ggcattcaaa    120
atccacaaca aaatctgggt tatcccggaa cgtgatacct ttactaaccc ggaagaaggt    180
gacctgaacc cgccaccgga agcgaaacag gtgccggtat cttactatga ctccacctac    240
ctgtctaccg ataacgaaaa ggacaactac ctgaaaggtg ttactaaact gttcgagcgt    300
```

```
atttactcca ccgacctggg ccgtatgctg ctgactagca tcgttcgcgg tatcccgttc    360
tggggcggtt ctaccatcga taccgaactg aaagtaatcg acactaactg catcaacgtt    420
attcagccgg acggttccta tcgttccgaa gaactgaacc tggtgatcat cggcccgtct    480
gctgatatca tccagttcga gtgtaagagc tttggtcacg aagttctgaa cctcacccgt    540
aacggctacg gttccactca gtacatccgt ttctctccgg acttcacctt cggttttgaa    600
gaatccctgg aagtagacac gaacccactg ctgggcgctg gtaaattcgc aactgatcct    660
gcggttaccc tggctcacga actgattcat gcaggccacc gcctgtacgg tatcgccatc    720
aatccgaacc gtgtcttcaa agttaacacc aacgcgtatt acgagatgtc cggtctggaa    780
gttagcttcg aagaactgcg tactttggc ggtcacgacg ctaaattcat cgactctctg    840
caagaaaacg agttccgtct gtactactat aacaagttca agatatcgc atccaccctg    900 aacaaagcga atccatcgt gggtaccact gcttctctcc agtacatgaa gaacgttttt    960
aaagaaaaat acctgctcag cgaagacacc tccggcaaat tctctgtaga caagttgaaa   1020
ttcgataaac tttacaaaat gctgactgaa atttacaccg aagacaactt cgttaagttc   1080
tttaaagttc tgaaccgcaa aacctatctg aacttcgaca aggcagtatt caaaatcaac   1140
atcgtgccga aagttaacta cactatctac gatggtttca acctgcgtaa caccaacctg   1200
gctgctaatt taacggcca gaacacgaaa atcaacaaca tgaacttcac aaaaactgaaa   1260 aacttcactg gtctgttcga gttttacaag ctgctgtgcg tcgacggcat cattacctcc   1320
aaaactaaat ctgacgatga cgataaaaac aaagcgctga acctgcagtg tatcaaggtt   1380
aacaactggg atttattctt cagcccgagt gaagacaact tcaccaacga cctgaacaaa   1440
ggtgaagaaa tcacctcaga tactaacatc gaagcagccg aagaaaacat ctcgctggac   1500
ctgatccagc agtactacct gacctttaat ttcgacaacg agccggaaaa catttctatc   1560
gaaaacctga gctctgatat catcggccag ctggaactga tgccgaacat cgaacgtttc   1620
ccaaacggta aaaagtacga gctggacaaa tataccatgt tccactacct gcgcgcgcag   1680
gaatttgaac acggcaaatc ccgtatcgca ctgactaact ccgttaacga agctctgctc   1740
aacccgtccc gtgtatacac cttcttctct agcgactacg tgaaaaaggt caacaaagcg   1800
actgaagctg caatgttctt gggttgggtt gaacagcttg tttatgattt taccgacgag   1860
acgtccgaag tatctactac cgacaaaatt gcggatatca ctatcatcat cccgtacatc   1920
ggtccggctc tgaacattgg caacatgctg tacaaagacg acttcgttgg cgcactgatc   1980
ttctccggtc cggtgatcct gctggagttc atcccgaaaa tcgccatccc ggtactgggc   2040
acctttgctc tggttctta cattgcaaac aaggttctga ctgtacaaac catcgacaac   2100
gcgctgagca acgtaacga aaatgggat gaagtttaca atatatcgt gaccaactgg   2160 ctggctaagg ttaatactca gatcgacctc atccgcaaaa aaatgaaaga agcactggaa   2220
aaccaggcga agctaccaa ggcaatcatt aactaccagt acaaccagta caccgaggaa   2280
gaaaaaaaca acatcaactt caacatcgac gatctgtcct ctaaactgaa cgaatccatc   2340
aacaaagcta tgatcaacat caacaagttc ctgaaccagt gctctgtaag ctatctgatg   2400
aactccatga tcccgtacgg tgttaaacgt ctggaggact cgatgcgtc tctgaaagac   2460 gccctgctga atacatttta cgacaaccgt ggcactctga tcggtcaggt tgatcgtctg   2520
aaggacaaag tgaacaatac cttatcgacc gacatcccct ttcagctcag taaatatgtc   2580
gataaccaac gccttttgtc cactctagaa ggtggcggtg gtccggtgg cggtggctca   2640
```

```
ggcgggggcg tagcgcact agacaactct gactctgaat gcccgctgtc tcacgacggt    2700
tactgcctgc acgacggtgt ttgcatgtac atcgaagctc tggacaaata cgcttgcaac    2760
tgcgttgttg gttacatcgg tgaacgttgc cagtaccgtg acctgaaatg gtgggaactg    2820
cgtgcgctag aagcacacca tcatcaccac catcaccatc accattaatg a            2871
```

<210> SEQ ID NO 8
<211> LENGTH: 955
<212> TYPE: PRT
<213> ORGANISM: Artificial sequence
<220> FEATURE:
<223> OTHER INFORMATION: Protein sequence of BoNT/A with Human EGF
      Targeting Moiety

<400> SEQUENCE: 8

```
Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
    130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
    290                 295                 300

Ser Ile Val Gly Thr Thr Ala Ser Leu Gln Tyr Met Lys Asn Val Phe
305                 310                 315                 320
```

-continued

Lys Glu Lys Tyr Leu Leu Ser Glu Asp Thr Ser Gly Lys Phe Ser Val
            325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Lys Val Leu Asn Arg Lys Thr
            355                 360                 365

Tyr Leu Asn Phe Asp Lys Ala Val Phe Lys Ile Asn Ile Val Pro Lys
370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
            405                 410                 415

Thr Lys Leu Lys Asn Phe Thr Gly Leu Phe Glu Phe Tyr Lys Leu Leu
            420                 425                 430

Cys Val Asp Gly Ile Ile Thr Ser Lys Thr Lys Ser Asp Asp Asp
            435                 440                 445

Lys Asn Lys Ala Leu Asn Leu Gln Cys Ile Lys Val Asn Asn Trp Asp
            450                 455                 460

Leu Phe Phe Ser Pro Ser Glu Asp Asn Phe Thr Asn Asp Leu Asn Lys
465                 470                 475                 480

Gly Glu Glu Ile Thr Ser Asp Thr Asn Ile Glu Ala Ala Glu Glu Asn
            485                 490                 495

Ile Ser Leu Asp Leu Ile Gln Gln Tyr Tyr Leu Thr Phe Asn Phe Asp
            500                 505                 510

Asn Glu Pro Glu Asn Ile Ser Ile Glu Asn Leu Ser Ser Asp Ile Ile
            515                 520                 525

Gly Gln Leu Glu Leu Met Pro Asn Ile Glu Arg Phe Pro Asn Gly Lys
            530                 535                 540

Lys Tyr Glu Leu Asp Lys Tyr Thr Met Phe His Tyr Leu Arg Ala Gln
545                 550                 555                 560

Glu Phe Glu His Gly Lys Ser Arg Ile Ala Leu Thr Asn Ser Val Asn
            565                 570                 575

Glu Ala Leu Leu Asn Pro Ser Arg Val Tyr Thr Phe Phe Ser Ser Asp
            580                 585                 590

Tyr Val Lys Lys Val Asn Lys Ala Thr Glu Ala Ala Met Phe Leu Gly
            595                 600                 605

Trp Val Glu Gln Leu Val Tyr Asp Phe Thr Asp Glu Thr Ser Glu Val
            610                 615                 620

Ser Thr Thr Asp Lys Ile Ala Asp Ile Thr Ile Ile Pro Tyr Ile
625                 630                 635                 640

Gly Pro Ala Leu Asn Ile Gly Asn Met Leu Tyr Lys Asp Asp Phe Val
            645                 650                 655

Gly Ala Leu Ile Phe Ser Gly Ala Val Ile Leu Leu Glu Phe Ile Pro
            660                 665                 670

Glu Ile Ala Ile Pro Val Leu Gly Thr Phe Ala Leu Val Ser Tyr Ile
            675                 680                 685

Ala Asn Lys Val Leu Thr Val Gln Thr Ile Asp Asn Ala Leu Ser Lys
            690                 695                 700

Arg Asn Glu Lys Trp Asp Glu Val Tyr Lys Tyr Ile Val Thr Asn Trp
705                 710                 715                 720

Leu Ala Lys Val Asn Thr Gln Ile Asp Leu Ile Arg Lys Lys Met Lys
            725                 730                 735

Glu Ala Leu Glu Asn Gln Ala Glu Ala Thr Lys Ala Ile Ile Asn Tyr

-continued

```
              740                 745                 750
Gln Tyr Asn Gln Tyr Thr Glu Glu Lys Asn Asn Ile Asn Phe Asn
            755                 760                 765
Ile Asp Asp Leu Ser Ser Lys Leu Asn Glu Ser Ile Asn Lys Ala Met
        770                 775                 780
Ile Asn Ile Asn Lys Phe Leu Asn Gln Cys Ser Val Ser Tyr Leu Met
785                 790                 795                 800
Asn Ser Met Ile Pro Tyr Gly Val Lys Arg Leu Glu Asp Phe Asp Ala
                805                 810                 815
Ser Leu Lys Asp Ala Leu Leu Lys Tyr Ile Tyr Asp Asn Arg Gly Thr
            820                 825                 830
Leu Ile Gly Gln Val Asp Arg Leu Lys Asp Lys Val Asn Asn Thr Leu
        835                 840                 845
Ser Thr Asp Ile Pro Phe Gln Leu Ser Lys Tyr Val Asp Asn Gln Arg
    850                 855                 860
Leu Leu Ser Thr Leu Glu Gly Gly Gly Ser Gly Gly Gly Gly Ser
865                 870                 875                 880
Gly Gly Gly Gly Ser Ala Leu Asp Asn Ser Asp Ser Glu Cys Pro Leu
                885                 890                 895
Ser His Asp Gly Tyr Cys Leu His Asp Gly Val Cys Met Tyr Ile Glu
            900                 905                 910
Ala Leu Asp Lys Tyr Ala Cys Asn Cys Val Val Gly Tyr Ile Gly Glu
        915                 920                 925
Arg Cys Gln Tyr Arg Asp Leu Lys Trp Trp Glu Leu Arg Ala Leu Glu
    930                 935                 940
Ala His His His His His His His His
945                 950                 955

<210> SEQ ID NO 9
<211> LENGTH: 2871
<212> TYPE: DNA
<213> ORGANISM: Artificial sequence
<220> FEATURE:
<223> OTHER INFORMATION: DNA sequence of BoNT/A with Human EGF Targeting
      Moiety and Thrombin Protease Cleavage Site

<400> SEQUENCE: 9
atgggatcca tggagttcgt taacaaacag ttcaactata agacccagt taacggtgtt      60 gacattgctt acatcaaaat cccgaacgct ggccagatgc agccggtaaa ggcattcaaa     120
atccacaaca aaatctgggt tatcccggaa cgtgatacct ttactaaccc ggaagaaggt     180
gacctgaacc cgccaccgga agcgaaacag gtgccggtat cttactatga ctccacctac     240
ctgtctaccg ataacgaaaa ggacaactac ctgaaaggtg ttactaaaact gttcgagcgt     300 atttactcca ccgacctggg ccgtggtctg ctgactagca tcgttcgcgg tatcccgttc     360
tggggcggtt ctaccatcga taccgaactg aaagtaatcg acactaactg catcaacgtt     420
attcagccgg acggttccta tcgttccgaa gaactgaacc tggtgatcat cggcccgtct     480
gctgatatca tccagttcga gtgtaagagc tttggtcacg aagttctgaa cctcacccgt     540
aacggctacg ttccactcca gtacatccgt ttctctccgg acttcacctt cggttttgaa     600
gaatccctgg aagtagacac gaacccactg ctgggcgctg gtaaattcgc aactgatcct     660
gcggttaccc tggctcacga actgattcat gcaggccacc gcctgtacgg tatcgccatc     720
aatccgaacc gtgtcttcaa agttaacacc aacgcgtatt acgagatgtc cggtctggaa     780
gttagcttcg aagaactgcg tacttttggc ggtcacgacg ctaaattcat cgactctctg     840
```

```
caagaaaacg agttccgtct gtactactat aacaagttca agatatcgc atccaccctg     900
aacaaagcga atccatcgt gggtaccact gcttctctcc agtacatgaa gaacgttttt    960
aaagaaaaat acctgctcag cgaagacacc tccggcaaat tctctgtaga caagttgaaa  1020
ttcgataaac tttacaaaat gctgactgaa atttacaccg aagacaactt cgttaagttc  1080
tttaaagttc tgaaccgcaa aacctatctg aacttcgaca aggcagtatt caaaatcaac  1140
atcgtgccga aagttaacta cactatctac gatggtttca acctgcgtaa caccaacctg  1200
gctgctaatt ttaacggcca gaacacggaa atcaacaaca tgaacttcac aaaactgaaa  1260
aacttcactg gtctgttcga gttttacaag ctgctgtgcg tcgacggcat cattacctcc  1320
aaaactaaat ctgacgatga cgataaaaac aaagcgctga acctgcagtg tatcaaggtt  1380
aacaactggg atttattctt cagcccgagt gaagacaact tcaccaacga cctgaacaaa  1440
ggtgaagaaa tcacctcaga tactaacatc gaagcagccg aagaaaacat ctcgctggac  1500
ctgatccagc agtactacct gacctttaat ttcgacaacg agccggaaaa catttctatc  1560
gaaaacctga gctctgatat catcggccag ctggaactga tgccgaacat cgaacgtttc  1620
ccaaacggta aaaagtacga gctggacaaa tataccatgt tccactacct gcgcgcgcag  1680
gaatttgaac acggcaaatc ccgtatcgca ctgactaact ccgttaacga agctctgctc  1740
aacccgtccc gtgtatacac cttcttctct agcgactacg tgaaaaaggt caacaaagcg  1800
actgaagctg caatgttctt gggttgggtt gaacagcttg tttatgattt taccgacgag  1860
acgtccgaag tatctactac cgacaaaatt gcggatatca ctatcatcat cccgtacatc  1920
ggtccggctc tgaacattgg caacatgctg tacaaagacg acttcgttgg cgcactgatc  1980
ttctccggtg cggtgatcct gctggagttc atcccggaaa tcgccatccc ggtactgggc  2040
acctttgctc tggtttctta cattgcaaac aaggttctga ctgtacaaac catcgacaac  2100
gcgctgagca acgtaacga aaaatgggat gaagtttaca atatatcgt gaccaactgg  2160
ctggctaagg ttaatactca gatcgacctc atccgcaaaa aatgaaaga agcactggaa  2220
aaccaggcgg aagctaccaa ggcaatcatt aactaccagt acaaccagta caccgaggaa  2280
gaaaaaaaca acatcaactt caacatcgac gatctgtcct ctaaactgaa cgaatccatc  2340
aacaaagcta tgatcaacat caacaagttc ctgaaccagt gctctgtaag ctatctgatg  2400
aactccatga tcccgtacgg tgttaaacgt ctggaggact cgatgcgtc tctgaaagac  2460
gccctgctga atacattta cgacaaccgt ggcactctga tcggtcaggt tgatcgtctg  2520
aaggacaaag tgaacaatac cttatcgacc gacatcccct tcagctcag taaatatgtc  2580
gataaccaac gccttttgtc cactctagaa ggtggcggtg gtccggtgg cggtggctca  2640
ggcggggggcg gtagcgcact agacaactct gactctgaat gcccgctgtc tcacgacggt  2700
tactgcctgc acgacggtgt ttgcatgtac atcgaagctc tggacaaata cgcttgcaac  2760
tgcgttgttg gttacatcgg tgaacgttgc cagtaccgtg acctgaaatg gtgggaactg  2820
cgtgcgctag aagcacacca tcatcaccac catcaccatc accattaatg a            2871
```

<210> SEQ ID NO 10
<211> LENGTH: 955
<212> TYPE: PRT
<213> ORGANISM: Artificial sequence
<220> FEATURE:
<223> OTHER INFORMATION: Protein sequence of BoNT/A with Human EGF
      Targeting Moiety and Thrombin Protease Cleavage Site

<400> SEQUENCE: 10

-continued

```
Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
            35                  40                  45

Pro Glu Arg Asp Thr Phe Thr Asn Pro Glu Glu Gly Asp Leu Asn Pro
50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Gly Leu Leu Thr
                100                 105                 110

Ser Ile Val Arg Gly Ile Pro Phe Trp Gly Gly Ser Thr Ile Asp Thr
                115                 120                 125

Glu Leu Lys Val Ile Asp Thr Asn Cys Ile Asn Val Ile Gln Pro Asp
130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
                180                 185                 190

Pro Asp Phe Thr Phe Gly Phe Glu Glu Ser Leu Glu Val Asp Thr Asn
                195                 200                 205

Pro Leu Leu Gly Ala Gly Lys Phe Ala Thr Asp Pro Ala Val Thr Leu
210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
                260                 265                 270

Asp Ala Lys Phe Ile Asp Ser Leu Gln Glu Asn Glu Phe Arg Leu Tyr
                275                 280                 285

Tyr Tyr Asn Lys Phe Lys Asp Ile Ala Ser Thr Leu Asn Lys Ala Lys
                290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
                340                 345                 350

Thr Glu Asp Asn Phe Val Lys Phe Phe Lys Val Leu Asn Arg Lys Thr
                355                 360                 365

Tyr Leu Asn Phe Asp Lys Ala Val Phe Lys Ile Asn Ile Val Pro Lys
                370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415
```

```
Thr Lys Leu Lys Asn Phe Thr Gly Leu Phe Glu Phe Tyr Lys Leu Leu
            420                 425                 430

Cys Val Asp Gly Ile Ile Thr Ser Lys Thr Lys Ser Asp Asp Asp
            435                 440                 445

Lys Asn Lys Ala Leu Asn Leu Gln Cys Ile Lys Val Asn Asn Trp Asp
            450                 455                 460

Leu Phe Phe Ser Pro Ser Glu Asp Asn Phe Thr Asn Asp Leu Asn Lys
465                 470                 475                 480

Gly Glu Glu Ile Thr Ser Asp Thr Asn Ile Glu Ala Ala Glu Glu Asn
                    485                 490                 495

Ile Ser Leu Asp Leu Ile Gln Gln Tyr Tyr Leu Thr Phe Asn Phe Asp
            500                 505                 510

Asn Glu Pro Glu Asn Ile Ser Ile Glu Asn Leu Ser Ser Asp Ile Ile
            515                 520                 525

Gly Gln Leu Glu Leu Met Pro Asn Ile Glu Arg Phe Pro Asn Gly Lys
            530                 535                 540

Lys Tyr Glu Leu Asp Lys Tyr Thr Met Phe His Tyr Leu Arg Ala Gln
545                 550                 555                 560

Glu Phe Glu His Gly Lys Ser Arg Ile Ala Leu Thr Asn Ser Val Asn
                    565                 570                 575

Glu Ala Leu Leu Asn Pro Ser Arg Val Tyr Thr Phe Phe Ser Ser Asp
            580                 585                 590

Tyr Val Lys Val Asn Lys Ala Thr Glu Ala Ala Met Phe Leu Gly
                    595                 600                 605

Trp Val Glu Gln Leu Val Tyr Asp Phe Thr Asp Glu Thr Ser Glu Val
            610                 615                 620

Ser Thr Thr Asp Lys Ile Ala Asp Ile Thr Ile Ile Pro Tyr Ile
625                 630                 635                 640

Gly Pro Ala Leu Asn Ile Gly Asn Met Leu Tyr Lys Asp Asp Phe Val
                    645                 650                 655

Gly Ala Leu Ile Phe Ser Gly Ala Val Ile Leu Leu Glu Phe Ile Pro
            660                 665                 670

Glu Ile Ala Ile Pro Val Leu Gly Thr Phe Ala Leu Val Ser Tyr Ile
            675                 680                 685

Ala Asn Lys Val Leu Thr Val Gln Thr Ile Asp Asn Ala Leu Ser Lys
            690                 695                 700

Arg Asn Glu Lys Trp Asp Glu Val Tyr Lys Tyr Ile Val Thr Asn Trp
705                 710                 715                 720

Leu Ala Lys Val Asn Thr Gln Ile Asp Leu Ile Arg Lys Lys Met Lys
                    725                 730                 735

Glu Ala Leu Glu Asn Gln Ala Glu Ala Thr Lys Ala Ile Ile Asn Tyr
            740                 745                 750

Gln Tyr Asn Gln Tyr Thr Glu Glu Lys Asn Asn Ile Asn Phe Asn
            755                 760                 765

Ile Asp Asp Leu Ser Ser Lys Leu Asn Glu Ser Ile Asn Lys Ala Met
770                 775                 780

Ile Asn Ile Asn Lys Phe Leu Asn Gln Cys Ser Val Ser Tyr Leu Met
785                 790                 795                 800

Asn Ser Met Ile Pro Tyr Gly Val Lys Arg Leu Glu Asp Phe Asp Ala
                    805                 810                 815

Ser Leu Lys Asp Ala Leu Leu Lys Tyr Ile Tyr Asp Asn Arg Gly Thr
            820                 825                 830

Leu Ile Gly Gln Val Asp Arg Leu Lys Asp Lys Val Asn Asn Thr Leu
```

```
                     835                 840                 845

Ser Thr Asp Ile Pro Phe Gln Leu Ser Lys Tyr Val Asp Asn Gln Arg
850                 855                 860

Leu Leu Ser Thr Leu Glu Gly Gly Gly Ser Gly Gly Gly Gly Ser
865                 870                 875                 880

Gly Gly Gly Gly Ser Ala Leu Asp Asn Ser Asp Ser Glu Cys Pro Leu
                885                 890                 895

Ser His Asp Gly Tyr Cys Leu His Asp Gly Val Cys Met Tyr Ile Glu
                900                 905                 910

Ala Leu Asp Lys Tyr Ala Cys Asn Cys Val Val Gly Tyr Ile Gly Glu
            915                 920                 925

Arg Cys Gln Tyr Arg Asp Leu Lys Trp Trp Glu Leu Arg Ala Leu Glu
            930                 935                 940

Ala His His His His His His His His
945                 950                 955

<210> SEQ ID NO 11
<211> LENGTH: 945
<212> TYPE: PRT
<213> ORGANISM: Artificial sequence
<220> FEATURE:
<223> OTHER INFORMATION: Protein sequence of BoNT/C with Human EGF
      Targeting Moiety and Furin Protease Cleavage Site

<400> SEQUENCE: 11

Ile Ser Glu Phe Gly Ser Glu Phe Met Pro Ile Thr Ile Asn Asn Phe
1               5                   10                  15

Asn Tyr Ser Asp Pro Val Asp Asn Lys Asn Ile Leu Tyr Leu Asp Thr
            20                  25                  30

His Leu Asn Thr Leu Ala Asn Glu Pro Glu Lys Ala Phe Arg Ile Thr
        35                  40                  45

Gly Asn Ile Trp Val Ile Pro Asp Arg Phe Ser Arg Asn Ser Asn Pro
    50                  55                  60

Asn Leu Asn Lys Pro Pro Arg Val Thr Ser Pro Lys Ser Gly Tyr Tyr
65                  70                  75                  80

Asp Pro Asn Tyr Leu Ser Thr Asp Ser Asp Lys Asp Thr Phe Leu Lys
                85                  90                  95

Glu Ile Ile Lys Leu Phe Lys Arg Ile Asn Ser Arg Glu Ile Gly Glu
            100                 105                 110

Glu Leu Ile Tyr Arg Leu Ser Thr Asp Ile Pro Phe Pro Gly Asn Asn
        115                 120                 125

Asn Thr Pro Ile Asn Thr Phe Asp Phe Asp Val Asp Phe Asn Ser Val
    130                 135                 140

Asp Val Lys Thr Arg Gln Gly Asn Asn Trp Val Lys Thr Gly Ser Ile
145                 150                 155                 160

Asn Pro Ser Val Ile Ile Thr Gly Pro Arg Glu Asn Ile Ile Asp Pro
                165                 170                 175

Glu Thr Ser Thr Phe Lys Leu Thr Asn Asn Thr Phe Ala Ala Gln Glu
            180                 185                 190

Gly Phe Gly Ala Leu Ser Ile Ile Ser Ile Ser Pro Arg Phe Met Leu
        195                 200                 205

Thr Tyr Ser Asn Ala Thr Asn Asp Val Arg Ser Arg Arg Phe Ser Lys
    210                 215                 220

Ser Glu Phe Cys Met Asp Pro Ile Leu Ile Leu Met His Glu Leu Asn
225                 230                 235                 240
```

```
His Ala Met His Asn Leu Tyr Gly Ile Ala Ile Pro Asn Asp Gln Thr
                245                 250                 255
Ile Ser Ser Val Thr Ser Asn Ile Phe Tyr Ser Gln Tyr Asn Val Lys
            260                 265                 270
Leu Glu Tyr Ala Glu Ile Tyr Ala Phe Gly Gly Pro Thr Ile Asp Leu
        275                 280                 285
Ile Pro Lys Ser Ala Arg Lys Tyr Phe Glu Lys Ala Leu Asp Tyr
290                 295                 300
Tyr Arg Ser Ile Ala Lys Arg Leu Asn Ser Ile Thr Ala Asn Pro
305                 310                 315                 320
Ser Ser Phe Asn Lys Tyr Ile Gly Glu Tyr Lys Gln Lys Leu Ile Arg
                325                 330                 335
Lys Tyr Arg Phe Val Val Glu Ser Ser Gly Glu Val Thr Val Asn Arg
            340                 345                 350
Asn Lys Phe Val Glu Leu Tyr Asn Glu Leu Thr Gln Ile Phe Thr Glu
        355                 360                 365
Phe Asn Tyr Ala Lys Ile Tyr Asn Val Gln Asn Arg Lys Ile Tyr Leu
    370                 375                 380
Ser Asn Val Tyr Thr Pro Val Thr Ala Asn Ile Leu Asp Asp Asn Val
385                 390                 395                 400
Tyr Asp Ile Gln Asn Gly Phe Asn Ile Pro Lys Ser Asn Leu Asn Val
                405                 410                 415
Leu Phe Met Gly Gln Asn Leu Ser Arg Asn Pro Ala Leu Arg Lys Val
            420                 425                 430
Asn Pro Glu Asn Met Leu Tyr Leu Phe Thr Lys Phe Cys Val Asp Ala
        435                 440                 445
Asp Asp Asp Asp Lys Leu Tyr Asn Lys Thr Leu Gln Cys Arg Glu Leu
    450                 455                 460
Leu Val Lys Asn Thr Asp Leu Pro Phe Ile Gly Asp Ile Ser Asp Val
465                 470                 475                 480
Lys Thr Asp Ile Phe Leu Arg Lys Asp Ile Asn Glu Glu Thr Glu Val
                485                 490                 495
Ile Pro Asp Asn Val Ser Val Asp Gln Val Ile Leu Ser Lys Asn Thr
            500                 505                 510
Ser Glu His Gly Gln Leu Asp Leu Leu Tyr Pro Ser Ile Asp Ser Glu
        515                 520                 525
Ser Glu Ile Leu Pro Gly Glu Asn Gln Val Phe Tyr Asp Asn Arg Thr
    530                 535                 540
Gln Asn Val Asp Tyr Leu Asn Ser Tyr Tyr Leu Glu Ser Gln Lys
545                 550                 555                 560
Leu Ser Asp Asn Val Glu Asp Phe Thr Phe Thr Arg Ser Ile Glu Glu
                565                 570                 575
Ala Leu Asp Asn Ser Ala Lys Val Tyr Thr Tyr Phe Pro Thr Leu Ala
            580                 585                 590
Asn Lys Val Asn Ala Gly Val Gln Gly Gly Leu Phe Leu Met Trp Ala
        595                 600                 605
Asn Asp Val Val Glu Asp Phe Thr Thr Asn Ile Leu Arg Lys Asp Thr
    610                 615                 620
Leu Asp Lys Ile Ser Asp Val Ser Ala Ile Ile Pro Tyr Ile Gly Pro
625                 630                 635                 640
Ala Leu Asn Ile Ser Asn Ser Val Arg Arg Gly Asn Phe Thr Glu Ala
                645                 650                 655
Phe Ala Val Thr Gly Val Thr Ile Leu Leu Glu Ala Phe Pro Glu Phe
```

-continued

```
                660             665             670
Thr Ile Pro Ala Leu Gly Ala Phe Val Ile Tyr Ser Lys Val Gln Glu
                675             680             685
Arg Asn Glu Ile Ile Lys Thr Ile Asp Asn Cys Leu Glu Gln Arg Ile
            690             695             700
Lys Arg Trp Lys Asp Ser Tyr Glu Trp Met Met Gly Thr Trp Leu Ser
705             710             715             720
Arg Ile Ile Thr Gln Phe Asn Asn Ile Ser Tyr Gln Met Tyr Asp Ser
                725             730             735
Leu Asn Tyr Gln Ala Gly Ala Ile Lys Ala Lys Ile Asp Leu Glu Tyr
                740             745             750
Lys Lys Tyr Ser Gly Ser Asp Lys Glu Asn Ile Lys Ser Gln Val Glu
            755             760             765
Asn Leu Lys Asn Ser Leu Asp Val Lys Ile Ser Glu Ala Met Asn Asn
        770             775             780
Ile Asn Lys Phe Ile Arg Glu Cys Ser Val Thr Tyr Leu Phe Lys Asn
785             790             795             800
Met Leu Pro Lys Val Ile Asp Glu Leu Asn Glu Phe Asp Arg Asn Thr
                805             810             815
Lys Ala Lys Leu Ile Asn Leu Ile Asp Ser His Asn Ile Ile Leu Val
                820             825             830
Gly Glu Val Asp Lys Leu Lys Ala Lys Val Asn Asn Ser Phe Gln Asn
            835             840             845
Thr Ile Pro Phe Asn Ile Phe Ser Tyr Thr Asn Asn Ser Leu Leu Lys
        850             855             860
Asp Ile Ile Asn Glu Tyr Phe Asn Leu Glu Gly Gly Gly Ser Gly
865             870             875             880
Gly Gly Gly Ser Gly Gly Gly Ser Ala Leu Asp Asn Ser Asp Ser
                885             890             895
Glu Cys Pro Leu Ser His Asp Gly Tyr Cys Leu His Asp Gly Val Cys
            900             905             910
Met Tyr Ile Glu Ala Leu Asp Lys Tyr Ala Cys Asn Cys Val Val Gly
                915             920             925
Tyr Ile Gly Glu Arg Cys Gln Tyr Arg Asp Leu Lys Trp Trp Glu Leu
            930             935             940
Arg
945

<210> SEQ ID NO 12
<211> LENGTH: 2871
<212> TYPE: DNA
<213> ORGANISM: Artificial sequence
<220> FEATURE:
<223> OTHER INFORMATION: DNA sequence of BoNT/A with Human EGF Targeting
      Moiety and Factor Xa Protease Cleavage Site

<400> SEQUENCE: 12
atgggatcca tggagttcgt taacaaacag ttcaactata agacccagt taacggtgtt      60 gacattgctt acatcaaaat cccgaacgct ggccagatgc agccggtaaa ggcattcaaa     120
atccacaaca aaatctgggt tatcccggaa cgtgataccc ttactaaccc ggaagaaggt     180
gacctgaacc cgccaccgga agcgaaacag gtgccggtat cttactatga ctccacctac     240
ctgtctaccg ataacgaaaa ggacaactac ctgaaaggtg ttactaaaact gttcgagcgt     300 atttactcca ccgacctggg ccgtatgctg ctgactagca tcgttcgcgg tatcccgttc     360
```

```
tggggcggtt ctaccatcga taccgaactg aaagtaatcg acactaactg catcaacgtt      420
attcagccgg acggttccta tcgttccgaa gaactgaacc tggtgatcat cggcccgtct      480
gctgatatca tccagttcga gtgtaagagc tttggtcacg aagttctgaa cctcacccgt      540
aacggctacg gttccactca gtacatccgt ttctctccgg acttcacctt cggttttgaa      600
gaatccctgg aagtagacac gaacccactg ctgggcgctg gtaaattcgc aactgatcct      660
gcggttaccc tggctcacga actgattcat gcaggccacc gcctgtacgg tatcgccatc      720
aatccgaacc gtgtcttcaa agttaacacc aacgcgtatt acgagatgtc cggtctggaa      780
gttagcttcg aagaactgcg tactttggc ggtcacgacg ctaaattcat cgactctctg      840
caagaaaacg agttccgtct gtactactat aacaagttca agatatcgc atccaccctg      900 aacaaagcga atccatcgt gggtaccact gcttctctcc agtacatgaa gaacgttttt      960
aaagaaaaat acctgctcag cgaagacacc tccggcaaat tctctgtaga caagttgaaa     1020
ttcgataaac tttacaaaat gctgactgaa atttacaccg aagacaactt cgttaagttc     1080
tttaaagttc tgaaccgcaa aacctatctg aacttcgaca aggcagtatt caaaatcaac     1140
atcgtgccga agttaactga cactatctac gatggtttca acctgcgtaa caccaacctg     1200
gctgctaatt ttaacggcca gaacacgaaa atcaacaaca tgaacttcac aaaactgaaa     1260
aacttcactg gtctgttcga gttttacaag ctgctgtgcg tcgacggcat cattacctcc     1320
aaaactaaat ctgacgatga cgataaaaac aaagcgctga acctgcagtg tatcaaggtt     1380
aacaactggg atttattctt cagcccgagt gaagacaact tcaccaacga cctgaacaaa     1440
ggtgaagaaa tcacctcaga tactaacatc gaagcagccg aagaaaacat ctcgctggac     1500
ctgatccagc agtactacct gacctttaat ttcgacaacg agccggaaaa catttctatc     1560
gaaaacctga gctctgatat catcggccag ctggaactga tgccgaacat cgaacgtttc     1620
ccaaacggta aaagtacga gctggacaaa tataccatgt tccactacct gcgcgcgcag     1680
gaatttgaac acatcgaagg ccgtatcgca ctgactaact ccgttaacga agctctgctc     1740
aacccgtccc gtgtatacac cttcttctct agcgactacg tgaaaaaggt caacaaagcg     1800
actgaagctg caatgttctt gggttgggtt gaacagcttg tttatgattt taccgacgag     1860
acgtccgaag tatctactac cgacaaaatt gcggatatca ctatcatcat cccgtacatc     1920
ggtccggctc tgaacattgg caacatgctg tacaaagacg acttcgttgg cgcactgatc     1980
ttctccggtg cggtgatcct gctggagttc atcccggaaa tcgccatccc ggtactgggc     2040
acctttgctc tggtttctta cattgcaaac aaggttctga ctgtacaaac catcgacaac     2100
gcgctgagca acgtaacga aaatgggat gaagtttaca aatatatcgt gaccaactgg     2160
ctggctaagg ttaatactca gatcgaccct atccgcaaaa aaatgaaaga agcactggaa     2220
aaccaggcgg aagctaccaa ggcaatcatt aactaccagt acaaccagta caccgaggaa     2280
gaaaaaaaca acatcaactt caacatcgac gatctgtcct ctaaactgaa cgaatccatc     2340
aacaaagcta tgatcaacat caacaagttc ctgaaccagt gctctgtaag ctatctgatg     2400
aactccatga tcccgtacgg tgttaaacgt ctggaggact cgatgcgtc tctgaaagac     2460 gccctgctga aatacattta cgacaaccgt ggcactctga tcggtcaggt tgatcgtctg     2520
aaggacaaag tgaacaatac cttatcgacc gacatccctt ttcagctcag taaatatgtc     2580
gataaccaac gccttttgtc cactctagaa ggtggcggtg gtccggtgg cggtggctca     2640 ggcggggcg gtagcgcact agacaactct gactctgaat gccgctgtc tcacgacggt     2700 tactgcctgc acgacggtgt tgcatgtac atcgaagctc tggacaaata cgcttgcaac     2760
```

```
tgcgttgttg gttacatcgg tgaacgttgc cagtaccgtg acctgaaatg gtgggaactg    2820
cgtgcgctag aagcacacca tcatcaccac catcaccatc accattaatg a            2871

<210> SEQ ID NO 13
<211> LENGTH: 954
<212> TYPE: PRT
<213> ORGANISM: Artificial sequence
<220> FEATURE:
<223> OTHER INFORMATION: Protein sequence of BoNT/A with Human EGF
      Targeting Moiety and Factor Xa Protease Cleavage Site

<400> SEQUENCE: 13
```

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
                340                 345                 350

Glu Asp Asn Phe Val Lys Phe Phe Lys Val Leu Asn Arg Lys Thr Tyr
            355                 360                 365

Leu Asn Phe Asp Lys Ala Val Phe Lys Ile Asn Ile Val Pro Lys Val
        370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Asp Asp Asp Asp Lys
        435                 440                 445

Asn Lys Ala Leu Asn Leu Gln Cys Ile Lys Val Asn Asn Trp Asp Leu
450                 455                 460

Phe Phe Ser Pro Ser Glu Asp Asn Phe Thr Asn Asp Leu Asn Lys Gly
465                 470                 475                 480

Glu Glu Ile Thr Ser Asp Thr Asn Ile Glu Ala Ala Glu Asn Ile
                485                 490                 495

Ser Leu Asp Leu Ile Gln Gln Tyr Tyr Leu Thr Phe Asn Phe Asp Asn
            500                 505                 510

Glu Pro Glu Asn Ile Ser Ile Glu Asn Leu Ser Ser Asp Ile Ile Gly
        515                 520                 525

Gln Leu Glu Leu Met Pro Asn Ile Glu Arg Phe Pro Asn Gly Lys Lys
    530                 535                 540

Tyr Glu Leu Asp Lys Tyr Thr Met Phe His Tyr Leu Arg Ala Gln Glu
545                 550                 555                 560

Phe Glu His Ile Glu Gly Arg Ile Ala Leu Thr Asn Ser Val Asn Glu
                565                 570                 575

Ala Leu Leu Asn Pro Ser Arg Val Tyr Thr Phe Phe Ser Ser Asp Tyr
            580                 585                 590

Val Lys Lys Val Asn Lys Ala Thr Glu Ala Ala Met Phe Leu Gly Trp
        595                 600                 605

Val Glu Gln Leu Val Tyr Asp Phe Thr Asp Glu Thr Ser Glu Val Ser
    610                 615                 620

Thr Thr Asp Lys Ile Ala Asp Ile Thr Ile Ile Pro Tyr Ile Gly
625                 630                 635                 640

Pro Ala Leu Asn Ile Gly Asn Met Leu Tyr Lys Asp Asp Phe Val Gly
                645                 650                 655

Ala Leu Ile Phe Ser Gly Ala Val Ile Leu Leu Glu Phe Ile Pro Glu
            660                 665                 670

Ile Ala Ile Pro Val Leu Gly Thr Phe Ala Leu Val Ser Tyr Ile Ala
        675                 680                 685

Asn Lys Val Leu Thr Val Gln Thr Ile Asp Asn Ala Leu Ser Lys Arg
    690                 695                 700

Asn Glu Lys Trp Asp Glu Val Tyr Lys Tyr Ile Val Thr Asn Trp Leu
705                 710                 715                 720

Ala Lys Val Asn Thr Gln Ile Asp Leu Ile Arg Lys Lys Met Lys Glu
                725                 730                 735

Ala Leu Glu Asn Gln Ala Glu Ala Thr Lys Ala Ile Ile Asn Tyr Gln
            740                 745                 750

Tyr Asn Gln Tyr Thr Glu Glu Glu Lys Asn Asn Ile Asn Phe Asn Ile

```
                    755                 760                 765
Asp Asp Leu Ser Ser Lys Leu Asn Glu Ser Ile Asn Lys Ala Met Ile
    770                 775                 780

Asn Ile Asn Lys Phe Leu Asn Gln Cys Ser Val Ser Tyr Leu Met Asn
785                 790                 795                 800

Ser Met Ile Pro Tyr Gly Val Lys Arg Leu Glu Asp Phe Asp Ala Ser
                805                 810                 815

Leu Lys Asp Ala Leu Leu Lys Tyr Ile Tyr Asp Asn Arg Gly Thr Leu
            820                 825                 830

Ile Gly Gln Val Asp Arg Leu Lys Asp Lys Val Asn Asn Thr Leu Ser
        835                 840                 845

Thr Asp Ile Pro Phe Gln Leu Ser Lys Tyr Val Asp Asn Gln Arg Leu
    850                 855                 860

Leu Ser Thr Leu Glu Gly Gly Gly Ser Gly Gly Gly Ser Gly
865                 870                 875                 880

Gly Gly Gly Ser Ala Leu Asp Asn Ser Asp Ser Glu Cys Pro Leu Ser
                885                 890                 895

His Asp Gly Tyr Cys Leu His Asp Gly Val Cys Met Tyr Ile Glu Ala
            900                 905                 910

Leu Asp Lys Tyr Ala Cys Asn Cys Val Val Gly Tyr Ile Gly Glu Arg
        915                 920                 925

Cys Gln Tyr Arg Asp Leu Lys Trp Trp Glu Leu Arg Ala Leu Glu Ala
    930                 935                 940

His His His His His His His His His
945                 950

<210> SEQ ID NO 14
<211> LENGTH: 2871
<212> TYPE: DNA
<213> ORGANISM: Artificial sequence
<220> FEATURE:
<223> OTHER INFORMATION: DNA sequence of BoNT/A with Human EGF Targeting
      Moiety and ADAM17 Protease Cleavage Site

<400> SEQUENCE: 14
atgggatcca tggagttcgt taacaaacag ttcaactata agacccagt taacggtgtt      60 gacattgctt acatcaaaat cccgaacgct ggccagatgc agccggtaaa ggcattcaaa    120
atccacaaca aaatctgggt tatcccggaa cgtgataccct tactaaccc ggaagaaggt    180 gacctgaacc cgccaccgga agcgaaacag gtgccggtat cttactatga ctccacctac    240
ctgtctaccg ataacgaaaa ggacaactac ctgaaaggtg ttactaaaact gttcgagcgt    300 atttactcca ccgacctggg ccgtatgctg ctgactagca tcgttcgcgg tatcccgttc    360
tggggcggtt ctaccatcga taccgaactg aaagtaatcg acactaactg catcaacgtt    420
attcagccgg acggttccta tcgttccgaa gaactgaacc tggtgatcat cggcccgtct    480
gctgatatca tccagttcga gtgtaagagc tttggtcacg aagttctgaa cctcacccgt    540
aacggctacg gttccactca gtacatccgt ttctctccgg acttcacctt cggttttgaa    600
gaatccctgg aagtagacac gaacccactg gcgcaggctg ttcgttcctc ttctgatcct    660
gcggttaccc tggctcacga actgattcat gcaggccacc gcctgtacgg tatcgccatc    720
aatccgaacc gtgtcttcaa agttaacacc aacgcgtatt acgagatgtc cggtctggaa    780
gttagcttcg aagaactgcg tacttttggc ggtcacgacg ctaaattcat cgactctctg    840
caagaaaacg agttccgtct gtactactat aacaagttca agatatcgc atccaccctg    900
```

```
aacaaagcga aatccatcgt gggtaccact gcttctctcc agtacatgaa gaacgttttt    960
aaagaaaaat acctgctcag cgaagacacc tccggcaaat tctctgtaga caagttgaaa   1020
ttcgataaac tttacaaaat gctgactgaa atttacaccg aagacaactt cgttaagttc   1080
tttaaagttc tgaaccgcaa aacctatctg aacttcgaca aggcagtatt caaaatcaac   1140
atcgtgccga aagttaacta cactatctac gatggtttca acctgcgtaa caccaacctg   1200
gctgctaatt ttaacggcca gaacacggaa atcaacaaca tgaacttcac aaaactgaaa   1260
aacttcactg gtctgttcga gttttacaag ctgctgtgcg tcgacggcat cattacctcc   1320
aaaactaaat ctgacgatga cgataaaaac aaagcgctga acctgcagtg tatcaaggtt   1380
aacaactggg atttattctt cagcccgagt gaagacaact tcaccaacga cctgaacaaa   1440
ggtgaagaaa tcacctcaga tactaacatc gaagcagccg aagaaaacat ctcgctggac   1500
ctgatccagc agtactacct gacctttaat ttcgacaacg agccggaaaa catttctatc   1560
gaaaacctga gctctgatat catcggccag ctggaactga tgccgaacat cgaacgtttc   1620
ccaaacggta aaaagtacga gctggacaaa tataccatgt tccactacct gcgcgcgcag   1680
gaatttgaac acggcaaatc ccgtatcgca ctgactaact ccgttaacga agctctgctc   1740
aacccgtccc gtgtatacac cttcttctct agcgactacg tgaaaaaggt caacaaagcg   1800
actgaagctg caatgttctt gggttgggtt gaacagcttg tttatgattt taccgacgag   1860
acgtccgaag tatctactac cgacaaaatt gcggatatca ctatcatcat cccgtacatc   1920
ggtccggctc tgaacattgg caacatgctg tacaaagacg acttcgttgg cgcactgatc   1980
ttctccggtg cggtgatcct gctggagttc atcccggaaa tcgccatccc ggtactgggc   2040
acctttgctc tggtttctta cattgcaaac aaggttctga ctgtacaaac catcgacaac   2100
gcgctgagca aacgtaacga aaaatgggat gaagtttaca aatatatcgt gaccaactgg   2160
ctggctaagg ttaatactca gatcgacctc atccgcaaaa aaatgaaaga agcactggaa   2220
aaccaggcgg aagctaccaa ggcaatcatt aactaccagt acaaccagta caccgaggaa   2280
gaaaaaaaca acatcaactt caacatcgac gatctgtcct ctaaactgaa cgaatccatc   2340
aacaaagcta tgatcaacat caacaagttc ctgaaccagt gctctgtaag ctatctgatg   2400
aactccatga tcccgtacgg tgttaaacgt ctggaggact tcgatgcgtc tctgaaagac   2460
gccctgctga aatacattta cgacaaccgt ggcactctga tcggtcaggt tgatcgtctg   2520
aaggacaaag tgaacaatac cttatcgacc gacatccctt ttcagctcag taaatatgtc   2580
gataaccaac gccttttgtc cactctagaa ggtggcggtg ggtccggtgg cggtggctca   2640
ggcgggggcg gtagcgcact agacaactct gactctgaat gcccgctgtc tcacgacggt   2700
tactgcctgc acgacggtgt ttgcatgtac atcgaagctc tggacaaata cgcttgcaac   2760
tgcgttgttg gttacatcgg tgaacgttgc cagtaccgtg acctgaaatg gtgggaactg   2820
cgtgcgctag aagcacacca tcatcaccac catcaccatc accattaatg a            2871
```

```
<210> SEQ ID NO 15
<211> LENGTH: 954
<212> TYPE: PRT
<213> ORGANISM: Artificial sequence
<220> FEATURE:
<223> OTHER INFORMATION: Protein sequence of BoNT/A with Human EGF
      Targeting Moiety and ADAM17 Protease Cleavage Site

<400> SEQUENCE: 15

Gly Ser Met Glu Phe Val Asn Lys Gln Phe Asn Tyr Lys Asp Pro Val
1               5                   10                  15
```

```
Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Ala Gln Ala Val Arg Ser Ser Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430
```

Val Asp Gly Ile Ile Thr Ser Lys Thr Lys Ser Asp Asp Asp Lys
            435                 440                 445

Asn Lys Ala Leu Asn Leu Gln Cys Ile Lys Val Asn Asn Trp Asp Leu
450                 455                 460

Phe Phe Ser Pro Ser Glu Asp Asn Phe Thr Asn Asp Leu Asn Lys Gly
465                 470                 475                 480

Glu Glu Ile Thr Ser Asp Thr Asn Ile Glu Ala Ala Glu Glu Asn Ile
                485                 490                 495

Ser Leu Asp Leu Ile Gln Gln Tyr Tyr Leu Thr Phe Asn Phe Asp Asn
            500                 505                 510

Glu Pro Glu Asn Ile Ser Ile Glu Asn Leu Ser Ser Asp Ile Ile Gly
            515                 520                 525

Gln Leu Glu Leu Met Pro Asn Ile Glu Arg Phe Pro Asn Gly Lys Lys
530                 535                 540

Tyr Glu Leu Asp Lys Tyr Thr Met Phe His Tyr Leu Arg Ala Gln Glu
545                 550                 555                 560

Phe Glu His Gly Lys Ser Arg Ile Ala Leu Thr Asn Ser Val Asn Glu
                565                 570                 575

Ala Leu Leu Asn Pro Ser Arg Val Tyr Thr Phe Phe Ser Ser Asp Tyr
            580                 585                 590

Val Lys Lys Val Asn Lys Ala Thr Glu Ala Ala Met Phe Leu Gly Trp
            595                 600                 605

Val Glu Gln Leu Val Tyr Asp Phe Thr Asp Glu Thr Ser Glu Val Ser
            610                 615                 620

Thr Thr Asp Lys Ile Ala Asp Ile Thr Ile Ile Pro Tyr Ile Gly
625                 630                 635                 640

Pro Ala Leu Asn Ile Gly Asn Met Leu Tyr Lys Asp Asp Phe Val Gly
                645                 650                 655

Ala Leu Ile Phe Ser Gly Ala Val Ile Leu Leu Glu Phe Ile Pro Glu
            660                 665                 670

Ile Ala Ile Pro Val Leu Gly Thr Phe Ala Leu Val Ser Tyr Ile Ala
            675                 680                 685

Asn Lys Val Leu Thr Val Gln Thr Ile Asp Asn Ala Leu Ser Lys Arg
690                 695                 700

Asn Glu Lys Trp Asp Glu Val Tyr Lys Tyr Ile Val Thr Asn Trp Leu
705                 710                 715                 720

Ala Lys Val Asn Thr Gln Ile Asp Leu Ile Arg Lys Lys Met Lys Glu
                725                 730                 735

Ala Leu Glu Asn Gln Ala Glu Ala Thr Lys Ala Ile Ile Asn Tyr Gln
            740                 745                 750

Tyr Asn Gln Tyr Thr Glu Glu Lys Asn Asn Ile Asn Phe Asn Ile
            755                 760                 765

Asp Asp Leu Ser Ser Lys Leu Asn Glu Ser Ile Asn Lys Ala Met Ile
770                 775                 780

Asn Ile Asn Lys Phe Leu Asn Gln Cys Ser Val Ser Tyr Leu Met Asn
785                 790                 795                 800

Ser Met Ile Pro Tyr Gly Val Lys Arg Leu Glu Asp Phe Asp Ala Ser
                805                 810                 815

Leu Lys Asp Ala Leu Leu Lys Tyr Ile Tyr Asp Asn Arg Gly Thr Leu
            820                 825                 830

Ile Gly Gln Val Asp Arg Leu Lys Asp Lys Val Asn Asn Thr Leu Ser
            835                 840                 845

Thr Asp Ile Pro Phe Gln Leu Ser Lys Tyr Val Asp Asn Gln Arg Leu

```
                850                 855                 860
Leu Ser Thr Leu Glu Gly Gly Gly Ser Gly Gly Gly Ser Gly
865                 870                 875                 880

Gly Gly Gly Ser Ala Leu Asp Asn Ser Asp Ser Glu Cys Pro Leu Ser
                885                 890                 895

His Asp Gly Tyr Cys Leu His Asp Gly Val Cys Met Tyr Ile Glu Ala
            900                 905                 910

Leu Asp Lys Tyr Ala Cys Asn Cys Val Val Gly Tyr Ile Gly Glu Arg
                915                 920                 925

Cys Gln Tyr Arg Asp Leu Lys Trp Trp Glu Leu Arg Ala Leu Glu Ala
            930                 935                 940

His His His His His His His His His
945                 950

<210> SEQ ID NO 16
<211> LENGTH: 3957
<212> TYPE: DNA
<213> ORGANISM: Artificial sequence
<220> FEATURE:
<223> OTHER INFORMATION: DNA sequence of BoNT/A with Engineered
      Enterokinase Activation Site

<400> SEQUENCE: 16
atgggatcca tggagttcgt taacaaacag ttcaactata agacccagt taacggtgtt      60 gacattgctt acatcaaaat cccgaacgct ggccagatgc agccggtaaa ggcattcaaa     120
atccacaaca aaatctgggt tatcccggaa cgtgatacct ttactaaccc ggaagaaggt    180
gacctgaacc cgccaccgga agcgaaacag gtgccggtat cttactatga ctccacctac    240
ctgtctaccg ataacgaaaa ggacaactac ctgaaaggtg ttactaaact gttcgagcgt    300
atttactcca ccgacctggg ccgtatgctg ctgactagca tcgttcgcgg tatcccgttc    360
tggggcggtt ctaccatcga taccgaactg aaagtaatcg acactaactg catcaacgtt    420
attcagccgg acggttccta tcgttccgaa gaactgaacc tggtgatcat cggcccgtct    480
gctgatatca tccagttcga gtgtaagagc tttggtcacg aagttctgaa cctcacccgt    540
aacggctacg gttccactca gtacatccgt ttctctccgg acttcacctt cggttttgaa    600
gaatccctgg aagtagacac gaacccactg ctgggcgctg gtaaattcgc aactgatcct    660
gcggttaccc tggctcacga actgattcat gcaggccacc gcctgtacgg tatcgccatc    720
aatccgaacc gtgtcttcaa agttaacacc aacgcgtatt acgagatgtc cggtctggaa    780
gttagcttcg aagaactgcg tactttggc ggtcacgacg ctaaattcat cgactctctg    840
caagaaaacg agttccgtct gtactactat aacaagttca agatatcgc atccaccctg    900 aacaaagcga atccatcgt gggtaccact gcttctctcc agtacatgaa gaacgttttt    960 aaagaaaat acctgctcag cgaagacacc tccggcaaat tctctgtaga caagttgaaa   1020
ttcgataaac tttacaaaat gctgactgaa atttacaccg aagacaactt cgttaagttc   1080
tttaaagttc tgaaccgcaa aacctatctg aacttcgaca aggcagtatt caaaatcaac   1140
atcgtgccga agttaactta cactatctac gatggtttca acctgcgtaa caccaacctg   1200
gctgctaatt taacggcca aacacgaa atcaacaaca tgaacttcac aaaactgaaa   1260
aacttcactg gtctgttcga gttttacaag ctgctgtgcg tcgacggcat cattacctcc   1320
aaaactaaat ctgacgatga cgataaaaac aaagcgctga acctgcagtg tatcaaggtt   1380
aacaactggg atttattctt cagcccgagt gaagacaact tcaccaacga cctgaacaaa   1440
```

```
ggtgaagaaa tcacctcaga tactaacatc gaagcagccg aagaaaacat ctcgctggac    1500
ctgatccagc agtactacct gacctttaat ttcgacaacg agccggaaaa catttctatc    1560
gaaaacctga gctctgatat catcggccag ctggaactga tgccgaacat cgaacgtttc    1620
ccaaacggta aaaagtacga gctggacaaa tataccatgt tccactacct gcgcgcgcag    1680
gaatttgaac acggcaaatc ccgtatcgca ctgactaact ccgttaacga agctctgctc    1740
aacccgtccc gtgtatacac cttcttctct agcgactacg tgaaaaaggt caacaaagcg    1800
actgaagctg caatgttctt gggttgggtt gaacagcttg tttatgattt taccgacgag    1860
acgtccgaag tatctactac cgacaaaatt gcggatatca ctatcatcat cccgtacatc    1920
ggtccggctc tgaacattgg caacatgctg tacaaagacg acttcgttgg cgcactgatc    1980
ttctccggtg cggtgatcct gctggagttc atcccggaaa tcgccatccc ggtactgggc    2040 accttttgctc tggtttctta cattgcaaac aaggttctga ctgtacaaac catcgacaac    2100
gcgctgagca acgtaacga aaaatgggat gaagtttaca atatatcgt gaccaactgg    2160 ctggctaagg ttaatactca gatcgacctc atccgcaaaa aaatgaaaga agcactggaa    2220
aaccaggcgg aagctaccaa ggcaatcatt aactaccagt acaaccagta caccgaggaa    2280
gaaaaaaaca acatcaactt caacatcgac gatctgtcct ctaaactgaa cgaatccatc    2340
aacaaagcta tgatcaacat caacaagttc ctgaaccagt gctctgtaag ctatctgatg    2400
aactccatga tcccgtacgg tgttaaacgt ctggaggact cgatgcgtc tctgaaagac    2460 gccctgctga atacattta cgacaaccgt ggcactctga tcggtcaggt tgatcgtctg    2520
aaggacaaag tgaacaatac cttatcgacc gacatcccct tccagctcag taaatatgtc    2580
gataaccaac gccttttgtc cactttcacc gaatacatca aaaacatcat caacaccagt    2640
ctagaaatcc tgaacctgcg ttacgaatct aaccacctga tcgacctgtc tcgttacgct    2700
tctaaaatca acatcggttc taaagttaac ttcgacccga tcgacaaaaa ccagatccag    2760
ctgttcaacc tggaatcttc taaaatcgaa gttatcctga aaaacgctat cgtttacaac    2820
tctatgtacg aaaacttctc tacctctttc tggattcgta tcccgaaata ctttaactct    2880
atctctctga caacgaata caccatcatc aactgcatgg aaaacaactc tggttggaaa    2940
gtttctctga actacggtga aatcatctgg accctgcaag acacccagga aatcaaacag    3000
cgtgttgttt tcaaatactc tcagatgatc aacatctctg actacatcaa ccgttggatc    3060
ttcgttacca tcaccaacaa ccgtctgaac aactctaaaa tctacatcaa cggtcgtctg    3120
atcgaccaga aaccgatctc taacctgggt aacatccacg cttctaacaa catcatgttc    3180
aaactggacg gttgccgtga cacccaccgt tacatctgga tcaaatactt caacctgttc    3240
gacaaagaac tgaacgaaaa agaaatcaaa gacctgtacg acaaccagtc taactctggt    3300
gcactagtga ttttgaagga cttttgggc gactatctcc agtacgacaa accttactat    3360
atgctgaatt tgtatgatcc caacaaatat gtggatgtga ataacgttgg tattaggggt    3420
tacatgtatt tgaagggtcc aagggggtca gtcatgacaa ccaatatcta cttaaattcc    3480
tctctttacc gagggacaaa attcattatc aaaaagtatg ctagtggaaa taagataat    3540 atagtcagaa acaatgatcg cgtttacatt aacgtggtag tcaaaaataa ggagtataga    3600
ctagctacga atgcatcgca ggcgggagtg gagaagatac tgagcgcact agaaatacct    3660
gacgtaggaa acttaagcca ggttgtcgtt atgaaatcaa agaacgatca aggaattact    3720
aataagtgta agatgaactt acaagataac aatggcaatg atataggctt catcgggttt    3780
catcaattta acaacatagc gaaactcgta gcctctaact ggtacaaccg tcaaatcgaa    3840
```

-continued

```
cgaagttccc gtactctagg ttgctcgtgg gagttcatcc cagtagacga cgggtggggc  3900
gaacggccgc ttgcgctagc acaccatcat caccaccatc accatcacca ttaatga    3957
```

<210> SEQ ID NO 17
<211> LENGTH: 1318
<212> TYPE: PRT
<213> ORGANISM: Artificial sequence
<220> FEATURE:
<223> OTHER INFORMATION: Protein sequence of BoNT/A with Engineered
      Enterokinase Activation Site

<400> SEQUENCE: 17

```
His Met Gly Ser Met Glu Phe Val Asn Lys Gln Phe Asn Tyr Lys Asp
1               5                   10                  15

Pro Val Asn Gly Val Asp Ile Ala Tyr Ile Lys Ile Pro Asn Ala Gly
            20                  25                  30

Gln Met Gln Pro Val Lys Ala Phe Lys Ile His Asn Lys Ile Trp Val
        35                  40                  45

Ile Pro Glu Arg Asp Thr Phe Thr Asn Pro Glu Glu Gly Asp Leu Asn
    50                  55                  60

Pro Pro Pro Glu Ala Lys Gln Val Pro Val Ser Tyr Tyr Asp Ser Thr
65                  70                  75                  80

Tyr Leu Ser Thr Asp Asn Glu Lys Asp Asn Tyr Leu Lys Gly Val Thr
                85                  90                  95

Lys Leu Phe Glu Arg Ile Tyr Ser Thr Asp Leu Gly Arg Met Leu Leu
            100                 105                 110

Thr Ser Ile Val Arg Gly Ile Pro Phe Trp Gly Gly Ser Thr Ile Asp
        115                 120                 125

Thr Glu Leu Lys Val Ile Asp Thr Asn Cys Ile Asn Val Ile Gln Pro
130                 135                 140

Asp Gly Ser Tyr Arg Ser Glu Glu Leu Asn Leu Val Ile Ile Gly Pro
145                 150                 155                 160

Ser Ala Asp Ile Ile Gln Phe Glu Cys Lys Ser Phe Gly His Glu Val
                165                 170                 175

Leu Asn Leu Thr Arg Asn Gly Tyr Gly Ser Thr Gln Tyr Ile Arg Phe
            180                 185                 190

Ser Pro Asp Phe Thr Phe Gly Phe Glu Glu Ser Leu Glu Val Asp Thr
        195                 200                 205

Asn Pro Leu Leu Gly Ala Gly Lys Phe Ala Thr Asp Pro Ala Val Thr
    210                 215                 220

Leu Ala His Glu Leu Ile His Ala Gly His Arg Leu Tyr Gly Ile Ala
225                 230                 235                 240

Ile Asn Pro Asn Arg Val Phe Lys Val Asn Thr Asn Ala Tyr Tyr Glu
                245                 250                 255

Met Ser Gly Leu Glu Val Ser Phe Glu Glu Leu Arg Thr Phe Gly Gly
            260                 265                 270

His Asp Ala Lys Phe Ile Asp Ser Leu Gln Glu Asn Glu Phe Arg Leu
        275                 280                 285

Tyr Tyr Tyr Asn Lys Phe Lys Asp Ile Ala Ser Thr Leu Asn Lys Ala
    290                 295                 300

Lys Ser Ile Val Gly Thr Thr Ala Ser Leu Gln Tyr Met Lys Asn Val
305                 310                 315                 320

Phe Lys Glu Lys Tyr Leu Leu Ser Glu Asp Thr Ser Gly Lys Phe Ser
                325                 330                 335
```

```
Val Asp Lys Leu Lys Phe Asp Lys Leu Tyr Lys Met Leu Thr Glu Ile
            340                 345                 350

Tyr Thr Glu Asp Asn Phe Val Lys Phe Phe Lys Val Leu Asn Arg Lys
        355                 360                 365

Thr Tyr Leu Asn Phe Asp Lys Ala Val Phe Lys Ile Asn Ile Val Pro
    370                 375                 380

Lys Val Asn Tyr Thr Ile Tyr Asp Gly Phe Asn Leu Arg Asn Thr Asn
385                 390                 395                 400

Leu Ala Ala Asn Phe Asn Gly Gln Asn Thr Glu Ile Asn Asn Met Asn
                405                 410                 415

Phe Thr Lys Leu Lys Asn Phe Thr Gly Leu Phe Glu Phe Tyr Lys Leu
            420                 425                 430

Leu Cys Val Asp Gly Ile Ile Thr Ser Lys Thr Lys Ser Asp Asp Asp
        435                 440                 445

Asp Lys Asn Lys Ala Leu Asn Leu Gln Cys Ile Lys Val Asn Asn Trp
    450                 455                 460

Asp Leu Phe Phe Ser Pro Ser Glu Asp Asn Phe Thr Asn Asp Leu Asn
465                 470                 475                 480

Lys Gly Glu Glu Ile Thr Ser Asp Thr Asn Ile Glu Ala Ala Glu Glu
                485                 490                 495

Asn Ile Ser Leu Asp Leu Ile Gln Gln Tyr Tyr Leu Thr Phe Asn Phe
            500                 505                 510

Asp Asn Glu Pro Glu Asn Ile Ser Ile Glu Asn Leu Ser Ser Asp Ile
        515                 520                 525

Ile Gly Gln Leu Glu Leu Met Pro Asn Ile Glu Arg Phe Pro Asn Gly
    530                 535                 540

Lys Lys Tyr Glu Leu Asp Lys Tyr Thr Met Phe His Tyr Leu Arg Ala
545                 550                 555                 560

Gln Glu Phe Glu His Gly Lys Ser Arg Ile Ala Leu Thr Asn Ser Val
                565                 570                 575

Asn Glu Ala Leu Leu Asn Pro Ser Arg Val Tyr Thr Phe Phe Ser Ser
            580                 585                 590

Asp Tyr Val Lys Lys Val Asn Lys Ala Thr Glu Ala Ala Met Phe Leu
        595                 600                 605

Gly Trp Val Glu Gln Leu Val Tyr Asp Phe Thr Asp Glu Thr Ser Glu
    610                 615                 620

Val Ser Thr Thr Asp Lys Ile Ala Asp Ile Thr Ile Ile Ile Pro Tyr
625                 630                 635                 640

Ile Gly Pro Ala Leu Asn Ile Gly Asn Met Leu Tyr Lys Asp Asp Phe
                645                 650                 655

Val Gly Ala Leu Ile Phe Ser Gly Ala Val Ile Leu Leu Glu Phe Ile
            660                 665                 670

Pro Glu Ile Ala Ile Pro Val Leu Gly Thr Phe Ala Leu Val Ser Tyr
        675                 680                 685

Ile Ala Asn Lys Val Leu Thr Val Gln Thr Ile Asp Asn Ala Leu Ser
    690                 695                 700

Lys Arg Asn Glu Lys Trp Asp Glu Val Tyr Lys Tyr Ile Val Thr Asn
705                 710                 715                 720

Trp Leu Ala Lys Val Asn Thr Gln Ile Asp Leu Ile Arg Lys Lys Met
                725                 730                 735

Lys Glu Ala Leu Glu Asn Gln Ala Glu Ala Thr Lys Ala Ile Ile Asn
            740                 745                 750

Tyr Gln Tyr Asn Gln Tyr Thr Glu Glu Glu Lys Asn Asn Ile Asn Phe
```

-continued

```
            755                 760                 765
Asn Ile Asp Asp Leu Ser Ser Lys Leu Asn Glu Ser Ile Asn Lys Ala
770                 775                 780
Met Ile Asn Ile Asn Lys Phe Leu Asn Gln Cys Ser Val Ser Tyr Leu
785                 790                 795                 800
Met Asn Ser Met Ile Pro Tyr Gly Val Lys Arg Leu Glu Asp Phe Asp
                805                 810                 815
Ala Ser Leu Lys Asp Ala Leu Leu Lys Tyr Ile Tyr Asp Asn Arg Gly
            820                 825                 830
Thr Leu Ile Gly Gln Val Asp Arg Leu Lys Asp Lys Val Asn Asn Thr
            835                 840                 845
Leu Ser Thr Asp Ile Pro Phe Gln Leu Ser Lys Tyr Val Asp Asn Gln
850                 855                 860
Arg Leu Leu Ser Thr Phe Thr Glu Tyr Ile Lys Asn Ile Ile Asn Thr
865                 870                 875                 880
Ser Leu Glu Ile Leu Asn Leu Arg Tyr Glu Ser Asn His Leu Ile Asp
                885                 890                 895
Leu Ser Arg Tyr Ala Ser Lys Ile Asn Ile Gly Ser Lys Val Asn Phe
            900                 905                 910
Asp Pro Ile Asp Lys Asn Gln Ile Gln Leu Phe Asn Leu Glu Ser Ser
            915                 920                 925
Lys Ile Glu Val Ile Leu Lys Asn Ala Ile Val Tyr Asn Ser Met Tyr
930                 935                 940
Glu Asn Phe Ser Thr Ser Phe Trp Ile Arg Ile Pro Lys Tyr Phe Asn
945                 950                 955                 960
Ser Ile Ser Leu Asn Asn Glu Tyr Thr Ile Ile Asn Cys Met Glu Asn
                965                 970                 975
Asn Ser Gly Trp Lys Val Ser Leu Asn Tyr Gly Glu Ile Ile Trp Thr
            980                 985                 990
Leu Gln Asp Thr Gln Glu Ile Lys Gln Arg Val Val Phe Lys Tyr Ser
            995                 1000                1005
Gln Met Ile Asn Ile Ser Asp Tyr Ile Asn Arg Trp Ile Phe Val
    1010                1015                1020
Thr Ile Thr Asn Asn Arg Leu Asn Asn Ser Lys Ile Tyr Ile Asn
    1025                1030                1035
Gly Arg Leu Ile Asp Gln Lys Pro Ile Ser Asn Leu Gly Asn Ile
    1040                1045                1050
His Ala Ser Asn Asn Ile Met Phe Lys Leu Asp Gly Cys Arg Asp
    1055                1060                1065
Thr His Arg Tyr Ile Trp Ile Lys Tyr Phe Asn Leu Phe Asp Lys
    1070                1075                1080
Glu Leu Asn Glu Lys Glu Ile Lys Asp Leu Tyr Asp Asn Gln Ser
    1085                1090                1095
Asn Ser Gly Ala Leu Val Ile Leu Lys Asp Phe Trp Gly Asp Tyr
    1100                1105                1110
Leu Gln Tyr Asp Lys Pro Tyr Tyr Met Leu Asn Leu Tyr Asp Pro
    1115                1120                1125
Asn Lys Tyr Val Asp Val Asn Asn Val Gly Ile Arg Gly Tyr Met
    1130                1135                1140
Tyr Leu Lys Gly Pro Arg Gly Ser Val Met Thr Thr Asn Ile Tyr
    1145                1150                1155
Leu Asn Ser Ser Leu Tyr Arg Gly Thr Lys Phe Ile Ile Lys Lys
    1160                1165                1170
```

-continued

| | | | | | | | | | | | |
|---|---|---|---|---|---|---|---|---|---|---|---|
| Tyr | Ala | Ser | Gly | Asn | Lys | Asp | Asn | Ile | Val | Arg | Asn Asn Asp Arg |
| | 1175 | | | | 1180 | | | | | 1185 | |
| Val | Tyr | Ile | Asn | Val | Val | Val | Lys | Asn | Lys | Glu | Tyr Arg Leu Ala |
| | 1190 | | | | 1195 | | | | | 1200 | |
| Thr | Asn | Ala | Ser | Gln | Ala | Gly | Val | Glu | Lys | Ile | Leu Ser Ala Leu |
| | 1205 | | | | 1210 | | | | | 1215 | |
| Glu | Ile | Pro | Asp | Val | Gly | Asn | Leu | Ser | Gln | Val | Val Met Lys |
| | 1220 | | | | 1225 | | | | | 1230 | |
| Ser | Lys | Asn | Asp | Gln | Gly | Ile | Thr | Asn | Lys | Cys | Lys Met Asn Leu |
| | 1235 | | | | 1240 | | | | | 1245 | |
| Gln | Asp | Asn | Asn | Gly | Asn | Asp | Ile | Gly | Phe | Ile | Gly Phe His Gln |
| | 1250 | | | | 1255 | | | | | 1260 | |
| Phe | Asn | Asn | Ile | Ala | Lys | Leu | Val | Ala | Ser | Asn | Trp Tyr Asn Arg |
| | 1265 | | | | 1270 | | | | | 1275 | |
| Gln | Ile | Glu | Arg | Ser | Ser | Arg | Thr | Leu | Gly | Cys | Ser Trp Glu Phe |
| | 1280 | | | | 1285 | | | | | 1290 | |
| Ile | Pro | Val | Asp | Asp | Gly | Trp | Gly | Glu | Arg | Pro | Leu Ala Leu Ala |
| | 1295 | | | | 1300 | | | | | 1305 | |
| His | His | His | His | His | His | His | His | His | | | |
| | 1310 | | | | 1315 | | | | | | |

<210> SEQ ID NO 18
<211> LENGTH: 3957
<212> TYPE: DNA
<213> ORGANISM: Artificial sequence
<220> FEATURE:
<223> OTHER INFORMATION: DNA sequence of BoNT/A with Engineered
      Enterokinase Activation Site and ADAM17 Protease Cleavage Site

<400> SEQUENCE: 18

| | |
|---|---|
| atgggatcca tggagttcgt taacaaacag ttcaactata agacccagt taacggtgtt | 60 |
| gacattgctt acatcaaaat cccgaacgct ggccagatgc agccggtaaa ggcattcaaa | 120 |
| atccacaaca aaatctgggt tatcccggaa cgtgatacct ttactaaccc ggaagaaggt | 180 |
| gacctgaacc cgccaccgga agcgaaacag gtgccggtat cttactatga ctccacctac | 240 |
| ctgtctaccg ataacgaaaa ggacaactac ctgaaaggtg ttactaaact gttcgagcgt | 300 |
| atttactcca ccgacctggg ccgtatgctg ctgactagca tcgttcgcgg tatcccgttc | 360 |
| tggggcggtt ctaccatcga taccgaactg aaagtaatcg acactaactg catcaacgtt | 420 |
| attcagccgg acggttccta tcgttccgaa gaactgaacc tggtgatcat cggcccgtct | 480 |
| gctgatatca tccagttcga gtgtaagagc tttggtcacg aagttctgaa cctcacccgt | 540 |
| aacggctacg gttccactca gtacatccgt ttctctccgg acttcacctt cggttttgaa | 600 |
| gaatccctgg aagtagacac gaacccactg cgcaggctg ttcgttcctc ttctgatcct | 660 |
| gcggttaccc tggctcacga actgattcat gcaggccacc gcctgtacgg tatcgccatc | 720 |
| aatccgaacc gtgtcttcaa agttaacacc aacgcgtatt acgagatgtc cggtctggaa | 780 |
| gttagcttcg aagaactgcg tacttttggc ggtcacgacg ctaaattcat cgactctctg | 840 |
| caagaaaacg agttccgtct gtactactat aacaagttca aagatatcgc atccaccctg | 900 |
| aacaaagcga atccatcgt gggtaccact gcttctctcc agtacatgaa gaacgttttt | 960 |
| aaagaaaaat acctgctcag cgaagacacc tccggcaaat ctctgtagaa caagttgaaa | 1020 |
| ttcgataaac tttacaaaat gctgactgaa atttacaccg aagacaactt cgttaagttc | 1080 |
| tttaaagttc tgaaccgcaa aacctatctg aacttcgaca aggcagtatt caaaatcaac | 1140 |

```
atcgtgccga aagttaacta cactatctac gatggtttca acctgcgtaa caccaacctg    1200
gctgctaatt ttaacggcca gaacacggaa atcaacaaca tgaacttcac aaaactgaaa    1260
aacttcactg gtctgttcga gttttacaag ctgctgtgcg tcgacggcat cattacctcc    1320
aaaactaaat ctgacgatga cgataaaaac aaagcgctga acctgcagtg tatcaaggtt    1380
aacaactggg atttattctt cagcccgagt gaagacaact tcaccaacga cctgaacaaa    1440
ggtgaagaaa tcacctcaga tactaacatc gaagcagccg aagaaaacat ctcgctggac    1500
ctgatccagc agtactacct gacctttaat ttcgacaacg agccggaaaa catttctatc    1560
gaaaacctga gctctgatat catcggccag ctggaactga tgccgaacat cgaacgtttc    1620
ccaaacggta aaagtacga gctggacaaa tataccatgt tccactacct gcgcgcgcag    1680
gaatttgaac acggcaaatc ccgtatcgca ctgactaact ccgttaacga agctctgctc    1740
aacccgtccc gtgtatacac cttcttctct agcgactacg tgaaaaaggt caacaaagcg    1800
actgaagctg caatgttctt gggttgggtt gaacagcttg tttatgattt taccgacgag    1860
acgtccgaag tatctactac cgacaaaatt gcggatatca ctatcatcat cccgtacatc    1920
ggtccggctc tgaacattgg caacatgctg tacaaagacg acttcgttgg cgcactgatc    1980
ttctccggtg cggtgatcct gctggagttc atcccggaaa tcgccatccc ggtactgggc    2040
acctttgctc tggtttctta cattgcaaac aaggttctga ctgtacaaac catcgacaac    2100
gcgctgagca acgtaacga aaatgggat gaagtttaca atatatcgt gaccaactgg    2160 ctggctaagg ttaatactca gatcgacctc atccgcaaaa aaatgaaaga agcactggaa    2220
aaccaggcgg aagctaccaa ggcaatcatt aactaccagt acaaccagta caccgaggaa    2280
gaaaaaaaca acatcaactt caacatcgac gatctgtcct ctaaactgaa cgaatccatc    2340
aacaaagcta tgatcaacat caacaagttc ctgaaccagt gctctgtaag ctatctgatg    2400
aactccatga tcccgtacgg tgttaaacgt ctggaggact cgatgcgtc tctgaaagac    2460 gccctgctga aatacattta cgacaaccgt ggcactctga tcggtcaggt tgatcgtctg    2520
aaggacaaag tgaacaatac cttatcgacc gacatcccct tcagctcag taaatatgtc    2580 gataaccaac gccttttgtc cactttcacc gaatacatca aaaacatcat caacaccagt    2640
ctagaaatcc tgaacctgcg ttacgaatct aaccacctga tcgacctgtc tcgttacgct    2700
tctaaaatca acatcggttc taaagttaac ttcgacccga tcgacaaaaa ccagatccag    2760
ctgttcaacc tggaatcttc taaaatcgaa gttatcctga aaacgctat cgtttacaac    2820 tctatgtacg aaaacttctc tacctctttc tggattcgta tcccgaaata ctttaactct    2880
atctctctga caacgaata caccatcatc aactgcatgg aaaacaactc tggttggaaa    2940
gtttctctga actacggtga aatcatctgg accctgcaag acacccagga atcaaacag    3000 cgtgttgttt tcaaatactc tcagatgatc aacatctctg actacatcaa ccgttggatc    3060
ttcgttacca tcaccaacaa ccgtctgaac aactctaaaa tctacatcaa cggtcgtctg    3120
atcgaccaga aaccgatctc taacctgggt aacatccacg cttctaacaa catcatgttc    3180
aaactggacg gttgccgtga cacccaccgt tacatctgga tcaaatactt caacctgttc    3240
gacaaagaac tgaacgaaaa agaaatcaaa gacctgtacg acaaccagtc taactctggt    3300
gcactagtga ttttgaagga cttttgggc gactatctcc agtacgacaa accttactat    3360
atgctgaatt tgtatgatcc caacaaatat gtggatgtga ataacgttgg tattaggggt    3420
tacatgtatt tgaagggtcc aaggggggtca gtcatgacaa ccaatatcta cttaaattcc    3480
```

-continued

```
tctctttacc gagggacaaa attcattatc aaaaagtatg ctagtggaaa taaagataat    3540
atagtcagaa acaatgatcg cgtttacatt aacgtggtag tcaaaaataa ggagtataga    3600
ctagctacga atgcatcgca ggcgggagtg gagaagatac tgagcgcact agaaatacct    3660
gacgtaggaa acttaagcca ggttgtcgtt atgaaatcaa agaacgatca aggaattact    3720
aataagtgta agatgaactt acaagataac aatggcaatg atataggctt catcgggttt    3780
catcaattta acaacatagc gaaactcgta gcctctaact ggtacaaccg tcaaatcgaa    3840
cgaagttccc gtactctagg ttgctcgtgg gagttcatcc cagtagacga cgggtggggc    3900
gaacggccgc ttgcgctagc acaccatcat caccaccatc accatcacca ttaatga      3957
```

<210> SEQ ID NO 19
<211> LENGTH: 1316
<212> TYPE: PRT
<213> ORGANISM: Artificial sequence
<220> FEATURE:
<223> OTHER INFORMATION: Protein sequence of BoNT/A with Engineered Enterokinase Activation Site and ADAM17 Protease Cleavage Site

<400> SEQUENCE: 19

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Ala Gln Ala Val Arg Ser Ser Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
```

```
            275                 280                 285
Tyr Asn Lys Phe Lys Asp Ile Ala Ser Thr Leu Asn Lys Ala Lys Ser
            290                 295                 300
Ile Val Gly Thr Thr Ala Ser Leu Gln Tyr Met Lys Asn Val Phe Lys
305                 310                 315                 320
Glu Lys Tyr Leu Leu Ser Glu Asp Thr Ser Gly Lys Phe Ser Val Asp
                325                 330                 335
Lys Leu Lys Phe Asp Lys Leu Tyr Lys Met Leu Thr Glu Ile Tyr Thr
            340                 345                 350
Glu Asp Asn Phe Val Lys Phe Lys Val Leu Asn Arg Lys Thr Tyr
            355                 360                 365
Leu Asn Phe Asp Lys Ala Val Phe Lys Ile Asn Ile Val Pro Lys Val
    370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
            405                 410                 415
Lys Leu Lys Asn Phe Thr Gly Leu Phe Glu Phe Tyr Lys Leu Leu Cys
            420                 425                 430
Val Asp Gly Ile Ile Thr Ser Lys Thr Lys Ser Asp Asp Asp Lys
            435                 440                 445
Asn Lys Ala Leu Asn Leu Gln Cys Ile Lys Val Asn Asn Trp Asp Leu
    450                 455                 460
Phe Phe Ser Pro Ser Glu Asp Asn Phe Thr Asn Asp Leu Asn Lys Gly
465                 470                 475                 480
Glu Glu Ile Thr Ser Asp Thr Asn Ile Glu Ala Ala Glu Asn Ile
                485                 490                 495
Ser Leu Asp Leu Ile Gln Gln Tyr Tyr Leu Thr Phe Asn Phe Asp Asn
            500                 505                 510
Glu Pro Glu Asn Ile Ser Ile Glu Asn Leu Ser Ser Asp Ile Ile Gly
            515                 520                 525
Gln Leu Glu Leu Met Pro Asn Ile Glu Arg Phe Pro Asn Gly Lys Lys
    530                 535                 540
Tyr Glu Leu Asp Lys Tyr Thr Met Phe His Tyr Leu Arg Ala Gln Glu
545                 550                 555                 560
Phe Glu His Gly Lys Ser Arg Ile Ala Leu Thr Asn Ser Val Asn Glu
                565                 570                 575
Ala Leu Leu Asn Pro Ser Arg Val Tyr Thr Phe Phe Ser Ser Asp Tyr
            580                 585                 590
Val Lys Lys Val Asn Lys Ala Thr Glu Ala Ala Met Phe Leu Gly Trp
            595                 600                 605
Val Glu Gln Leu Val Tyr Asp Phe Thr Asp Glu Thr Ser Glu Val Ser
    610                 615                 620
Thr Thr Asp Lys Ile Ala Asp Ile Thr Ile Ile Pro Tyr Ile Gly
625                 630                 635                 640
Pro Ala Leu Asn Ile Gly Asn Met Leu Tyr Lys Asp Asp Phe Val Gly
                645                 650                 655
Ala Leu Ile Phe Ser Gly Ala Val Ile Leu Leu Glu Phe Ile Pro Glu
            660                 665                 670
Ile Ala Ile Pro Val Leu Gly Thr Phe Ala Leu Val Ser Tyr Ile Ala
            675                 680                 685
Asn Lys Val Leu Thr Val Gln Thr Ile Asp Asn Ala Leu Ser Lys Arg
    690                 695                 700
```

-continued

```
Asn Glu Lys Trp Asp Glu Val Tyr Lys Tyr Ile Val Thr Asn Trp Leu
705                 710                 715                 720

Ala Lys Val Asn Thr Gln Ile Asp Leu Ile Arg Lys Lys Met Lys Glu
                725                 730                 735

Ala Leu Glu Asn Gln Ala Glu Ala Thr Lys Ala Ile Ile Asn Tyr Gln
            740                 745                 750

Tyr Asn Gln Tyr Thr Glu Glu Lys Asn Asn Ile Asn Phe Asn Ile
        755                 760                 765

Asp Asp Leu Ser Ser Lys Leu Asn Glu Ser Ile Asn Lys Ala Met Ile
        770                 775                 780

Asn Ile Asn Lys Phe Leu Asn Gln Cys Ser Val Ser Tyr Leu Met Asn
785                 790                 795                 800

Ser Met Ile Pro Tyr Gly Val Lys Arg Leu Glu Asp Phe Asp Ala Ser
                805                 810                 815

Leu Lys Asp Ala Leu Leu Lys Tyr Ile Tyr Asp Asn Arg Gly Thr Leu
            820                 825                 830

Ile Gly Gln Val Asp Arg Leu Lys Asp Lys Val Asn Asn Thr Leu Ser
            835                 840                 845

Thr Asp Ile Pro Phe Gln Leu Ser Lys Tyr Val Asp Asn Gln Arg Leu
        850                 855                 860

Leu Ser Thr Phe Thr Glu Tyr Ile Lys Asn Ile Ile Asn Thr Ser Leu
865                 870                 875                 880

Glu Ile Leu Asn Leu Arg Tyr Glu Ser Asn His Leu Ile Asp Leu Ser
                885                 890                 895

Arg Tyr Ala Ser Lys Ile Asn Ile Gly Ser Lys Val Asn Phe Asp Pro
            900                 905                 910

Ile Asp Lys Asn Gln Ile Gln Leu Phe Asn Leu Glu Ser Ser Lys Ile
        915                 920                 925

Glu Val Ile Leu Lys Asn Ala Ile Val Tyr Asn Ser Met Tyr Glu Asn
        930                 935                 940

Phe Ser Thr Ser Phe Trp Ile Arg Ile Pro Lys Tyr Phe Asn Ser Ile
945                 950                 955                 960

Ser Leu Asn Asn Glu Tyr Thr Ile Ile Asn Cys Met Glu Asn Asn Ser
                965                 970                 975

Gly Trp Lys Val Ser Leu Asn Tyr Gly Glu Ile Ile Trp Thr Leu Gln
            980                 985                 990

Asp Thr Gln Glu Ile Lys Gln Arg  Val Val Phe Lys Tyr  Ser Gln Met
        995                 1000                1005

Ile Asn  Ile Ser Asp Tyr Ile  Asn Arg Trp Ile Phe  Val Thr Ile
    1010                 1015                1020

Thr Asn  Asn Arg Leu Asn Asn  Ser Lys Ile Tyr Ile  Asn Gly Arg
    1025                 1030                1035

Leu Ile  Asp Gln Lys Pro Ile  Ser Asn Leu Gly Asn  Ile His Ala
    1040                 1045                1050

Ser Asn  Asn Ile Met Phe Lys  Leu Asp Gly Cys Arg  Asp Thr His
    1055                 1060                1065

Arg Tyr  Ile Trp Ile Lys Tyr  Phe Asn Leu Phe Asp  Lys Glu Leu
    1070                 1075                1080

Asn Glu  Lys Glu Ile Lys Asp  Leu Tyr Asp Asn Gln  Ser Asn Ser
    1085                 1090                1095

Gly Ala  Leu Val Ile Leu Lys  Asp Phe Trp Gly Asp  Tyr Leu Gln
    1100                 1105                1110
```

-continued

| | | | | | | | | | |
|---|---|---|---|---|---|---|---|---|---|
|Tyr|Asp|Lys|Pro|Tyr|Tyr|Met|Leu|Asn|Leu|Tyr|Asp|Pro|Asn|Lys|
|   |1115|   |   |   |   |1120|   |   |   |1125|   |   |   |   |

Tyr Asp Lys Pro Tyr Tyr Met Leu Asn Leu Tyr Asp Pro Asn Lys
    1115                1120                1125

Tyr Val Asp Val Asn Val Gly Ile Arg Gly Tyr Met Tyr Leu
    1130                1135                1140

Lys Gly Pro Arg Gly Ser Val Met Thr Thr Asn Ile Tyr Leu Asn
    1145                1150                1155

Ser Ser Leu Tyr Arg Gly Thr Lys Phe Ile Ile Lys Lys Tyr Ala
    1160                1165                1170

Ser Gly Asn Lys Asp Asn Ile Val Arg Asn Asn Asp Arg Val Tyr
    1175                1180                1185

Ile Asn Val Val Val Lys Asn Lys Glu Tyr Arg Leu Ala Thr Asn
    1190                1195                1200

Ala Ser Gln Ala Gly Val Glu Lys Ile Leu Ser Ala Leu Glu Ile
    1205                1210                1215

Pro Asp Val Gly Asn Leu Ser Gln Val Val Val Met Lys Ser Lys
    1220                1225                1230

Asn Asp Gln Gly Ile Thr Asn Lys Cys Lys Met Asn Leu Gln Asp
    1235                1240                1245

Asn Asn Gly Asn Asp Ile Gly Phe Ile Gly Phe His Gln Phe Asn
    1250                1255                1260

Asn Ile Ala Lys Leu Val Ala Ser Asn Trp Tyr Asn Arg Gln Ile
    1265                1270                1275

Glu Arg Ser Ser Arg Thr Leu Gly Cys Ser Trp Glu Phe Ile Pro
    1280                1285                1290

Val Asp Asp Gly Trp Gly Glu Arg Pro Leu Ala Leu Ala His His
    1295                1300                1305

His His His His His His His
    1310            1315

<210> SEQ ID NO 20
<211> LENGTH: 3960
<212> TYPE: DNA
<213> ORGANISM: Artificial sequence
<220> FEATURE:
<223> OTHER INFORMATION: DNA sequence of BoNT/A with Engineered
      Enterokinase Activation Site and Furin Protease Cleavage Site

<400> SEQUENCE: 20

| | |
|---|---|
|atgggatcca tggagttcgt taacaaacag ttcaactata aagacccagt taacggtgtt|60|
|gacattgctt acatcaaaat cccgaacgct ggccagatgc agccggtaaa ggcattcaaa|120|
|atccacaaca aaatctgggt tatcccggaa cgtgataccct tactaaccc ggaagaaggt|180|
|gacctgaacc cgccaccgga agcgaaacag gtgccggtat cttactatga ctccacctac|240|
|ctgtctaccg ataacgaaaa ggacaactac ctgaaaggtg ttactaaaac tgttcgagcgt|300|
|attactccaa ccgacctggg ccgtatgctg ctgactagca tcgttcgcgg tatcccgttc|360|
|tggggcggtt ctaccatcga taccgaactg aaagtaatcg acactaactg catcaacgtt|420|
|attcagccgg acgttcccta tcgttccgaa gaactgaacc tggtgatcat cggcccgtct|480|
|gctgatatca tccagttcga gtgtaagagc tttggtcacg aagttctgaa cctcacccgt|540|
|aacggctacg ttccactcaa gtacatccgt ttctctccgg acttcacctt cggttttgaa|600|
|gaatccctgg aagtagacac gaacccactg ctgggcgctg gtaaattcgc aactgatcct|660|
|gcggttaccc tggctcacga actgattcat gcaggccacc gcctgtacgg tatcgccatc|720|
|aatccgaacc gtgtcttcaa agttaacacc aacgcgtatt acgagatgtc cggtctggaa|780|

```
gttagcttcg aagaactgcg tacttttggc ggtcacgacg ctaaattcat cgactctctg      840
caagaaaacg agttccgtct gtactactat aacaagttca agatatcgc atccaccctg       900 aacaaagcga atccatcgt gggtaccact gcttctctcc agtacatgaa gaacgttttt       960
aaagaaaaat acctgctcag cgaagacacc tccggcaaat tctctgtaga caagttgaaa     1020
ttcgataaac tttacaaaat gctgactgaa atttacaccg aagacaactt cgttaagttc     1080
tttaaagttc tgaaccgcaa aacctatctg aacttcgaca aggcagtatt caaaatcaac     1140
atcgtgccga aagttaacta cactatctac gatggtttca acctgcgtaa caccaacctg     1200
gctgctaatt ttaacggcca gaacacggaa atcaacaaca tgaacttcac aaaactgaaa     1260
aacttcactg gtctgttcga gttttacaag ctgctgtgcg tcgacggcat cattacctcc     1320
aaaactaaat ctgacgatga cgataaaaac aaagcgctga acctgcagtg tatcaaggtt     1380
aacaactggg atttattctt cagcccgagt gaagacaact tcaccaacga cctgaacaaa     1440
ggtgaagaaa tcacctcaga tactaacatc gaagcagccg aagaaaacat ctcgctggac     1500
ctgatccagc agtactacct gacctttaat ttcgacaacag agccggaaaa catttctatc     1560
gaaaacctga gctctgatat catcggccag ctggaactga tgccgaacat cgaacgtttc     1620
ccaaacggta aaaagtacga gctggacaaa tataccatgt tccactacct gcgcgcgcag     1680
gaatttgaac acggccgttc ccgtcgcatc gcactgacta actccgttaa cgaagctctg     1740
ctcaacccgt cccgtgtata caccttcttc tctagcgact acgtgaaaaa ggtcaacaaa     1800
gcgactgaag ctgcaatgtt cttgggttgg gttgaacagc ttgtttatga ttttaccgac     1860
gagacgtccg aagtatctac taccgacaaa attgcggata tcactatcat catcccgtac     1920
atcggtccgg ctctgaacat tggcaacatg ctgtacaaag acgacttcgt tggcgcactg     1980
atcttctccg gtgcggtgat cctgctggag ttcatcccgg aaatcgccat cccggtactg     2040
ggcacctttg ctctggtttc ttacattgca acaaggttc tgactgtaca aaccatcgac      2100
aacgcgctga gcaaacgtaa cgaaaaatgg gatgaagttt acaaatatat cgtgaccaac     2160
tggctggcta aggttaatac tcagatcgac ctcatccgca aaaaaatgaa agaagcactg     2220
gaaaaccagg cggaagctac caaggcaatc attaactacc agtacaacca gtacaccgag     2280
gaagaaaaaa acaacatcaa cttcaacatc gacgatctgt cctctaaact gaacgaatcc     2340
atcaacaaag ctatgatcaa catcaacaag ttcctgaacc agtgctctgt aagctatctg     2400
atgaactcca tgatcccgta cggtgttaaa cgtctggagg acttcgatgc gtctctgaaa     2460
gacgccctgc tgaaatacat ttacgacaac cgtggcactc tgatcggtca ggttgatcgt     2520
ctgaaggaca aagtgaacaa taccttatcg accgacatcc cttttcagct cagtaaatat     2580
gtcgataacc aacgcctttt gtccactttc accgaataca tcaaaaacat catcaacacc     2640
agtctagaaa tcctgaacct gcgttacgaa tctaaccacc tgatcgacct gtctcgttac     2700
gcttctaaaa tcaacatcgg ttctaaagtt aacttcgacc cgatcgacaa aaaccagatc     2760
cagctgttca acctggaatc ttctaaaatc gaagttatcc tgaaaaacgc tatcgtttac     2820
aactctatgt acgaaaactt ctctacctct ttctggattc gtatcccgaa atactttaac     2880
tctatctctc tgaacaacga atacaccatc atcaactgca tggaaaacaa ctctggttgg     2940
aaagtttctc tgaactacgg tgaaatcatc tggaccctgc aagacaccca ggaaatcaaa     3000
cagcgtgttg ttttcaaata ctctcagatg atcaacatct ctgactacat caaccgttgg     3060
atcttcgtta ccatcaccaa caaccgtctg aacaactcta aaatctacat caacggtcgt     3120
ctgatcgacc agaaaccgat ctctaacctg ggtaacatcc acgcttctaa caacatcatg     3180
```

-continued

```
ttcaaactgg acggttgccg tgacacccac cgttacatct ggatcaaata cttcaacctg    3240
ttcgacaaag aactgaacga aaaagaaatc aaagacctgt acgacaacca gtctaactct    3300
ggtgcactag tgattttgaa ggacttttgg ggcgactatc tccagtacga caaaccttac    3360
tatatgctga atttgtatga tcccaacaaa tatgtggatg tgaataacgt tggtattagg    3420
ggttacatgt atttgaaggg tccaaggggg tcagtcatga caaccaatat ctacttaaat    3480
tcctctcttt accgagggac aaaattcatt atcaaaaagt atgctagtgg aaataaagat    3540
aatatagtca gaaacaatga tcgcgtttac attaacgtgg tagtcaaaaa taaggagtat    3600
agactagcta cgaatgcatc gcaggcggga gtggagaaga tactgagcgc actagaaata    3660
cctgacgtag gaaacttaag ccaggttgtc gttatgaaat caaagaacga tcaaggaatt    3720
actaataagt gtaagatgaa cttacaagat aacaatggca atgatatagg cttcatcggg    3780
tttcatcaat ttaacaacat agcgaaactc gtagcctcta actggtacaa ccgtcaaatc    3840
gaacgaagtt cccgtactct aggttgctcg tgggagttca tcccagtaga cgacgggtgg    3900
ggcgaacggc cgcttgcgct agcacaccat catcaccacc atcaccatca ccattaatga    3960
```

<210> SEQ ID NO 21
<211> LENGTH: 1317
<212> TYPE: PRT
<213> ORGANISM: Artificial sequence
<220> FEATURE:
<223> OTHER INFORMATION: Protein sequence of BoNT/A with Engineered
      Enterokinase Activation Site and Furin Protease Cleavage Site

<400> SEQUENCE: 21

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220
```

-continued

```
His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
            245                 250                 255

Gly Leu Glu Val Ser Phe Glu Glu Leu Arg Thr Phe Gly Gly His Asp
        260                 265                 270

Ala Lys Phe Ile Asp Ser Leu Gln Glu Asn Glu Phe Arg Leu Tyr Tyr
    275                 280                 285

Tyr Asn Lys Phe Lys Asp Ile Ala Ser Thr Leu Asn Lys Ala Lys Ser
290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
            325                 330                 335

Lys Leu Lys Phe Asp Lys Leu Tyr Lys Met Leu Thr Glu Ile Tyr Thr
        340                 345                 350

Glu Asp Asn Phe Val Lys Phe Lys Val Leu Asn Arg Lys Thr Tyr
    355                 360                 365

Leu Asn Phe Asp Lys Ala Val Phe Lys Ile Asn Ile Val Pro Lys Val
370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
            405                 410                 415

Lys Leu Lys Asn Phe Thr Gly Leu Phe Glu Phe Tyr Lys Leu Leu Cys
        420                 425                 430

Val Asp Gly Ile Ile Thr Ser Lys Thr Lys Ser Asp Asp Asp Lys
    435                 440                 445

Asn Lys Ala Leu Asn Leu Gln Cys Ile Lys Val Asn Asn Trp Asp Leu
450                 455                 460

Phe Phe Ser Pro Ser Glu Asp Asn Phe Thr Asn Asp Leu Asn Lys Gly
465                 470                 475                 480

Glu Glu Ile Thr Ser Asp Thr Asn Ile Glu Ala Ala Glu Glu Asn Ile
            485                 490                 495

Ser Leu Asp Leu Ile Gln Gln Tyr Tyr Leu Thr Phe Asn Phe Asp Asn
        500                 505                 510

Glu Pro Glu Asn Ile Ser Ile Glu Asn Leu Ser Ser Asp Ile Ile Gly
    515                 520                 525

Gln Leu Glu Leu Met Pro Asn Ile Glu Arg Phe Pro Asn Gly Lys Lys
530                 535                 540

Tyr Glu Leu Asp Lys Tyr Thr Met Phe His Tyr Leu Arg Ala Gln Glu
545                 550                 555                 560

Phe Glu His Gly Arg Ser Arg Arg Ile Ala Leu Thr Asn Ser Val Asn
            565                 570                 575

Glu Ala Leu Leu Asn Pro Ser Arg Val Tyr Thr Phe Phe Ser Ser Asp
        580                 585                 590

Tyr Val Lys Lys Val Asn Lys Ala Thr Glu Ala Ala Met Phe Leu Gly
    595                 600                 605

Trp Val Glu Gln Leu Val Tyr Asp Phe Thr Asp Glu Thr Ser Glu Val
610                 615                 620

Ser Thr Thr Asp Lys Ile Ala Asp Ile Thr Ile Ile Pro Tyr Ile
625                 630                 635                 640
```

-continued

```
Gly Pro Ala Leu Asn Ile Gly Asn Met Leu Tyr Lys Asp Asp Phe Val
                645                 650                 655

Gly Ala Leu Ile Phe Ser Gly Val Ile Leu Leu Glu Phe Ile Pro
            660                 665                 670

Glu Ile Ala Ile Pro Val Leu Gly Thr Phe Ala Leu Val Ser Tyr Ile
        675                 680                 685

Ala Asn Lys Val Leu Thr Val Gln Thr Ile Asp Asn Ala Leu Ser Lys
    690                 695                 700

Arg Asn Glu Lys Trp Asp Glu Val Tyr Lys Tyr Ile Val Thr Asn Trp
705                 710                 715                 720

Leu Ala Lys Val Asn Thr Gln Ile Asp Leu Ile Arg Lys Lys Met Lys
                725                 730                 735

Glu Ala Leu Glu Asn Gln Ala Glu Ala Thr Lys Ala Ile Ile Asn Tyr
            740                 745                 750

Gln Tyr Asn Gln Tyr Thr Glu Glu Lys Asn Asn Ile Asn Phe Asn
        755                 760                 765

Ile Asp Asp Leu Ser Ser Lys Leu Asn Glu Ser Ile Asn Lys Ala Met
    770                 775                 780

Ile Asn Ile Asn Lys Phe Leu Asn Gln Cys Ser Val Ser Tyr Leu Met
785                 790                 795                 800

Asn Ser Met Ile Pro Tyr Gly Val Lys Arg Leu Glu Asp Phe Asp Ala
                805                 810                 815

Ser Leu Lys Asp Ala Leu Leu Lys Tyr Ile Tyr Asp Asn Arg Gly Thr
            820                 825                 830

Leu Ile Gly Gln Val Asp Arg Leu Lys Asp Lys Val Asn Asn Thr Leu
        835                 840                 845

Ser Thr Asp Ile Pro Phe Gln Leu Ser Lys Tyr Val Asp Asn Gln Arg
    850                 855                 860

Leu Leu Ser Thr Phe Thr Glu Tyr Ile Lys Asn Ile Ile Asn Thr Ser
865                 870                 875                 880

Leu Glu Ile Leu Asn Leu Arg Tyr Glu Ser Asn His Leu Ile Asp Leu
                885                 890                 895

Ser Arg Tyr Ala Ser Lys Ile Asn Ile Gly Ser Lys Val Asn Phe Asp
            900                 905                 910

Pro Ile Asp Lys Asn Gln Ile Gln Leu Phe Asn Leu Glu Ser Ser Lys
        915                 920                 925

Ile Glu Val Ile Leu Lys Asn Ala Ile Val Tyr Asn Ser Met Tyr Glu
    930                 935                 940

Asn Phe Ser Thr Ser Phe Trp Ile Arg Ile Pro Lys Tyr Phe Asn Ser
945                 950                 955                 960

Ile Ser Leu Asn Asn Glu Tyr Thr Ile Ile Asn Cys Met Glu Asn Asn
                965                 970                 975

Ser Gly Trp Lys Val Ser Leu Asn Tyr Gly Glu Ile Ile Trp Thr Leu
            980                 985                 990

Gln Asp Thr Gln Glu Ile Lys Gln Arg Val Val Phe Lys Tyr Ser Gln
        995                 1000                1005

Met Ile Asn Ile Ser Asp Tyr Ile Asn Arg Trp Ile Phe Val Thr
        1010                1015                1020

Ile Thr Asn Asn Arg Leu Asn Asn Ser Lys Ile Tyr Ile Asn Gly
        1025                1030                1035

Arg Leu Ile Asp Gln Lys Pro Ile Ser Asn Leu Gly Asn Ile His
        1040                1045                1050

Ala Ser Asn Asn Ile Met Phe Lys Leu Asp Gly Cys Arg Asp Thr
```

|      |      |      |
|------|------|------|
| 1055 | 1060 | 1065 |

His Arg Tyr Ile Trp Ile Lys Tyr Phe Asn Leu Phe Asp Lys Glu
    1070                1075                1080

Leu Asn Glu Lys Glu Ile Lys Asp Leu Tyr Asp Asn Gln Ser Asn
    1085                1090                1095

Ser Gly Ala Leu Val Ile Leu Lys Asp Phe Trp Gly Asp Tyr Leu
    1100                1105                1110

Gln Tyr Asp Lys Pro Tyr Tyr Met Leu Asn Leu Tyr Asp Pro Asn
    1115                1120                1125

Lys Tyr Val Asp Val Asn Asn Val Gly Ile Arg Gly Tyr Met Tyr
    1130                1135                1140

Leu Lys Gly Pro Arg Gly Ser Val Met Thr Thr Asn Ile Tyr Leu
    1145                1150                1155

Asn Ser Ser Leu Tyr Arg Gly Thr Lys Phe Ile Ile Lys Lys Tyr
    1160                1165                1170

Ala Ser Gly Asn Lys Asp Asn Ile Val Arg Asn Asn Asp Arg Val
    1175                1180                1185

Tyr Ile Asn Val Val Val Lys Asn Lys Glu Tyr Arg Leu Ala Thr
    1190                1195                1200

Asn Ala Ser Gln Ala Gly Val Glu Lys Ile Leu Ser Ala Leu Glu
    1205                1210                1215

Ile Pro Asp Val Gly Asn Leu Ser Gln Val Val Val Met Lys Ser
    1220                1225                1230

Lys Asn Asp Gln Gly Ile Thr Asn Lys Cys Lys Met Asn Leu Gln
    1235                1240                1245

Asp Asn Asn Gly Asn Asp Ile Gly Phe Ile Gly Phe His Gln Phe
    1250                1255                1260

Asn Asn Ile Ala Lys Leu Val Ala Ser Asn Trp Tyr Asn Arg Gln
    1265                1270                1275

Ile Glu Arg Ser Ser Arg Thr Leu Gly Cys Ser Trp Glu Phe Ile
    1280                1285                1290

Pro Val Asp Asp Gly Trp Gly Glu Arg Pro Leu Ala Leu Ala His
    1295                1300                1305

His His His His His His His
    1310                1315

<210> SEQ ID NO 22
<211> LENGTH: 2811
<212> TYPE: DNA
<213> ORGANISM: Artificial sequence
<220> FEATURE:
<223> OTHER INFORMATION: DNA sequence of BoNT/C with Human EGF Targeting
      Moiety and Furin Protease Cleavage Site

<400> SEQUENCE: 22

```
atgccgatca ccatcaacaa cttcaactac agcgatccgg tggataacaa aaacatcctg      60
tacctggata cccatctgaa taccctggcg aacgaaccgg aaaaagcgtt tcgtatcacc     120
ggcaacattt gggttattcc ggatcgtttt agccgtaaca gcaacccgaa tctgaataaa     180
ccgccgcgtg ttaccagccc gaaaagcggt tattacgatc cgaactatct gagcaccgat     240
agcgataaag ataccttcct gaaagaaatc atcaaactgt tcaaacgcat caacagccgt     300
gaaattggcg aagaactgat ctatcgcctg agcaccgata ttccgtttcc gggcaacaac     360 aacacccccga tcaacaccct tgatttcgat gtggatttca acagcgttga tgttaaaacc     420
cgccagggta caattgggt gaaaaccggc agcattaacc cgagcgtgat tattaccggt     480
```

```
ccgcgcgaaa acattattga tccggaaacc agcacccttta aactgaccaa caacaccttt    540
gcggcgcagg aaggttttgg cgcgctgagc attattagca ttagcccgcg ctttatgctg    600
acctatagca acgcgaccaa cgatgttatt gaaggccgtt tcagcaaaag cgaattttgc    660
atggacccga tcctgatcct gatgcatgaa ctgaaccatg cgatgcataa cctgtatggc    720
atcgcgattc cgaacgatca gaccattagc agcgtgacca gcaacatctt ttacagccag    780
tacaacgtga aactggaata tgcggaaatc tatgcgtttg gcggtccgac cattgatctg    840
attccgaaaa gcgcgcgcaa atacttcgaa gaaaaagcgc tggattacta cgcagcatt    900 gcgaaacgtc tgaacagcat taccaccgcg aatccgagca gcttcaacaa atatatcggc    960
gaatataaac agaaactgat ccgcaaatat cgctttgtgg tggaaagcag cggcgaagtt   1020
accgttaacc gcaataaatt cgtggaactg tacaacgaac tgacccagat cttcaccgaa   1080
tttaactatg cgaaaatcta taacgtgcag aaccgtaaaa tctacctgag caacgtgtat   1140
accccggtga ccgcgaatat tctggatgat aacgtgtacg atatccagaa cggctttaac   1200
atcccgaaaa gcaacctgaa cgttctgttt atgggccaga acctgagccg taatccggcg   1260
ctgcgtaaag tgaacccgga aaacatgctg tacctgttca ccaaattttg cgtcgacgcg   1320
gacgatgacg ataaactgta caacaaaacc ctgcagtgtc gtgaactgct ggtgaaaaac   1380
accgatctgc cgtttattgg cgatatcagc gatgtgaaaa ccgatatctt cctgcgcaaa   1440
gatatcaacg aagaaccgaa agtgatcccg gataacgtga gcgttgatca ggtgatcctg   1500
agcaaaaaca ccagcgaaca tggtcagctg gatctgctgt atccgagcat tgatagcgaa   1560
agcgaaattc tgccgggcga aaaccaggtg ttttacgata accgtaccca gaacgtggat   1620
tacctgaaca gctattacta cctggaaagc cagaaactga gcgataacgt ggaagatttt   1680
accttacccc gcagcattga agaagcgctg gataacagcg cgaaagttta cacctatttt   1740
ccgaccctgg cgaacaaagt taatgcgggt gttcagggcg gtctgtttct gatgtgggcg   1800
aacgatgtgg tggaagattt caccaccaac atcctgcgta aagataccct ggataaaatc   1860
agcgatgtta gcgcgattat tccgtatatt ggtccggcgc tgaacattag caatagcgtg   1920
cgtcgtggca attttaccga agcgtttgcg gttaccggtg tgaccattct gctggaagcg   1980
tttccggaat taccattcc ggcgctgggt gcgtttgtga tctatagcaa agtgcaggaa   2040
cgcaacgaaa tcatcaaaac catcgataac tgcctggaac agcgtattaa acgctggaaa   2100
gatagctatg aatggatgat gggcacctgg ctgagccgta ttatcaccca gttcaacaac   2160
atcagctacc agatgtacga tagcctgaac tatcaggcgg tgcgattaa agcgaaaatc   2220 gatctggaat acaaaaaata cagcggcagc gataaagaaa acatcaaaag ccaggttgaa   2280
aacctgaaaa cagcctgga tgtgaaaatt agcgaagcga tgaataacat caacaaattc   2340
atccgcgaat gcagcgtgac ctacctgttc aaaaacatgc tgccgaaagt gatcgatgaa   2400
ctgaacgaat tgatcgcaa caccaaagcg aaactgatca acctgatcga tagccacaac   2460
attattctgg tgggcgaagt ggataaactg aaagcgaaag ttaacaacag cttccagaac   2520
accatcccgt taacatctt cagctatacc aacaacagcc tgctgaaaga tatcatcaac   2580
gaatacttca atctagaagg tggcggtggg tccggtggcg gtggctcagg cggggcggt   2640 agcgcactag acaactctga ctctgaatgc ccgctgtctc acgacggtta ctgcctgcac   2700
gacggtgttt gcatgtacat cgaagctctg gacaaatacg cttgcaactg cgttgttggt   2760
tacatcggtg aacgttgcca gtaccgtgac ctgaaatggt gggaactgcg t            2811
```

<210> SEQ ID NO 23
<211> LENGTH: 937
<212> TYPE: PRT
<213> ORGANISM: Artificial sequence
<220> FEATURE:
<223> OTHER INFORMATION: Protein sequence of BoNT/C with Human EGF
      Targeting Moiety and Furin Protease Cleavage Site

<400> SEQUENCE: 23

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Ile Glu Gly Arg Phe Ser Lys Ser Glu Phe Cys Met Asp Pro Ile
210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365
```

```
Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Lys Leu Tyr Asn
        435                 440                 445

Lys Thr Leu Gln Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Pro Asp Asn Val Ser Val Asp
                485                 490                 495

Gln Val Ile Leu Ser Lys Asn Thr Ser Glu His Gly Gln Leu Asp Leu
                500                 505                 510

Leu Tyr Pro Ser Ile Asp Ser Glu Ser Glu Ile Leu Pro Gly Glu Asn
    515                 520                 525

Gln Val Phe Tyr Asp Asn Arg Thr Gln Asn Val Asp Tyr Leu Asn Ser
    530                 535                 540

Tyr Tyr Tyr Leu Glu Ser Gln Lys Leu Ser Asp Asn Val Glu Asp Phe
545                 550                 555                 560

Thr Phe Thr Arg Ser Ile Glu Glu Ala Leu Asp Asn Ser Ala Lys Val
                565                 570                 575

Tyr Thr Tyr Phe Pro Thr Leu Ala Asn Lys Val Asn Ala Gly Val Gln
                580                 585                 590

Gly Gly Leu Phe Leu Met Trp Ala Asn Asp Val Val Glu Asp Phe Thr
            595                 600                 605

Thr Asn Ile Leu Arg Lys Asp Thr Leu Asp Lys Ile Ser Asp Val Ser
610                 615                 620

Ala Ile Ile Pro Tyr Ile Gly Pro Ala Leu Asn Ile Ser Asn Ser Val
625                 630                 635                 640

Arg Arg Gly Asn Phe Thr Glu Ala Phe Ala Val Thr Gly Val Thr Ile
                645                 650                 655

Leu Leu Glu Ala Phe Pro Glu Phe Thr Ile Pro Ala Leu Gly Ala Phe
                660                 665                 670

Val Ile Tyr Ser Lys Val Gln Glu Arg Asn Glu Ile Ile Lys Thr Ile
            675                 680                 685

Asp Asn Cys Leu Glu Gln Arg Ile Lys Arg Trp Lys Asp Ser Tyr Glu
            690                 695                 700

Trp Met Met Gly Thr Trp Leu Ser Arg Ile Ile Thr Gln Phe Asn Asn
705                 710                 715                 720

Ile Ser Tyr Gln Met Tyr Asp Ser Leu Asn Tyr Gln Ala Gly Ala Ile
                725                 730                 735

Lys Ala Lys Ile Asp Leu Glu Tyr Lys Lys Tyr Ser Gly Ser Asp Lys
            740                 745                 750

Glu Asn Ile Lys Ser Gln Val Glu Asn Leu Lys Asn Ser Leu Asp Val
    755                 760                 765

Lys Ile Ser Glu Ala Met Asn Asn Ile Asn Lys Phe Ile Arg Glu Cys
    770                 775                 780
```

```
Ser Val Thr Tyr Leu Phe Lys Asn Met Leu Pro Lys Val Ile Asp Glu
785                 790                 795                 800

Leu Asn Glu Phe Asp Arg Asn Thr Lys Ala Lys Leu Ile Asn Leu Ile
            805                 810                 815

Asp Ser His Asn Ile Ile Leu Val Gly Glu Val Asp Lys Leu Lys Ala
        820                 825                 830

Lys Val Asn Asn Ser Phe Gln Asn Thr Ile Pro Phe Asn Ile Phe Ser
    835                 840                 845

Tyr Thr Asn Asn Ser Leu Leu Lys Asp Ile Ile Asn Glu Tyr Phe Asn
850                 855                 860

Leu Glu Gly Gly Gly Ser Gly Gly Gly Ser Gly Gly Gly Gly
865                 870                 875                 880

Ser Ala Leu Asp Asn Ser Asp Ser Glu Cys Pro Leu Ser His Asp Gly
            885                 890                 895

Tyr Cys Leu His Asp Gly Val Cys Met Tyr Ile Glu Ala Leu Asp Lys
        900                 905                 910

Tyr Ala Cys Asn Cys Val Val Gly Tyr Ile Gly Glu Arg Cys Gln Tyr
    915                 920                 925

Arg Asp Leu Lys Trp Trp Glu Leu Arg
930                 935
```

<210> SEQ ID NO 24
<211> LENGTH: 939
<212> TYPE: PRT
<213> ORGANISM: Artificial sequence
<220> FEATURE:
<223> OTHER INFORMATION: Protein sequence of BoNT/C with Human EGF
      Targeting Moiety and Thrombin Protease Cleavage Site

<400> SEQUENCE: 24

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Val Pro Arg Phe Ser Leu Thr Tyr Ser Asn Ala Thr Asn Asp
        195                 200                 205
```

```
Val Gly Glu Gly Arg Phe Ser Lys Ser Glu Phe Cys Met Asp Pro Ile
    210                 215                 220
Leu Ile Leu Met His Glu Leu Asn His Ala Met His Asn Leu Tyr Gly
225                 230                 235                 240
Ile Ala Ile Pro Asn Asp Gln Thr Ile Ser Ser Val Thr Ser Asn Ile
                245                 250                 255
Phe Tyr Ser Gln Tyr Asn Val Lys Leu Glu Tyr Ala Glu Ile Tyr Ala
            260                 265                 270
Phe Gly Gly Pro Thr Ile Asp Leu Ile Pro Lys Ser Ala Arg Lys Tyr
        275                 280                 285
Phe Glu Glu Lys Ala Leu Asp Tyr Tyr Arg Ser Ile Ala Lys Arg Leu
    290                 295                 300
Asn Ser Ile Thr Thr Ala Asn Pro Ser Ser Phe Asn Lys Tyr Ile Gly
305                 310                 315                 320
Glu Tyr Lys Gln Lys Leu Ile Arg Lys Tyr Arg Phe Val Val Glu Ser
                325                 330                 335
Ser Gly Glu Val Thr Val Asn Arg Asn Lys Phe Val Glu Leu Tyr Asn
            340                 345                 350
Glu Leu Thr Gln Ile Phe Thr Glu Phe Asn Tyr Ala Lys Ile Tyr Asn
        355                 360                 365
Val Gln Asn Arg Lys Ile Tyr Leu Ser Asn Val Tyr Thr Pro Val Thr
    370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
                405                 410                 415
Arg Asn Pro Ala Leu Arg Lys Val Asn Pro Glu Asn Met Leu Tyr Leu
            420                 425                 430
Phe Thr Lys Phe Cys Val Asp Ala Asp Asp Asp Lys Leu Tyr Asn
        435                 440                 445
Lys Thr Leu Gln Cys Arg Glu Leu Leu Val Lys Asn Thr Asp Leu Pro
    450                 455                 460
Phe Ile Gly Asp Ile Ser Asp Val Lys Thr Asp Ile Phe Leu Arg Lys
465                 470                 475                 480
Asp Ile Asn Glu Glu Thr Glu Val Ile Tyr Tyr Pro Asp Asn Val Ser
                485                 490                 495
Val Asp Gln Val Ile Leu Ser Lys Asn Thr Ser Glu His Gly Gln Leu
            500                 505                 510
Asp Leu Leu Tyr Pro Ser Ile Asp Ser Glu Ser Glu Ile Leu Pro Gly
        515                 520                 525
Glu Asn Gln Val Phe Tyr Asp Asn Arg Thr Gln Asn Val Asp Tyr Leu
    530                 535                 540
Asn Ser Tyr Tyr Tyr Leu Glu Ser Gln Lys Leu Ser Asp Asn Val Glu
545                 550                 555                 560
Asp Phe Thr Phe Thr Arg Ser Ile Glu Glu Ala Leu Asp Asn Ser Ala
                565                 570                 575
Lys Val Tyr Thr Tyr Phe Pro Thr Leu Ala Asn Lys Val Asn Ala Gly
            580                 585                 590
Val Gln Gly Gly Leu Phe Leu Met Trp Ala Asn Asp Val Val Glu Asp
        595                 600                 605
Phe Thr Thr Asn Ile Leu Arg Lys Asp Thr Leu Asp Lys Ile Ser Asp
    610                 615                 620
```

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
            645                 650                 655

Thr Ile Leu Leu Glu Ala Phe Pro Glu Phe Thr Ile Pro Ala Leu Gly
        660                 665                 670

Ala Phe Val Ile Tyr Ser Lys Val Gln Glu Arg Asn Glu Ile Ile Lys
    675                 680                 685

Thr Ile Asp Asn Cys Leu Glu Gln Arg Ile Lys Arg Trp Lys Asp Ser
690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
            725                 730                 735

Ala Ile Lys Ala Lys Ile Asp Leu Glu Tyr Lys Lys Tyr Ser Gly Ser
        740                 745                 750

Asp Lys Glu Asn Ile Lys Ser Gln Val Glu Asn Leu Lys Asn Ser Leu
    755                 760                 765

Asp Val Lys Ile Ser Glu Ala Met Asn Asn Ile Asn Lys Phe Ile Arg
770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
            805                 810                 815

Leu Ile Asp Ser His Asn Ile Ile Leu Val Gly Glu Val Asp Lys Leu
        820                 825                 830

Lys Ala Lys Val Asn Asn Ser Phe Gln Asn Thr Ile Pro Phe Asn Ile
    835                 840                 845

Phe Ser Tyr Thr Asn Asn Ser Leu Leu Lys Asp Ile Ile Asn Glu Tyr
850                 855                 860

Phe Asn Leu Glu Gly Gly Gly Ser Gly Gly Gly Ser Gly
865                 870                 875                 880

Gly Gly Ser Ala Leu Asp Asn Ser Asp Ser Glu Cys Pro Leu Ser His
            885                 890                 895

Asp Gly Tyr Cys Leu His Asp Gly Val Cys Met Tyr Ile Glu Ala Leu
        900                 905                 910

Asp Lys Tyr Ala Cys Asn Cys Val Val Gly Tyr Ile Gly Glu Arg Cys
    915                 920                 925

Gln Tyr Arg Asp Leu Lys Trp Trp Glu Leu Arg
930                 935

<210> SEQ ID NO 25
<211> LENGTH: 939
<212> TYPE: PRT
<213> ORGANISM: Artificial sequence
<220> FEATURE:
<223> OTHER INFORMATION: Protein sequence of BoNT/C with Human EGF
      Targeting Moiety and Thrombin Protease Cleavage Site

<400> SEQUENCE: 25

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

```
Arg Phe Ser Arg Asn Ser Asn Pro Asn Leu Asn Lys Pro Pro Arg Val
 50                  55                  60

Thr Ser Pro Lys Ser Gly Tyr Tyr Asp Pro Asn Tyr Leu Ser Thr Asp
 65                  70                  75                  80

Ser Asp Lys Asp Thr Phe Leu Lys Glu Ile Ile Lys Leu Phe Lys Arg
                 85                  90                  95

Ile Asn Ser Arg Glu Ile Gly Glu Leu Ile Tyr Arg Leu Ser Thr
            100                 105                 110

Asp Ile Pro Phe Pro Gly Asn Asn Thr Pro Ile Asn Thr Phe Asp
            115                 120                 125

Phe Asp Val Asp Phe Asn Ser Val Asp Val Lys Thr Arg Gln Gly Asn
        130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Gly Thr Ser Thr Phe Lys Leu Thr
                    165                 170                 175

Asn Asn Thr Phe Ala Ala Gln Glu Gly Phe Gly Ala Leu Ser Ile Ile
                180                 185                 190

Ser Ile Ser Pro Arg Phe Met Leu Thr Tyr Ser Asn Ala Thr Asn Asp
        195                 200                 205

Val Gly Thr Pro Arg Phe Ser Lys Ser Glu Phe Cys Met Asp Pro Ile
        210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                    245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
                275                 280                 285

Phe Glu Glu Lys Ala Leu Asp Tyr Tyr Arg Ser Ile Ala Lys Arg Leu
        290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
        370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Lys Leu Tyr Asn
        435                 440                 445

Lys Thr Leu Gln Cys Arg Glu Leu Leu Val Lys Asn Thr Asp Leu Pro
450                 455                 460
```

```
Phe Ile Gly Asp Ile Ser Asp Val Lys Thr Asp Ile Phe Leu Arg Lys
465                 470                 475                 480

Asp Ile Asn Glu Thr Glu Val Ile Tyr Tyr Pro Asp Asn Val Ser
            485                 490                 495

Val Asp Gln Val Ile Leu Ser Lys Asn Thr Ser Glu His Gly Gln Leu
                500                 505                 510

Asp Leu Leu Tyr Pro Ser Ile Asp Ser Glu Ser Glu Ile Leu Pro Gly
            515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
    595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
            690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
            725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
            755                 760                 765

Asp Val Lys Ile Ser Glu Ala Met Asn Asn Ile Asn Lys Phe Ile Arg
            770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
            805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
            835                 840                 845

Phe Ser Tyr Thr Asn Asn Ser Leu Leu Lys Asp Ile Ile Asn Glu Tyr
            850                 855                 860

Phe Asn Leu Glu Gly Gly Gly Ser Gly Gly Gly Ser Gly
865                 870                 875                 880

Gly Gly Ser Ala Leu Asp Asn Ser Asp Ser Glu Cys Pro Leu Ser His
```

-continued

```
                        885                 890                 895
Asp Gly Tyr Cys Leu His Asp Gly Val Cys Met Tyr Ile Glu Ala Leu
            900                 905                 910

Asp Lys Tyr Ala Cys Asn Cys Val Val Gly Tyr Ile Gly Glu Arg Cys
            915                 920                 925

Gln Tyr Arg Asp Leu Lys Trp Trp Glu Leu Arg
            930                 935

<210> SEQ ID NO 26
<211> LENGTH: 939
<212> TYPE: PRT
<213> ORGANISM: Artificial sequence
<220> FEATURE:
<223> OTHER INFORMATION: Protein sequence of BoNT/C with Human EGF
      Targeting Moiety and Factor Xa Protease Cleavage Site

<400> SEQUENCE: 26

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300
```

-continued

```
Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
            325                 330                 335

Ser Gly Glu Val Thr Val Asn Arg Asn Lys Phe Val Glu Leu Tyr Asn
        340                 345                 350

Glu Leu Thr Gln Ile Phe Thr Glu Phe Asn Tyr Ala Lys Ile Tyr Asn
    355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
            405                 410                 415

Arg Asn Pro Ala Leu Arg Lys Val Asn Pro Glu Asn Met Leu Tyr Leu
        420                 425                 430

Phe Thr Lys Phe Cys Val Asp Ala Asp Asp Asp Lys Leu Tyr Asn
    435                 440                 445

Lys Thr Leu Gln Cys Arg Glu Leu Leu Val Lys Asn Thr Asp Leu Pro
450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
            485                 490                 495

Val Asp Gln Val Ile Leu Ser Lys Asn Thr Ser Glu His Gly Gln Leu
        500                 505                 510

Asp Leu Leu Tyr Pro Ser Ile Asp Ser Glu Ser Glu Ile Leu Pro Gly
    515                 520                 525

Glu Asn Gln Val Phe Tyr Asp Asn Arg Thr Gln Asn Val Asp Tyr Leu
530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
            565                 570                 575

Lys Val Tyr Thr Tyr Phe Pro Thr Leu Ala Asn Lys Val Asn Ala Gly
        580                 585                 590

Val Gln Gly Gly Leu Phe Leu Met Trp Ala Asn Asp Val Val Glu Asp
    595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
            645                 650                 655

Thr Ile Leu Leu Glu Ala Phe Pro Glu Phe Thr Ile Pro Ala Leu Gly
        660                 665                 670

Ala Phe Val Ile Tyr Ser Lys Val Gln Glu Arg Asn Glu Ile Ile Lys
    675                 680                 685

Thr Ile Asp Asn Cys Leu Glu Gln Arg Ile Lys Arg Trp Lys Asp Ser
690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
```

```
                    725                 730                 735
Ala Ile Lys Ala Lys Ile Asp Gly Arg Tyr Lys Lys Tyr Ser Gly Ser
                740                 745                 750

Asp Lys Glu Asn Ile Lys Ser Gln Val Glu Asn Leu Lys Asn Ser Leu
                755                 760                 765

Asp Val Lys Ile Ser Glu Ala Met Asn Asn Ile Asn Lys Phe Ile Arg
            770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
                820                 825                 830

Lys Ala Lys Val Asn Asn Ser Phe Gln Asn Thr Ile Pro Phe Asn Ile
                835                 840                 845

Phe Ser Tyr Thr Asn Asn Ser Leu Leu Lys Asp Ile Ile Asn Glu Tyr
                850                 855                 860

Phe Asn Leu Glu Gly Gly Gly Ser Gly Gly Gly Ser Gly Gly
865                 870                 875                 880

Gly Gly Ser Ala Leu Asp Asn Ser Asp Ser Glu Cys Pro Leu Ser His
                885                 890                 895

Asp Gly Tyr Cys Leu His Asp Gly Val Cys Met Tyr Ile Glu Ala Leu
                900                 905                 910

Asp Lys Tyr Ala Cys Asn Cys Val Val Gly Tyr Ile Gly Glu Arg Cys
                915                 920                 925

Gln Tyr Arg Asp Leu Lys Trp Trp Glu Leu Arg
                930                 935
```

<210> SEQ ID NO 27
<211> LENGTH: 939
<212> TYPE: PRT
<213> ORGANISM: Artificial sequence
<220> FEATURE:
<223> OTHER INFORMATION: Protein sequence of BoNT/C with Human EGF
      Targeting Moiety and Factor Xa Protease Cleavage Site

<400> SEQUENCE: 27

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
                20                  25                  30

Pro Glu Lys Ala Phe Arg Ile Thr Gly Asn Ile Trp Val Ile Pro Asp
            35                  40                  45

Arg Phe Ser Arg Asn Ser Asn Pro Asn Leu Asn Lys Pro Pro Arg Val
50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
                100                 105                 110

Asp Ile Pro Phe Pro Gly Asn Asn Asn Thr Pro Ile Asn Thr Phe Asp
            115                 120                 125

Phe Asp Val Asp Phe Asn Ser Val Asp Val Lys Thr Arg Gln Gly Asn
        130                 135                 140
```

```
Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
                180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
                260                 265                 270

Phe Gly Gly Pro Thr Ile Asp Leu Ile Pro Lys Ser Ala Arg Lys Tyr
                275                 280                 285

Phe Glu Glu Lys Ala Leu Asp Tyr Tyr Arg Ser Ile Ala Lys Arg Leu
290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
                340                 345                 350

Glu Leu Thr Gln Ile Phe Thr Glu Phe Asn Tyr Ala Lys Ile Tyr Asn
                355                 360                 365

Val Gln Asn Arg Lys Ile Tyr Leu Ser Asn Val Tyr Thr Pro Val Thr
                370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
                420                 425                 430

Phe Thr Lys Phe Cys Val Asp Ala Asp Asp Asp Lys Leu Tyr Asn
                435                 440                 445

Lys Thr Leu Gln Cys Arg Glu Leu Leu Val Lys Asn Thr Asp Leu Pro
450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
                500                 505                 510

Asp Leu Leu Tyr Pro Ser Ile Asp Ser Glu Ser Glu Ile Leu Pro Gly
                515                 520                 525

Glu Asn Gln Val Phe Tyr Asp Asn Arg Thr Gln Asn Val Asp Tyr Leu
                530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
```

```
                565                 570                 575
Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ile Asp Gly
            740                 745                 750

Arg Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
850                 855                 860

Phe Asn Leu Glu Gly Gly Gly Ser Gly Gly Gly Ser Gly Gly
865                 870                 875                 880

Gly Gly Ser Ala Leu Asp Asn Ser Asp Ser Glu Cys Pro Leu Ser His
                885                 890                 895

Asp Gly Tyr Cys Leu His Asp Gly Val Cys Met Tyr Ile Glu Ala Leu
            900                 905                 910

Asp Lys Tyr Ala Cys Asn Cys Val Val Gly Tyr Ile Gly Glu Arg Cys
        915                 920                 925

Gln Tyr Arg Asp Leu Lys Trp Trp Glu Leu Arg
930                 935
```

<210> SEQ ID NO 28
<211> LENGTH: 939
<212> TYPE: PRT
<213> ORGANISM: Artificial sequence
<220> FEATURE:
<223> OTHER INFORMATION: Protein sequence of BoNT/C with Human EGF
      Targeting Moiety and Thrombin Protease Cleavage Site

<400> SEQUENCE: 28

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
            35                  40                  45

Arg Phe Ser Arg Asn Ser Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
                100                 105                 110

Asp Ile Pro Phe Pro Gly Asn Asn Asn Thr Pro Ile Asn Thr Phe Asp
            115                 120                 125

Phe Asp Val Asp Phe Asn Ser Val Asp Val Lys Thr Arg Gln Gly Asn
130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
    195                 200                 205

Val Gly Glu Gly Arg Phe Ser Lys Ser Glu Phe Cys Met Asp Pro Ile
210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
            245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
            275                 280                 285

Phe Glu Glu Lys Ala Leu Asp Tyr Tyr Arg Ser Ile Ala Lys Arg Leu
290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
```

```
            405                 410                 415
Arg Asn Pro Ala Leu Arg Lys Val Asn Pro Glu Asn Met Leu Tyr Leu
            420                 425                 430

Phe Thr Lys Phe Cys Val Asp Ala Asp Asp Asp Lys Leu Tyr Asn
            435                 440                 445

Lys Thr Leu Gln Cys Arg Glu Leu Leu Val Lys Asn Thr Asp Leu Pro
            450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
            485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
            515                 520                 525

Glu Asn Gln Val Phe Tyr Asp Asn Arg Thr Gln Asn Val Asp Tyr Leu
            530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                        565                 570                 575

Lys Val Tyr Thr Tyr Phe Pro Thr Leu Ala Asn Lys Val Asn Ala Gly
                        580                 585                 590

Val Gln Gly Gly Leu Phe Leu Met Trp Ala Asn Asp Val Val Glu Asp
            595                 600                 605

Phe Thr Thr Asn Ile Leu Arg Lys Asp Thr Leu Asp Lys Ile Ser Asp
            610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                        645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
            690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                        725                 730                 735

Ala Ile Lys Ala Lys Ile Asp Leu Glu Tyr Lys Lys Tyr Gly Val Pro
                        740                 745                 750

Arg Lys Glu Asn Ile Lys Ser Gln Val Glu Asn Leu Lys Asn Ser Leu
            755                 760                 765

Asp Val Lys Ile Ser Glu Ala Met Asn Asn Ile Asn Lys Phe Ile Arg
            770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                        805                 810                 815

Leu Ile Asp Ser His Asn Ile Ile Leu Val Gly Glu Val Asp Lys Leu
                        820                 825                 830
```

```
Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Leu Glu Gly Gly Gly Ser Gly Gly Gly Ser Gly Gly
865                 870                 875                 880

Gly Gly Ser Ala Leu Asp Asn Ser Asp Ser Glu Cys Pro Leu Ser His
                885                 890                 895

Asp Gly Tyr Cys Leu His Asp Gly Val Cys Met Tyr Ile Glu Ala Leu
                900                 905                 910

Asp Lys Tyr Ala Cys Asn Cys Val Val Gly Tyr Ile Gly Glu Arg Cys
                915                 920                 925

Gln Tyr Arg Asp Leu Lys Trp Trp Glu Leu Arg
                930                 935

<210> SEQ ID NO 29
<211> LENGTH: 917
<212> TYPE: PRT
<213> ORGANISM: Artificial sequence
<220> FEATURE:
<223> OTHER INFORMATION: Protein sequence of BoNT/D with Human
      Vasoactive Intestinal Peptide Targeting Moiety and Factor Xa
      Protease Cleavage Site

<400> SEQUENCE: 29

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240
```

```
Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
            275                 280                 285

Leu Arg Glu Lys Ala Leu Gly His Tyr Lys Asp Ile Ala Lys Arg Leu
        290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
        370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Val Asp Gly Gly Gly Ser Ala Asp Asp Asp
            435                 440                 445

Asp Lys His Ser Asp Ala Val Phe Thr Asp Asn Tyr Thr Arg Leu Arg
        450                 455                 460

Arg Gln Leu Ala Val Arg Arg Tyr Leu Asn Ser Ile Leu Asn Ala Leu
465                 470                 475                 480

Ala Gly Gly Gly Ser Gly Gly Gly Ser Gly Gly Gly Ser
                485                 490                 495

Ala Leu Ala Leu Gln Cys Ile Lys Val Lys Asn Asn Arg Leu Pro Tyr
            500                 505                 510

Val Ala Asp Lys Asp Ser Ile Ser Gln Glu Ile Phe Glu Asn Lys Ile
            515                 520                 525

Ile Thr Asp Glu Thr Asn Val Gln Asn Tyr Ser Asp Lys Phe Ser Leu
            530                 535                 540

Asp Glu Ser Ile Leu Asp Gly Gln Val Pro Ile Asn Pro Glu Ile Val
545                 550                 555                 560

Asp Pro Leu Leu Pro Asn Val Asn Met Glu Pro Leu Asn Leu Pro Gly
            565                 570                 575

Glu Glu Ile Val Phe Tyr Asp Asp Ile Thr Lys Tyr Val Asp Tyr Leu
            580                 585                 590

Asn Ser Tyr Tyr Tyr Leu Glu Ser Gln Lys Leu Ser Asn Asn Val Glu
        595                 600                 605

Asn Ile Thr Leu Thr Thr Ser Val Glu Glu Ala Leu Gly Tyr Ser Asn
        610                 615                 620

Lys Ile Tyr Thr Phe Leu Pro Ser Leu Ala Glu Lys Val Asn Lys Gly
625                 630                 635                 640

Val Gln Ala Gly Leu Phe Leu Asn Trp Ala Asn Glu Val Val Glu Asp
                645                 650                 655

Phe Thr Thr Asn Ile Met Lys Lys Asp Thr Leu Asp Lys Ile Ser Asp
```

```
                    660                 665                 670
Val Ser Val Ile Ile Pro Tyr Ile Gly Pro Ala Leu Asn Ile Gly Asn
                675                 680                 685

Ser Ala Leu Arg Gly Asn Phe Asn Gln Ala Phe Ala Thr Ala Gly Val
            690                 695                 700

Ala Phe Leu Leu Glu Gly Phe Pro Glu Phe Thr Ile Pro Ala Leu Gly
705                 710                 715                 720

Val Phe Thr Phe Tyr Ser Ser Ile Gln Glu Arg Glu Lys Ile Ile Lys
                725                 730                 735

Thr Ile Glu Asn Cys Leu Glu Gln Arg Val Lys Arg Trp Lys Asp Ser
                740                 745                 750

Tyr Gln Trp Met Val Ser Asn Trp Leu Ser Arg Ile Thr Thr Gln Phe
            755                 760                 765

Asn His Ile Asn Tyr Gln Met Tyr Asp Ser Leu Ser Tyr Gln Ala Asp
                770                 775                 780

Ala Ile Lys Ala Lys Ile Asp Leu Glu Tyr Lys Lys Tyr Ile Asp Gly
785                 790                 795                 800

Arg Lys Glu Asn Ile Lys Ser Gln Val Glu Asn Leu Lys Asn Ser Leu
                805                 810                 815

Asp Val Lys Ile Ser Glu Ala Met Asn Asn Ile Asn Lys Phe Ile Arg
                820                 825                 830

Glu Cys Ser Val Thr Tyr Leu Phe Lys Asn Met Leu Pro Lys Val Ile
            835                 840                 845

Asp Glu Leu Asn Lys Phe Asp Leu Arg Thr Lys Thr Glu Leu Ile Asn
850                 855                 860

Leu Ile Asp Ser His Asn Ile Ile Leu Val Gly Glu Val Asp Arg Leu
865                 870                 875                 880

Lys Ala Lys Val Asn Glu Ser Phe Glu Asn Thr Met Pro Phe Asn Ile
                885                 890                 895

Phe Ser Tyr Thr Asn Asn Ser Leu Leu Lys Asp Ile Ile Asn Glu Tyr
            900                 905                 910

Phe Asn Leu Glu Ala
        915

<210> SEQ ID NO 30
<211> LENGTH: 938
<212> TYPE: PRT
<213> ORGANISM: Artificial sequence
<220> FEATURE:
<223> OTHER INFORMATION: Protein sequence of BoNT/A with Human EGF
      Targeting Moiety and Thrombin Protease Cleavage Site

<400> SEQUENCE: 30

Met Glu Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95
```

-continued

Arg Ile Tyr Ser Thr Asp Leu Gly Arg Gly Leu Leu Thr Ser Ile Val
            100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
            130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
            210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Asp
            420                 425                 430

Gly Ile Ile Thr Ser Lys Thr Lys Ser Asp Asp Asp Lys Asn Lys
            435                 440                 445

Ala Leu Asn Leu Gln Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu

```
              515                 520                 525
Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Leu Glu Gly Gly Gly Gly Ser Gly Gly Gly Ser Gly Gly Gly
865                 870                 875                 880

Gly Ser Ala Leu Asp Asn Ser Asp Ser Glu Cys Pro Leu Ser His Asp
                885                 890                 895

Gln Tyr Cys Leu His Asp Gly Val Cys Met Tyr Ile Glu Ala Leu Asp
            900                 905                 910

Lys Tyr Ala Cys Asn Cys Val Val Gly Tyr Ile Gly Glu Arg Cys Gln
        915                 920                 925

Tyr Arg Asp Leu Lys Trp Trp Glu Leu Arg
    930                 935
```

<210> SEQ ID NO 31
<211> LENGTH: 938
<212> TYPE: PRT
<213> ORGANISM: Artificial sequence
<220> FEATURE:
<223> OTHER INFORMATION: Protein sequence of BoNT/A with Human EGF
      Targeting Moiety and Thrombin Protease Cleavage Site

<400> SEQUENCE: 31

Met Glu

```
            355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
            405                 410                 415
Lys Asn Phe Thr Gly Leu Phe Glu Phe Tyr Lys Leu Leu Cys Val Asp
            420                 425                 430
Gly Ile Ile Thr Ser Lys Thr Lys Ser Asp Asp Asp Lys Asn Lys
            435                 440                 445
Ala Leu Asn Leu Gln Cys Ile Lys Val Asn Asn Trp Asp Leu Phe Phe
            450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
            485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
            530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
            565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Ala Met Phe Leu Gly Trp Val Glu
            595                 600                 605
Gln Leu Val Tyr Asp Phe Thr Asp Glu Thr Ser Glu Val Ser Thr Thr
            610                 615                 620
Asp Lys Ile Ala Asp Ile Thr Ile Ile Ile Pro Tyr Ile Gly Pro Ala
625                 630                 635                 640
Leu Asn Ile Gly Asn Met Leu Tyr Lys Asp Asp Phe Val Gly Ala Leu
            645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
            675                 680                 685
Val Leu Thr Val Gln Thr Ile Asp Asn Ala Leu Ser Lys Arg Asn Glu
            690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Met Lys Glu Ala Leu
            725                 730                 735
Glu Asn Gln Ala Glu Ala Thr Lys Ala Ile Ile Asn Tyr Gln Tyr Asn
            740                 745                 750
Gln Tyr Thr Glu Glu Glu Lys Asn Asn Ile Asn Phe Asn Ile Asp Asp
            755                 760                 765
Leu Ser Ser Lys Leu Asn Glu Ser Ile Asn Lys Ala Met Ile Asn Ile
            770                 775                 780
```

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
850                 855                 860

Thr Leu Glu Gly Gly Gly Gly Ser Gly Gly Gly Gly Ser Gly Gly Gly
865                 870                 875                 880

Gly Ser Ala Leu Asp Asn Ser Asp Ser Glu Cys Pro Leu Ser His Asp
            885                 890                 895

Gln Tyr Cys Leu His Asp Gly Val Cys Met Tyr Ile Glu Ala Leu Asp
            900                 905                 910

Lys Tyr Ala Cys Asn Cys Val Val Gly Tyr Ile Gly Glu Arg Cys Gln
            915                 920                 925

Tyr Arg Asp Leu Lys Trp Trp Glu Leu Arg
            930                 935

<210> SEQ ID NO 32
<211> LENGTH: 1318
<212> TYPE: PRT
<213> ORGANISM: Artificial sequence
<220> FEATURE:
<223> OTHER INFORMATION: Protein sequence of BoNT/A with Engineered
      Enterokinase Activation Site and Thrombin Protease Cleavage Site

<400> SEQUENCE: 32

His Met Gly Ser Met Glu Phe Val Asn Lys Gln Phe Asn Tyr Lys Asp
1               5                   10                  15

Pro Val Asn Gly Val Asp Ile Ala Tyr Ile Lys Ile Pro Asn Ala Gly
            20                  25                  30

Gln Met Gln Pro Val Lys Ala Phe Lys Ile His Asn Lys Ile Trp Val
        35                  40                  45

Ile Pro Glu Arg Asp Thr Phe Thr Asn Pro Glu Glu Gly Asp Leu Asn
    50                  55                  60

Pro Pro Pro Glu Ala Lys Gln Val Pro Val Ser Tyr Tyr Asp Ser Thr
65                  70                  75                  80

Tyr Leu Ser Thr Asp Asn Glu Lys Asp Asn Tyr Leu Lys Gly Val Thr
                85                  90                  95

Lys Leu Phe Glu Arg Ile Tyr Ser Thr Asp Leu Gly Arg Gly Leu Leu
            100                 105                 110

Thr Ser Ile Val Arg Gly Ile Pro Phe Trp Gly Gly Ser Thr Ile Asp
        115                 120                 125

Thr Glu Leu Lys Val Ile Asp Thr Asn Cys Ile Asn Val Ile Gln Pro
130                 135                 140

Asp Gly Ser Tyr Arg Ser Glu Glu Leu Asn Leu Val Ile Ile Gly Pro
145                 150                 155                 160

Ser Ala Asp Ile Ile Gln Phe Glu Cys Lys Ser Phe Gly His Glu Val
                165                 170                 175

Leu Asn Leu Thr Arg Asn Gly Tyr Gly Ser Thr Gln Tyr Ile Arg Phe
            180                 185                 190

Ser Pro Asp Phe Thr Phe Gly Phe Glu Glu Ser Leu Glu Val Asp Thr

-continued

```
                195                 200                 205
Asn Pro Leu Leu Gly Ala Gly Lys Phe Ala Thr Asp Pro Ala Val Thr
210                 215                 220

Leu Ala His Glu Leu Ile His Ala Gly His Arg Leu Tyr Gly Ile Ala
225                 230                 235                 240

Ile Asn Pro Asn Arg Val Phe Lys Val Asn Thr Asn Ala Tyr Tyr Glu
                245                 250                 255

Met Ser Gly Leu Glu Val Ser Phe Glu Glu Leu Arg Thr Phe Gly Gly
                260                 265                 270

His Asp Ala Lys Phe Ile Asp Ser Leu Gln Glu Asn Glu Phe Arg Leu
                275                 280                 285

Tyr Tyr Tyr Asn Lys Phe Lys Asp Ile Ala Ser Thr Leu Asn Lys Ala
                290                 295                 300

Lys Ser Ile Val Gly Thr Thr Ala Ser Leu Gln Tyr Met Lys Asn Val
305                 310                 315                 320

Phe Lys Glu Lys Tyr Leu Leu Ser Glu Asp Thr Ser Gly Lys Phe Ser
                325                 330                 335

Val Asp Lys Leu Lys Phe Asp Lys Leu Tyr Lys Met Leu Thr Glu Ile
                340                 345                 350

Tyr Thr Glu Asp Asn Phe Val Lys Phe Phe Lys Val Leu Asn Arg Lys
                355                 360                 365

Thr Tyr Leu Asn Phe Asp Lys Ala Val Phe Lys Ile Asn Ile Val Pro
                370                 375                 380

Lys Val Asn Tyr Thr Ile Tyr Asp Gly Phe Asn Leu Arg Asn Thr Asn
385                 390                 395                 400

Leu Ala Ala Asn Phe Asn Gly Gln Asn Thr Glu Ile Asn Asn Met Asn
                405                 410                 415

Phe Thr Lys Leu Lys Asn Phe Thr Gly Leu Phe Glu Phe Tyr Lys Leu
                420                 425                 430

Leu Cys Val Asp Gly Ile Ile Thr Ser Lys Thr Lys Ser Asp Asp Asp
                435                 440                 445

Asp Lys Asn Lys Ala Leu Asn Leu Gln Cys Ile Lys Val Asn Asn Trp
                450                 455                 460

Asp Leu Phe Phe Ser Pro Ser Glu Asp Asn Phe Thr Asn Asp Leu Asn
465                 470                 475                 480

Lys Gly Glu Glu Ile Thr Ser Asp Thr Asn Ile Glu Ala Ala Glu Glu
                485                 490                 495

Asn Ile Ser Leu Asp Leu Ile Gln Gln Tyr Tyr Leu Thr Phe Asn Phe
                500                 505                 510

Asp Asn Glu Pro Glu Asn Ile Ser Ile Glu Asn Leu Ser Ser Asp Ile
                515                 520                 525

Ile Gly Gln Leu Glu Leu Met Pro Asn Ile Glu Arg Phe Pro Asn Gly
                530                 535                 540

Lys Lys Tyr Glu Leu Asp Lys Tyr Thr Met Phe His Tyr Leu Arg Ala
545                 550                 555                 560

Gln Glu Phe Glu His Gly Lys Ser Arg Ile Ala Leu Thr Asn Ser Val
                565                 570                 575

Asn Glu Ala Leu Leu Asn Pro Ser Arg Val Tyr Thr Phe Phe Ser Ser
                580                 585                 590

Asp Tyr Val Lys Lys Val Asn Lys Ala Thr Glu Ala Ala Met Phe Leu
                595                 600                 605

Gly Trp Val Glu Gln Leu Val Tyr Asp Phe Thr Asp Glu Thr Ser Glu
610                 615                 620
```

```
Val Ser Thr Thr Asp Lys Ile Ala Asp Ile Thr Ile Ile Ile Pro Tyr
625                 630                 635                 640

Ile Gly Pro Ala Leu Asn Ile Gly Asn Met Leu Tyr Lys Asp Asp Phe
            645                 650                 655

Val Gly Ala Leu Ile Phe Ser Gly Ala Val Ile Leu Glu Phe Ile
        660                 665                 670

Pro Glu Ile Ala Ile Pro Val Leu Gly Thr Phe Ala Leu Val Ser Tyr
            675                 680                 685

Ile Ala Asn Lys Val Leu Thr Val Gln Thr Ile Asp Asn Ala Leu Ser
690                 695                 700

Lys Arg Asn Glu Lys Trp Asp Glu Val Tyr Lys Tyr Ile Val Thr Asn
705                 710                 715                 720

Trp Leu Ala Lys Val Asn Thr Gln Ile Asp Leu Ile Arg Lys Lys Met
                725                 730                 735

Lys Glu Ala Leu Glu Asn Gln Ala Glu Ala Thr Lys Ala Ile Ile Asn
            740                 745                 750

Tyr Gln Tyr Asn Gln Tyr Thr Glu Glu Lys Asn Asn Ile Asn Phe
            755                 760                 765

Asn Ile Asp Asp Leu Ser Ser Lys Leu Asn Glu Ser Ile Asn Lys Ala
770                 775                 780

Met Ile Asn Ile Asn Lys Phe Leu Asn Gln Cys Ser Val Ser Tyr Leu
785                 790                 795                 800

Met Asn Ser Met Ile Pro Tyr Gly Val Lys Arg Leu Glu Asp Phe Asp
                805                 810                 815

Ala Ser Leu Lys Asp Ala Leu Leu Lys Tyr Ile Tyr Asp Asn Arg Gly
            820                 825                 830

Thr Leu Ile Gly Gln Val Asp Arg Leu Lys Asp Lys Val Asn Asn Thr
            835                 840                 845

Leu Ser Thr Asp Ile Pro Phe Gln Leu Ser Lys Tyr Val Asp Asn Gln
850                 855                 860

Arg Leu Leu Ser Thr Phe Thr Glu Tyr Ile Lys Asn Ile Ile Asn Thr
865                 870                 875                 880

Ser Leu Glu Ile Leu Asn Leu Arg Tyr Glu Ser Asn His Leu Ile Asp
                885                 890                 895

Leu Ser Arg Tyr Ala Ser Lys Ile Asn Ile Gly Ser Lys Val Asn Phe
            900                 905                 910

Asp Pro Ile Asp Lys Asn Gln Ile Gln Leu Phe Asn Leu Glu Ser Ser
    915                 920                 925

Lys Ile Glu Val Ile Leu Lys Asn Ala Ile Val Tyr Asn Ser Met Tyr
            930                 935                 940

Glu Asn Phe Ser Thr Ser Phe Trp Ile Arg Ile Pro Lys Tyr Phe Asn
945                 950                 955                 960

Ser Ile Ser Leu Asn Asn Glu Tyr Thr Ile Ile Asn Cys Met Glu Asn
                965                 970                 975

Asn Ser Gly Trp Lys Val Ser Leu Asn Tyr Gly Glu Ile Ile Trp Thr
            980                 985                 990

Leu Gln Asp Thr Gln Glu Ile Lys  Gln Arg Val Val Phe  Lys Tyr Ser
            995                 1000                1005

Gln Met  Ile Asn Ile Ser Asp  Tyr Ile Asn Arg Trp  Ile Phe Val
        1010                1015                1020

Thr Ile  Thr Asn Asn Arg Leu  Asn Asn Ser Lys Ile  Tyr Ile Asn
        1025                1030                1035
```

Gly Arg Leu Ile Asp Gln Lys Pro Ile Ser Asn Leu Gly Asn Ile
    1040                1045                1050

His Ala Ser Asn Asn Ile Met Phe Lys Leu Asp Gly Cys Arg Asp
    1055                1060                1065

Thr His Arg Tyr Ile Trp Ile Lys Tyr Phe Asn Leu Phe Asp Lys
    1070                1075                1080

Glu Leu Asn Glu Lys Glu Ile Lys Asp Leu Tyr Asp Asn Gln Ser
    1085                1090                1095

Asn Ser Gly Ala Leu Val Ile Leu Lys Asp Phe Trp Gly Asp Tyr
    1100                1105                1110

Leu Gln Tyr Asp Lys Pro Tyr Tyr Met Leu Asn Leu Tyr Asp Pro
    1115                1120                1125

Asn Lys Tyr Val Asp Val Asn Asn Val Gly Ile Arg Gly Tyr Met
    1130                1135                1140

Tyr Leu Lys Gly Pro Arg Gly Ser Val Met Thr Thr Asn Ile Tyr
    1145                1150                1155

Leu Asn Ser Ser Leu Tyr Arg Gly Thr Lys Phe Ile Ile Lys Lys
    1160                1165                1170

Tyr Ala Ser Gly Asn Lys Asp Asn Ile Val Arg Asn Asn Asp Arg
    1175                1180                1185

Val Tyr Ile Asn Val Val Val Lys Asn Lys Glu Tyr Arg Leu Ala
    1190                1195                1200

Thr Asn Ala Ser Gln Ala Gly Val Glu Lys Ile Leu Ser Ala Leu
    1205                1210                1215

Glu Ile Pro Asp Val Gly Asn Leu Ser Gln Val Val Val Met Lys
    1220                1225                1230

Ser Lys Asn Asp Gln Gly Ile Thr Asn Lys Cys Lys Met Asn Leu
    1235                1240                1245

Gln Asp Asn Asn Gly Asn Asp Ile Gly Phe Ile Gly Phe His Gln
    1250                1255                1260

Phe Asn Asn Ile Ala Lys Leu Val Ala Ser Asn Trp Tyr Asn Arg
    1265                1270                1275

Gln Ile Glu Arg Ser Ser Arg Thr Leu Gly Cys Ser Trp Glu Phe
    1280                1285                1290

Ile Pro Val Asp Asp Gly Trp Gly Glu Arg Pro Leu Ala Leu Ala
    1295                1300                1305

His His His His His His His His His
    1310                1315

<210> SEQ ID NO 33
<211> LENGTH: 1318
<212> TYPE: PRT
<213> ORGANISM: Artificial sequence
<220> FEATURE:
<223> OTHER INFORMATION: Protein sequence of BoNT/A with Engineered
      Enterokinase Activation Site and Factor Xa Protease Cleavage Site

<400> SEQUENCE: 33

His Met Gly Ser Met Glu Phe Val Asn Lys Gln Phe Asn Tyr Lys Asp
1               5                   10                  15

Pro Val Asn Gly Val Asp Ile Ala Tyr Ile Lys Ile Pro Asn Ala Gly
                20                  25                  30

Gln Met Gln Pro Val Lys Ala Phe Lys Ile His Asn Lys Ile Trp Val
            35                  40                  45

Ile Pro Glu Arg Asp Thr Phe Thr Asn Pro Glu Glu Gly Asp Leu Asn
        50                  55                  60

-continued

```
Pro Pro Pro Glu Ala Lys Gln Val Pro Val Ser Tyr Asp Ser Thr
65                  70                  75                  80

Tyr Leu Ser Thr Asp Asn Glu Lys Asp Asn Tyr Leu Lys Gly Val Thr
            85                  90                  95

Lys Leu Phe Glu Arg Ile Tyr Ser Thr Asp Leu Gly Arg Met Leu Leu
            100                 105                 110

Thr Ser Ile Val Arg Gly Ile Pro Phe Trp Gly Ser Thr Ile Asp
        115                 120                 125

Thr Glu Leu Lys Val Ile Asp Thr Asn Cys Ile Asn Val Ile Gln Pro
        130                 135                 140

Asp Gly Ser Tyr Arg Ser Glu Glu Leu Asn Leu Val Ile Ile Gly Pro
145                 150                 155                 160

Ser Ala Asp Ile Ile Gln Phe Glu Cys Lys Ser Phe Gly His Glu Val
                165                 170                 175

Leu Asn Leu Thr Arg Asn Gly Tyr Gly Ser Thr Gln Tyr Ile Arg Phe
            180                 185                 190

Ser Pro Asp Phe Thr Phe Gly Phe Glu Glu Ser Leu Glu Val Asp Thr
        195                 200                 205

Asn Pro Leu Leu Gly Ala Gly Lys Phe Ala Thr Asp Pro Ala Val Thr
210                 215                 220

Leu Ala His Glu Leu Ile His Ala Gly His Arg Leu Tyr Gly Ile Ala
225                 230                 235                 240

Ile Asn Pro Asn Arg Val Phe Lys Val Asn Thr Asn Ala Tyr Tyr Glu
                245                 250                 255

Met Ser Gly Leu Glu Val Ser Phe Glu Glu Leu Arg Thr Phe Gly Gly
            260                 265                 270

His Asp Ala Lys Phe Ile Asp Gly Arg Gln Glu Asn Glu Phe Arg Leu
        275                 280                 285

Tyr Tyr Tyr Asn Lys Phe Lys Asp Ile Ala Ser Thr Leu Asn Lys Ala
    290                 295                 300

Lys Ser Ile Val Gly Thr Thr Ala Ser Leu Gln Tyr Met Lys Asn Val
305                 310                 315                 320

Phe Lys Glu Lys Tyr Leu Leu Ser Glu Asp Thr Ser Gly Lys Phe Ser
                325                 330                 335

Val Asp Lys Leu Lys Phe Asp Lys Leu Tyr Lys Met Leu Thr Glu Ile
            340                 345                 350

Tyr Thr Glu Asp Asn Phe Val Lys Phe Phe Lys Val Leu Asn Arg Lys
        355                 360                 365

Thr Tyr Leu Asn Phe Asp Lys Ala Val Phe Lys Ile Asn Ile Val Pro
        370                 375                 380

Lys Val Asn Tyr Thr Ile Tyr Asp Gly Phe Asn Leu Arg Asn Thr Asn
385                 390                 395                 400

Leu Ala Ala Asn Phe Asn Gly Gln Asn Thr Glu Ile Asn Asn Met Asn
                405                 410                 415

Phe Thr Lys Leu Lys Asn Phe Thr Gly Leu Phe Glu Phe Tyr Lys Leu
            420                 425                 430

Leu Cys Val Asp Gly Ile Ile Thr Ser Lys Thr Lys Ser Asp Asp
        435                 440                 445

Asp Lys Asn Lys Ala Leu Asn Leu Gln Cys Ile Lys Val Asn Asn Trp
    450                 455                 460

Asp Leu Phe Phe Ser Pro Ser Glu Asp Asn Phe Thr Asn Asp Leu Asn
465                 470                 475                 480
```

-continued

```
Lys Gly Glu Glu Ile Thr Ser Asp Thr Asn Ile Glu Ala Ala Glu Glu
                485                 490                 495

Asn Ile Ser Leu Asp Leu Ile Gln Gln Tyr Tyr Leu Thr Phe Asn Phe
            500                 505                 510

Asp Asn Glu Pro Glu Asn Ile Ser Ile Glu Asn Leu Ser Ser Asp Ile
            515                 520                 525

Ile Gly Gln Leu Glu Leu Met Pro Asn Ile Glu Arg Phe Pro Asn Gly
            530                 535                 540

Lys Lys Tyr Glu Leu Asp Lys Tyr Thr Met Phe His Tyr Leu Arg Ala
545                 550                 555                 560

Gln Glu Phe Glu His Gly Lys Ser Arg Ile Ala Leu Thr Asn Ser Val
                565                 570                 575

Asn Glu Ala Leu Leu Asn Pro Ser Arg Val Tyr Thr Phe Phe Ser Ser
            580                 585                 590

Asp Tyr Val Lys Lys Val Asn Lys Ala Thr Glu Ala Ala Met Phe Leu
            595                 600                 605

Gly Trp Val Glu Gln Leu Val Tyr Asp Phe Thr Asp Glu Thr Ser Glu
            610                 615                 620

Val Ser Thr Thr Asp Lys Ile Ala Asp Ile Thr Ile Ile Ile Pro Tyr
625                 630                 635                 640

Ile Gly Pro Ala Leu Asn Ile Gly Asn Met Leu Tyr Lys Asp Asp Phe
            645                 650                 655

Val Gly Ala Leu Ile Phe Ser Gly Ala Val Ile Leu Leu Glu Phe Ile
            660                 665                 670

Pro Glu Ile Ala Ile Pro Val Leu Gly Thr Phe Ala Leu Val Ser Tyr
            675                 680                 685

Ile Ala Asn Lys Val Leu Thr Val Gln Thr Ile Asp Asn Ala Leu Ser
            690                 695                 700

Lys Arg Asn Glu Lys Trp Asp Glu Val Tyr Lys Tyr Ile Val Thr Asn
705                 710                 715                 720

Trp Leu Ala Lys Val Asn Thr Gln Ile Asp Leu Ile Arg Lys Lys Met
            725                 730                 735

Lys Glu Ala Leu Glu Asn Gln Ala Glu Ala Thr Lys Ala Ile Ile Asn
            740                 745                 750

Tyr Gln Tyr Asn Gln Tyr Thr Glu Glu Glu Lys Asn Asn Ile Asn Phe
            755                 760                 765

Asn Ile Asp Asp Leu Ser Ser Lys Leu Asn Glu Ser Ile Asn Lys Ala
            770                 775                 780

Met Ile Asn Ile Asn Lys Phe Leu Asn Gln Cys Ser Val Ser Tyr Leu
785                 790                 795                 800

Met Asn Ser Met Ile Pro Tyr Gly Val Lys Arg Leu Glu Asp Phe Asp
                805                 810                 815

Ala Ser Leu Lys Asp Ala Leu Leu Lys Tyr Ile Tyr Asp Asn Arg Gly
            820                 825                 830

Thr Leu Ile Gly Gln Val Asp Arg Leu Lys Asp Lys Val Asn Asn Thr
            835                 840                 845

Leu Ser Thr Asp Ile Pro Phe Gln Leu Ser Lys Tyr Val Asp Asn Gln
            850                 855                 860

Arg Leu Leu Ser Thr Phe Thr Glu Tyr Ile Lys Asn Ile Ile Asn Thr
865                 870                 875                 880

Ser Leu Glu Ile Leu Asn Leu Arg Tyr Glu Ser Asn His Leu Ile Asp
            885                 890                 895

Leu Ser Arg Tyr Ala Ser Lys Ile Asn Ile Gly Ser Lys Val Asn Phe
```

-continued

```
                900             905             910
Asp Pro Ile Asp Lys Asn Gln Ile Gln Leu Phe Asn Leu Glu Ser Ser
            915             920             925

Lys Ile Glu Val Ile Leu Lys Asn Ala Ile Val Tyr Asn Ser Met Tyr
            930             935             940

Glu Asn Phe Ser Thr Ser Phe Trp Ile Arg Ile Pro Lys Tyr Phe Asn
945             950             955             960

Ser Ile Ser Leu Asn Asn Glu Tyr Thr Ile Ile Asn Cys Met Glu Asn
            965             970             975

Asn Ser Gly Trp Lys Val Ser Leu Asn Tyr Gly Glu Ile Ile Trp Thr
            980             985             990

Leu Gln Asp Thr Gln Glu Ile Lys  Gln Arg Val Val Phe  Lys Tyr Ser
            995             1000            1005

Gln Met  Ile Asn Ile Ser Asp  Tyr Ile Asn Arg Trp  Ile Phe Val
    1010            1015            1020

Thr Ile  Thr Asn Asn Arg Leu  Asn Asn Ser Lys Ile  Tyr Ile Asn
    1025            1030            1035

Gly Arg  Leu Ile Asp Gln Lys  Pro Ile Ser Asn Leu  Gly Asn Ile
    1040            1045            1050

His Ala  Ser Asn Asn Ile Met  Phe Lys Leu Asp Gly  Cys Arg Asp
    1055            1060            1065

Thr His  Arg Tyr Ile Trp Ile  Lys Tyr Phe Asn Leu  Phe Asp Lys
    1070            1075            1080

Glu Leu  Asn Glu Lys Glu Ile  Lys Asp Leu Tyr Asp  Asn Gln Ser
    1085            1090            1095

Asn Ser  Gly Ala Leu Val Ile  Leu Lys Asp Phe Trp  Gly Asp Tyr
    1100            1105            1110

Leu Gln  Tyr Asp Lys Pro Tyr  Tyr Met Leu Asn Leu  Tyr Asp Pro
    1115            1120            1125

Asn Lys  Tyr Val Asp Val Asn  Asn Val Gly Ile Arg  Gly Tyr Met
    1130            1135            1140

Tyr Leu  Lys Gly Pro Arg Gly  Ser Val Met Thr Thr  Asn Ile Tyr
    1145            1150            1155

Leu Asn  Ser Ser Leu Tyr Arg  Gly Thr Lys Phe Ile  Ile Lys Lys
    1160            1165            1170

Tyr Ala  Ser Gly Asn Lys Asp  Asn Ile Val Arg Asn  Asn Asp Arg
    1175            1180            1185

Val Tyr  Ile Asn Val Val Val  Lys Asn Lys Glu Tyr  Arg Leu Ala
    1190            1195            1200

Thr Asn  Ala Ser Gln Ala Gly  Val Glu Lys Ile Leu  Ser Ala Leu
    1205            1210            1215

Glu Ile  Pro Asp Val Gly Asn  Leu Ser Gln Val Val  Val Met Lys
    1220            1225            1230

Ser Lys  Asn Asp Gln Gly Ile  Thr Asn Lys Cys Lys  Met Asn Leu
    1235            1240            1245

Gln Asp  Asn Asn Gly Asn Asp  Ile Gly Phe Ile Gly  Phe His Gln
    1250            1255            1260

Phe Asn  Asn Ile Ala Lys Leu  Val Ala Ser Asn Trp  Tyr Asn Arg
    1265            1270            1275

Gln Ile  Glu Arg Ser Ser Arg  Thr Leu Gly Cys Ser  Trp Glu Phe
    1280            1285            1290

Ile Pro  Val Asp Asp Gly Trp  Gly Glu Arg Pro Leu  Ala Leu Ala
    1295            1300            1305
```

His His His His His His His His His His
    1310                    1315

<210> SEQ ID NO 34
<211> LENGTH: 1318
<212> TYPE: PRT
<213> ORGANISM: Artificial sequence
<220> FEATURE:
<223> OTHER INFORMATION: Protein sequence of BoNT/A with Engineered
      Enterokinase Activation Site and Factor Xa Protease Cleavage Site

<400> SEQUENCE: 34

His Met Gly Ser Met Glu Phe Val Asn Lys Gln Phe Asn Tyr Lys Asp
1               5                   10                  15

Pro Val Asn Gly Val Asp Ile Ala Tyr Ile Lys Ile Pro Asn Ala Gly
            20                  25                  30

Gln Met Gln Pro Val Lys Ala Phe Lys Ile His Asn Lys Ile Trp Val
        35                  40                  45

Ile Pro Glu Arg Asp Thr Phe Thr Asn Pro Glu Glu Gly Asp Leu Asn
    50                  55                  60

Pro Pro Pro Glu Ala Lys Gln Val Pro Val Ser Tyr Tyr Asp Ser Thr
65                  70                  75                  80

Tyr Leu Ser Thr Asp Asn Glu Lys Asp Asn Tyr Leu Lys Gly Val Thr
                85                  90                  95

Lys Leu Phe Glu Arg Ile Tyr Ser Thr Asp Leu Gly Arg Met Leu Leu
            100                 105                 110

Thr Ser Ile Val Arg Gly Ile Pro Phe Trp Gly Gly Ser Thr Ile Asp
        115                 120                 125

Thr Glu Leu Lys Val Ile Asp Thr Asn Cys Ile Asn Val Ile Gln Pro
    130                 135                 140

Asp Gly Ser Tyr Arg Ser Glu Glu Leu Asn Leu Val Ile Ile Gly Pro
145                 150                 155                 160

Ser Ala Asp Ile Ile Gln Phe Glu Cys Lys Ser Phe Gly His Glu Val
                165                 170                 175

Leu Asn Leu Thr Arg Asn Gly Tyr Gly Ser Thr Gln Tyr Ile Arg Phe
            180                 185                 190

Ser Pro Asp Phe Thr Phe Gly Phe Glu Glu Ser Leu Glu Val Asp Thr
        195                 200                 205

Asn Pro Leu Leu Gly Ala Gly Lys Phe Ala Thr Asp Pro Ala Val Thr
    210                 215                 220

Leu Ala His Glu Leu Ile His Ala Gly His Arg Leu Tyr Gly Ile Ala
225                 230                 235                 240

Ile Asn Pro Asn Arg Val Phe Lys Val Asn Thr Asn Ala Tyr Tyr Glu
                245                 250                 255

Met Ser Gly Leu Glu Val Ser Phe Glu Glu Leu Arg Thr Phe Gly Gly
            260                 265                 270

His Asp Ala Lys Phe Ile Asp Ser Leu Gln Glu Asn Glu Phe Arg Leu
        275                 280                 285

Tyr Tyr Tyr Asn Lys Phe Lys Asp Ile Ala Ser Thr Leu Asn Lys Ala
    290                 295                 300

Lys Ser Ile Val Gly Thr Thr Ala Ser Leu Gln Tyr Met Lys Asn Val
305                 310                 315                 320

Phe Lys Glu Lys Tyr Leu Leu Ser Glu Asp Thr Ser Gly Lys Phe Ser
                325                 330                 335

Val Asp Lys Leu Lys Phe Asp Lys Leu Tyr Lys Met Leu Thr Glu Ile

```
                340                 345                 350
Tyr Thr Glu Asp Asn Phe Val Lys Phe Phe Lys Val Leu Asn Arg Lys
            355                 360                 365

Thr Tyr Leu Asn Phe Asp Lys Ala Val Phe Lys Ile Asn Ile Val Pro
        370                 375                 380

Lys Val Asn Tyr Thr Ile Tyr Asp Gly Phe Asn Leu Arg Asn Thr Asn
385                 390                 395                 400

Leu Ala Ala Asn Phe Asn Gly Gln Asn Thr Glu Ile Asn Asn Met Asn
                405                 410                 415

Phe Thr Lys Leu Lys Asn Phe Thr Gly Leu Phe Glu Phe Tyr Lys Leu
            420                 425                 430

Leu Cys Val Asp Gly Ile Ile Thr Ser Lys Thr Lys Ser Asp Asp Asp
        435                 440                 445

Asp Lys Asn Lys Ala Leu Asn Leu Gln Cys Ile Lys Val Asn Asn Trp
    450                 455                 460

Asp Leu Phe Phe Ser Pro Ser Glu Asp Asn Phe Thr Asn Asp Leu Asn
465                 470                 475                 480

Lys Gly Glu Glu Ile Thr Ser Asp Thr Asn Ile Glu Ala Ala Glu Glu
                485                 490                 495

Asn Ile Ser Leu Asp Leu Ile Gln Gln Tyr Tyr Leu Thr Phe Asn Phe
            500                 505                 510

Asp Asn Glu Pro Glu Asn Ile Ser Ile Glu Asn Leu Ser Ser Asp Ile
        515                 520                 525

Ile Gly Gln Leu Glu Leu Met Pro Asn Ile Glu Arg Phe Pro Asn Gly
    530                 535                 540

Lys Lys Tyr Glu Leu Asp Lys Tyr Thr Met Phe His Tyr Leu Arg Ala
545                 550                 555                 560

Gln Glu Phe Glu His Ile Glu Gly Arg Ile Ala Leu Thr Asn Ser Val
                565                 570                 575

Asn Glu Ala Leu Leu Asn Pro Ser Arg Val Tyr Thr Phe Phe Ser Ser
            580                 585                 590

Asp Tyr Val Lys Lys Val Asn Lys Ala Thr Glu Ala Ala Met Phe Leu
        595                 600                 605

Gly Trp Val Glu Gln Leu Val Tyr Asp Phe Thr Asp Glu Thr Ser Glu
    610                 615                 620

Val Ser Thr Thr Asp Lys Ile Ala Asp Ile Thr Ile Ile Pro Tyr
625                 630                 635                 640

Ile Gly Pro Ala Leu Asn Ile Gly Asn Met Leu Tyr Lys Asp Asp Phe
                645                 650                 655

Val Gly Ala Leu Ile Phe Ser Gly Ala Val Ile Leu Leu Glu Phe Ile
            660                 665                 670

Pro Glu Ile Ala Ile Pro Val Leu Gly Thr Phe Ala Leu Val Ser Tyr
        675                 680                 685

Ile Ala Asn Lys Val Leu Thr Val Gln Thr Ile Asp Asn Ala Leu Ser
    690                 695                 700

Lys Arg Asn Glu Lys Trp Asp Glu Val Tyr Lys Tyr Ile Val Thr Asn
705                 710                 715                 720

Trp Leu Ala Lys Val Asn Thr Gln Ile Asp Leu Ile Arg Lys Lys Met
                725                 730                 735

Lys Glu Ala Leu Glu Asn Gln Ala Glu Ala Thr Lys Ala Ile Ile Asn
            740                 745                 750

Tyr Gln Tyr Asn Gln Tyr Thr Glu Glu Lys Asn Asn Ile Asn Phe
        755                 760                 765
```

```
Asn Ile Asp Asp Leu Ser Ser Lys Leu Asn Glu Ser Ile Asn Lys Ala
        770                 775                 780

Met Ile Asn Ile Asn Lys Phe Leu Asn Gln Cys Ser Val Ser Tyr Leu
785                 790                 795                 800

Met Asn Ser Met Ile Pro Tyr Gly Val Lys Arg Leu Glu Asp Phe Asp
                805                 810                 815

Ala Ser Leu Lys Asp Ala Leu Leu Lys Tyr Ile Tyr Asp Asn Arg Gly
            820                 825                 830

Thr Leu Ile Gly Gln Val Asp Arg Leu Lys Asp Lys Val Asn Asn Thr
        835                 840                 845

Leu Ser Thr Asp Ile Pro Phe Gln Leu Ser Lys Tyr Val Asp Asn Gln
850                 855                 860

Arg Leu Leu Ser Thr Phe Thr Glu Tyr Ile Lys Asn Ile Ile Asn Thr
865                 870                 875                 880

Ser Leu Glu Ile Leu Asn Leu Arg Tyr Glu Ser Asn His Leu Ile Asp
                885                 890                 895

Leu Ser Arg Tyr Ala Ser Lys Ile Asn Ile Gly Ser Lys Val Asn Phe
            900                 905                 910

Asp Pro Ile Asp Lys Asn Gln Ile Gln Leu Phe Asn Leu Glu Ser Ser
        915                 920                 925

Lys Ile Glu Val Ile Leu Lys Asn Ala Ile Val Tyr Asn Ser Met Tyr
    930                 935                 940

Glu Asn Phe Ser Thr Ser Phe Trp Ile Arg Ile Pro Lys Tyr Phe Asn
945                 950                 955                 960

Ser Ile Ser Leu Asn Asn Glu Tyr Thr Ile Ile Asn Cys Met Glu Asn
                965                 970                 975

Asn Ser Gly Trp Lys Val Ser Leu Asn Tyr Gly Glu Ile Ile Trp Thr
            980                 985                 990

Leu Gln Asp Thr Gln Glu Ile Lys  Gln Arg Val Val Phe  Lys Tyr Ser
        995                 1000                1005

Gln Met  Ile Asn Ile Ser Asp  Tyr Ile Asn Arg Trp  Ile Phe Val
    1010                1015                1020

Thr Ile  Thr Asn Asn Arg Leu  Asn Asn Ser Lys Ile  Tyr Ile Asn
    1025                1030                1035

Gly Arg  Leu Ile Asp Gln Lys  Pro Ile Ser Asn Leu  Gly Asn Ile
    1040                1045                1050

His Ala  Ser Asn Asn Ile Met  Phe Lys Leu Asp Gly  Cys Arg Asp
    1055                1060                1065

Thr His  Arg Tyr Ile Trp Ile  Lys Tyr Phe Asn Leu  Phe Asp Lys
    1070                1075                1080

Glu Leu  Asn Glu Lys Glu Ile  Lys Asp Leu Tyr Asp  Asn Gln Ser
    1085                1090                1095

Asn Ser  Gly Ala Leu Val Ile  Leu Lys Asp Phe Trp  Gly Asp Tyr
    1100                1105                1110

Leu Gln  Tyr Asp Lys Pro Tyr  Tyr Met Leu Asn Leu  Tyr Asp Pro
    1115                1120                1125

Asn Lys  Tyr Val Asp Val Asn  Asn Val Gly Ile Arg  Gly Tyr Met
    1130                1135                1140

Tyr Leu  Lys Gly Pro Arg Gly  Ser Val Met Thr Thr  Asn Ile Tyr
    1145                1150                1155

Leu Asn  Ser Ser Leu Tyr Arg  Gly Thr Lys Phe Ile  Ile Lys Lys
    1160                1165                1170
```

Tyr Ala Ser Gly Asn Lys Asp Asn Ile Val Arg Asn Asn Asp Arg
    1175                1180                1185

Val Tyr Ile Asn Val Val Lys Asn Lys Glu Tyr Arg Leu Ala
    1190                1195                1200

Thr Asn Ala Ser Gln Ala Gly Val Glu Lys Ile Leu Ser Ala Leu
    1205                1210                1215

Glu Ile Pro Asp Val Gly Asn Leu Ser Gln Val Val Met Lys
    1220                1225                1230

Ser Lys Asn Asp Gln Gly Ile Thr Asn Lys Cys Lys Met Asn Leu
    1235                1240                1245

Gln Asp Asn Asn Gly Asn Asp Ile Gly Phe Ile Gly Phe His Gln
    1250                1255                1260

Phe Asn Asn Ile Ala Lys Leu Val Ala Ser Asn Trp Tyr Asn Arg
    1265                1270                1275

Gln Ile Glu Arg Ser Ser Arg Thr Leu Gly Cys Ser Trp Glu Phe
    1280                1285                1290

Ile Pro Val Asp Asp Gly Trp Gly Glu Arg Pro Leu Ala Leu Ala
    1295                1300                1305

His His His His His His His His His
    1310                1315

<210> SEQ ID NO 35
<211> LENGTH: 1252
<212> TYPE: PRT
<213> ORGANISM: Artificial sequence
<220> FEATURE:
<223> OTHER INFORMATION: Protein sequence of BoNT/E with Engineered
      Enterokinase Activation Site and Thrombin Protease Cleavage Site

<400> SEQUENCE: 35

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln His Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Ile Val Pro Arg Phe Ser Phe
            180                 185                 190

Arg Phe Asn Asp Asn Ser Ile Asn Glu Phe Ile Gln Asp Pro Ala Leu
        195                 200                 205

-continued

```
Thr Leu Met His Glu Leu Ile His Ser Leu His Gly Leu Tyr Gly Ala
    210                 215                 220
Lys Gly Ile Thr Thr Thr Cys Ile Ile Thr Gln Gln Gln Asn Pro Leu
225                 230                 235                 240
Ile Thr Asn Arg Lys Gly Ile Asn Ile Glu Glu Phe Leu Thr Phe Gly
                245                 250                 255
Gly Asn Asp Leu Asn Ile Ile Thr Val Ala Gln Tyr Asn Asp Ile Tyr
                260                 265                 270
Thr Asn Leu Leu Asn Asp Tyr Arg Lys Ile Ala Ser Lys Leu Ser Lys
            275                 280                 285
Val Gln Val Ser Asn Pro Gln Leu Asn Pro Tyr Lys Asp Ile Phe Gln
290                 295                 300
Glu Lys Tyr Gly Leu Asp Lys Asp Ala Ser Gly Ile Tyr Ser Val Asn
305                 310                 315                 320
Ile Asn Lys Phe Asp Asp Ile Leu Lys Lys Leu Tyr Ser Phe Thr Glu
                325                 330                 335
Phe Asp Leu Ala Thr Lys Phe Gln Val Lys Cys Arg Glu Thr Tyr Ile
                340                 345                 350
Gly Gln Tyr Lys Tyr Phe Lys Leu Ser Asn Leu Leu Asn Asp Ser Ile
            355                 360                 365
Tyr Asn Ile Ser Glu Gly Tyr Asn Ile Asn Asn Leu Lys Val Asn Phe
    370                 375                 380
Arg Gly Gln Asn Ala Asn Leu Asn Pro Arg Ile Ile Lys Pro Ile Thr
385                 390                 395                 400
Gly Arg Gly Leu Val Lys Lys Ile Ile Arg Phe Cys Lys Asn Ile Val
                405                 410                 415
Ser Val Lys Gly Ile Arg Lys Ser Ile Cys Ile Glu Ile Asn Asn Gly
                420                 425                 430
Glu Leu Phe Phe Val Ala Ser Glu Asn Ser Tyr Asn Asp Asp Asn Ile
            435                 440                 445
Asn Thr Pro Lys Glu Ile Asp Asp Thr Val Thr Ser Asn Asn Asn Tyr
    450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
                500                 505                 510
Asp Val Asn Glu Leu Asn Val Phe Phe Tyr Leu Asp Ala Gln Lys Val
            515                 520                 525
Pro Glu Gly Glu Asn Asn Val Asn Leu Thr Ser Ser Ile Asp Thr Ala
    530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
                565                 570                 575
Gln Gln Val Leu Val Asp Phe Thr Thr Glu Ala Asn Gln Lys Ser Thr
            580                 585                 590
Val Asp Lys Ile Ala Asp Ile Ser Ile Val Val Pro Tyr Ile Gly Leu
            595                 600                 605
Ala Leu Asn Ile Gly Asn Glu Ala Gln Lys Gly Asn Phe Lys Asp Ala
    610                 615                 620
```

-continued

Leu Glu Leu Leu Gly Ala Gly Ile Leu Glu Phe Glu Pro Glu Leu
625                 630                 635                 640

Leu Ile Pro Thr Ile Leu Val Phe Thr Ile Lys Ser Phe Leu Gly Ser
            645                 650                 655

Ser Asp Asn Lys Asn Lys Val Ile Lys Ala Ile Asn Asn Ala Leu Lys
        660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
            725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
            805                 810                 815

Asp Thr Leu Asn Asn Ser Ile Pro Phe Lys Leu Ser Ser Tyr Thr Asp
        820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
            885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
            965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
        995                 1000                1005

Gly Asn Leu Ile Asp Gln Lys Ser Ile Leu Asn Leu Gly Asn Ile
        1010                1015                1020

His Val Ser Asp Asn Ile Leu Phe Lys Ile Val Asn Cys Ser Tyr
    1025                1030                1035

Thr Arg Tyr Ile Gly Ile Arg Tyr Phe Asn Ile Phe Asp Lys Glu

```
                  1040                1045                1050

Leu Asp Glu Thr Glu Ile Gln Thr Leu Tyr Ser Asn Glu Pro Asn
        1055                1060                1065

Thr Asn Ile Leu Lys Asp Phe Trp Gly Asn Tyr Leu Leu Tyr Asp
    1070                1075                1080

Lys Glu Tyr Tyr Leu Leu Asn Val Leu Lys Pro Asn Asn Phe Ile
1085                1090                1095

Asp Arg Arg Lys Asp Ser Thr Leu Ser Ile Asn Asn Ile Arg Ser
        1100                1105                1110

Thr Ile Leu Leu Ala Asn Arg Leu Tyr Ser Gly Ile Lys Val Lys
    1115                1120                1125

Ile Gln Arg Val Asn Asn Ser Ser Thr Asn Asp Asn Leu Val Arg
1130                1135                1140

Lys Asn Asp Gln Val Tyr Ile Asn Phe Val Ala Ser Lys Thr His
        1145                1150                1155

Leu Phe Pro Leu Tyr Ala Asp Thr Ala Thr Thr Asn Lys Glu Lys
    1160                1165                1170

Thr Ile Lys Ile Ser Ser Ser Gly Asn Arg Phe Asn Gln Val Val
1175                1180                1185

Val Met Asn Ser Val Gly Asn Asn Cys Thr Met Asn Phe Lys Asn
        1190                1195                1200

Asn Asn Gly Asn Asn Ile Gly Leu Leu Gly Phe Lys Ala Asp Thr
    1205                1210                1215

Val Val Ala Ser Thr Trp Tyr Tyr Thr His Met Arg Asp His Thr
1220                1225                1230

Asn Ser Asn Gly Cys Phe Trp Asn Phe Ile Ser Glu Glu His Gly
        1235                1240                1245

Trp Gln Glu Lys
    1250

<210> SEQ ID NO 36
<211> LENGTH: 1252
<212> TYPE: PRT
<213> ORGANISM: Artificial sequence
<220> FEATURE:
<223> OTHER INFORMATION: Protein sequence of BoNT/E with Engineered
      Enterokinase Activation Site and Factor Xa Protease Cleavage Site

<400> SEQUENCE: 36

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125
```

```
Ala Ser Ala Val Glu Ile Lys Phe Ser Asn Gly Ser Gln His Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
            165                 170                 175

Gly Phe Gly Ser Ile Ala Ile Val Thr Phe Ser Pro Glu Tyr Ser Phe
            180                 185                 190

Arg Phe Asn Asp Asn Ser Ile Asn Glu Phe Ile Gln Asp Pro Ala Leu
            195                 200                 205

Thr Leu Met His Glu Leu Ile His Ser Leu His Gly Leu Tyr Gly Ala
210                 215                 220

Lys Gly Ile Thr Thr Thr Cys Ile Ile Thr Gln Gln Gln Asn Pro Leu
225                 230                 235                 240

Ile Thr Asn Arg Lys Gly Ile Asn Ile Glu Glu Phe Leu Thr Phe Gly
                245                 250                 255

Gly Asn Asp Leu Asn Ile Ile Thr Val Ala Gln Tyr Asn Asp Ile Tyr
            260                 265                 270

Thr Asn Leu Leu Asn Asp Tyr Arg Lys Ile Ala Ser Lys Leu Ser Lys
    275                 280                 285

Val Gln Val Ser Asn Pro Gln Leu Asn Pro Tyr Lys Asp Ile Phe Gln
290                 295                 300

Glu Lys Tyr Gly Leu Asp Lys Asp Ala Ser Gly Ile Tyr Ser Val Asn
305                 310                 315                 320

Ile Asn Lys Phe Asp Asp Ile Leu Lys Lys Leu Tyr Ser Phe Thr Glu
                325                 330                 335

Phe Asp Leu Ala Thr Lys Phe Gln Val Lys Cys Arg Glu Thr Tyr Ile
            340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Lys Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
            435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
530                 535                 540

Leu Leu Glu Gln Pro Lys Ile Tyr Thr Phe Phe Ser Ser Glu Phe Ile
```

```
                545                 550                 555                 560
            Asn Asn Val Asn Lys Pro Val Gln Ala Ala Leu Phe Val Ser Trp Ile
                            565                 570                 575

Gln Gln Val Leu Val Asp Phe Thr Thr Glu Ala Asn Gln Lys Ser Thr
                            580                 585                 590

Val Asp Lys Ile Ala Asp Ile Ser Ile Val Val Pro Tyr Ile Gly Leu
                            595                 600                 605

Ala Leu Asn Ile Gly Asn Glu Ala Gln Lys Gly Asn Phe Lys Asp Ala
                            610                 615                 620

Leu Glu Leu Leu Gly Ala Gly Ile Leu Leu Glu Phe Glu Pro Glu Leu
            625                 630                 635                 640

Leu Ile Pro Thr Ile Leu Val Phe Thr Ile Lys Ser Phe Leu Gly Ser
                            645                 650                 655

Ser Asp Asn Lys Asn Lys Val Ile Lys Ala Ile Asn Asn Ala Leu Lys
                            660                 665                 670

Glu Arg Asp Glu Lys Trp Lys Glu Val Tyr Ser Phe Ile Val Ser Asn
                            675                 680                 685

Trp Met Thr Lys Ile Asn Thr Gln Phe Asn Lys Arg Lys Glu Gln Met
            690                 695                 700

Tyr Gln Ala Leu Gln Asn Gln Val Asn Ala Ile Lys Thr Ile Ile Glu
            705                 710                 715                 720

Ser Lys Tyr Asn Ser Tyr Ile Glu Gly Arg Lys Asn Glu Leu Thr Asn
                            725                 730                 735

Lys Tyr Asp Ile Lys Gln Ile Glu Asn Glu Leu Asn Gln Lys Val Ser
                            740                 745                 750

Ile Ala Met Asn Asn Ile Asp Arg Phe Leu Thr Glu Ser Ser Ile Ser
                            755                 760                 765

Tyr Leu Met Lys Leu Ile Asn Glu Val Lys Ile Asn Lys Leu Arg Glu
                            770                 775                 780

Tyr Asp Glu Asn Val Lys Thr Tyr Leu Leu Asn Tyr Ile Ile Gln His
            785                 790                 795                 800

Gly Ser Ile Leu Gly Glu Ser Gln Gln Glu Leu Asn Ser Met Val Thr
                            805                 810                 815

Asp Thr Leu Asn Asn Ser Ile Pro Phe Lys Leu Ser Ser Tyr Thr Asp
                            820                 825                 830

Asp Lys Ile Leu Ile Ser Tyr Phe Asn Lys Phe Phe Lys Arg Ile Lys
                            835                 840                 845

Ser Ser Ser Val Leu Asn Met Arg Tyr Lys Asn Asp Lys Tyr Val Asp
            850                 855                 860

Thr Ser Gly Tyr Asp Ser Asn Ile Asn Ile Asn Gly Asp Val Tyr Lys
            865                 870                 875                 880

Tyr Pro Thr Asn Lys Asn Gln Phe Gly Ile Tyr Asn Asp Lys Leu Ser
                            885                 890                 895

Glu Val Asn Ile Ser Gln Asn Asp Tyr Ile Tyr Asp Asn Lys Tyr
                            900                 905                 910

Lys Asn Phe Ser Ile Ser Phe Trp Val Arg Ile Pro Asn Tyr Asp Asn
                            915                 920                 925

Lys Ile Val Asn Val Asn Asn Glu Tyr Thr Ile Ile Asn Cys Met Arg
                            930                 935                 940

Asp Asn Asn Ser Gly Trp Lys Val Ser Leu Asn His Asn Glu Ile Ile
            945                 950                 955                 960

Trp Thr Leu Gln Asp Asn Ala Gly Ile Asn Gln Lys Leu Ala Phe Asn
                            965                 970                 975
```

```
Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
            995                 1000                1005

Gly Asn  Leu Ile Asp Gln Lys  Ser Ile Leu Asn Leu  Gly Asn Ile
            1010                1015                1020

His Val  Ser Asp Asn Ile Leu  Phe Lys Ile Val Asn  Cys Ser Tyr
            1025                1030                1035

Thr Arg  Tyr Ile Gly Ile Arg  Tyr Phe Asn Ile Phe  Asp Lys Glu
            1040                1045                1050

Leu Asp  Glu Thr Glu Ile Gln  Thr Leu Tyr Ser Asn  Glu Pro Asn
            1055                1060                1065

Thr Asn  Ile Leu Lys Asp Phe  Trp Gly Asn Tyr Leu  Leu Tyr Asp
            1070                1075                1080

Lys Glu  Tyr Tyr Leu Leu Asn  Val Leu Lys Pro Asn  Asn Phe Ile
            1085                1090                1095

Asp Arg  Arg Lys Asp Ser Thr  Leu Ser Ile Asn Asn  Ile Arg Ser
            1100                1105                1110

Thr Ile  Leu Leu Ala Asn Arg  Leu Tyr Ser Gly Ile  Lys Val Lys
            1115                1120                1125

Ile Gln  Arg Val Asn Asn Ser  Ser Thr Asn Asp Asn  Leu Val Arg
            1130                1135                1140

Lys Asn  Asp Gln Val Tyr Ile  Asn Phe Val Ala Ser  Lys Thr His
            1145                1150                1155

Leu Phe  Pro Leu Tyr Ala Asp  Thr Ala Thr Thr Asn  Lys Glu Lys
            1160                1165                1170

Thr Ile  Lys Ile Ser Ser Ser  Gly Asn Arg Phe Asn  Gln Val Val
            1175                1180                1185

Val Met  Asn Ser Val Gly Asn  Asn Cys Thr Met Asn  Phe Lys Asn
            1190                1195                1200

Asn Asn  Gly Asn Asn Ile Gly  Leu Leu Gly Phe Lys  Ala Asp Thr
            1205                1210                1215

Val Val  Ala Ser Thr Trp Tyr  Tyr Thr His Met Arg  Asp His Thr
            1220                1225                1230

Asn Ser  Asn Gly Cys Phe Trp  Asn Phe Ile Ser Glu  Glu His Gly
            1235                1240                1245

Trp Gln  Glu Lys
            1250

<210> SEQ ID NO 37
<211> LENGTH: 900
<212> TYPE: PRT
<213> ORGANISM: Artificial sequence
<220> FEATURE:
<223> OTHER INFORMATION: Protein sequence of BoNT/E with Human
      Vasoactive Intestinal Peptide Targeting Moiety and Thrombin
      Protease Cleavage Site

<400> SEQUENCE: 37

Met Gly Ser Met Pro Lys Ile Asn Ser Phe Asn Tyr Asn Asp Pro Val
1               5                   10                  15

Asn Asp Arg Thr Ile Leu Tyr Ile Lys Pro Gly Gly Cys Gln Glu Phe
            20                  25                  30

Tyr Lys Ser Phe Asn Ile Met Lys Asn Ile Trp Ile Ile Pro Glu Arg
        35                  40                  45
```

Asn Val Ile Gly Thr Thr Pro Gln Asp Phe His Pro Pro Thr Ser Leu
50                    55                    60

Lys Asn Gly Asp Ser Ser Tyr Tyr Asp Pro Asn Tyr Leu Gln Ser Asp
65                    70                    75                    80

Glu Glu Lys Asp Arg Phe Leu Lys Ile Val Thr Lys Ile Phe Asn Arg
                85                    90                    95

Ile Asn Asn Asn Leu Ser Gly Arg Gly Leu Leu Glu Glu Leu Ser Lys
            100                   105                   110

Ala Asn Pro Tyr Leu Gly Asn Asp Asn Thr Pro Asp Asn Gln Phe His
            115                   120                   125

Ile Gly Asp Ala Ser Ala Val Glu Ile Lys Phe Ser Asn Gly Ser Gln
130                   135                   140

His Ile Leu Leu Pro Asn Val Ile Ile Met Gly Ala Glu Pro Asp Leu
145                   150                   155                   160

Phe Glu Thr Asn Ser Ser Asn Ile Ser Leu Arg Asn Asn Tyr Met Pro
                165                   170                   175

Ser Asn His Gly Phe Gly Ser Ile Ala Ile Val Thr Phe Ser Pro Glu
            180                   185                   190

Tyr Ser Phe Arg Phe Asn Asp Asn Ser Ile Asn Glu Phe Ile Gln Asp
            195                   200                   205

Pro Ala Leu Thr Leu Met His Glu Leu Ile His Ser Leu His Gly Leu
210                   215                   220

Tyr Gly Ala Lys Gly Ile Thr Thr Thr Cys Ile Ile Thr Gln Gln Gln
225                   230                   235                   240

Asn Pro Leu Ile Thr Asn Arg Lys Gly Ile Asn Ile Glu Glu Phe Leu
                245                   250                   255

Thr Phe Gly Gly Asn Asp Leu Asn Ile Ile Thr Val Ala Gln Tyr Asn
            260                   265                   270

Asp Ile Tyr Thr Asn Leu Leu Asn Asp Tyr Arg Lys Ile Ala Ser Lys
            275                   280                   285

Leu Ser Lys Val Gln Val Ser Asn Pro Gln Leu Asn Pro Tyr Lys Asp
290                   295                   300

Ile Phe Gln Glu Lys Tyr Gly Leu Asp Lys Asp Ala Ser Gly Ile Tyr
305                   310                   315                   320

Ser Val Asn Ile Asn Lys Phe Asp Asp Ile Leu Lys Lys Leu Tyr Ser
                325                   330                   335

Phe Thr Glu Phe Asp Leu Ala Thr Lys Phe Gln Val Lys Cys Arg Glu
            340                   345                   350

Thr Tyr Ile Gly Gln Tyr Lys Tyr Phe Lys Leu Ser Asn Leu Leu Asn
            355                   360                   365

Asp Ser Ile Tyr Asn Ile Ser Glu Gly Tyr Asn Ile Asn Asn Leu Lys
370                   375                   380

Val Asn Phe Arg Gly Gln Asn Ala Asn Leu Asn Pro Arg Ile Ile Lys
385                   390                   395                   400

Pro Ile Thr Gly Arg Gly Leu Val Lys Lys Ile Ile Arg Phe Cys Val
                405                   410                   415

Asp Gly Gly Gly Gly Ser Ala Asp Asp Asp Lys His Ser Asp Ala
            420                   425                   430

Val Phe Thr Asp Asn Tyr Thr Arg Leu Arg Arg Gln Leu Ala Val Arg
            435                   440                   445

Arg Tyr Leu Asn Ser Ile Leu Asn Ala Leu Ala Gly Gly Gly Ser
450                   455                   460

Gly Gly Gly Gly Ser Gly Gly Gly Gly Ser Ala Leu Val Leu Gln Cys

```
            465                 470                 475                 480
        Ile Glu Ile Asn Asn Gly Glu Leu Phe Phe Val Ala Ser Glu Asn Ser
                        485                 490                 495
        Tyr Asn Asp Asp Asn Ile Asn Thr Pro Lys Glu Ile Asp Asp Thr Val
                        500                 505                 510
        Thr Ser Asn Asn Asn Tyr Glu Asn Asp Leu Asp Gln Val Ile Leu Asn
                        515                 520                 525
        Phe Asn Ser Glu Ser Ala Pro Gly Leu Ser Asp Glu Lys Leu Asn Leu
                        530                 535                 540
        Thr Ile Gln Asn Asp Ala Tyr Ile Pro Lys Tyr Asp Ser Asn Gly Thr
        545                 550                 555                 560
        Ser Asp Ile Glu Gln His Asp Val Asn Glu Leu Asn Val Phe Phe Tyr
                        565                 570                 575
        Leu Asp Ala Gln Lys Val Pro Glu Gly Glu Asn Asn Val Asn Leu Thr
                        580                 585                 590
        Ser Ser Ile Asp Thr Ala Leu Leu Glu Gln Pro Lys Ile Tyr Thr Phe
                        595                 600                 605
        Phe Ser Ser Glu Phe Ile Asn Asn Val Asn Lys Pro Val Gln Ala Ala
                        610                 615                 620
        Leu Phe Val Ser Trp Ile Gln Gln Val Leu Val Asp Phe Thr Thr Glu
        625                 630                 635                 640
        Ala Asn Gln Lys Ser Thr Val Asp Lys Ile Ala Asp Ile Ser Ile Val
                        645                 650                 655
        Val Pro Tyr Ile Gly Leu Ala Leu Asn Ile Gly Asn Glu Ala Gln Lys
                        660                 665                 670
        Gly Asn Phe Lys Asp Ala Leu Glu Leu Leu Gly Ala Gly Ile Leu Leu
                        675                 680                 685
        Glu Phe Glu Pro Glu Leu Leu Ile Pro Thr Ile Leu Val Phe Thr Ile
                        690                 695                 700
        Lys Ser Phe Leu Gly Ser Ser Asp Asn Lys Asn Lys Val Ile Lys Ala
        705                 710                 715                 720
        Ile Asn Asn Ala Leu Lys Glu Arg Asp Glu Lys Trp Lys Glu Val Tyr
                        725                 730                 735
        Ser Phe Ile Val Ser Asn Trp Met Thr Lys Ile Asn Thr Gln Phe Asn
                        740                 745                 750
        Lys Arg Lys Glu Gln Met Tyr Gln Ala Leu Gln Asn Gln Val Asn Ala
                        755                 760                 765
        Ile Lys Thr Ile Ile Glu Ser Lys Tyr Asn Ser Tyr Thr Leu Glu Glu
                        770                 775                 780
        Lys Asn Glu Leu Thr Asn Lys Tyr Asp Ile Lys Gln Ile Glu Asn Glu
        785                 790                 795                 800
        Leu Asn Gln Lys Val Ser Ile Ala Met Asn Asn Ile Asp Arg Phe Leu
                        805                 810                 815
        Thr Glu Ser Ser Ile Ser Tyr Leu Met Lys Ile Ile Asn Glu Val Lys
                        820                 825                 830
        Ile Asn Lys Leu Arg Glu Tyr Asp Glu Asn Val Lys Thr Tyr Leu Leu
                        835                 840                 845
        Asn Tyr Ile Ile Gln His Gly Ser Ile Leu Gly Glu Ser Gln Gln Glu
                        850                 855                 860
        Leu Asn Ser Met Val Thr Asp Thr Leu Asn Asn Ser Ile Pro Phe Lys
        865                 870                 875                 880
        Leu Ser Ser Tyr Thr Asp Asp Lys Ile Leu Ile Ser Tyr Phe Asn Lys
                        885                 890                 895
```

```
Phe Phe Lys Gly
            900

<210> SEQ ID NO 38
<211> LENGTH: 900
<212> TYPE: PRT
<213> ORGANISM: Artificial sequence
<220> FEATURE:
<223> OTHER INFORMATION: Protein sequence of BoNT/E with Human
      Vasoactive Intenstinal Peptide Targeting Moiety and Factor Xa
      Protease Cleavage Site

<400> SEQUENCE: 38

Met Gly Ser Met Pro Lys Ile Asn Ser Phe Asn Tyr Asn Asp Pro Val
1               5                   10                  15

Asn Asp Arg Thr Ile Leu Tyr Ile Lys Pro Gly Gly Cys Gln Glu Phe
            20                  25                  30

Tyr Lys Ser Phe Asn Ile Met Lys Asn Ile Trp Ile Ile Pro Glu Arg
        35                  40                  45

Asn Val Ile Gly Thr Thr Pro Gln Asp Phe His Pro Pro Thr Ser Leu
    50                  55                  60

Lys Asn Gly Asp Ser Ser Tyr Tyr Asp Pro Asn Tyr Leu Gln Ser Asp
65                  70                  75                  80

Glu Glu Lys Asp Arg Phe Leu Lys Ile Val Thr Lys Ile Phe Asn Arg
                85                  90                  95

Ile Asn Asn Asn Leu Ser Gly Gly Ile Leu Leu Glu Glu Leu Ser Lys
            100                 105                 110

Ala Asn Pro Tyr Leu Gly Asn Asp Asn Thr Pro Asp Asn Gln Phe His
        115                 120                 125

Ile Gly Asp Ala Ser Ala Val Glu Ile Lys Phe Ser Asn Gly Ser Gln
    130                 135                 140

His Ile Leu Leu Pro Asn Val Ile Ile Met Gly Ala Glu Pro Asp Leu
145                 150                 155                 160

Phe Glu Thr Asn Ser Ser Asn Ile Ser Leu Arg Asn Asn Tyr Met Pro
                165                 170                 175

Ser Asn His Gly Phe Gly Ser Ile Ala Ile Val Thr Phe Ser Pro Glu
            180                 185                 190

Tyr Ser Phe Arg Phe Asn Asp Asn Ser Ile Asn Glu Phe Ile Gln Asp
        195                 200                 205

Pro Ala Leu Thr Leu Met His Glu Leu Ile His Ser Leu His Gly Leu
    210                 215                 220

Tyr Gly Ala Lys Gly Ile Thr Thr Cys Ile Ile Thr Gln Gln Gln
225                 230                 235                 240

Asn Pro Leu Ile Thr Asn Arg Lys Gly Ile Asn Ile Glu Glu Phe Leu
                245                 250                 255

Thr Phe Gly Gly Asn Asp Leu Asn Ile Ile Thr Val Ala Gln Tyr Asn
            260                 265                 270

Asp Ile Tyr Thr Asn Leu Leu Asn Asp Tyr Arg Lys Ile Ala Ser Lys
        275                 280                 285

Leu Ser Lys Val Gln Val Ser Asn Pro Gln Leu Asn Pro Tyr Lys Asp
    290                 295                 300

Ile Phe Gln Glu Lys Tyr Gly Leu Asp Lys Asp Ala Ser Gly Ile Tyr
305                 310                 315                 320

Ser Val Asn Ile Asn Lys Phe Asp Asp Ile Leu Lys Lys Leu Tyr Ser
                325                 330                 335
```

```
Phe Thr Glu Phe Asp Leu Ala Thr Lys Phe Gln Val Lys Cys Arg Glu
            340                 345                 350

Thr Tyr Ile Gly Gln Tyr Lys Tyr Phe Lys Leu Ser Asn Leu Leu Asn
            355                 360                 365

Asp Ser Ile Tyr Asn Ile Ser Glu Gly Tyr Asn Ile Asn Asn Leu Lys
370                 375                 380

Val Asn Phe Arg Gly Gln Asn Ala Asn Leu Asn Pro Arg Ile Ile Lys
385                 390                 395                 400

Pro Ile Thr Gly Arg Gly Leu Val Lys Lys Ile Ile Arg Phe Cys Val
            405                 410                 415

Asp Gly Gly Gly Ser Ala Asp Asp Asp Lys His Ser Asp Ala
            420                 425                 430

Val Phe Thr Asp Asn Tyr Thr Arg Leu Arg Arg Gln Leu Ala Val Arg
            435                 440                 445

Arg Tyr Leu Asn Ser Ile Leu Asn Ala Leu Ala Gly Gly Gly Gly Ser
            450                 455                 460

Gly Gly Gly Gly Ser Gly Gly Gly Ser Ala Leu Val Leu Gln Cys
465                 470                 475                 480

Ile Glu Ile Asn Asn Gly Glu Leu Phe Phe Val Ala Ser Glu Asn Ser
            485                 490                 495

Tyr Asn Asp Asp Asn Ile Asn Thr Pro Lys Glu Ile Asp Asp Thr Val
            500                 505                 510

Thr Ser Asn Asn Asn Tyr Glu Asn Asp Leu Asp Gln Val Ile Leu Asn
            515                 520                 525

Phe Asn Ser Glu Ser Ala Pro Gly Leu Ser Asp Glu Lys Leu Asn Leu
530                 535                 540

Thr Ile Gln Asn Asp Ala Tyr Ile Pro Lys Tyr Asp Ser Asn Gly Thr
545                 550                 555                 560

Ser Asp Ile Glu Gln His Asp Val Asn Glu Leu Asn Val Phe Phe Tyr
            565                 570                 575

Leu Asp Ala Gln Lys Val Pro Glu Ile Glu Gly Arg Val Asn Leu Thr
            580                 585                 590

Ser Ser Ile Asp Thr Ala Leu Leu Glu Gln Pro Lys Ile Tyr Thr Phe
            595                 600                 605

Phe Ser Ser Glu Phe Ile Asn Asn Val Asn Lys Pro Val Gln Ala Ala
            610                 615                 620

Leu Phe Val Ser Trp Ile Gln Gln Val Leu Val Asp Phe Thr Thr Glu
625                 630                 635                 640

Ala Asn Gln Lys Ser Thr Val Asp Lys Ile Ala Asp Ile Ser Ile Val
            645                 650                 655

Val Pro Tyr Ile Gly Leu Ala Leu Asn Ile Gly Asn Glu Ala Gln Lys
            660                 665                 670

Gly Asn Phe Lys Asp Ala Leu Glu Leu Leu Gly Ala Gly Ile Leu Leu
            675                 680                 685

Glu Phe Glu Pro Glu Leu Leu Ile Pro Thr Ile Leu Val Phe Thr Ile
            690                 695                 700

Lys Ser Phe Leu Gly Ser Ser Asp Asn Lys Asn Lys Val Ile Lys Ala
705                 710                 715                 720

Ile Asn Asn Ala Leu Lys Glu Arg Asp Glu Lys Trp Lys Glu Val Tyr
            725                 730                 735

Ser Phe Ile Val Ser Asn Trp Met Thr Lys Ile Asn Thr Gln Phe Asn
            740                 745                 750

Lys Arg Lys Glu Gln Met Tyr Gln Ala Leu Gln Asn Gln Val Asn Ala
```

```
                    755                 760                 765
Ile Lys Thr Ile Ile Glu Ser Lys Tyr Asn Ser Tyr Thr Leu Glu Glu
                770                 775                 780

Lys Asn Glu Leu Thr Asn Lys Tyr Asp Ile Lys Gln Ile Glu Asn Glu
785                 790                 795                 800

Leu Asn Gln Lys Val Ser Ile Ala Met Asn Asn Ile Asp Arg Phe Leu
                805                 810                 815

Thr Glu Ser Ser Ile Ser Tyr Leu Met Lys Ile Ile Asn Glu Val Lys
                820                 825                 830

Ile Asn Lys Leu Arg Glu Tyr Asp Glu Asn Val Lys Thr Tyr Leu Leu
                835                 840                 845

Asn Tyr Ile Ile Gln His Gly Ser Ile Leu Gly Glu Ser Gln Gln Glu
                850                 855                 860

Leu Asn Ser Met Val Thr Asp Thr Leu Asn Asn Ser Ile Pro Phe Lys
865                 870                 875                 880

Leu Ser Ser Tyr Thr Asp Asp Lys Ile Leu Ile Ser Tyr Phe Asn Lys
                885                 890                 895

Phe Phe Lys Gly
                900

<210> SEQ ID NO 39
<211> LENGTH: 900
<212> TYPE: PRT
<213> ORGANISM: Artificial sequence
<220> FEATURE:
<223> OTHER INFORMATION: Protein sequence of BoNT/E with Human
      Vasoactive Intestinal Peptide Targeting Moiety and Factor Xa
      Protease Cleavage Site

<400> SEQUENCE: 39

Met Gly Ser Met Pro Lys Ile Asn Ser Phe Asn Tyr Asn Asp Pro Val
1               5                   10                  15

Asn Asp Arg Thr Ile Leu Tyr Ile Lys Pro Gly Gly Cys Gln Glu Phe
                20                  25                  30

Tyr Lys Ser Phe Asn Ile Met Lys Asn Ile Trp Ile Ile Pro Glu Arg
                35                  40                  45

Asn Val Ile Gly Thr Thr Pro Gln Asp Phe His Pro Pro Thr Ser Leu
50                  55                  60

Lys Asn Gly Asp Ser Ser Tyr Tyr Asp Pro Asn Tyr Leu Gln Ser Asp
65                  70                  75                  80

Glu Glu Lys Asp Arg Phe Leu Lys Ile Val Thr Lys Ile Phe Asn Arg
                85                  90                  95

Ile Asn Asn Asn Leu Ser Gly Gly Ile Leu Leu Glu Glu Leu Ser Lys
                100                 105                 110

Ala Asn Pro Tyr Leu Gly Asn Asp Asn Thr Pro Asp Asn Gln Phe His
                115                 120                 125

Ile Gly Asp Ala Ser Ala Val Glu Ile Lys Phe Ser Asn Gly Ser Gln
                130                 135                 140

His Ile Leu Leu Pro Asn Val Ile Ile Met Gly Ala Glu Pro Asp Leu
145                 150                 155                 160

Phe Glu Thr Asn Ser Ser Asn Ile Ser Leu Arg Asn Asn Tyr Met Pro
                165                 170                 175

Ser Asn His Gly Phe Gly Ser Ile Ala Ile Val Thr Phe Ser Pro Glu
                180                 185                 190

Tyr Ser Phe Arg Phe Asn Asp Asn Ser Ile Asn Glu Phe Ile Gln Asp
                195                 200                 205
```

-continued

```
Pro Ala Leu Thr Leu Met His Glu Leu Ile His Ser Leu His Gly Leu
    210                 215                 220
Tyr Gly Ala Asp Gly Ile Thr Thr Thr Cys Ile Ile Thr Gln Gln Gln
225                 230                 235                 240
Asn Pro Leu Ile Thr Asn Arg Lys Gly Ile Asn Ile Glu Glu Phe Leu
                245                 250                 255
Thr Phe Gly Gly Asn Asp Leu Asn Ile Ile Thr Ile Glu Gly Arg Asn
            260                 265                 270
Asp Ile Tyr Thr Asn Leu Leu Asn Asp Tyr Arg Lys Ile Ala Ser Lys
        275                 280                 285
Leu Ser Lys Val Gln Val Ser Asn Pro Gln Leu Asn Pro Tyr Lys Asp
    290                 295                 300
Ile Phe Gln Glu Lys Tyr Gly Leu Asp Lys Asp Ala Ser Gly Ile Tyr
305                 310                 315                 320
Ser Val Asn Ile Asn Lys Phe Asp Asp Ile Leu Lys Lys Leu Tyr Ser
                325                 330                 335
Phe Thr Glu Phe Asp Leu Ala Thr Lys Phe Gln Val Lys Cys Arg Glu
            340                 345                 350
Thr Tyr Ile Gly Gln Tyr Lys Tyr Phe Lys Leu Ser Asn Leu Leu Asn
        355                 360                 365
Asp Ser Ile Tyr Asn Ile Ser Glu Gly Tyr Asn Ile Asn Asn Leu Lys
    370                 375                 380
Val Asn Phe Arg Gly Gln Asn Ala Asn Leu Asn Pro Arg Ile Ile Lys
385                 390                 395                 400
Pro Ile Thr Gly Arg Gly Leu Val Lys Lys Ile Ile Arg Phe Cys Val
                405                 410                 415
Asp Gly Gly Gly Ser Ala Asp Asp Asp Lys His Ser Asp Ala
            420                 425                 430
Val Phe Thr Asp Asn Tyr Thr Arg Leu Arg Arg Gln Leu Ala Val Arg
        435                 440                 445
Arg Tyr Leu Asn Ser Ile Leu Asn Ala Leu Ala Gly Gly Gly Gly Ser
    450                 455                 460
Gly Gly Gly Gly Ser Gly Gly Gly Ser Ala Leu Val Leu Gln Cys
465                 470                 475                 480
Ile Glu Ile Asn Asn Gly Glu Leu Phe Phe Val Ala Ser Glu Asn Ser
                485                 490                 495
Tyr Asn Asp Asp Asn Ile Asn Thr Pro Lys Glu Ile Asp Asp Thr Val
            500                 505                 510
Thr Ser Asn Asn Asn Tyr Glu Asn Asp Leu Asp Gln Val Ile Leu Asn
        515                 520                 525
Phe Asn Ser Glu Ser Ala Pro Gly Leu Ser Asp Glu Lys Leu Asn Leu
    530                 535                 540
Thr Ile Gln Asn Asp Ala Tyr Ile Pro Lys Tyr Asp Ser Asn Gly Thr
545                 550                 555                 560
Ser Asp Ile Glu Gln His Asp Val Asn Glu Leu Asn Val Phe Phe Tyr
                565                 570                 575
Leu Asp Ala Gln Lys Val Pro Glu Gly Glu Asn Asn Val Asn Leu Thr
            580                 585                 590
Ser Ser Ile Asp Thr Ala Leu Leu Glu Gln Pro Lys Ile Tyr Thr Phe
        595                 600                 605
Phe Ser Ser Glu Phe Ile Asn Asn Val Asn Lys Pro Val Gln Ala Ala
    610                 615                 620
```

-continued

```
Leu Phe Val Ser Trp Ile Gln Gln Val Leu Val Asp Phe Thr Thr Glu
625                 630                 635                 640

Ala Asn Gln Lys Ser Thr Val Asp Lys Ile Ala Asp Ile Ser Ile Val
            645                 650                 655

Val Pro Tyr Ile Gly Leu Ala Leu Asn Ile Gly Asn Glu Ala Gln Lys
        660                 665                 670

Gly Asn Phe Lys Asp Ala Leu Glu Leu Leu Gly Ala Gly Ile Leu Leu
    675                 680                 685

Glu Phe Glu Pro Glu Leu Leu Ile Pro Thr Ile Leu Val Phe Thr Ile
690                 695                 700

Lys Ser Phe Leu Gly Ser Ser Asp Asn Lys Asn Lys Val Ile Lys Ala
705                 710                 715                 720

Ile Asn Asn Ala Leu Lys Glu Arg Asp Glu Lys Trp Lys Glu Val Tyr
                725                 730                 735

Ser Phe Ile Val Ser Asn Trp Met Thr Lys Ile Asn Thr Gln Phe Asn
            740                 745                 750

Lys Arg Lys Glu Gln Met Tyr Gln Ala Leu Gln Asn Gln Val Asn Ala
        755                 760                 765

Ile Lys Thr Ile Ile Glu Ser Lys Tyr Asn Ser Tyr Thr Leu Glu Glu
    770                 775                 780

Lys Asn Glu Leu Thr Asn Lys Tyr Asp Ile Lys Gln Ile Glu Asn Glu
785                 790                 795                 800

Leu Asn Gln Lys Val Ser Ile Ala Met Asn Asn Ile Asp Arg Phe Leu
                805                 810                 815

Thr Glu Ser Ser Ile Ser Tyr Leu Met Lys Ile Ile Asn Glu Val Lys
            820                 825                 830

Ile Asn Lys Leu Arg Glu Tyr Asp Glu Asn Val Lys Thr Tyr Leu Leu
        835                 840                 845

Asn Tyr Ile Ile Gln His Gly Ser Ile Leu Gly Glu Ser Gln Gln Glu
    850                 855                 860

Leu Asn Ser Met Val Thr Asp Thr Leu Asn Asn Ser Ile Pro Phe Lys
865                 870                 875                 880

Leu Ser Ser Tyr Thr Asp Asp Lys Ile Leu Ile Ser Tyr Phe Asn Lys
                885                 890                 895

Phe Phe Lys Gly
            900

<210> SEQ ID NO 40
<211> LENGTH: 6
<212> TYPE: PRT
<213> ORGANISM: Artificial sequence
<220> FEATURE:
<223> OTHER INFORMATION: Thrombin recognition sequence

<400> SEQUENCE: 40

Leu Val Pro Arg Gly Ser
1               5

<210> SEQ ID NO 41
<211> LENGTH: 4
<212> TYPE: PRT
<213> ORGANISM: Artificial sequence
<220> FEATURE:
<223> OTHER INFORMATION: Factor Xa recognition sequence

<400> SEQUENCE: 41

Ile Glu Gly Arg
1
```

```
<210> SEQ ID NO 42
<211> LENGTH: 10
<212> TYPE: PRT
<213> ORGANISM: Artificial sequence
<220> FEATURE:
<223> OTHER INFORMATION: ADAM17 recognition sequence

<400> SEQUENCE: 42

Pro Leu Ala Gln Ala Val Arg Ser Ser Ser
1               5                   10

<210> SEQ ID NO 43
<211> LENGTH: 10
<212> TYPE: PRT
<213> ORGANISM: Artificial sequence
<220> FEATURE:
<223> OTHER INFORMATION: Human airway trypsin-like protease (HAT)
      recognition sequence

<400> SEQUENCE: 43

Ser Lys Gly Arg Ser Leu Ile Gly Arg Val
1               5                   10

<210> SEQ ID NO 44
<211> LENGTH: 6
<212> TYPE: PRT
<213> ORGANISM: Artificial sequence
<220> FEATURE:
<223> OTHER INFORMATION: Elastase (leukocyte) recognition sequence

<400> SEQUENCE: 44

Met Glu Ala Val Thr Tyr
1               5

<210> SEQ ID NO 45
<211> LENGTH: 4
<212> TYPE: PRT
<213> ORGANISM: Artificial sequence
<220> FEATURE:
<223> OTHER INFORMATION: Granzyme recognition sequence

<400> SEQUENCE: 45

Ile Glu Pro Asp
1

<210> SEQ ID NO 46
<211> LENGTH: 4
<212> TYPE: PRT
<213> ORGANISM: Artificial sequence
<220> FEATURE:
<223> OTHER INFORMATION: Caspase 2 recognition sequence

<400> SEQUENCE: 46

Asp Val Ala Asp
1

<210> SEQ ID NO 47
<211> LENGTH: 4
<212> TYPE: PRT
<213> ORGANISM: Artificial sequence
<220> FEATURE:
<223> OTHER INFORMATION: Caspase 3 recognition sequence

<400> SEQUENCE: 47

Asp Met Gln Asp
1
```

<210> SEQ ID NO 48
<211> LENGTH: 4
<212> TYPE: PRT
<213> ORGANISM: Artificial sequence
<220> FEATURE:
<223> OTHER INFORMATION: Caspase 4 recognition sequence

<400> SEQUENCE: 48

Leu Glu Val Asp
1

<210> SEQ ID NO 49
<211> LENGTH: 4
<212> TYPE: PRT
<213> ORGANISM: Artificial sequence
<220> FEATURE:
<223> OTHER INFORMATION: Caspase 7 recognition sequence

<400> SEQUENCE: 49

Asp Glu Val Asp
1

<210> SEQ ID NO 50
<211> LENGTH: 4
<212> TYPE: PRT
<213> ORGANISM: Artificial sequence
<220> FEATURE:
<223> OTHER INFORMATION: Caspase 9 recognition sequence

<400> SEQUENCE: 50

Leu Glu His Asp
1

<210> SEQ ID NO 51
<211> LENGTH: 4
<212> TYPE: PRT
<213> ORGANISM: Artificial sequence
<220> FEATURE:
<223> OTHER INFORMATION: Caspase 10 recognition sequence

<400> SEQUENCE: 51

Ile Glu His Asp
1

<210> SEQ ID NO 52
<211> LENGTH: 7
<212> TYPE: PRT
<213> ORGANISM: Artificial sequence
<220> FEATURE:
<223> OTHER INFORMATION: Region of BoNT/A

<400> SEQUENCE: 52

Tyr Ser Thr Asp Leu Gly Arg
1               5

<210> SEQ ID NO 53
<211> LENGTH: 7
<212> TYPE: PRT
<213> ORGANISM: Artificial sequence
<220> FEATURE:
<223> OTHER INFORMATION: Region of BoNT/B

<400> SEQUENCE: 53

Lys Ser Lys Pro Leu Gly Glu
1 5

<210> SEQ ID NO 54
<211> LENGTH: 7
<212> TYPE: PRT
<213> ORGANISM: Artificial sequence
<220> FEATURE:
<223> OTHER INFORMATION: Region of BoNT/C1

<400> SEQUENCE: 54

Asn Ser Arg Glu Ile Gly Glu
1               5

<210> SEQ ID NO 55
<211> LENGTH: 7
<212> TYPE: PRT
<213> ORGANISM: Artificial sequence
<220> FEATURE:
<223> OTHER INFORMATION: Region of BoNT/D

<400> SEQUENCE: 55

Asn Glu Arg Asp Ile Gly Lys
1               5

<210> SEQ ID NO 56
<211> LENGTH: 7
<212> TYPE: PRT
<213> ORGANISM: Artificial sequence
<220> FEATURE:
<223> OTHER INFORMATION: Region of BoNT/E

<400> SEQUENCE: 56

Asn Asn Asn Leu Ser Gly Gly
1               5

<210> SEQ ID NO 57
<211> LENGTH: 7
<212> TYPE: PRT
<213> ORGANISM: Artificial sequence
<220> FEATURE:
<223> OTHER INFORMATION: Region of BoNT/F

<400> SEQUENCE: 57

Asn Ser Asn Pro Ala Gly Gln
1               5

<210> SEQ ID NO 58
<211> LENGTH: 7
<212> TYPE: PRT
<213> ORGANISM: Artificial sequence
<220> FEATURE:
<223> OTHER INFORMATION: Region of BoNT/G

<400> SEQUENCE: 58

Asn Ser Lys Pro Ser Gly Gln
1               5

<210> SEQ ID NO 59
<211> LENGTH: 13
<212> TYPE: PRT
<213> ORGANISM: Artificial sequence
<220> FEATURE:
<223> OTHER INFORMATION: Region of BoNT/A

<400> SEQUENCE: 59

Val Asp Thr Asn Pro Leu Leu Gly Ala Gly Lys Phe Ala
1               5                   10

-continued

```
<210> SEQ ID NO 60
<211> LENGTH: 13
<212> TYPE: PRT
<213> ORGANISM: Artificial sequence
<220> FEATURE:
<223> OTHER INFORMATION: Region of BoNT/B

<400> SEQUENCE: 60

Asn Lys Gly Ala Ser Ile Phe Asn Arg Arg Gly Tyr Phe
1               5                   10

<210> SEQ ID NO 61
<211> LENGTH: 13
<212> TYPE: PRT
<213> ORGANISM: Artificial sequence
<220> FEATURE:
<223> OTHER INFORMATION: Region of BoNT/C1

<400> SEQUENCE: 61

Asp Val Gly Glu Gly Arg Phe Ser Lys Ser Glu Phe Cys
1               5                   10

<210> SEQ ID NO 62
<211> LENGTH: 13
<212> TYPE: PRT
<213> ORGANISM: Artificial sequence
<220> FEATURE:
<223> OTHER INFORMATION: Region of BoNT/D

<400> SEQUENCE: 62

Asn Gln Ser Ser Ala Val Leu Gly Lys Ser Ile Phe Cys
1               5                   10

<210> SEQ ID NO 63
<211> LENGTH: 14
<212> TYPE: PRT
<213> ORGANISM: Artificial sequence
<220> FEATURE:
<223> OTHER INFORMATION: Region of BoNT/G

<400> SEQUENCE: 63

Glu Asn Lys Asp Thr Ser Ile Phe Ser Arg Arg Ala Tyr Phe
1               5                   10

<210> SEQ ID NO 64
<211> LENGTH: 11
<212> TYPE: PRT
<213> ORGANISM: Artificial sequence
<220> FEATURE:
<223> OTHER INFORMATION: Region of BoNT/A

<400> SEQUENCE: 64

Gln Glu Phe Glu His Gly Lys Ser Arg Ile Ala
1               5                   10

<210> SEQ ID NO 65
<211> LENGTH: 11
<212> TYPE: PRT
<213> ORGANISM: Artificial sequence
<220> FEATURE:
<223> OTHER INFORMATION: Region of BoNT/B

<400> SEQUENCE: 65

Gln Thr Phe Pro Leu Asp Ile Arg Asp Ile Ser
1               5                   10

<210> SEQ ID NO 66
```

<211> LENGTH: 11
<212> TYPE: PRT
<213> ORGANISM: Artificial sequence
<220> FEATURE:
<223> OTHER INFORMATION: Region of BoNT/C1

<400> SEQUENCE: 66

Gln Lys Leu Ser Asp Asn Val Glu Asp Phe Thr
1               5                   10

<210> SEQ ID NO 67
<211> LENGTH: 11
<212> TYPE: PRT
<213> ORGANISM: Artificial sequence
<220> FEATURE:
<223> OTHER INFORMATION: Region of BoNT/D

<400> SEQUENCE: 67

Gln Lys Leu Ser Asn Asn Val Glu Asn Ile Thr
1               5                   10

<210> SEQ ID NO 68
<211> LENGTH: 11
<212> TYPE: PRT
<213> ORGANISM: Artificial sequence
<220> FEATURE:
<223> OTHER INFORMATION: Region of BoNT/E

<400> SEQUENCE: 68

Gln Lys Val Pro Glu Gly Glu Asn Asn Val Asn
1               5                   10

<210> SEQ ID NO 69
<211> LENGTH: 11
<212> TYPE: PRT
<213> ORGANISM: Artificial sequence
<220> FEATURE:
<223> OTHER INFORMATION: Region of BoNT/F

<400> SEQUENCE: 69

Gln Lys Ala Pro Glu Gly Glu Ser Ala Ile Ser
1               5                   10

<210> SEQ ID NO 70
<211> LENGTH: 11
<212> TYPE: PRT
<213> ORGANISM: Artificial sequence
<220> FEATURE:
<223> OTHER INFORMATION: Region of BoNT/G

<400> SEQUENCE: 70

Gln Thr Phe Pro Ser Asn Ile Glu Asn Leu Gln
1               5                   10

<210> SEQ ID NO 71
<211> LENGTH: 16
<212> TYPE: PRT
<213> ORGANISM: Artificial sequence
<220> FEATURE:
<223> OTHER INFORMATION: Region of BoNT/A

<400> SEQUENCE: 71

Tyr Asn Gln Tyr Thr Glu Glu Glu Lys Asn Asn Ile Asn Asn Ile Asp
1               5                   10                  15

<210> SEQ ID NO 72
<211> LENGTH: 19

-continued

```
<212> TYPE: PRT
<213> ORGANISM: Artificial sequence
<220> FEATURE:
<223> OTHER INFORMATION: Region of BoNT/B
<220> FEATURE:
<221> NAME/KEY: VARIANT
<222> LOCATION: (14)..(15)
<223> OTHER INFORMATION: Xaa = Any Amino Acid

<400> SEQUENCE: 72

Tyr Asn Ile Tyr Ser Glu Lys Glu Lys Ser Asn Ile Asn Xaa Xaa Ile
1               5                   10                  15

Asp Phe Asn

<210> SEQ ID NO 73
<211> LENGTH: 19
<212> TYPE: PRT
<213> ORGANISM: Artificial sequence
<220> FEATURE:
<223> OTHER INFORMATION: Region of BoNT/C1 and BoNT/D
<220> FEATURE:
<221> NAME/KEY: VARIANT
<222> LOCATION: (15)..(16)
<223> OTHER INFORMATION: Xaa = Any Amino Acid

<400> SEQUENCE: 73

Tyr Lys Lys Tyr Ser Gly Ser Asp Lys Glu Asn Ile Lys Ser Xaa Xaa
1               5                   10                  15

Gln Val Glu

<210> SEQ ID NO 74
<211> LENGTH: 19
<212> TYPE: PRT
<213> ORGANISM: Artificial sequence
<220> FEATURE:
<223> OTHER INFORMATION: Region of BoNT/E

<400> SEQUENCE: 74

Tyr Asn Ser Tyr Thr Leu Glu Glu Lys Asn Glu Leu Thr Asn Lys Tyr
1               5                   10                  15

Asp Ile Lys

<210> SEQ ID NO 75
<211> LENGTH: 19
<212> TYPE: PRT
<213> ORGANISM: Artificial sequence
<220> FEATURE:
<223> OTHER INFORMATION: Region of BoNT/F

<400> SEQUENCE: 75

Tyr Asn Asn Tyr Thr Leu Asp Glu Lys Asn Arg Leu Arg Ala Glu Tyr
1               5                   10                  15

Asn Ile Tyr

<210> SEQ ID NO 76
<211> LENGTH: 19
<212> TYPE: PRT
<213> ORGANISM: Artificial sequence
<220> FEATURE:
<223> OTHER INFORMATION: Region of BoNT/G
<220> FEATURE:
<221> NAME/KEY: VARIANT
<222> LOCATION: (14)..(15)
<223> OTHER INFORMATION: Xaa = Any Amino Acid

<400> SEQUENCE: 76
```

```
Tyr Asn Arg Tyr Ser Glu Glu Asp Lys Met Asn Ile Asn Xaa Xaa Ile
1               5                   10                  15

Asp Phe Asn

<210> SEQ ID NO 77
<211> LENGTH: 5
<212> TYPE: PRT
<213> ORGANISM: Artificial sequence
<220> FEATURE:
<223> OTHER INFORMATION: Enterokinase recognition site

<400> SEQUENCE: 77

Asp Asp Asp Asp Lys
1               5

<210> SEQ ID NO 78
<211> LENGTH: 4
<212> TYPE: PRT
<213> ORGANISM: Artificial sequence
<220> FEATURE:
<223> OTHER INFORMATION: Factor Xa recognition sequence

<400> SEQUENCE: 78

Ile Asp Gly Arg
1

<210> SEQ ID NO 79
<211> LENGTH: 7
<212> TYPE: PRT
<213> ORGANISM: Artificial sequence
<220> FEATURE:
<223> OTHER INFORMATION: Tobacco Etch Virus (TEV) recognition sequence

<400> SEQUENCE: 79

Glu Asn Leu Tyr Phe Gln Gly
1               5

<210> SEQ ID NO 80
<211> LENGTH: 8
<212> TYPE: PRT
<213> ORGANISM: Artificial sequence
<220> FEATURE:
<223> OTHER INFORMATION: PreScission recognition sequence

<400> SEQUENCE: 80

Leu Glu Val Leu Phe Gln Gly Pro
1               5

<210> SEQ ID NO 81
<211> LENGTH: 10
<212> TYPE: PRT
<213> ORGANISM: Artificial sequence
<220> FEATURE:
<223> OTHER INFORMATION: Fragment of TGF-alpha
<220> FEATURE:
<221> NAME/KEY: MOD_RES
<222> LOCATION: (1)..(1)
<223> OTHER INFORMATION: N-terminus acetylated
<220> FEATURE:
<221> NAME/KEY: MOD_RES
<222> LOCATION: (10)..(10)
<223> OTHER INFORMATION: Cys-methyl ester

<400> SEQUENCE: 81

Cys His Ser Gly Tyr Val Gly Ala Arg Cys
1               5                   10
```

```
<210> SEQ ID NO 82
<211> LENGTH: 12
<212> TYPE: PRT
<213> ORGANISM: Artificial sequence
<220> FEATURE:
<223> OTHER INFORMATION: Lab Synthesized GE11 Peptide

<400> SEQUENCE: 82

Tyr His Trp Tyr Gly Tyr Thr Pro Gln Asn Val Ile
1               5                   10

<210> SEQ ID NO 83
<211> LENGTH: 23
<212> TYPE: PRT
<213> ORGANISM: Artificial sequence
<220> FEATURE:
<223> OTHER INFORMATION: Influenza virus haemagglutinin

<400> SEQUENCE: 83

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 84
<211> LENGTH: 6
<212> TYPE: PRT
<213> ORGANISM: Artificial sequence
<220> FEATURE:
<223> OTHER INFORMATION: Region of BoNT/C

<400> SEQUENCE: 84

Ile Ser Pro Arg Phe Met
1               5

<210> SEQ ID NO 85
<211> LENGTH: 6
<212> TYPE: PRT
<213> ORGANISM: Artificial sequence
<220> FEATURE:
<223> OTHER INFORMATION: Thrombin Cleavage Site

<400> SEQUENCE: 85

Ile Val Pro Arg Phe Ser
1               5

<210> SEQ ID NO 86
<211> LENGTH: 10
<212> TYPE: PRT
<213> ORGANISM: Artificial sequence
<220> FEATURE:
<223> OTHER INFORMATION: Region of BoNT/A

<400> SEQUENCE: 86

Pro Leu Leu Gly Ala Gly Lys Phe Ala Thr
1               5                   10

<210> SEQ ID NO 87
<211> LENGTH: 4
<212> TYPE: PRT
<213> ORGANISM: Artificial sequence
<220> FEATURE:
<223> OTHER INFORMATION: Furin Cleavage Site

<400> SEQUENCE: 87

Arg Ser Arg Arg
1
```

<210> SEQ ID NO 88
<211> LENGTH: 6
<212> TYPE: PRT
<213> ORGANISM: Artificial sequence
<220> FEATURE:
<223> OTHER INFORMATION: Thrombin Cleavage Site

<400> SEQUENCE: 88

Gly Glu Gly Arg Phe Ser
1               5

<210> SEQ ID NO 89
<211> LENGTH: 6
<212> TYPE: PRT
<213> ORGANISM: Artificial sequence
<220> FEATURE:
<223> OTHER INFORMATION: Thrombin Cleavage Site

<400> SEQUENCE: 89

Gly Thr Pro Arg Phe Ser
1               5

<210> SEQ ID NO 90
<211> LENGTH: 4
<212> TYPE: PRT
<213> ORGANISM: Artificial sequence
<220> FEATURE:
<223> OTHER INFORMATION: Factor Xa Cleavage Site

<400> SEQUENCE: 90

Ser Gly Ser Asp
1

<210> SEQ ID NO 91
<211> LENGTH: 4
<212> TYPE: PRT
<213> ORGANISM: Artificial sequence
<220> FEATURE:
<223> OTHER INFORMATION: Thrombin Cleavage Site

<400> SEQUENCE: 91

Gly Val Pro Arg
1

<210> SEQ ID NO 92
<211> LENGTH: 4
<212> TYPE: PRT
<213> ORGANISM: Artificial sequence
<220> FEATURE:
<223> OTHER INFORMATION: Region of BoNT/A LC Domain

<400> SEQUENCE: 92

Ile Asp Ser Leu
1

<210> SEQ ID NO 93
<211> LENGTH: 6
<212> TYPE: PRT
<213> ORGANISM: Artificial sequence
<220> FEATURE:
<223> OTHER INFORMATION: Region of BoNT/E LC Domain

<400> SEQUENCE: 93

Phe Ser Pro Glu Tyr Ser
1               5

```
<210> SEQ ID NO 94
<211> LENGTH: 4
<212> TYPE: PRT
<213> ORGANISM: Artificial sequence
<220> FEATURE:
<223> OTHER INFORMATION: Region of BoNT/E HN Domain

<400> SEQUENCE: 94

Thr Leu Glu Glu
1

<210> SEQ ID NO 95
<211> LENGTH: 4
<212> TYPE: PRT
<213> ORGANISM: Artificial sequence
<220> FEATURE:
<223> OTHER INFORMATION: Region of BoNT/E HN Domain

<400> SEQUENCE: 95

Gly Glu Asn Asn
1

<210> SEQ ID NO 96
<211> LENGTH: 4
<212> TYPE: PRT
<213> ORGANISM: Artificial sequence
<220> FEATURE:
<223> OTHER INFORMATION: Region of BoNT/E LC Domain

<400> SEQUENCE: 96

Val Ala Gln Tyr
1

<210> SEQ ID NO 97
<211> LENGTH: 4
<212> TYPE: PRT
<213> ORGANISM: Artificial sequence
<220> FEATURE:
<223> OTHER INFORMATION: Region of BoNT/C LC Domain

<400> SEQUENCE: 97

Gly Glu Gly Arg
1

<210> SEQ ID NO 98
<211> LENGTH: 4
<212> TYPE: PRT
<213> ORGANISM: Artificial sequence
<220> FEATURE:
<223> OTHER INFORMATION: Region of BoNT/C HN Domain

<400> SEQUENCE: 98

Ile Asp Leu Glu
1

<210> SEQ ID NO 99
<211> LENGTH: 4
<212> TYPE: PRT
<213> ORGANISM: Artificial sequence
<220> FEATURE:
<223> OTHER INFORMATION: Region of BoNT/A HN Domain

<400> SEQUENCE: 99

Gly Lys Ser Arg
1
```

```
<210> SEQ ID NO 100
<211> LENGTH: 4
<212> TYPE: PRT
<213> ORGANISM: Artificial sequence
<220> FEATURE:
<223> OTHER INFORMATION: Recognition site for furin
<220> FEATURE:
<221> NAME/KEY: VARIANT
<222> LOCATION: (2)
<223> OTHER INFORMATION: Xaa = Any Amino Acid
<220> FEATURE:
<221> NAME/KEY: VARIANT
<222> LOCATION: (4)
<223> OTHER INFORMATION: Xaa = Lys or Arg

<400> SEQUENCE: 100

Arg Xaa Arg Xaa
 1

<210> SEQ ID NO 101
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (2)..(4)
<223> OTHER INFORMATION: Xaa = Any Amino Acid

<400> SEQUENCE: 101

Asp Xaa Xaa Xaa
 1

<210> SEQ ID NO 102
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (1),(3)..(4)
<223> OTHER INFORMATION: Xaa = Any Amino Acid

<400> SEQUENCE: 102

Xaa Met Xaa Xaa
 1

<210> SEQ ID NO 103
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (1)..(2),(4)
<223> OTHER INFORMATION: Xaa = Any Amino Acid

<400> SEQUENCE: 103

Xaa Xaa Gln Xaa
 1

<210> SEQ ID NO 104
<211> LENGTH: 4
<212> TYPE: PRT
<213> ORGANISM: Artificial sequence
```

```
<220> FEATURE:
<223> OTHER INFORMATION: Preferred insertion position for Caspase 3
      cleavage site
<220> FEATURE:
<221> NAME/KEY: VARIANT
<222> LOCATION: (1)..(3)
<223> OTHER INFORMATION: Xaa = Any Amino Acid

<400> SEQUENCE: 104

Xaa Xaa Xaa Asp
1

<210> SEQ ID NO 105
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (3),(4)
<223> OTHER INFORMATION: Xaa = Any Amino Acid

<400> SEQUENCE: 105

Asp Met Xaa Xaa
1

<210> SEQ ID NO 106
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (2),(4)
<223> OTHER INFORMATION: Xaa = Any Amino Acid

<400> SEQUENCE: 106

Asp Xaa Gln Xaa
1

<210> SEQ ID NO 107
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (2),(3)
<223> OTHER INFORMATION: Xaa = Any Amino Acid

<400> SEQUENCE: 107

Asp Xaa Xaa Asp
1

<210> SEQ ID NO 108
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (1),(4)
<223> OTHER INFORMATION: Xaa = Any Amino Acid
```

```
<400> SEQUENCE: 108

Xaa Met Gln Xaa
1

<210> SEQ ID NO 109
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (1),(3)
<223> OTHER INFORMATION: Xaa = Any Amino Acid

<400> SEQUENCE: 109

Xaa Met Xaa Asp
1

<210> SEQ ID NO 110
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (1),(2)
<223> OTHER INFORMATION: Xaa = Any Amino Acid

<400> SEQUENCE: 110

Xaa Xaa Gln Asp
1

<210> SEQ ID NO 111
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (4)
<223> OTHER INFORMATION: Xaa = Any Amino Acid

<400> SEQUENCE: 111

Asp Met Gln Xaa
1

<210> SEQ ID NO 112
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (1)
<223> OTHER INFORMATION: Xaa = Any Amino Acid

<400> SEQUENCE: 112

Xaa Met Gln Asp
1
```

-continued

<210> SEQ ID NO 113
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (2)
<223> OTHER INFORMATION: Xaa = Any Amino Acid

<400> SEQUENCE: 113

Asp Xaa Gln Asp
1

<210> SEQ ID NO 114
<211> LENGTH: 4
<212> TYPE: PRT
<213> ORGANISM: Artificial sequence
<220> FEATURE:
<223> OTHER INFORMATION: Preferred insertion position for Caspase 3
      cleavage site
<220> FEATURE:
<221> NAME/KEY: VARIANT
<222> LOCATION: (3)
<223> OTHER INFORMATION: Xaa = Any Amino Acid

<400> SEQUENCE: 114

Asp Met Xaa Asp
1

<210> SEQ ID NO 115
<211> LENGTH: 14
<212> TYPE: PRT
<213> ORGANISM: Artificial sequence
<220> FEATURE:
<223> OTHER INFORMATION: Region of BoNT/E
<220> FEATURE:
<221> NAME/KEY: VARIANT
<222> LOCATION: (4)..(7),(10),(11)
<223> OTHER INFORMATION: Xaa = Any Amino Acid

<400> SEQUENCE: 115

Asp Asn Cys Xaa Xaa Xaa Xaa Met Asn Xaa Xaa Glu Phe Ile
1               5                   10

<210> SEQ ID NO 116
<211> LENGTH: 14
<212> TYPE: PRT
<213> ORGANISM: Artificial sequence
<220> FEATURE:
<223> OTHER INFORMATION: Region of BoNT/F
<220> FEATURE:
<221> NAME/KEY: VARIANT
<222> LOCATION: (3)..(7),(10),(11)
<223> OTHER INFORMATION: Xaa = Any Amino Acid

<400> SEQUENCE: 116

Asp Asn Xaa Xaa Xaa Xaa Xaa Thr Asp Xaa Xaa Leu Phe Ile
1               5                   10

<210> SEQ ID NO 117
<211> LENGTH: 871
<212> TYPE: PRT
<213> ORGANISM: Clostridium botulinum serotype A

<400> SEQUENCE: 117

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
    20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Pro Glu
        50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

```
Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
```

```
            850                 855                 860
Thr Phe Thr Glu Tyr Ile Lys
865                 870

<210> SEQ ID NO 118
<211> LENGTH: 858
<212> TYPE: PRT
<213> ORGANISM: Clostridium botulinum serotype B

<400> SEQUENCE: 118

Met Pro Val Thr Ile Asn Asn Phe Asn Tyr Asn Asp Pro Ile Asp Asn
 1               5                  10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350
```

-continued

```
Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Ile Ser Lys Glu His Leu Ala Val Tyr
            420                 425                 430

Lys Ile Gln Met Cys Lys Ser Val Lys Ala Pro Gly Ile Cys Ile Asp
    435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
    515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
    595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
    675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Lys Ser Asn Ile Asn Ile Asp
            740                 745                 750

Phe Asn Asp Ile Asn Ser Lys Leu Asn Glu Gly Ile Asn Gln Ala Ile
    755                 760                 765

Asp Asn Ile Asn Asn Phe Ile Asn Gly Cys Ser Val Ser Tyr Leu Met
```

```
                770                 775                 780
Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
                835                 840                 845

Leu Ile Glu Met Phe Asn Lys Tyr Asn Ser
    850                 855

<210> SEQ ID NO 119
<211> LENGTH: 866
<212> TYPE: PRT
<213> ORGANISM: Clostridium botulinum serotype C1

<400> SEQUENCE: 119

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
                20                  25                  30

Pro Glu Lys Ala Phe Arg Ile Thr Gly Asn Ile Trp Val Ile Pro Asp
            35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285
```

```
Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
690                 695                 700

Tyr Glu Trp Met Met Gly Thr Trp Leu Ser Arg Ile Ile Thr Gln Phe
```

```
                705                 710                 715                 720
Asn Asn Ile Ser Tyr Gln Met Tyr Asp Ser Leu Asn Tyr Gln Ala Gly
                    725                 730                 735

Ala Ile Lys Ala Lys Ile Asp Leu Glu Tyr Lys Lys Tyr Ser Gly Ser
                    740                 745                 750

Asp Lys Glu Asn Ile Lys Ser Gln Val Glu Asn Leu Lys Asn Ser Leu
                    755                 760                 765

Asp Val Lys Ile Ser Glu Ala Met Asn Asn Ile Asn Lys Phe Ile Arg
                    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                    805                 810                 815

Leu Ile Asp Ser His Asn Ile Ile Leu Val Gly Glu Val Asp Lys Leu
                    820                 825                 830

Lys Ala Lys Val Asn Asn Ser Phe Gln Asn Thr Ile Pro Phe Asn Ile
                    835                 840                 845

Phe Ser Tyr Thr Asn Asn Ser Leu Leu Lys Asp Ile Ile Asn Glu Tyr
    850                 855                 860

Phe Asn
865

<210> SEQ ID NO 120
<211> LENGTH: 862
<212> TYPE: PRT
<213> ORGANISM: Clostridium botulinum serotype D

<400> SEQUENCE: 120

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
                20                  25                  30

Pro Val Lys Ala Phe Met Ile Thr Gln Asn Ile Trp Val Ile Pro Glu
            35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
                100                 105                 110

Gly Ser Pro Phe Met Gly Asp Ser Ser Thr Pro Glu Asp Thr Phe Asp
            115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
                180                 185                 190

Lys Val Ala Pro Glu Phe Leu Leu Thr Phe Ser Asp Val Thr Ser Asn
            195                 200                 205
```

```
Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
        435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
        515                 520                 525

Phe Tyr Asp Asp Ile Thr Lys Tyr Val Asp Tyr Leu Asn Ser Tyr Tyr
    530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Val Ile
    610                 615                 620

Ile Pro Tyr Ile Gly Pro Ala Leu Asn Ile Gly Asn Ser Ala Leu Arg
```

```
                625                 630                 635                 640
        Gly Asn Phe Asn Gln Ala Phe Thr Ala Gly Val Ala Phe Leu Leu
                            645                 650                 655

Glu Gly Phe Pro Glu Phe Thr Ile Pro Ala Leu Gly Val Phe Thr Phe
                            660                 665                 670

Tyr Ser Ser Ile Gln Glu Arg Glu Lys Ile Ile Lys Thr Ile Glu Asn
                            675                 680                 685

Cys Leu Glu Gln Arg Val Lys Arg Trp Lys Asp Ser Tyr Gln Trp Met
                690                 695                 700

Val Ser Asn Trp Leu Ser Arg Ile Thr Thr Gln Phe Asn His Ile Asn
        705                 710                 715                 720

Tyr Gln Met Tyr Asp Ser Leu Ser Tyr Gln Ala Asp Ala Ile Lys Ala
                            725                 730                 735

Lys Ile Asp Leu Glu Tyr Lys Lys Tyr Ser Gly Ser Asp Lys Glu Asn
                            740                 745                 750

Ile Lys Ser Gln Val Glu Asn Leu Lys Asn Ser Leu Asp Val Lys Ile
                            755                 760                 765

Ser Glu Ala Met Asn Asn Ile Asn Lys Phe Ile Arg Glu Cys Ser Val
        770                 775                 780

Thr Tyr Leu Phe Lys Asn Met Leu Pro Lys Val Ile Asp Glu Leu Asn
        785                 790                 795                 800

Lys Phe Asp Leu Arg Thr Lys Thr Glu Leu Ile Asn Leu Ile Asp Ser
                            805                 810                 815

His Asn Ile Ile Leu Val Gly Glu Val Asp Arg Leu Lys Ala Lys Val
                            820                 825                 830

Asn Glu Ser Phe Glu Asn Thr Met Pro Phe Asn Ile Phe Ser Tyr Thr
                            835                 840                 845

Asn Asn Ser Leu Leu Lys Asp Ile Ile Asn Glu Tyr Phe Asn
                            850                 855                 860

<210> SEQ ID NO 121
<211> LENGTH: 845
<212> TYPE: PRT
<213> ORGANISM: Clostridium botulinum serotype E

<400> SEQUENCE: 121

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140
```

-continued

```
Leu Pro Asn Val Ile Ile Met Gly Ala Glu Pro Asp Leu Phe Glu Thr
145                 150                 155                 160

Asn Ser Ser Asn Ile Ser Leu Arg Asn Tyr Met Pro Ser Asn His
            165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
            195                 200                 205

Thr Leu Met His Glu Leu Ile His Ser Leu His Gly Leu Tyr Gly Ala
            210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Asn Asn Leu Lys Val Asn Phe
            370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
                420                 425                 430

Glu Leu Phe Phe Val Ala Ser Glu Asn Ser Tyr Asn Asp Asp Asn Ile
            435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
            485                 490                 495

Tyr Ile Pro Lys Tyr Asp Ser Asn Gly Thr Ser Asp Ile Glu Gln His
                500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
            530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
```

```
                          565                 570                 575
Gln Gln Val Leu Val Asp Phe Thr Thr Glu Ala Asn Gln Lys Ser Thr
            580                 585                 590

Val Asp Lys Ile Ala Asp Ile Ser Ile Val Pro Tyr Ile Gly Leu
            595                 600                 605

Ala Leu Asn Ile Gly Asn Glu Ala Gln Lys Gly Asn Phe Lys Asp Ala
            610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
                660                 665                 670

Glu Arg Asp Glu Lys Trp Lys Glu Val Tyr Ser Phe Ile Val Ser Asn
                675                 680                 685

Trp Met Thr Lys Ile Asn Thr Gln Phe Asn Lys Arg Lys Glu Gln Met
            690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
                740                 745                 750

Ile Ala Met Asn Asn Ile Asp Arg Phe Leu Thr Glu Ser Ser Ile Ser
            755                 760                 765

Tyr Leu Met Lys Leu Ile Asn Glu Val Lys Ile Asn Lys Leu Arg Glu
            770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
                820                 825                 830

Asp Lys Ile Leu Ile Ser Tyr Phe Asn Lys Phe Phe Lys
                835                 840                 845

<210> SEQ ID NO 122
<211> LENGTH: 863
<212> TYPE: PRT
<213> ORGANISM: Clostridium botulinum serotype F

<400> SEQUENCE: 122

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95
```

```
Arg Ile Asn Ser Asn Pro Ala Gly Lys Val Leu Leu Gln Glu Ile Ser
                100                 105                 110

Tyr Ala Lys Pro Tyr Leu Gly Asn Asp His Thr Pro Ile Asp Glu Phe
            115                 120                 125

Ser Pro Val Thr Arg Thr Thr Ser Val Asn Ile Lys Leu Ser Thr Asn
130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
            210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
            325                 330                 335

Asn Glu Asn Lys Phe Asn Glu Ile Tyr Lys Lys Leu Tyr Ser Phe Thr
        340                 345                 350

Glu Ser Asp Leu Ala Asn Lys Phe Lys Val Lys Cys Arg Asn Thr Tyr
    355                 360                 365

Phe Ile Lys Tyr Glu Phe Leu Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Ser Glu Leu Phe Phe Val Ala Ser Glu Ser Ser Tyr Asn Glu
450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
```

```
            515                 520                 525
Glu Glu Tyr Asp Val Val Asp Phe Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
                565                 570                 575

Phe Ile Asp Thr Ile Asn Lys Pro Val Asn Ala Ala Leu Phe Ile Asp
                580                 585                 590

Trp Ile Ser Lys Val Ile Arg Asp Phe Thr Thr Glu Ala Thr Gln Lys
                595                 600                 605

Ser Thr Val Asp Lys Ile Ala Asp Ile Ser Leu Ile Val Pro Tyr Val
610                 615                 620

Gly Leu Ala Leu Asn Ile Ile Ile Glu Ala Lys Gly Asn Phe Glu
625                 630                 635                 640

Glu Ala Phe Glu Leu Leu Gly Val Gly Ile Leu Leu Glu Phe Val Pro
                645                 650                 655

Glu Leu Thr Ile Pro Val Ile Leu Val Phe Thr Ile Lys Ser Tyr Ile
                660                 665                 670

Asp Ser Tyr Glu Asn Lys Asn Lys Ala Ile Lys Ala Ile Asn Asn Ser
                675                 680                 685

Leu Ile Glu Arg Glu Ala Lys Trp Lys Glu Ile Tyr Ser Trp Ile Val
690                 695                 700

Ser Asn Trp Leu Thr Arg Ile Asn Thr Gln Phe Asn Lys Arg Lys Glu
705                 710                 715                 720

Gln Met Tyr Gln Ala Leu Gln Asn Gln Val Asp Ala Ile Lys Thr Ala
                725                 730                 735

Ile Glu Tyr Lys Tyr Asn Asn Tyr Thr Ser Asp Glu Lys Asn Arg Leu
                740                 745                 750

Glu Ser Glu Tyr Asn Ile Asn Asn Ile Glu Glu Leu Asn Lys Lys
                755                 760                 765

Val Ser Leu Ala Met Lys Asn Ile Glu Arg Phe Met Thr Glu Ser Ser
770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
                820                 825                 830

Val Thr Ser Thr Leu Asn Ser Ser Ile Pro Phe Glu Leu Ser Ser Tyr
                835                 840                 845

Thr Asn Asp Lys Ile Leu Ile Ile Tyr Phe Asn Arg Leu Tyr Lys
                850                 855                 860

<210> SEQ ID NO 123
<211> LENGTH: 863
<212> TYPE: PRT
<213> ORGANISM: Clostridium botulinum serotype G

<400> SEQUENCE: 123

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
                20                  25                  30
```

Tyr Tyr Lys Ala Phe Arg Ile Ile Asp Arg Ile Trp Ile Val Pro Glu
            35                  40                  45

Arg Phe Thr Tyr Gly Phe Gln Pro Asp Gln Phe Asn Ala Ser Thr Gly
 50                  55                  60

Val Phe Ser Lys Asp Val Tyr Glu Tyr Tyr Asp Pro Thr Tyr Leu Lys
 65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
            115                 120                 125

Phe Ala Ala Asn Val Ala Asn Val Ser Ile Asn Lys Lys Ile Ile Gln
130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
            195                 200                 205

Asn Lys Asp Thr Ser Ile Phe Ser Arg Arg Ala Tyr Phe Ala Asp Pro
            210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
            275                 280                 285

Tyr Asn Lys Ala Leu Gln Asn Phe Gln Asp Ile Ala Asn Arg Leu Asn
290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
            355                 360                 365

Arg Tyr Ser Tyr Phe Ser Glu Tyr Leu Pro Pro Ile Lys Thr Glu Lys
370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
            435                 440                 445

Gln Cys Ile Ile Val Asn Asn Glu Asp Leu Phe Phe Ile Ala Asn Lys

```
              450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
                    485                 490                 495
Leu Asp Asn Asp Leu Ser Ser Gly Ile Asp Leu Pro Asn Glu Asn Thr
                500                 505                 510
Glu Pro Phe Thr Asn Phe Asp Asp Ile Asp Ile Pro Val Tyr Ile Lys
            515                 520                 525
Gln Ser Ala Leu Lys Lys Ile Phe Val Asp Gly Asp Ser Leu Phe Glu
        530                 535                 540
Tyr Leu His Ala Gln Thr Phe Pro Ser Asn Ile Glu Asn Leu Gln Leu
545                 550                 555                 560
Thr Asn Ser Leu Asn Asp Ala Leu Arg Asn Asn Asn Lys Val Tyr Thr
                    565                 570                 575
Phe Phe Ser Thr Asn Leu Val Glu Lys Ala Asn Thr Val Val Gly Ala
                580                 585                 590
Ser Leu Phe Val Asn Trp Val Lys Gly Val Ile Asp Asp Phe Thr Ser
            595                 600                 605
Glu Ser Thr Gln Lys Ser Thr Ile Asp Lys Val Ser Asp Val Ser Ile
        610                 615                 620
Ile Ile Pro Tyr Ile Gly Pro Ala Leu Asn Val Gly Asn Glu Thr Ala
625                 630                 635                 640
Lys Glu Asn Phe Lys Asn Ala Phe Glu Ile Gly Gly Ala Ala Ile Leu
                    645                 650                 655
Met Glu Phe Ile Pro Glu Leu Ile Val Pro Ile Val Gly Phe Phe Thr
                660                 665                 670
Leu Glu Ser Tyr Val Gly Asn Lys Gly His Ile Ile Met Thr Ile Ser
            675                 680                 685
Asn Ala Leu Lys Lys Arg Asp Gln Lys Trp Thr Asp Met Tyr Gly Leu
        690                 695                 700
Ile Val Ser Gln Trp Leu Ser Thr Val Asn Thr Gln Phe Tyr Thr Ile
705                 710                 715                 720
Lys Glu Arg Met Tyr Asn Ala Leu Asn Asn Gln Ser Gln Ala Ile Glu
                    725                 730                 735
Lys Ile Ile Glu Asp Gln Tyr Asn Arg Tyr Ser Glu Glu Asp Lys Met
                740                 745                 750
Asn Ile Asn Ile Asp Phe Asn Asp Ile Asp Phe Lys Leu Asn Gln Ser
            755                 760                 765
Ile Asn Leu Ala Ile Asn Asn Ile Asp Asp Phe Ile Asn Gln Cys Ser
        770                 775                 780
Ile Ser Tyr Leu Met Asn Arg Met Ile Pro Leu Ala Val Lys Lys Leu
785                 790                 795                 800
Lys Asp Phe Asp Asp Asn Leu Lys Arg Asp Leu Leu Glu Tyr Ile Asp
                    805                 810                 815
Thr Asn Glu Leu Tyr Leu Leu Asp Glu Val Asn Ile Leu Lys Ser Lys
                820                 825                 830
Val Asn Arg His Leu Lys Asp Ser Ile Pro Phe Asp Leu Ser Leu Tyr
            835                 840                 845
Thr Lys Asp Thr Ile Leu Ile Gln Val Phe Asn Asn Tyr Ile Ser
        850                 855                 860
```

The invention claimed is:

1. A polypeptide comprising an amino acid sequence having at least 95% sequence identity with an amino acid sequence selected from the group consisting of: SEQ ID NOs: 4, 6, 10, 11, 13, 15, 19, 21, 23, 24, 25, 26, 27, 28, 29, 30, 32, 33, 34, 35, 36, 37, 38, and 39, wherein the amino acid sequence comprises, in N-C order:

a non-cytotoxic protease that is capable of cleaving a SNARE protein, wherein the non-cytotoxic protease is the L-chain of a botulinum neurotoxin;

a translocation domain that is capable of translocating the non-cytotoxic protease from within an endosome of a motor neuron of a neuromuscular junction, across the endosomal membrane thereof and into the cytosol of the motor neuron, wherein the translocation domain is the $H_N$ of a botulinum neurotoxin; and a targeting moiety that binds to a Binding Site on the motor neuron, which Binding Site is capable of undergoing endocytosis to be incorporated into an endosome within the motor neuron;

wherein the amino acid sequence comprises a cleavage site that is cleavable by a second protease and not by the non-cytotoxic protease, wherein the cleavage site is located in the non-cytotoxic protease or translocation domain; and wherein, when the targeting moiety of the polypeptide binds to a Binding Site on the motor neuron, the translocation domain can translocate the non-cytotoxic protease into the cytosol of the motor neuron such that the non-cytotoxic protease can cleave the SNARE protein; and wherein after cleavage of the cleavage site by the second protease, the polypeptide has reduced potency as measured by a reduced ability to cleave said SNARE protein and/or a reduced ability to translocate said non-cytotoxic protease.

2. The polypeptide according to claim 1, wherein said polypeptide comprises an amino acid sequence having at least 95% sequence identity with an amino acid sequence selected from the group consisting of: SEQ ID NOs: 13, 26, 27, 28 and 29.

3. A polypeptide comprising:

(a) a non-cytotoxic protease that is capable of cleaving a SNARE protein, the non-cytotoxic protease being selected from the group consisting of: the light chain of BoNT/A, the light chain of BoNT/B, the light chain of BoNT/C1, the light chain of BoNT/D, the light chain of BoNT/E, the light chain of BoNT/F, and the light chain of BoNT/G;

b) a translocation domain that is capable of translocating the non-cytotoxic protease from within an endosome of a motor neuron of a neuromuscular junction, across the endosomal membrane thereof and into the cytosol of the motor neuron, the translocation domain being selected from the group consisting of: the translocation domain of BoNT/A, the translocation domain of BoNT/B, the translocation domain of BoNT/C1, the translocation domain of BoNT/D, the translocation domain of BoNT/E, the translocation domain of BoNT/F, and the translocation domain of BoNT/G;

c) a cleavage site that is cleavable by a second protease and not by the non-cytotoxic protease, and d) a Targeting Moiety that binds to a Binding Site on the motor neuron, the Binding Site being capable of undergoing endocytosis to be incorporated into an endosome within the motor neuron;

wherein:

when the Targeting Moiety binds to a motor neuron of the neuromuscular junction, the translocation domain transports the non-cytotoxic protease into the cytosol of the motor neuron and inhibits the exocytic fusion process of the motor neuron;

after cleavage of the polypeptide by the second protease, the polypeptide has reduced potency as measured by a reduced ability to cleave the SNARE protein and/or a reduced ability to translocate the non-cytotoxic protease;

when the polypeptide comprises the light chain or the translocation domain of BoNT/A, the cleavage site is inserted within the sequence of SEQ ID NO: 52, 64 or 71;

when the polypeptide comprises the light chain or the translocation domain of BoNT/B, the cleavage site is inserted within the sequence of SEQ ID NO: 53, 65 or 72;

when the polypeptide comprises the light chain or the translocation domain of BoNT/C1, the cleavage site is inserted within the sequence of SEQ ID NO.: 54, 66 or 73;

when the polypeptide comprises the light chain or the translocation domain of BoNT/D, the cleavage site is inserted within the sequence of SEQ ID NO.: 55, 67 or 73;

when the polypeptide comprises the light chain or the translocation domain of BoNT/E, the cleavage site is inserted within the sequence SEQ ID NO.: 56, 68 or 74;

when the polypeptide comprises the light chain or the translocation domain of BoNT/F, the cleavage site is inserted within the sequence SEQ ID NO.: 57, 69 or 75; and when the polypeptide comprises the light chain or the translocation domain of BoNT/G, the cleavage site is inserted within the sequence SEQ ID NO.: 58, 70 or 76.

4. The polypeptide of claim 3, wherein:

when the polypeptide comprises the translocation domain of BoNT/A, the cleavage site is inserted within the sequence of SEQ ID NO: 71;

when the polypeptide comprises the translocation domain of BoNT/B, the cleavage site is inserted within the sequence of SEQ ID NO: 72;

when the polypeptide comprises the translocation domain of BoNT/C1, the cleavage site is inserted within the sequence of SEQ ID NO.: 73;

when the polypeptide comprises the translocation domain of BoNT/D, the cleavage site is inserted within the sequence of SEQ ID NO.: 73;

when the polypeptide comprises the translocation domain of BoNT/E, the cleavage site is inserted within the sequence of SEQ ID NO.: 74;

when the polypeptide comprises the translocation domain of BoNT/F, the cleavage site is inserted within the sequence of SEQ ID NO.: 75;

when the polypeptide comprises the translocation domain of BoNT/G, the cleavage site is inserted within the sequence of SEQ ID NO.: 76.

5. The polypeptide of claim 1, wherein said polypeptide comprises an amino acid sequence having at least 95% sequence identity with SEQ ID NO: 13.

* * * * *